(12) United States Patent
Heron et al.

(10) Patent No.: US 9,797,009 B2
(45) Date of Patent: Oct. 24, 2017

(54) ENZYME CONSTRUCT

(71) Applicant: OXFORD NANOPORE TECHNOLOGIES LIMITED, Oxford (GB)

(72) Inventors: Andrew Heron, Oxford (GB); James Clarke, Oxford (GB); Ruth Moysey, Oxford (GB); Elizabeth Jayne Wallace, Oxford (GB); Mark Bruce, Oxford (GB); Lakmal Jayasinghe, Oxford (GB); Domenico Caprotti, Oxford (GB); Szabolcs Soeroes, Oxford (GB); Luke McNeill, Oxford (GB); Mihaela Misca, Oxford (GB)

(73) Assignee: Oxford Nanopore Technologies Limited, Oxford (GB)

( * ) Notice: Subject to any disclaimer, the term of this patent is extended or adjusted under 35 U.S.C. 154(b) by 305 days.

(21) Appl. No.: 14/415,533

(22) PCT Filed: Jul. 18, 2013

(86) PCT No.: PCT/GB2013/051928
§ 371 (c)(1),
(2) Date: Jan. 16, 2015

(87) PCT Pub. No.: WO2014/013262
PCT Pub. Date: Jan. 23, 2014

(65) Prior Publication Data
US 2015/0218629 A1  Aug. 6, 2015

Related U.S. Application Data

(60) Provisional application No. 61/774,694, filed on Mar. 8, 2013, provisional application No. 61/673,446, filed on Jul. 19, 2012.

(51) Int. Cl.
*C12Q 1/68* (2006.01)
*C12N 9/14* (2006.01)

(52) U.S. Cl.
CPC ............ *C12Q 1/6869* (2013.01); *C12N 9/14* (2013.01); *C07K 2319/00* (2013.01); *C12Y 306/04* (2013.01)

(58) Field of Classification Search
None
See application file for complete search history.

(56) References Cited

U.S. PATENT DOCUMENTS

| | | | |
|---|---|---|---|
| 7,338,807 B2 | 3/2008 | Harris et al. | |
| 7,625,706 B2 * | 12/2009 | Akeson | B01L 3/502707 435/6.1 |
| 7,745,116 B2 | 6/2010 | Williams | |
| 8,105,846 B2 | 1/2012 | Bayley et al. | |
| 8,785,211 B2 | 7/2014 | Bayley et al. | |
| 8,828,208 B2 | 9/2014 | Canas et al. | |
| 2006/0063171 A1 | 3/2006 | Akeson et al. | |
| 2009/0256116 A1 | 10/2009 | Shumaker-Parry et al. | |
| 2010/0092960 A1 | 4/2010 | Fehr | |
| 2010/0120098 A1 | 5/2010 | Grunenwald et al. | |
| 2010/0221212 A1 | 9/2010 | Stagliano et al. | |
| 2011/0177498 A1 | 7/2011 | Clarke et al. | |
| 2011/0229877 A1 | 9/2011 | Jayasinghe et al. | |
| 2012/0058468 A1 | 3/2012 | Mckeown | |
| 2012/0107802 A1 | 5/2012 | Stoddart et al. | |
| 2013/0149769 A1 | 6/2013 | Kizaki et al. | |
| 2014/0051069 A1 | 2/2014 | Jayasinghe et al. | |
| 2014/0186823 A1 | 7/2014 | Clarke et al. | |
| 2014/0255921 A1 | 9/2014 | Moysey et al. | |
| 2014/0262784 A1 | 9/2014 | Clarke et al. | |
| 2014/0335512 A1 | 11/2014 | Moysey et al. | |
| 2015/0008126 A1 | 1/2015 | Maglia et al. | |
| 2015/0031020 A1 | 1/2015 | Jayasinghe et al. | |
| 2015/0065354 A1 | 3/2015 | Moysey et al. | |
| 2015/0152492 A1 | 6/2015 | Brown et al. | |
| 2015/0191709 A1 | 7/2015 | Heron et al. | |
| 2015/0197796 A1 | 7/2015 | White et al. | |
| 2016/0257942 A1 | 9/2016 | Bruce et al. | |
| 2017/0002406 A1 | 1/2017 | Bowen et al. | |

FOREIGN PATENT DOCUMENTS

| | | |
|---|---|---|
| WO | 00/28312 A1 | 5/2000 |
| WO | 2005/124888 A1 | 12/2005 |
| WO | WO 2006/028508 | 3/2006 |
| WO | 2006/100484 A2 | 9/2006 |
| WO | 2007/057668 A1 | 5/2007 |

(Continued)

OTHER PUBLICATIONS

Portakal et al. (Construction of recB-recD genetic fusion and functional analysis of RecBDC fusion enzyme in *Escherichia coli*, BMC Biochemistry 2008, 9:27, published Oct. 10, 2008).*
Blast® NCBI. Sequence ID No. 10; ZSYBNHWV114. Sep. 18, 2015.
Blast® NCBI. Sequence ID No. 52; ZT1133A811N. Sep. 18, 2015.
UniProt Database accession No. D0KN27. Dec. 15, 2009.
UniProt Database accession No. I7J3V8 sequence. Oct. 3, 2012.

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

The invention relates to methods using constructs comprising a helicase and an additional polynucleotide binding moiety. The helicase is attached to the polynucleotide binding moiety and the construct has the ability to control the movement of a polynucleotide. The constructs can be used to control the movement of polynucleotides and are particularly useful for sequencing polynucleotides.

20 Claims, 28 Drawing Sheets

(56) References Cited

FOREIGN PATENT DOCUMENTS

| WO | 2008102120 A1 | 8/2008 |
|---|---|---|
| WO | 2008102121 A1 | 8/2008 |
| WO | 2009/035647 A1 | 3/2009 |
| WO | 2009/044170 A1 | 4/2009 |
| WO | 2009/077734 A2 | 6/2009 |
| WO | 2010/004265 A1 | 1/2010 |
| WO | 2010/004273 A1 | 1/2010 |
| WO | WO 2010/034018 | 3/2010 |
| WO | 2010/086602 A1 | 8/2010 |
| WO | 2010/086603 A1 | 8/2010 |
| WO | WO 2010/086622 | 8/2010 |
| WO | 2010/109197 A2 | 9/2010 |
| WO | 2010/122293 A1 | 10/2010 |
| WO | 2011/067559 A1 | 6/2011 |
| WO | WO 2012/033524 A2 | 3/2012 |
| WO | 2012/098561 A2 | 7/2012 |
| WO | 2012/098562 A2 | 7/2012 |
| WO | WO 2012/164270 A1 | 12/2012 |
| WO | WO 2013/014451 A1 | 1/2013 |
| WO | WO 2013/041878 | 3/2013 |
| WO | 2013/057495 A2 | 4/2013 |
| WO | 2013/098561 A1 | 7/2013 |
| WO | 2013/098562 A2 | 7/2013 |
| WO | WO 2013/153359 | 10/2013 |
| WO | 2014/013259 A1 | 1/2014 |
| WO | 2014/013260 A1 | 1/2014 |
| WO | WO 2014/013262 A1 | 1/2014 |
| WO | WO 2014/158665 A1 | 10/2014 |

OTHER PUBLICATIONS

UniProt Database accession No. K7NRI8 sequence. Feb. 6, 2013.
UniProt Database accession No. Q7Y5C3 sequence. Oct. 1, 2003.
Sequence ID No. 2 Search Results. US-14-351-038-2. Sep. 16, 2015. 69 pages.
Genbank Submission. NCBI; Accession No. AM778123. Richards et al.; Sep. 18, 2008.
[No Author Listed] Antibodies bind specific molecules through their hypervariable loops. 33.3 Antibody Binding. 6th edition. 2007;953-954.
Allen et al., The genome sequence of the psychrophilic archaeon, Methanococcoides burtonii: the role of genome evolution in cold adaptation. ISME J. Sep. 2009;3(9):1012-35. doi: 10.1038/ismej.2009.45.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Buttner et al., Structural basis for DNA duplex separation by a superfamily-2 helicase. Nat Struct Mol Biol. Jul. 2007;14(7):647-52.
Byrd et al., A parallel quadruplex DNA is bound tightly but unfolded slowly by pif1 helicase. J Biol Chem. Mar. 6, 2015;290(10):6482-94. doi:10.1074/jbc.M114.630749. Epub Jan. 14, 2015.
Colas et al., Microscopical investigations of nisin-loaded nanoliposomes prepared by Mozafari method and their bacterial targeting. Micron. 2007;38(8):841-7.
Comer et al., Microscopic mechanics of hairpin DNA translocation through synthetic nanopores. Biophys J. Jan. 2009;96(2):593-608. doi: 10.1016/j.bpj.2008.09.023.
Deamer, Nanopore analysis of nucleic acids bound to exonucleases and polymerases. Annu Rev Biophys. 2010;39:79-90. doi:10.1146/annurev.biophys.093008.131250.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Dostál et al., Tracking F plasmid TraI relaxase processing reactions provides insight into F plasmid transfer. Nucleic Acids Res. Apr. 2011;39(7):2658-70. doi: 10.1093/nar/gkq1137. Epub Nov. 24, 2010.
Dou et al., The DNA binding properties of the *Escherichia coli* RecQ helicase. J Biol Chem. Feb. 20, 2004;279(8):6354-63. Epub Dec. 9, 2003.
Eliseev et al., Molecular Recognition of Nucleotides, Nucleosides, and Sugars by Aminocyclodextrins. J. Am. Chem. Soc., vol. 116:6081-6088 (1994).
Garalde et al., Highly parallel direct RNA sequencing on an array of nanopores. bioRxiv. 2016. doi: http://dx.doi.org/10.1101/068809.
Graham et al., Sequence-specific assembly of FtsK hexamers establishes directional translocation on DNA. Proc Natl Acad Sci U S A. Nov. 23, 2010;107(47):20263-8. doi: 10.1073/pnas.1007518107. Epub Nov. 3, 2010.
He et al, The T4 phage SF1B helicase Dda is structurally optimized to perform DNA strand separation. Structure. Jul. 3, 2012;20(7):1189-200. doi:10.1016/j.str.2012.04.013. Epub May 31, 2012.
Hopfner et al., Mechanisms of nucleic acid translocases: lessons from structural biology and single-molecule biophysics. Curr Opin Struct Biol. Feb. 2007;17(1):87-95. Epub Dec. 6, 2006.
Hornblower et al., Single-molecule analysis of DNA-protein complexes using nanopores. Nat Methods. Apr. 2007;4(4):315-7. Epub Mar. 4, 2007.
Howorka et al., Nanopore analytics: sensing of single molecules. Chem Soc Rev. Aug. 2009;38(8):2360-84. doi: 10.1039/b813796j. Epub Jun. 15, 2009.
James, Aptamers. Encyclopedia of Analytical Chemistry. R.A. Meyers (Ed.). 4848-4871. John Wiley & Sons Ltd, Chichester, 2000.
Jezewska et al., Interactions of *Escherichia coli* replicative helicase PriA protein with single-stranded DNA. Biochemistry. Aug. 29, 2000;39(34):10454-67.
Kafri et al., Dynamics of molecular motors and polymer translocation with sequence heterogeneity. Biophys J. Jun. 2004;86(6):3373-91.
Kar et al., Defining the structure-function relationships of bluetongue virus helicase protein VP6. J Virol. Nov. 2003;77(21):11347-56.
Keyser, Controlling molecular transport through nanopores. J R Soc Interface. Oct. 7, 2011;8(63):1369-78. doi: 10.1098/rsif.2011.0222. Epub Jun. 29, 2011.
Khafizov, Single Molecule Force Spectroscopy of Single Stranded Dna Binding Protein and Rep Helicase. University of Illinois at Urbana-Champaign Dissertation. 2012.
Korolev et al., Major domain swiveling revealed by the crystal structures of complexes of E. coli Rep helicase bound to single-stranded DNA and ADP. Cell. Aug. 22, 1997;90(4):635-47.
Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Kuper et al., Functional and structural studies of the nucleotide excision repair helicase XPD suggest a polarity for DNA translocation. EMBO J. Jan. 18, 2012;31(2):494-502. doi: 10.1038/emboj.2011.374.
Langecker et al., Synthetic lipid membrane channels formed by designed DNA nanostructures. Science. Nov. 16, 2012;338(6109):932-6. doi: 10.1126/science.1225624.
Lee et al., Direct imaging of single UvrD helicase dynamics on long single-stranded DNA. Nat Commun. 2013;4:1878. doi:10.1038/ncomms2882.
Lohman et al., Mechanisms of helicase-catalyzed DNA unwinding. Annu Rev Biochem. 1996;65:169-214.
Maddox et al., Elevated serum levels in human pregnancy of a molecule immunochemically similar to eosinophil granule major basic protein. J Exp Med. Oct. 1, 1983;158(4):1211-26.

(56) References Cited

OTHER PUBLICATIONS

Marini et al., A human DNA helicase homologous to the DNA cross-link sensitivity protein Mus308. J Biol Chem. Mar. 8, 2002;277(10):8716-23. Epub Dec. 18, 2001.
Morris et al., Evidence for a functional monomeric form of the bacteriophage T4 DdA helicase. Dda does not form stable oligomeric structures. J Biol Chem. Jun. 8, 2001;276(23):19691-8. Epub Feb. 27, 2001.
Pinero-Fernandez et al., Indole transport across *Escherichia coli* membranes. J Bacteriol. Apr. 2011;193(8):1793-8. doi:10.1128/JB.01477-10. Epub Feb. 4, 2011.
Raney et al., Structure and Mechanisms of SF1 DNA Helicases. Adv Exp Med Biol. 2013;767:17-46. doi: 10.1007/978-1-4614-5037-5_2.
Rudolf et al., The DNA repair helicases XPD and FancJ have essential iron-sulfur domains. Mol Cell. Sep. 15, 2006;23(6):801-8.
Rudolf et al., The helicase XPD unwinds bubble structures and is not stalled by DNA lesions removed by the nucleotide excision repair pathway. Nucleic Acids Res. Jan. 2010;38(3):931-41. doi:10.1093/nar/gkp1058.
Saariaho et al., Characteristics of MuA transposase-catalyzed processing of model transposon end DNA hairpin substrates. Nucleic Acids Res. Jun. 6, 2006;34(10):3139-49. Print 2006.
Sathiyamoorthy et al., The crystal structure of *Escherichia coli* group 4 capsule protein GfcC reveals a domain organization resembling that of Wza. Biochemistry. Jun. 21, 2011;50(24):5465-76. doi: 10.1021/bi101869h.
Singleton et al., Structure and mechanism of helicases and nucleic acid translocases. Annu Rev Biochem. 2007;76:23-50.
Wang et al., DNA helicase activity of the RecD protein from Deinococcus radiodurans. J Biol Chem. Dec. 10, 2004;279(50):52024-32.
White, Structure, function and evolution of the XPD family of iron—sulfur-containing 5'→>3' DNA helicases. Biochem Soc Trans. 2009;37:547-551.
Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.
Woodman et al., Molecular biology of Hel308 helicase in archaea. Biochem Soc Trans. Feb. 2009;37(Pt 1):74-8. doi: 10.1042/BST0370074.
Woodman et al., Winged helix domains with unknown function in Hel308 and related helicases. Biochem Soc Trans. Jan. 2011;39(1):140-4. doi:10.1042/BST0390140.
Zhang et al., Structural evidence for consecutive Hel308-like modules in the spliceosomal ATPase Brr2. Nat Struct Mol Biol. Jul. 2009;16(7):731-9. doi: 10.1038/nsmb.1625.
Activating signal cointegrator 1 complex subunit 3-like [Strongylocentrotus purpuratus]Database accession No. XP_003728286 abstract.
Altschul S. F. (1993) J Mol Evol 36:290-300.
Altschul, S.F et al (1990) J Mol Biol 215:403-10.
Braha, et al., Chem Biol. Jul. 1997; 4(7):497-505.
Cheng, Y. et al., J Biol Chem.Apr. 8, 2001; 286(14): 12670-12682. Epub Feb. 2, 2011.
G123225 Database accession No. B4KAC8 sequence.
DEAD/DEAH box helicase Database accession No. I3D0E7 sequence.
Devereux et al (1984) Nucleic Acids Research 12, p. 387-395.
Fairman-Williams et al., Curr. Opin. Struct Biol., 2010, 20 (3), 313-324.
Garcilláen-Barcia MP, et al., FEMS Microbiol Rev. May 2009; 33(3): 657-687.
Gonzalez-Perez et al., Langmuir, 2009, 25, 10447-10450.
Grant, G. P. et al., (2007), Nucleic Acids Res 35(10): e77.
Green et al., Protein Science 2001, vol. 10, 1293-1304.
Hammerstein et al. J Biol Chem. Apr. 22, 2001; 286(16): 14324-14334.
Holden et al., J Am Chem Soc. Jul. 11, 2007;129(27):8650-8655.
International Preliminary Report on Patentability, PCT/GB2013/051928, dated Jan. 20, 2015, pp. 1-8.
International Search Report and Written Opinion, PCT/GB2013/051928, Oct. 9, 2013, 1-12.
Ivanov AP et al., Nano Lett. Jan. 12, 2011;11(1):279-85.
Keyser U F, Journal of Bacteriology, 2011, vol. 193, Nr:8, pp. 1793-1378.
Kumar, A. et al. (1988). Anal Biochem; 169(2): 376-82.
Lieberman KR et al, J Am Chem Soc. 2010;132(50):17961-72.
Liu C. C. et al., Annu. Rev. Biochem., 2010, 79, 413-444.
Liu H, et al., Cell, May 30, 2008, 133(5):801-812.
Lohman et al., Nature Reviews Molecular Cell Biology, 2008, 9, 391-401.
M.A. Holden, H. Bayley. J. Am. Chem. Soc. 2005, 127, 6502-6503.
Montal and Mueller (Proc. Natl. Acad. Sci. USA., 1972; 69: 3561-3566).
Nikolov, V., R. Lipowsky, et al. (2007). "Behavior of giant vesicles with anchored DNA molecules." Biophys J 92(12): 4356-68.
O'Shea et al., Science 254 (5031): 539-544.
Pfeiffer, I. and F. Hook (2004). "Bivalent cholesterol-based coupling of oligonucleotides to lipid membrane assemblies." J Am Chem Soc 126(33): 10224-5.
Predicted protein Database accession No. A4S1E1 sequence.
Press release: Oxford Nanopore introduces DNA 'strand sequencing' on the high-throughput GridION platform and presents MinION, a sequencer the size of a USB; memory stick, Feb. 2012.
Putative ski2-type helicase; EC=3.6.4.—Database accession No. E1QUS6 sequence.
Putative ski2-type helicase; EC=3.6.4.—Database accession No. K0IM99 sequence.
Remaut and Waksman Trends Biochem. Sci. (2006) 31 436-444.
Richards et al, J BioChem 2008, vol. 283, 5118-5128.
Satapathy AK, et al., FEBS J.; Apr. 2008; 275(8): 1835-1851. Epub Mar. 9, 2008.
Schneider et al, Nature Biotech 2012, vol. 30, 326-328.
Soni GV et al., Rev Sci Instrum. Jan. 2010;81(1):014301.
Stoddart et al., PNAS, 2009; 106(19): 7702-7707.
Troutt, A. B., et al. (1992). Proc Natl Acad Sci U S A 89(20): 9823-9825.
Tuteja and Tuteja, Eur. J. Biochem. 271, 1849-1863 (2004).
Van Heel M, et al., Q Rev Biophys.(2000) 33: 307-369.
Van Lengerich, B., R. J. Rawle, et al. "Covalent attachment of lipid vesicles to a fluid-supported bilayer allows observation of DNA-mediated vesicle interactions." Langmuir 26(11): 8666-72.
Venkatesan & Rashid, Nature Nanotechnology, vol. 6, Nr:10, pp. 615-624.
Vinson, Science, 2009: 324(5924): 197.
Xiang Ma, et al., Chem. Soc. Rev., 2010,39, 70-80.
Yoshina-Ishii, C. and S. G. Boxer (2003). "Arrays of mobile tethered vesicles on supported lipid bilayers." J Am Chem Soc 125(13): 3696-7.
U.S. Appl. No. 14/415,459, filed Jan. 16, 2015, James White.
U.S. Appl. No. 14/415,453, filed Jan. 16, 2015, Andrew Heron.
U.S. Appl. No. 14/369,024, filed Jun. 26, 2014, Ruth Moysey.
U.S. Appl. No. 14/369,072, filed Jun. 26, 2014, Ruth Moysey.
U.S. Appl. No. 14/351,038, filed Apr. 10, 2014, Ruth Moysey.
U.S. Appl. No. 13/260,178, filed Jan. 17, 2012, David Stoddart.
U.S. Appl. No. 13/147,159, filed Nov. 15, 2011, Brian Mckeown.
U.S. Appl. No. 14/234,698, filed Apr. 25, 2014, Clive Gavin Brown.
U.S. Appl. No. 14/122,573, filed Apr. 16, 2014, James Clarke.
U.S. Appl. No. 14/334,285, filed Jul. 17, 2014, Giovanni Maglia.
U.S. Appl. No. 13/984,628, filed Feb. 27, 2014, James Clarke.
U.S. Appl. No. 13/002,717, filed Mar. 30, 2011, James Clarke.
U.S. Appl. No. 14/455,394, filed Aug. 8, 2014, Lakmal Jayasinghe.
U.S. Appl. No. 13/968,778, filed Aug. 16, 2013, Lakmal Jayasinghe.
U.S. Appl. No. 12/093,610, filed Jul. 28, 2008, Hagan Bayley.
U.S. Appl. No. 15/441,695, filed Feb. 24, 2017, Moysey et al.
U.S. Appl. No. 14/773,164, filed Sep. 4, 2015, Andrew John Heron.
U.S. Appl. No. 14/858,138, filed Sep. 18, 2015, Lakmal Jayasinghe.

\* cited by examiner

SEQUENCE LISTING

<160> NUMBER OF SEQ ID NOS: 115

<210> SEQ ID NO 1
<211> LENGTH: 558
<212> TYPE: DNA
<213> ORGANISM: Artificial sequence
<220> FEATURE:
<223> OTHER INFORMATION: Mycobacterium smegmatis porin A mutant
      (D90N/D91N/D93N/D118R/D134R/E139K)

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558
```

<210> SEQ ID NO 2
<211> LENGTH: 184
<212> TYPE: PRT
<213> ORGANISM: Artificial sequence
<220> FEATURE:
<223> OTHER INFORMATION: Mycobacterium smegmatis porin A mutant
      (D90N/D91N/D93N/D118R/D134R/E139K)

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 885
<212> TYPE: DNA
<213> ORGANISM: Artificial sequence
<220> FEATURE:
<223> OTHER INFORMATION: alpha-hemolysin mutant E111N/K147N

<400> SEQUENCE: 3

```
atggcagatt ctgatattaa tattaaaacc ggtactacag atattggaag caatactaca    60
gtaaaaacag gtgatttagt cacttatgat aaagaaaatg gcatgcacaa aaaagtattt   120
tatagtttta tcgatgataa aaatcacaat aaaaaactgc tagttattag aacaaaaggt   180
accattgctg gtcaatatag agtttatagc gaagaaggtg ctaacaaaag tggtttagcc   240
tggccttcag cctttaaggt acagttgcaa ctacctgata tgaagtagc tcaaatatct    300
gattactatc caagaaattc gattgataca aaaaactata tgagtacttt aacttatgga   360
ttcaacggta atgttactgg tgatgataca ggaaaaattg gcggccttat tggtgcaaat   420
gtttcgattg gtcatacact gaactatgtt caacctgatt tcaaaacaat tttagagagc   480
ccaactgata aaaagtagg ctggaaagtg atatttaaca atatggtgaa tcaaaattgg    540
ggaccatacg atcgagattc ttggaacccg gtatatggca atcaactttt catgaaaact   600
agaaatggtt ctatgaaagc agcagataac ttccttgatc ctaacaaagc aagttctcta   660
ttatcttcag ggttttcacc agacttcgct acagttatta ctatggatag aaaagcatcc   720
aaacaacaaa caaatataga tgtaatatac gaacgagttc gtgatgatta ccaattgcat   780
tggacttcaa caaattggaa aggtaccaat actaaagata aatggacaga tcgttcttca   840
gaaagatata aaatcgattg ggaaaaagaa gaaatgacaa attaa                    885
```

<210> SEQ ID NO 4
<211> LENGTH: 293
<212> TYPE: PRT
<213> ORGANISM: Artificial sequence
<220> FEATURE:
<223> OTHER INFORMATION: alpha-hemolysin mutant E111N/K147N

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
```

```
            145                 150                 155                 160
        Thr Asp Lys Lys Val Gly Trp Lys Val Ile Phe Asn Asn Met Val Asn
                        165                 170                 175

Gln Asn Trp Gly Pro Tyr Asp Arg Asp Ser Trp Asn Pro Val Tyr Gly
                        180                 185                 190

Asn Gln Leu Phe Met Lys Thr Arg Asn Gly Ser Met Lys Ala Ala Asp
                        195                 200                 205

Asn Phe Leu Asp Pro Asn Lys Ala Ser Ser Leu Leu Ser Ser Gly Phe
                210                 215                 220

Ser Pro Asp Phe Ala Thr Val Ile Thr Met Asp Arg Lys Ala Ser Lys
        225                 230                 235                 240

Gln Gln Thr Asn Ile Asp Val Ile Tyr Glu Arg Val Arg Asp Asp Tyr
                        245                 250                 255

Gln Leu His Trp Thr Ser Thr Asn Trp Lys Gly Thr Asn Thr Lys Asp
                        260                 265                 270

Lys Trp Thr Asp Arg Ser Ser Glu Arg Tyr Lys Ile Asp Trp Glu Lys
                        275                 280                 285

Glu Glu Met Thr Asn
                290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
        1               5                   10                  15

Thr Val Gln Gln Trp Asp Thr Phe Leu Asn Gly Val Phe Pro Leu Asp
                        20                  25                  30

Arg Asn Arg Leu Thr Arg Glu Trp Phe His Ser Gly Arg Ala Lys Tyr
                        35                  40                  45

Ile Val Ala Gly Pro Gly Ala Asp Glu Phe Glu Gly Thr Leu Glu Leu
                50                  55                  60

Gly Tyr Gln Ile Gly Phe Pro Trp Ser Leu Gly Val Gly Ile Asn Phe
        65                  70                  75                  80

Ser Tyr Thr Thr Pro Asn Ile Leu Ile Asp Asp Gly Asp Ile Thr Ala
                        85                  90                  95

Pro Pro Phe Gly Leu Asn Ser Val Ile Thr Pro Asn Leu Phe Pro Gly
                        100                 105                 110

Val Ser Ile Ser Ala Asp Leu Gly Asn Gly Pro Gly Ile Gln Glu Val
                        115                 120                 125

Ala Thr Phe Ser Val Asp Val Ser Gly Pro Ala Gly Gly Val Ala Val
                        130                 135                 140

Ser Asn Ala His Gly Thr Val Thr Gly Ala Ala Gly Gly Val Leu Leu
        145                 150                 155                 160

Arg Pro Phe Ala Arg Leu Ile Ala Ser Thr Gly Asp Ser Val Thr Thr
                        165                 170                 175

Tyr Gly Glu Pro Trp Asn Met Asn
                        180

<210> SEQ ID NO 6
<211> LENGTH: 184
<212> TYPE: PRT
<213> ORGANISM: Mycobacterium smegmatis
```

```
<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175
```

Gly Glu Pro Trp Asn Met Asn
            180

<210> SEQ ID NO 8
<211> LENGTH: 8
<212> TYPE: PRT
<213> ORGANISM: Artificial sequence
<220> FEATURE:
<223> OTHER INFORMATION: Amino acid sequence of the Hel308 motif
<220> FEATURE:
<221> NAME/KEY: MISC_FEATURE
<222> LOCATION: (2)..(2)
<223> OTHER INFORMATION: Xaa = C, M or L
<220> FEATURE:
<221> NAME/KEY: MISC_FEATURE
<222> LOCATION: (3)..(3)
<223> OTHER INFORMATION: Xaa = any amino acid

<400> SEQUENCE: 8

Gln Xaa Xaa Gly Arg Ala Gly Arg
1               5

<210> SEQ ID NO 9
<211> LENGTH: 9
<212> TYPE: PRT
<213> ORGANISM: Artificial sequence
<220> FEATURE:
<223> OTHER INFORMATION: Amino acid sequence of the extended Hel308
      motif
<220> FEATURE:
<221> NAME/KEY: MISC_FEATURE
<222> LOCATION: (2)..(2)
<223> OTHER INFORMATION: Xaa = C, M or L
<220> FEATURE:
<221> NAME/KEY: MISC_FEATURE
<222> LOCATION: (3)..(3)
<223> OTHER INFORMATION: Xaa = any amino acid

<400> SEQUENCE: 9

Gln Xaa Xaa Gly Arg Ala Gly Arg Pro
1               5

<210> SEQ ID NO 10
<211> LENGTH: 760
<212> TYPE: PRT
<213> ORGANISM: Methanococcoides burtonii

<400> SEQUENCE: 10

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp

```
            130                 135                 140
Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
                180                 185                 190

Ala Ala Leu Val Leu Ser Glu Trp Arg Pro Thr Asp Leu His Glu Gly
                195                 200                 205

Val Leu Phe Gly Asp Ala Ile Asn Phe Pro Gly Ser Gln Lys Lys Ile
                210                 215                 220

Asp Arg Leu Glu Lys Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
                260                 265                 270

Asn Asp Ile Met Ile Lys Leu Ala Gly Ile Ala Glu Glu Val Glu Ser
                275                 280                 285

Thr Gly Glu Thr Asp Thr Ala Ile Val Leu Ala Asn Cys Ile Arg Lys
                290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
                340                 345                 350

Arg Ser Tyr Arg Arg Phe Asp Ser Asn Phe Gly Met Gln Pro Ile Pro
                355                 360                 365

Val Leu Glu Tyr Lys Gln Met Ala Gly Arg Ala Gly Arg Pro His Leu
                370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
                420                 425                 430

Ile Val Asn Gly Phe Ala Ser Thr Arg Gln Glu Leu Phe Asp Phe Phe
                435                 440                 445

Gly Ala Thr Phe Phe Ala Tyr Gln Gln Asp Lys Trp Met Leu Glu Glu
                450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
                500                 505                 510

Ser Lys Ile Val Asp Gly Phe Lys Asp Ile Gly Lys Ser Thr Gly Gly
                515                 520                 525

Asn Met Gly Ser Leu Glu Asp Asp Lys Gly Asp Asp Ile Thr Val Thr
                530                 535                 540

Asp Met Thr Leu Leu His Leu Val Cys Ser Thr Pro Asp Met Arg Gln
545                 550                 555                 560
```

```
Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Val Lys Thr Ala Met Leu Leu Glu
        595                 600                 605

Glu Trp Val Thr Glu Val Ser Ala Glu Asp Ile Thr Arg His Phe Asn
610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
                660                 665                 670

Asp Leu Met Glu Leu Val Gly Ile Arg Gly Val Gly Arg Val Arg Ala
            675                 680                 685

Arg Lys Leu Tyr Asn Ala Gly Phe Val Ser Val Ala Lys Leu Lys Gly
        690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
                740                 745                 750

Gln Lys Thr Phe Asn Asp Phe Gln
        755                 760

<210> SEQ ID NO 11
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 11

Gln Met Ala Gly Arg Ala Gly Arg
1               5

<210> SEQ ID NO 12
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 12

Gln Met Ala Gly Arg Ala Gly Arg Pro
1               5

<210> SEQ ID NO 13
<211> LENGTH: 707
<212> TYPE: PRT
<213> ORGANISM: Cenarchaeum symbiosum

<400> SEQUENCE: 13

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30
```

```
Lys Ala Gly Leu Thr Asp Gly Lys Ser Val Leu Val Ser Ala Pro Thr
            35                  40                  45

Ala Ser Gly Lys Thr Leu Ile Ala Ala Ile Ala Met Ile Ser His Leu
 50                  55                  60

Ser Arg Asn Arg Gly Lys Ala Val Tyr Leu Ser Pro Leu Arg Ala Leu
 65                  70                  75                  80

Ala Ala Glu Lys Phe Ala Glu Phe Gly Lys Ile Gly Gly Ile Pro Leu
                 85                  90                  95

Gly Arg Pro Val Arg Val Gly Val Ser Thr Gly Asp Phe Glu Lys Ala
                100                 105                 110

Gly Arg Ser Leu Gly Asn Asn Asp Ile Leu Val Leu Thr Asn Glu Arg
                115                 120                 125

Met Asp Ser Leu Ile Arg Arg Arg Pro Asp Trp Met Asp Glu Val Gly
        130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
                180                 185                 190

Ala Gly Trp Leu Asp Cys Thr Leu Val His Ser Thr Trp Arg Pro Val
                195                 200                 205

Pro Leu Ser Glu Gly Val Tyr Gln Asp Gly Glu Val Ala Met Gly Asp
        210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
                260                 265                 270

Ile Pro Glu Ala Lys Gly Ala Asp Ala Ala Lys Leu Ala Ala Ala Ala
        275                 280                 285

Lys Lys Ile Ile Ser Ser Gly Glu Thr Lys Leu Ala Lys Thr Leu
        290                 295                 300

Ala Glu Leu Val Glu Lys Gly Ala Ala Phe His His Ala Gly Leu Asn
305                 310                 315                 320

Gln Asp Cys Arg Ser Val Val Glu Glu Glu Phe Arg Ser Gly Arg Ile
                325                 330                 335

Arg Leu Leu Ala Ser Thr Pro Thr Leu Ala Ala Gly Val Asn Leu Pro
                340                 345                 350

Ala Arg Arg Val Val Ile Ser Ser Val Met Arg Tyr Asn Ser Ser Ser
                355                 360                 365

Gly Met Ser Glu Pro Ile Ser Ile Leu Glu Tyr Lys Gln Leu Cys Gly
        370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415

Pro Glu Pro Ile Arg Ser Ala Met Val Asp Asp Arg Ala Leu Arg Ile
                420                 425                 430

His Val Leu Ser Leu Val Thr Thr Ser Pro Gly Ile Lys Glu Asp Asp
        435                 440                 445
```

Val Thr Glu Phe Phe Leu Gly Thr Leu Gly Gly Gln Gln Ser Gly Glu
            450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
                500                 505                 510

Leu Arg Asp Ala Val Gly Glu Ala Ser Pro Gly Arg Met His Thr Leu
                515                 520                 525

Gly Phe Leu His Leu Val Ser Glu Cys Ser Gly Phe Met Pro Arg Phe
                530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
                580                 585                 590

Leu Ala Glu Asp Leu Lys Phe Glu Ser Gly Asp Val His Arg Met Val
                595                 600                 605

Glu Ser Ser Gly Trp Leu Leu Arg Cys Ile Trp Glu Ile Ser Lys His
                610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
                660                 665                 670

Gly Pro Gly Asp Leu Ala Ala Val Pro Val Glu Arg Leu Ser Arg Val
                675                 680                 685

Glu Gly Ile Gly Ala Thr Leu Ala Asn Asn Ile Lys Ser Gln Leu Arg
                690                 695                 700

Lys Gly Gly
705

<210> SEQ ID NO 14
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 14

Gln Leu Cys Gly Arg Ala Gly Arg
1               5

<210> SEQ ID NO 15
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 15

Gln Leu Cys Gly Arg Ala Gly Arg Pro
1               5

<210> SEQ ID NO 16

```
<211> LENGTH: 720
<212> TYPE: PRT
<213> ORGANISM: Thermococcus gammatolerans

<400> SEQUENCE: 16
```

| | | | | | | | | | | | | | | |
|---|---|---|---|---|---|---|---|---|---|---|---|---|---|---|
| Met | Lys | Val | Asp | Glu | Leu | Pro | Val | Asp | Glu | Arg | Leu | Lys | Ala | Val | Leu |
| 1 | | | | 5 | | | | | 10 | | | | | 15 | |

Lys Glu Arg Gly Ile Glu Glu Leu Tyr Pro Pro Gln Ala Glu Ala Leu
                20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
        115                 120                 125

Leu Arg His Gly Ala Arg Trp Ile Asn Asp Val Lys Leu Val Val Ala
130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
            180                 185                 190

Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
370                 375                 380

Ala Arg Thr Asp Glu Pro Gly Lys Leu Met Glu Arg Tyr Ile Arg Gly

```
                385                 390                 395                 400
Lys Pro Glu Lys Leu Phe Ser Met Leu Ala Asn Glu Gln Ala Phe Arg
                    405                 410                 415
Ser Gln Val Leu Ala Leu Ile Thr Asn Phe Gly Ile Arg Ser Phe Pro
                420                 425                 430
Glu Leu Val Arg Phe Leu Glu Arg Thr Phe Tyr Ala His Gln Arg Lys
                435                 440                 445
Asp Leu Ser Ser Leu Glu Tyr Lys Ala Lys Glu Val Val Tyr Phe Leu
                450                 455                 460
Ile Glu Asn Glu Phe Ile Asp Leu Asp Leu Glu Asp Arg Phe Ile Pro
465                 470                 475                 480
Leu Pro Phe Gly Lys Arg Thr Ser Gln Leu Tyr Ile Asp Pro Leu Thr
                    485                 490                 495
Ala Lys Lys Phe Lys Asp Ala Phe Pro Ala Ile Glu Arg Asn Pro Asn
                500                 505                 510
Pro Phe Gly Ile Phe Gln Leu Ile Ala Ser Thr Pro Asp Met Ala Thr
                515                 520                 525
Leu Thr Ala Arg Arg Arg Glu Met Glu Asp Tyr Leu Asp Leu Ala Tyr
                530                 535                 540
Glu Leu Glu Asp Lys Leu Tyr Ala Ser Ile Pro Tyr Tyr Glu Asp Ser
545                 550                 555                 560
Arg Phe Gln Gly Phe Leu Gly Gln Val Lys Thr Ala Lys Val Leu Leu
                    565                 570                 575
Asp Trp Ile Asn Glu Val Pro Glu Ala Arg Ile Tyr Glu Thr Tyr Ser
                580                 585                 590
Ile Asp Pro Gly Asp Leu Tyr Arg Leu Leu Glu Leu Ala Asp Trp Leu
                595                 600                 605
Met Tyr Ser Leu Ile Glu Leu Tyr Lys Leu Phe Glu Pro Lys Glu Glu
                610                 615                 620
Ile Leu Asn Tyr Leu Arg Asp Leu His Leu Arg Leu Arg His Gly Val
625                 630                 635                 640
Arg Glu Glu Leu Leu Glu Leu Val Arg Leu Pro Asn Ile Gly Arg Lys
                    645                 650                 655
Arg Ala Arg Ala Leu Tyr Asn Ala Gly Phe Arg Ser Val Glu Ala Ile
                660                 665                 670
Ala Asn Ala Lys Pro Ala Glu Leu Leu Ala Val Glu Gly Ile Gly Ala
                675                 680                 685
Lys Ile Leu Asp Gly Ile Tyr Arg His Leu Gly Ile Glu Lys Arg Val
                690                 695                 700
Thr Glu Glu Lys Pro Lys Arg Lys Gly Thr Leu Glu Asp Phe Leu Arg
705                 710                 715                 720

<210> SEQ ID NO 17
<211> LENGTH: 8
<212> TYPE: PRT
<213> ORGANISM: Artificial sequence
<220> FEATURE:
<223> OTHER INFORMATION: Exemplary extended Hel308 motif

<400> SEQUENCE: 17

Gln Met Met Gly Arg Ala Gly Arg
1               5

<210> SEQ ID NO 18
<211> LENGTH: 9
<212> TYPE: PRT
```

```
<213> ORGANISM: Artificial sequence
<220> FEATURE:
<223> OTHER INFORMATION: Exemplary extended Hel308 motif

<400> SEQUENCE: 18

Gln Met Met Gly Arg Ala Gly Arg Pro
1               5

<210> SEQ ID NO 19
<211> LENGTH: 799
<212> TYPE: PRT
<213> ORGANISM: Methanospirillum hungatei

<400> SEQUENCE: 19

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
            20                  25                  30

Glu Lys Gly Leu Leu Glu Gly Lys Asn Leu Leu Ile Ser Ile Pro Thr
        35                  40                  45

Ala Ser Gly Lys Thr Leu Leu Ala Glu Met Ala Met Trp Ser Arg Ile
    50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
        115                 120                 125

Arg Thr Pro Trp Leu Ser Gln Ile Thr Cys Ile Val Leu Asp Glu Val
    130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
        195                 200                 205

Tyr Asn Gly Lys Ile Arg Phe Ser Asp Ser Glu Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
                245                 250                 255

Phe Ala Lys Lys Ala Ala Gly Leu Lys Ala Gly Ser Pro Asp Ser
            260                 265                 270

Lys Ala Leu Ala Gln Glu Leu Arg Arg Leu Arg Asp Arg Asp Glu Gly
        275                 280                 285

Asn Val Leu Ala Asp Cys Val Glu Arg Gly Ala Ala Phe His His Ala
    290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                325                 330                 335
```

```
Asn Leu Pro Ala Arg Arg Val Ile Ile Arg Asp Tyr Asn Arg Phe Ala
            340                 345                 350

Ser Gly Leu Gly Met Val Pro Ile Pro Val Gly Glu Tyr His Gln Met
        355                 360                 365

Ala Gly Arg Ala Gly Arg Pro His Leu Asp Pro Tyr Gly Glu Ala Val
    370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
        435                 440                 445

Gln His Pro Lys Thr Arg Ser Leu Pro Arg Leu Val Ala Asp Ala Ile
    450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
        515                 520                 525

Arg Leu Tyr Leu Lys Ala Ala Asp Thr Gln Leu Leu Arg Thr Phe Leu
    530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
        595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
        675                 680                 685

Gln Val Ile Asp Glu Ile Thr Gly Val Lys Arg Ser Gly Ile His Ser
    690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
            740                 745                 750
```

```
Val Leu Gly Ala Ala Arg Ala Arg Lys Val Leu Ala Phe Leu Ser Asn
        755                 760                 765

Ser Glu Lys Glu Asn Ser Ser Ser Asp Lys Thr Glu Glu Ile Pro Asp
        770                 775                 780

Thr Gln Lys Ile Arg Gly Gln Ser Ser Trp Glu Asp Phe Gly Cys
785                 790                 795

<210> SEQ ID NO 20
<211> LENGTH: 8
<212> TYPE: PRT
<213> ORGANISM: Artificial sequence
<220> FEATURE:
<223> OTHER INFORMATION: RecD-like motif I
<220> FEATURE:
<221> NAME/KEY: MISC_FEATURE
<222> LOCATION: (1)..(1)
<223> OTHER INFORMATION: Xaa = G, S or A
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = P, A, S or G
<220> FEATURE:
<221> NAME/KEY: MISC_FEATURE
<222> LOCATION: (5)..(5)
<223> OTHER INFORMATION: Xaa = T, A, V, S or C
<220> FEATURE:
<221> NAME/KEY: MISC_FEATURE
<222> LOCATION: (6)..(6)
<223> OTHER INFORMATION: Xaa = G or A
<220> FEATURE:
<221> NAME/KEY: MISC_FEATURE
<222> LOCATION: (7)..(7)
<223> OTHER INFORMATION: Xaa = K or R
<220> FEATURE:
<221> NAME/KEY: MISC_FEATURE
<222> LOCATION: (8)..(8)
<223> OTHER INFORMATION: Xaa = T or S

<400> SEQUENCE: 20

Xaa Xaa Xaa Gly Xaa Xaa Xaa Xaa
1               5

<210> SEQ ID NO 21
<211> LENGTH: 25
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(17)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = G, S or A
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = P, A, S or G
<220> FEATURE:
<221> NAME/KEY: MISC_FEATURE
<222> LOCATION: (22)..(22)
<223> OTHER INFORMATION: Xaa = T, A, V, S or C
<220> FEATURE:
<221> NAME/KEY: MISC_FEATURE
```

<222> LOCATION: (23)..(23)
<223> OTHER INFORMATION: Xaa = G or A
<220> FEATURE:
<221> NAME/KEY: MISC_FEATURE
<222> LOCATION: (24)..(24)
<223> OTHER INFORMATION: Xaa = K or R
<220> FEATURE:
<221> NAME/KEY: MISC_FEATURE
<222> LOCATION: (25)..(25)
<223> OTHER INFORMATION: Xaa = T or S

<400> SEQUENCE: 21

Gln Xaa Xaa Xaa Xaa Xaa Xaa Xaa Xaa Xaa Xaa Xaa Xaa Xaa Xaa
1               5                   10                  15

Xaa Xaa Xaa Xaa Gly Xaa Xaa Xaa Xaa
            20                  25

<210> SEQ ID NO 22
<211> LENGTH: 26
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = G, S or A
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = P, A, S or G
<220> FEATURE:
<221> NAME/KEY: MISC_FEATURE
<222> LOCATION: (23)..(23)
<223> OTHER INFORMATION: Xaa = T, A, V, S or C
<220> FEATURE:
<221> NAME/KEY: MISC_FEATURE
<222> LOCATION: (24)..(24)
<223> OTHER INFORMATION: Xaa = G or A
<220> FEATURE:
<221> NAME/KEY: MISC_FEATURE
<222> LOCATION: (25)..(25)
<223> OTHER INFORMATION: Xaa = K or A
<220> FEATURE:
<221> NAME/KEY: MISC_FEATURE
<222> LOCATION: (26)..(26)
<223> OTHER INFORMATION: Xaa = T or S

<400> SEQUENCE: 22

Gln Xaa Xaa Xaa Xaa Xaa Xaa Xaa Xaa Xaa Xaa Xaa Xaa Xaa Xaa
1               5                   10                  15

Xaa Xaa Xaa Xaa Xaa Gly Xaa Xaa Xaa Xaa
            20                  25

<210> SEQ ID NO 23
<211> LENGTH: 27
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(19)
<223> OTHER INFORMATION: Xaa = any amino acid
<220> FEATURE:

```
<221> NAME/KEY: MISC_FEATURE
<222> LOCATION: (20)..(20)
<223> OTHER INFORMATION: Xaa = G, S or A
<220> FEATURE:
<221> NAME/KEY: MISC_FEATURE
<222> LOCATION: (21)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = P, A, S or G
<220> FEATURE:
<221> NAME/KEY: MISC_FEATURE
<222> LOCATION: (24)..(24)
<223> OTHER INFORMATION: Xaa = T, A, V, S or C
<220> FEATURE:
<221> NAME/KEY: MISC_FEATURE
<222> LOCATION: (25)..(25)
<223> OTHER INFORMATION: Xaa = G or A
<220> FEATURE:
<221> NAME/KEY: MISC_FEATURE
<222> LOCATION: (26)..(26)
<223> OTHER INFORMATION: Xaa = K or R
<220> FEATURE:
<221> NAME/KEY: MISC_FEATURE
<222> LOCATION: (27)..(27)
<223> OTHER INFORMATION: Xaa = T or S

<400> SEQUENCE: 23

Gln Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Gly Xaa Xaa Xaa Xaa
            20                  25

<210> SEQ ID NO 24
<211> LENGTH: 8
<212> TYPE: PRT
<213> ORGANISM: Artificial sequence
<220> FEATURE:
<223> OTHER INFORMATION: RecD motif I
<220> FEATURE:
<221> NAME/KEY: MISC_FEATURE
<222> LOCATION: (5)..(5)
<223> OTHER INFORMATION: Xaa = T, V or C
<220> FEATURE:
<221> NAME/KEY: MISC_FEATURE
<222> LOCATION: (8)..(8)
<223> OTHER INFORMATION: Xaa = T or S

<400> SEQUENCE: 24

Gly Gly Pro Gly Xaa Gly Lys Xaa
1               5

<210> SEQ ID NO 25
<211> LENGTH: 8
<212> TYPE: PRT
<213> ORGANISM: Artificial sequence
<220> FEATURE:
<223> OTHER INFORMATION: Preferred RecD motif I

<400> SEQUENCE: 25

Gly Gly Pro Gly Thr Gly Lys Thr
1               5

<210> SEQ ID NO 26
<211> LENGTH: 25
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
```

```
<222> LOCATION: (2)..(17)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = T, V or C
<220> FEATURE:
<221> NAME/KEY: MISC_FEATURE
<222> LOCATION: (25)..(25)
<223> OTHER INFORMATION: Xaa = T or S

<400> SEQUENCE: 26

Gln Xaa Xaa Xaa Xaa Xaa Xaa Xaa Xaa Xaa Xaa Xaa Xaa Xaa Xaa
1               5                   10                  15

Xaa Gly Gly Pro Gly Xaa Gly Lys Xaa
            20                  25

<210> SEQ ID NO 27
<211> LENGTH: 26
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(18)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = T, V or C
<220> FEATURE:
<221> NAME/KEY: MISC_FEATURE
<222> LOCATION: (26)..(26)
<223> OTHER INFORMATION: Xaa = T or S

<400> SEQUENCE: 27

Gln Xaa Xaa Xaa Xaa Xaa Xaa Xaa Xaa Xaa Xaa Xaa Xaa Xaa Xaa
1               5                   10                  15

Xaa Xaa Gly Gly Pro Gly Xaa Gly Lys Xaa
            20                  25

<210> SEQ ID NO 28
<211> LENGTH: 27
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(19)
<223> OTHER INFORMATION: Xaa = any amino acid
<220> FEATURE:
<221> NAME/KEY: MISC_FEATURE
<222> LOCATION: (24)..(24)
<223> OTHER INFORMATION: Xaa = T, V or C
<220> FEATURE:
<221> NAME/KEY: MISC_FEATURE
<222> LOCATION: (27)..(27)
<223> OTHER INFORMATION: Xaa = T or S

<400> SEQUENCE: 28

Gln Xaa Xaa Xaa Xaa Xaa Xaa Xaa Xaa Xaa Xaa Xaa Xaa Xaa Xaa
1               5                   10                  15

Xaa Xaa Xaa Gly Gly Pro Gly Xaa Gly Lys Xaa
            20                  25

<210> SEQ ID NO 29
<211> LENGTH: 10
<212> TYPE: PRT
```

```
<213> ORGANISM: Artificial sequence
<220> FEATURE:
<223> OTHER INFORMATION: RecD-like motif V
<220> FEATURE:
<221> NAME/KEY: MISC_FEATURE
<222> LOCATION: (1)..(1)
<223> OTHER INFORMATION: Xaa = Y, W or F
<220> FEATURE:
<221> NAME/KEY: MISC_FEATURE
<222> LOCATION: (2)..(2)
<223> OTHER INFORMATION: Xaa = A, T, S, M, C or V
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = T, N or S
<220> FEATURE:
<221> NAME/KEY: MISC_FEATURE
<222> LOCATION: (5)..(5)
<223> OTHER INFORMATION: Xaa = A, T, G, S, V or I
<220> FEATURE:
<221> NAME/KEY: MISC_FEATURE
<222> LOCATION: (6)..(8)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = G or S

<400> SEQUENCE: 29

Xaa Xaa Xaa Xaa Xaa Xaa Xaa Xaa Gln Xaa
1               5                   10

<210> SEQ ID NO 30
<211> LENGTH: 10
<212> TYPE: PRT
<213> ORGANISM: Artificial sequence
<220> FEATURE:
<223> OTHER INFORMATION: RecD motif V
<220> FEATURE:
<221> NAME/KEY: MISC_FEATURE
<222> LOCATION: (1)..(1)
<223> OTHER INFORMATION: Xaa = Y, W or F
<220> FEATURE:
<221> NAME/KEY: MISC_FEATURE
<222> LOCATION: (2)..(2)
<223> OTHER INFORMATION: Xaa = A, M, C or V
<220> FEATURE:
<221> NAME/KEY: MISC_FEATURE
<222> LOCATION: (3)..(3)
<223> OTHER INFORMATION: Xaa = I, M or L
<220> FEATURE:
<221> NAME/KEY: MISC_FEATURE
<222> LOCATION: (4)..(4)
<223> OTHER INFORMATION: Xaa = T or S
<220> FEATURE:
<221> NAME/KEY: MISC_FEATURE
<222> LOCATION: (5)..(5)
<223> OTHER INFORMATION: Xaa = V or I

<400> SEQUENCE: 30

Xaa Xaa Xaa Xaa Xaa His Lys Ser Gln Gly
1               5                   10

<210> SEQ ID NO 31
<211> LENGTH: 13
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
```

```
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(10)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = any amino acid except D, E, R and K

<400> SEQUENCE: 31

His Xaa Xaa Xaa Arg Xaa Xaa Xaa Xaa Xaa His Xaa His
1               5                   10

<210> SEQ ID NO 32
<211> LENGTH: 14
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(11)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid except D, E, R and K

<400> SEQUENCE: 32

His Xaa Xaa Xaa Arg Xaa Xaa Xaa Xaa Xaa His Xaa His
1               5                   10

<210> SEQ ID NO 33
<211> LENGTH: 15
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(12)
<223> OTHER INFORMATION: Xaa = any amino acid
<220> FEATURE:
<221> NAME/KEY: MISC_FEATURE
<222> LOCATION: (14)..(14)
<223> OTHER INFORMATION: Xaa = any amino acid except D, E, R and K

<400> SEQUENCE: 33

His Xaa Xaa Xaa Arg Xaa Xaa Xaa Xaa Xaa Xaa His Xaa His
1               5                   10                  15
```

-continued

```
<210> SEQ ID NO 34
<211> LENGTH: 16
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(13)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid except D, E, R and K

<400> SEQUENCE: 34

His Xaa Xaa Xaa Arg Xaa Xaa Xaa Xaa Xaa Xaa Xaa Xaa His Xaa His
1               5                   10                  15

<210> SEQ ID NO 35
<211> LENGTH: 17
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(14)
<223> OTHER INFORMATION: Xaa = any amino acid
<220> FEATURE:
<221> NAME/KEY: MISC_FEATURE
<222> LOCATION: (16)..(16)
<223> OTHER INFORMATION: Xaa = any amino acid except D, E, R and K

<400> SEQUENCE: 35

His Xaa Xaa Xaa Arg Xaa Xaa Xaa Xaa Xaa Xaa Xaa Xaa Xaa His Xaa
1               5                   10                  15

His

<210> SEQ ID NO 36
<211> LENGTH: 18
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(15)
<223> OTHER INFORMATION: Xaa = any amino acid
<220> FEATURE:
```

```
<221> NAME/KEY: MISC_FEATURE
<222> LOCATION: (17)..(17)
<223> OTHER INFORMATION: Xaa = any amino acid except D, E, R and K

<400> SEQUENCE: 36

His Xaa Xaa Xaa Arg Xaa Xaa Xaa Xaa Xaa Xaa Xaa Xaa Xaa Xaa His
1               5                   10                  15

Xaa His

<210> SEQ ID NO 37
<211> LENGTH: 19
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid except D, E, R and K

<400> SEQUENCE: 37

His Xaa Xaa Xaa Arg Xaa Xaa Xaa Xaa Xaa Xaa Xaa Xaa Xaa Xaa Xaa
1               5                   10                  15

His Xaa His

<210> SEQ ID NO 38
<211> LENGTH: 20
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(17)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid

<400> SEQUENCE: 38

His Xaa Xaa Xaa Arg Xaa Xaa Xaa Xaa Xaa Xaa Xaa Xaa Xaa Xaa Xaa
1               5                   10                  15

Xaa His Xaa His
            20

<210> SEQ ID NO 39
<211> LENGTH: 17
<212> TYPE: PRT
<213> ORGANISM: Artificial sequence
```

```
-continued

<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(15)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid except D, E, K and R

<400> SEQUENCE: 39

Gly Xaa Xaa Xaa Xaa Xaa Xaa Xaa His Xaa Xaa Xaa Xaa Xaa Xaa His
1               5                   10                  15

Xaa

<210> SEQ ID NO 40
<211> LENGTH: 18
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid except D, E, K and R

<400> SEQUENCE: 40

Gly Xaa Xaa Xaa Xaa Xaa Xaa Xaa His Xaa Xaa Xaa Xaa Xaa Xaa Xaa
1               5                   10                  15

His Xaa

<210> SEQ ID NO 41
<211> LENGTH: 19
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
```

```
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(17)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid except D, E, K and R

<400> SEQUENCE: 41

Gly Xaa Xaa Xaa Xaa Xaa Xaa Xaa His Xaa Xaa Xaa Xaa Xaa Xaa Xaa
1               5                   10                  15

Xaa His Xaa

<210> SEQ ID NO 42
<211> LENGTH: 20
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(18)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid except D, E, K and R

<400> SEQUENCE: 42

Gly Xaa Xaa Xaa Xaa Xaa Xaa Xaa His Xaa Xaa Xaa Xaa Xaa Xaa Xaa
1               5                   10                  15

Xaa Xaa His Xaa
            20

<210> SEQ ID NO 43
<211> LENGTH: 21
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(19)
```

-continued

```
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = any amino acid

<400> SEQUENCE: 43

Gly Xaa Xaa Xaa Xaa Xaa Xaa Xaa His Xaa Xaa Xaa Xaa Xaa Xaa Xaa
1               5                   10                  15

Xaa Xaa Xaa His Xaa
            20

<210> SEQ ID NO 44
<211> LENGTH: 22
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(20)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except D, E, K and R

<400> SEQUENCE: 44

Gly Xaa Xaa Xaa Xaa Xaa Xaa Xaa His Xaa Xaa Xaa Xaa Xaa Xaa Xaa
1               5                   10                  15

Xaa Xaa Xaa Xaa His Xaa
            20

<210> SEQ ID NO 45
<211> LENGTH: 23
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = any amino acid except D, E, K and R

<400> SEQUENCE: 45
```

-continued

```
Gly Xaa Xaa Xaa Xaa Xaa Xaa His Xaa Xaa Xaa Xaa Xaa Xaa
1               5                   10                  15

Xaa Xaa Xaa Xaa Xaa His Xaa
            20
```

<210> SEQ ID NO 46
<211> LENGTH: 1756
<212> TYPE: PRT
<213> ORGANISM: Escherichia coli

<400> SEQUENCE: 46

```
Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
        275                 280                 285

Arg Ala Tyr Arg Asp Ala Ala Asp Gln Arg Thr Glu Ile Arg Thr Gln
    290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
```

```
                340             345             350
Val Ile Glu Arg Ala Arg Ala Gly Ile Asp Glu Ala Ile Ser Arg Glu
            355                 360                 365

Gln Leu Ile Pro Leu Asp Arg Glu Lys Gly Leu Phe Thr Ser Gly Ile
            370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Ala Ala Gly Gln Arg Glu Arg
            435                 440                 445

Val Ala Glu Leu Val Met Met Ala Arg Glu Gln Gly Arg Glu Val Gln
            450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
            485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
            515                 520                 525

Asn Val Gln Val Leu Ile Thr Asp Ser Gly Gln Arg Thr Gly Thr Gly
            530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
            565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
            595                 600                 605

Ile Leu Thr Gln Ala Ile Arg Ser Glu Leu Lys Thr Gln Gly Val Leu
            610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
            645                 650                 655

Glu Gln Trp Asn Pro Glu Thr Arg Ser His Asp Arg Tyr Val Ile Asp
            660                 665                 670

Arg Val Thr Ala Gln Ser His Ser Leu Thr Leu Arg Asp Ala Gln Gly
            675                 680                 685

Glu Thr Gln Val Val Arg Ile Ser Ser Leu Asp Ser Ser Trp Ser Leu
            690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
            725                 730                 735

Val Ala Ser Val Ser Glu Asp Ala Met Thr Val Val Pro Gly Arg
            740                 745                 750

Ala Glu Pro Ala Ser Leu Pro Val Ser Asp Ser Pro Phe Thr Ala Leu
            755                 760                 765
```

```
Lys Leu Glu Asn Gly Trp Val Glu Thr Pro Gly His Ser Val Ser Asp
770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
            805                 810                 815

Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
        835                 840                 845

Leu Glu Thr Ala Ile Ser Leu Gln Lys Ala Gly Leu His Thr Pro Ala
    850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
        915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Gln Gly
            980                 985                 990

Tyr Ala Gly Val Gly Lys Thr Thr Gln Phe Arg Ala Val Met Ser Ala
        995                 1000                1005

Val Asn Met Leu Pro Ala Ser Glu Arg Pro Arg Val Val Gly Leu
    1010                1015                1020

Gly Pro Thr His Arg Ala Val Gly Glu Met Arg Ser Ala Gly Val
    1025                1030                1035

Asp Ala Gln Thr Leu Ala Ser Phe Leu His Asp Thr Gln Leu Gln
    1040                1045                1050

Gln Arg Ser Gly Glu Thr Pro Asp Phe Ser Asn Thr Leu Phe Leu
    1055                1060                1065

Leu Asp Glu Ser Ser Met Val Gly Asn Thr Glu Met Ala Arg Ala
    1070                1075                1080

Tyr Ala Leu Ile Ala Ala Gly Gly Gly Arg Ala Val Ala Ser Gly
    1085                1090                1095

Asp Thr Asp Gln Leu Gln Ala Ile Ala Pro Gly Gln Ser Phe Arg
    1100                1105                1110

Leu Gln Gln Thr Arg Ser Ala Ala Asp Val Val Ile Met Lys Glu
    1115                1120                1125

Ile Val Arg Gln Thr Pro Glu Leu Arg Glu Ala Val Tyr Ser Leu
    1130                1135                1140

Ile Asn Arg Asp Val Glu Arg Ala Leu Ser Gly Leu Glu Ser Val
    1145                1150                1155

Lys Pro Ser Gln Val Pro Arg Leu Glu Gly Ala Trp Ala Pro Glu
    1160                1165                1170
```

-continued

```
His Ser Val Thr Glu Phe Ser His Ser Gln Glu Ala Lys Leu Ala
    1175                1180                1185
Glu Ala Gln Gln Lys Ala Met Leu Lys Gly Glu Ala Phe Pro Asp
    1190                1195                1200
Ile Pro Met Thr Leu Tyr Glu Ala Ile Val Arg Asp Tyr Thr Gly
    1205                1210                1215
Arg Thr Pro Glu Ala Arg Glu Gln Thr Leu Ile Val Thr His Leu
    1220                1225                1230
Asn Glu Asp Arg Arg Val Leu Asn Ser Met Ile His Asp Ala Arg
    1235                1240                1245
Glu Lys Ala Gly Glu Leu Gly Lys Glu Gln Val Met Val Pro Val
    1250                1255                1260
Leu Asn Thr Ala Asn Ile Arg Asp Gly Glu Leu Arg Arg Leu Ser
    1265                1270                1275
Thr Trp Glu Lys Asn Pro Asp Ala Leu Ala Leu Val Asp Asn Val
    1280                1285                1290
Tyr His Arg Ile Ala Gly Ile Ser Lys Asp Asp Gly Leu Ile Thr
    1295                1300                1305
Leu Gln Asp Ala Glu Gly Asn Thr Arg Leu Ile Ser Pro Arg Glu
    1310                1315                1320
Ala Val Ala Glu Gly Val Thr Leu Tyr Thr Pro Asp Lys Ile Arg
    1325                1330                1335
Val Gly Thr Gly Asp Arg Met Arg Phe Thr Lys Ser Asp Arg Glu
    1340                1345                1350
Arg Gly Tyr Val Ala Asn Ser Val Trp Thr Val Thr Ala Val Ser
    1355                1360                1365
Gly Asp Ser Val Thr Leu Ser Asp Gly Gln Gln Thr Arg Val Ile
    1370                1375                1380
Arg Pro Gly Gln Glu Arg Ala Glu Gln His Ile Asp Leu Ala Tyr
    1385                1390                1395
Ala Ile Thr Ala His Gly Ala Gln Gly Ala Ser Glu Thr Phe Ala
    1400                1405                1410
Ile Ala Leu Glu Gly Thr Glu Gly Asn Arg Lys Leu Met Ala Gly
    1415                1420                1425
Phe Glu Ser Ala Tyr Val Ala Leu Ser Arg Met Lys Gln His Val
    1430                1435                1440
Gln Val Tyr Thr Asp Asn Arg Gln Gly Trp Thr Asp Ala Ile Asn
    1445                1450                1455
Asn Ala Val Gln Lys Gly Thr Ala His Asp Val Leu Glu Pro Lys
    1460                1465                1470
Pro Asp Arg Glu Val Met Asn Ala Gln Arg Leu Phe Ser Thr Ala
    1475                1480                1485
Arg Glu Leu Arg Asp Val Ala Ala Gly Arg Ala Val Leu Arg Gln
    1490                1495                1500
Ala Gly Leu Ala Gly Gly Asp Ser Pro Ala Arg Phe Ile Ala Pro
    1505                1510                1515
Gly Arg Lys Tyr Pro Gln Pro Tyr Val Ala Leu Pro Ala Phe Asp
    1520                1525                1530
Arg Asn Gly Lys Ser Ala Gly Ile Trp Leu Asn Pro Leu Thr Thr
    1535                1540                1545
Asp Asp Gly Asn Gly Leu Arg Gly Phe Ser Gly Glu Gly Arg Val
    1550                1555                1560
Lys Gly Ser Gly Asp Ala Gln Phe Val Ala Leu Gln Gly Ser Arg
```

```
                1565                1570                1575

Asn Gly Glu Ser Leu Leu Ala Asp Asn Met Gln Asp Gly Val Arg
            1580                1585                1590

Ile Ala Arg Asp Asn Pro Asp Ser Gly Val Val Arg Ile Ala
        1595                1600                1605

Gly Glu Gly Arg Pro Trp Asn Pro Gly Ala Ile Thr Gly Gly Arg
    1610                1615                1620

Val Trp Gly Asp Ile Pro Asp Asn Ser Val Gln Pro Gly Ala Gly
1625                1630                1635

Asn Gly Glu Pro Val Thr Ala Glu Val Leu Ala Gln Arg Gln Ala
    1640                1645                1650

Glu Glu Ala Ile Arg Arg Glu Thr Glu Arg Arg Ala Asp Glu Ile
    1655                1660                1665

Val Arg Lys Met Ala Glu Asn Lys Pro Asp Leu Pro Asp Gly Lys
    1670                1675                1680

Thr Glu Leu Ala Val Arg Asp Ile Ala Gly Gln Glu Arg Asp Arg
    1685                1690                1695

Ser Ala Ile Ser Glu Arg Glu Thr Ala Leu Pro Glu Ser Val Leu
    1700                1705                1710

Arg Glu Ser Gln Arg Glu Arg Glu Ala Val Arg Glu Val Ala Arg
    1715                1720                1725

Glu Asn Leu Leu Gln Glu Arg Leu Gln Gln Met Glu Arg Asp Met
    1730                1735                1740

Val Arg Asp Leu Gln Lys Glu Lys Thr Leu Gly Gly Asp
    1745                1750                1755

<210> SEQ ID NO 47
<211> LENGTH: 8
<212> TYPE: PRT
<213> ORGANISM: Artificial sequence
<220> FEATURE:
<223> OTHER INFORMATION: RecD-like motif I of TraI Eco

<400> SEQUENCE: 47

Gly Tyr Ala Gly Val Gly Lys Thr
1               5

<210> SEQ ID NO 48
<211> LENGTH: 10
<212> TYPE: PRT
<213> ORGANISM: Artificial sequence
<220> FEATURE:
<223> OTHER INFORMATION: RecD-like motif V of TraI Eco

<400> SEQUENCE: 48

Tyr Ala Ile Thr Ala His Gly Ala Gln Gly
1               5                   10

<210> SEQ ID NO 49
<211> LENGTH: 14
<212> TYPE: PRT
<213> ORGANISM: Artificial sequence
<220> FEATURE:
<223> OTHER INFORMATION: MobF  motif III of TraI Eco

<400> SEQUENCE: 49

His Asp Thr Ser Arg Asp Gln Glu Pro Gln Leu His Thr His
1               5                   10

<210> SEQ ID NO 50
```

```
<211> LENGTH: 9
<212> TYPE: PRT
<213> ORGANISM: Artificial Sequence
<220> FEATURE:
<223> OTHER INFORMATION: XPD motif V
<220> FEATURE:
<221> NAME/KEY: MISC_FEATURE
<222> LOCATION: (1)..(1)
<223> OTHER INFORMATION: Any amino acid except D, E, K or R. Preferably
      not charged or H. More preferably V, L, I, S or Y.
<220> FEATURE:
<221> NAME/KEY: MISC_FEATURE
<222> LOCATION: (2)..(2)
<223> OTHER INFORMATION: Any amino acid except D, E, K or R. Preferably
      not charged or H.
<220> FEATURE:
<221> NAME/KEY: MISC_FEATURE
<222> LOCATION: (3)..(3)
<223> OTHER INFORMATION: Any amino acid.
<220> FEATURE:
<221> NAME/KEY: MISC_FEATURE
<222> LOCATION: (5)..(5)
<223> OTHER INFORMATION: Any amino acid.  Preferably K, R or T.
<220> FEATURE:
<221> NAME/KEY: MISC_FEATURE
<222> LOCATION: (6)..(6)
<223> OTHER INFORMATION: Any amino acid except D, E, K or R. Preferably
      not charged or H. More preferably V, L, I, N or F.
<220> FEATURE:
<221> NAME/KEY: MISC_FEATURE
<222> LOCATION: (7)..(7)
<223> OTHER INFORMATION: Any amino acid except D, E, K or R. Preferably
      not charged or H. More preferably S or A.

<400> SEQUENCE: 50

Xaa Xaa Xaa Gly Xaa Xaa Xaa Glu Gly
1               5

<210> SEQ ID NO 51
<211> LENGTH: 22
<212> TYPE: PRT
<213> ORGANISM: Artificial Sequence
<220> FEATURE:
<223> OTHER INFORMATION: XPD motif VI
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid except D, E, K, R. Typically G,
      P, A, V, L, I, M, C, F, Y, W, H, Q, N, S or T.  Preferably not
      charged. Preferably not H.  More preferably V, A, L, I or M.
<220> FEATURE:
<221> NAME/KEY: MISC_FEATURE
<222> LOCATION: (6)..(6)
<223> OTHER INFORMATION: Any amino acid except D, E, K, R. Typically G,
      P, A, V, L, I, M, C, F, Y, W, H, Q, N, S or T.  Preferably not
      charged. Preferably not H.  More preferably V, A, L, I, M or C.
<220> FEATURE:
<221> NAME/KEY: MISC_FEATURE
<222> LOCATION: (7)..(7)
<223> OTHER INFORMATION: Any amino acid except D, E, K, R. Typically G,
      P, A, V, L, I, M, C, F, Y, W, H, Q, N, S or T.  Preferably not
      charged. Preferably not H.  More preferably I, H, L, F, M or V.
<220> FEATURE:
<221> NAME/KEY: MISC_FEATURE
<222> LOCATION: (9)..(11)
<223> OTHER INFORMATION: Any amino acid.
<220> FEATURE:
<221> NAME/KEY: MISC_FEATURE
<222> LOCATION: (12)..(12)
<223> OTHER INFORMATION: D or E
<220> FEATURE:
<221> NAME/KEY: MISC_FEATURE
<222> LOCATION: (13)..(13)
```

```
<223> OTHER INFORMATION: Any amino acid.
<220> FEATURE:
<221> NAME/KEY: MISC_FEATURE
<222> LOCATION: (14)..(14)
<223> OTHER INFORMATION: Any amino acid.  Preferably G, A, S or C
<220> FEATURE:
<221> NAME/KEY: MISC_FEATURE
<222> LOCATION: (15)..(16)
<223> OTHER INFORMATION: Any amino acid.
<220> FEATURE:
<221> NAME/KEY: MISC_FEATURE
<222> LOCATION: (17)..(17)
<223> OTHER INFORMATION: Any amino acid. Preferably F, V, L, I, M, A, W
      or Y
<220> FEATURE:
<221> NAME/KEY: MISC_FEATURE
<222> LOCATION: (18)..(18)
<223> OTHER INFORMATION: Any amino acid. Preferably L, F, Y, M, I or V.
<220> FEATURE:
<221> NAME/KEY: MISC_FEATURE
<222> LOCATION: (19)..(19)
<223> OTHER INFORMATION: Any amino acid. Preferably A, C, V, L, I, M or
      S.

<400> SEQUENCE: 51

Gln Xaa Xaa Gly Arg Xaa Xaa Arg Xaa Xaa Xaa Xaa Xaa Xaa Xaa
1               5                   10                  15

Xaa Xaa Xaa Asp Asn Arg
            20

<210> SEQ ID NO 52
<211> LENGTH: 726
<212> TYPE: PRT
<213> ORGANISM: Methanococcoides burtonii

<400> SEQUENCE: 52

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
            20                  25                  30

Gln Gln Gln Leu Val Leu Phe Glu Gly Ala Cys Gly Thr Gly Lys Thr
        35                  40                  45

Leu Ser Ala Leu Val Pro Ala Leu His Val Gly Lys Met Leu Gly Lys
    50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
    130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205
```

```
His Ala Ile Lys Asp Gly Met Cys Gly Tyr Glu Leu Val Lys Arg Glu
    210                 215                 220
Leu Lys His Ala Asp Leu Leu Ile Cys Asn Tyr His His Val Leu Asn
225                 230                 235                 240
Pro Asp Ile Phe Ser Thr Val Leu Gly Trp Ile Glu Lys Glu Pro Gln
                245                 250                 255
Glu Thr Ile Val Ile Phe Asp Glu Ala His Asn Leu Glu Ser Ala Ala
            260                 265                 270
Arg Ser His Ser Ser Leu Ser Leu Thr Glu His Ser Ile Glu Lys Ala
        275                 280                 285
Ile Thr Glu Leu Glu Ala Asn Leu Asp Leu Leu Ala Asp Asp Asn Ile
    290                 295                 300
His Asn Leu Phe Asn Ile Phe Leu Glu Val Ile Ser Asp Thr Tyr Asn
305                 310                 315                 320
Ser Arg Phe Lys Phe Gly Glu Arg Glu Arg Val Arg Lys Asn Trp Tyr
                325                 330                 335
Asp Ile Arg Ile Ser Asp Pro Tyr Glu Arg Asn Asp Ile Val Arg Gly
            340                 345                 350
Lys Phe Leu Arg Gln Ala Lys Gly Asp Phe Gly Glu Lys Asp Ile
        355                 360                 365
Gln Ile Leu Leu Ser Glu Ala Ser Glu Leu Gly Ala Lys Leu Asp Glu
    370                 375                 380
Thr Tyr Arg Asp Gln Tyr Lys Lys Gly Leu Ser Ser Val Met Lys Arg
385                 390                 395                 400
Ser His Ile Arg Tyr Val Ala Asp Phe Met Ser Ala Tyr Ile Glu Leu
                405                 410                 415
Ser His Asn Leu Asn Tyr Tyr Pro Ile Leu Asn Val Arg Arg Asp Met
            420                 425                 430
Asn Asp Glu Ile Tyr Gly Arg Val Glu Leu Phe Thr Cys Ile Pro Lys
        435                 440                 445
Asn Val Thr Glu Pro Leu Phe Asn Ser Leu Phe Ser Val Ile Leu Met
    450                 455                 460
Ser Ala Thr Leu His Pro Phe Glu Met Val Lys Lys Thr Leu Gly Ile
465                 470                 475                 480
Thr Arg Asp Thr Cys Glu Met Ser Tyr Gly Thr Ser Phe Pro Glu Glu
                485                 490                 495
Lys Arg Leu Ser Ile Ala Val Ser Ile Pro Pro Leu Phe Ala Lys Asn
            500                 505                 510
Arg Asp Asp Arg His Val Thr Glu Leu Leu Gln Val Leu Leu Asp
        515                 520                 525
Ser Ile Glu Asn Ser Lys Gly Asn Val Ile Leu Phe Phe Gln Ser Ala
    530                 535                 540
Phe Glu Ala Lys Arg Tyr Tyr Ser Lys Ile Glu Pro Leu Val Asn Val
545                 550                 555                 560
Pro Val Phe Leu Asp Glu Val Gly Ile Ser Ser Gln Asp Val Arg Glu
                565                 570                 575
Glu Phe Phe Ser Ile Gly Glu Glu Asn Gly Lys Ala Val Leu Leu Ser
            580                 585                 590
Tyr Leu Trp Gly Thr Leu Ser Glu Gly Ile Asp Tyr Arg Asp Gly Arg
        595                 600                 605
Gly Arg Thr Val Ile Ile Gly Val Gly Tyr Pro Ala Leu Asn Asp
    610                 615                 620
Arg Met Asn Ala Val Glu Ser Ala Tyr Asp His Val Phe Gly Tyr Gly
```

-continued

```
            625                 630                 635                 640
Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
                660                 665                 670

Ile Leu Leu Asp Gly Arg Phe Leu Thr Asp Ser Lys Lys Arg Phe Gly
                675                 680                 685

Lys Phe Ser Val Phe Glu Val Phe Pro Pro Ala Glu Arg Ser Glu Phe
                690                 695                 700

Val Asp Val Asp Pro Glu Lys Val Lys Tyr Ser Leu Met Asn Phe Phe
705                 710                 715                 720

Met Asp Asn Asp Glu Gln
                725

<210> SEQ ID NO 53
<211> LENGTH: 9
<212> TYPE: PRT
<213> ORGANISM: Artificial Sequence
<220> FEATURE:
<223> OTHER INFORMATION: Motif V

<400> SEQUENCE: 53

Tyr Leu Trp Gly Thr Leu Ser Glu Gly
1               5

<210> SEQ ID NO 54
<211> LENGTH: 22
<212> TYPE: PRT
<213> ORGANISM: Artificial Sequence
<220> FEATURE:
<223> OTHER INFORMATION: Motif VI

<400> SEQUENCE: 54

Gln Ala Met Gly Arg Val Val Arg Ser Pro Thr Asp Tyr Gly Ala Arg
1               5                   10                  15

Ile Leu Leu Asp Gly Arg
                20

<210> SEQ ID NO 55
<211> LENGTH: 65
<212> TYPE: PRT
<213> ORGANISM: Artificial sequence
<220> FEATURE:
<223> OTHER INFORMATION: HhH domain

<400> SEQUENCE: 55

Gly Thr Gly Ser Gly Ala Trp Lys Glu Trp Leu Glu Arg Lys Val Gly
1               5                   10                  15

Glu Gly Arg Ala Arg Arg Leu Ile Glu Tyr Phe Gly Ser Ala Gly Glu
                20                  25                  30

Val Gly Lys Leu Val Glu Asn Ala Glu Val Ser Lys Leu Leu Glu Val
                35                  40                  45

Pro Gly Ile Gly Asp Glu Ala Val Ala Arg Leu Val Pro Gly Gly Ser
        50                  55                  60

Ser
65

<210> SEQ ID NO 56
<211> LENGTH: 299
<212> TYPE: PRT
<213> ORGANISM: Bacteriophage RB69
```

<400> SEQUENCE: 56

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Ser Asp
        275                 280                 285

Asp Gly Asp Leu Asp Asp Leu Leu Ala Gly Leu
    290                 295

<210> SEQ ID NO 57
<211> LENGTH: 232
<212> TYPE: PRT
<213> ORGANISM: Bacteriophage T7

<400> SEQUENCE: 57

Met Ala Lys Lys Ile Phe Thr Ser Ala Leu Gly Thr Ala Glu Pro Tyr
1               5                   10                  15

Ala Tyr Ile Ala Lys Pro Asp Tyr Gly Asn Glu Glu Arg Gly Phe Gly
            20                  25                  30

Asn Pro Arg Gly Val Tyr Lys Val Asp Leu Thr Ile Pro Asn Lys Asp
        35                  40                  45

Pro Arg Cys Gln Arg Met Val Asp Glu Ile Val Lys Cys His Glu Glu
    50                  55                  60

```
Ala Tyr Ala Ala Val Glu Glu Tyr Glu Asn Pro Pro Ala Val
 65                  70                  75                  80

Ala Arg Gly Lys Lys Pro Leu Lys Pro Tyr Glu Gly Asp Met Pro Phe
                 85                  90                  95

Phe Asp Asn Gly Asp Gly Thr Thr Phe Lys Phe Lys Cys Tyr Ala
            100                 105                 110

Ser Phe Gln Asp Lys Lys Thr Lys Glu Thr Lys His Ile Asn Leu Val
            115                 120                 125

Val Val Asp Ser Lys Gly Lys Lys Met Glu Asp Val Pro Ile Ile Gly
        130                 135                 140

Gly Gly Ser Lys Leu Lys Val Lys Tyr Ser Leu Val Pro Tyr Lys Trp
145                 150                 155                 160

Asn Thr Ala Val Gly Ala Ser Val Lys Leu Gln Leu Glu Ser Val Met
                165                 170                 175

Leu Val Glu Leu Ala Thr Phe Gly Gly Gly Glu Asp Asp Trp Ala Asp
            180                 185                 190

Glu Val Glu Glu Asn Gly Tyr Val Ala Ser Gly Ser Ala Lys Ala Ser
        195                 200                 205

Lys Pro Arg Asp Glu Glu Ser Trp Asp Glu Asp Glu Glu Ser Glu
210                 215                 220

Glu Ala Asp Glu Asp Gly Asp Phe
225                 230
```

<210> SEQ ID NO 58
<211> LENGTH: 324
<212> TYPE: PRT
<213> ORGANISM: Herpes simplex virus 1

<400> SEQUENCE: 58

```
Met Asp Ser Pro Gly Gly Val Ala Pro Ala Ser Pro Val Glu Asp Ala
 1                5                  10                  15

Ser Asp Ala Ser Leu Gly Gln Pro Glu Glu Gly Ala Pro Cys Gln Val
                 20                  25                  30

Val Leu Gln Gly Ala Glu Leu Asn Gly Ile Leu Gln Ala Phe Ala Pro
            35                  40                  45

Leu Arg Thr Ser Leu Leu Asp Ser Leu Leu Val Met Gly Asp Arg Gly
 50                  55                  60

Ile Leu Ile His Asn Thr Ile Phe Gly Glu Gln Val Phe Leu Pro Leu
 65                  70                  75                  80

Glu His Ser Gln Phe Ser Arg Tyr Arg Trp Arg Gly Pro Thr Ala Ala
                 85                  90                  95

Phe Leu Ser Leu Val Asp Gln Lys Arg Ser Leu Leu Ser Val Phe Arg
            100                 105                 110

Ala Asn Gln Tyr Pro Asp Leu Arg Arg Val Glu Leu Ala Ile Thr Gly
            115                 120                 125

Gln Ala Pro Phe Arg Thr Leu Val Gln Arg Ile Trp Thr Thr Thr Ser
        130                 135                 140

Asp Gly Glu Ala Val Glu Leu Ala Ser Glu Thr Leu Met Lys Arg Glu
145                 150                 155                 160

Leu Thr Ser Phe Val Val Leu Val Pro Gln Gly Thr Pro Asp Val Gln
                165                 170                 175

Leu Arg Leu Thr Arg Pro Gln Leu Thr Lys Val Leu Asn Ala Thr Gly
            180                 185                 190

Ala Asp Ser Ala Thr Pro Thr Thr Phe Glu Leu Gly Val Asn Gly Lys
```

-continued

```
                195                 200                 205
Phe Ser Val Phe Thr Thr Ser Thr Cys Val Thr Phe Ala Ala Arg Glu
    210                 215                 220

Glu Gly Val Ser Ser Thr Ser Thr Gln Val Gln Ile Leu Ser Asn
225                 230                 235                 240

Ala Leu Thr Lys Ala Gly Gln Ala Ala Asn Ala Lys Thr Val Tyr
                245                 250                 255

Gly Glu Asn Thr His Arg Thr Phe Ser Val Val Asp Asp Cys Ser
                260                 265                 270

Met Arg Ala Val Leu Arg Arg Leu Gln Val Gly Gly Thr Leu Lys
                275                 280                 285

Phe Phe Leu Thr Thr Pro Val Pro Ser Leu Cys Val Thr Ala Thr Gly
290                 295                 300

Pro Asn Ala Val Ser Ala Val Phe Leu Leu Lys Pro Gln Lys His His
305                 310                 315                 320

His His His His

<210> SEQ ID NO 59
<211> LENGTH: 251
<212> TYPE: PRT
<213> ORGANISM: Artificial sequence
<220> FEATURE:
<223> OTHER INFORMATION: PCNA subunit 1

<400> SEQUENCE: 59

Met Phe Lys Ile Val Tyr Pro Asn Ala Lys Asp Phe Ser Phe Ile
1               5                   10                  15

Asn Ser Ile Thr Asn Val Thr Asp Ser Ile Ile Leu Asn Phe Thr Glu
                20                  25                  30

Asp Gly Ile Phe Ser Arg His Leu Thr Glu Asp Lys Val Leu Met Ala
                35                  40                  45

Ile Met Arg Ile Pro Lys Asp Val Leu Ser Glu Tyr Ser Ile Asp Ser
    50                  55                  60

Pro Thr Ser Val Lys Leu Asp Val Ser Ser Val Lys Lys Ile Leu Ser
65                  70                  75                  80

Lys Ala Ser Ser Lys Lys Ala Thr Ile Glu Leu Thr Glu Thr Asp Ser
                85                  90                  95

Gly Leu Lys Ile Ile Ile Arg Asp Glu Lys Ser Gly Ala Lys Ser Thr
                100                 105                 110

Ile Tyr Ile Lys Ala Glu Lys Gly Gln Val Glu Gln Leu Thr Glu Pro
            115                 120                 125

Lys Val Asn Leu Ala Val Asn Phe Thr Thr Asp Glu Ser Val Leu Asn
    130                 135                 140

Val Ile Ala Ala Asp Val Thr Leu Val Gly Glu Met Arg Ile Ser
145                 150                 155                 160

Thr Glu Glu Asp Lys Ile Lys Ile Glu Ala Gly Glu Glu Gly Lys Arg
                165                 170                 175

Tyr Val Ala Phe Leu Met Lys Asp Lys Pro Leu Lys Glu Leu Ser Ile
            180                 185                 190

Asp Thr Ser Ala Ser Ser Ser Tyr Ser Ala Glu Met Phe Lys Asp Ala
    195                 200                 205

Val Lys Gly Leu Arg Gly Phe Ser Ala Pro Thr Met Val Ser Phe Gly
    210                 215                 220

Glu Asn Leu Pro Met Lys Ile Asp Val Glu Ala Val Ser Gly Gly His
225                 230                 235                 240
```

```
Met Ile Phe Trp Ile Ala Pro Arg Leu Leu Glu
            245                 250

<210> SEQ ID NO 60
<211> LENGTH: 245
<212> TYPE: PRT
<213> ORGANISM: Artificial sequence
<220> FEATURE:
<223> OTHER INFORMATION: PCNA subunit 2

<400> SEQUENCE: 60

Met Lys Ala Lys Val Ile Asp Ala Val Ser Phe Ser Tyr Ile Leu Arg
1               5                   10                  15

Thr Val Gly Asp Phe Leu Ser Glu Ala Asn Phe Ile Val Thr Lys Glu
            20                  25                  30

Gly Ile Arg Val Ser Gly Ile Asp Pro Ser Arg Val Val Phe Leu Asp
        35                  40                  45

Ile Phe Leu Pro Ser Ser Tyr Phe Glu Gly Phe Glu Val Ser Gln Glu
    50                  55                  60

Lys Glu Ile Ile Gly Phe Lys Leu Glu Asp Val Asn Asp Ile Leu Lys
65                  70                  75                  80

Arg Val Leu Lys Asp Asp Thr Leu Ile Leu Ser Ser Asn Glu Ser Lys
                85                  90                  95

Leu Thr Leu Thr Phe Asp Gly Glu Phe Thr Arg Ser Phe Glu Leu Pro
            100                 105                 110

Leu Ile Gln Val Glu Ser Thr Gln Pro Pro Ser Val Asn Leu Glu Phe
        115                 120                 125

Pro Phe Lys Ala Gln Leu Leu Thr Ile Thr Phe Ala Asp Ile Ile Asp
    130                 135                 140

Glu Leu Ser Asp Leu Gly Glu Val Leu Asn Ile His Ser Lys Glu Asn
145                 150                 155                 160

Lys Leu Tyr Phe Glu Val Ile Gly Asp Leu Ser Thr Ala Lys Val Glu
                165                 170                 175

Leu Ser Thr Asp Asn Gly Thr Leu Leu Glu Ala Ser Gly Ala Asp Val
            180                 185                 190

Ser Ser Ser Tyr Gly Met Glu Tyr Val Ala Asn Thr Thr Lys Met Arg
        195                 200                 205

Arg Ala Ser Asp Ser Met Glu Leu Tyr Phe Gly Ser Gln Ile Pro Leu
    210                 215                 220

Lys Leu Arg Phe Lys Leu Pro Gln Glu Gly Tyr Gly Asp Phe Tyr Ile
225                 230                 235                 240

Ala Pro Arg Ala Asp
                245

<210> SEQ ID NO 61
<211> LENGTH: 246
<212> TYPE: PRT
<213> ORGANISM: Artificial sequence
<220> FEATURE:
<223> OTHER INFORMATION: PCNA subunit 3

<400> SEQUENCE: 61

Met Lys Val Val Tyr Asp Asp Val Arg Val Leu Lys Asp Ile Ile Gln
1               5                   10                  15

Ala Leu Ala Arg Leu Val Asp Glu Ala Val Leu Lys Phe Lys Gln Asp
            20                  25                  30

Ser Val Glu Leu Val Ala Leu Asp Arg Ala His Ile Ser Leu Ile Ser
```

```
                35                  40                  45
Val Asn Leu Pro Arg Glu Met Phe Lys Glu Tyr Asp Val Asn Asp Glu
     50                  55                  60

Phe Lys Phe Gly Phe Asn Thr Gln Tyr Leu Met Lys Ile Leu Lys Val
 65                  70                  75                  80

Ala Lys Arg Lys Glu Ala Ile Glu Ile Ala Ser Glu Ser Pro Asp Ser
                 85                  90                  95

Val Ile Ile Asn Ile Ile Gly Ser Thr Asn Arg Glu Phe Asn Val Arg
            100                 105                 110

Asn Leu Glu Val Ser Glu Gln Ile Pro Glu Ile Asn Leu Gln Phe
        115                 120                 125

Asp Ile Ser Ala Thr Ile Ser Ser Asp Gly Phe Lys Ser Ala Ile Ser
    130                 135                 140

Glu Val Ser Thr Val Thr Asp Asn Val Val Glu Gly His Glu Asp
145                 150                 155                 160

Arg Ile Leu Ile Lys Ala Glu Gly Glu Ser Glu Val Glu Val Glu Phe
                165                 170                 175

Ser Lys Asp Thr Gly Gly Leu Gln Asp Leu Glu Phe Ser Lys Glu Ser
            180                 185                 190

Lys Asn Ser Tyr Ser Ala Glu Tyr Leu Asp Asp Val Leu Ser Leu Thr
        195                 200                 205

Lys Leu Ser Asp Tyr Val Lys Ile Ser Phe Gly Asn Gln Lys Pro Leu
    210                 215                 220

Gln Leu Phe Phe Asn Met Glu Gly Gly Gly Lys Val Thr Tyr Leu Leu
225                 230                 235                 240

Ala Pro Lys Val Leu Glu
                245

<210> SEQ ID NO 62
<211> LENGTH: 608
<212> TYPE: PRT
<213> ORGANISM: Bacteriophage phi-29

<400> SEQUENCE: 62

Met Lys His Met Pro Arg Lys Met Tyr Ser Cys Ala Phe Glu Thr Thr
 1               5                  10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
 50                  55                  60

Phe Asp Gly Ala Phe Ile Ile Asn Trp Leu Glu Arg Asn Gly Phe Lys
 65                  70                  75                  80

Trp Ser Ala Asp Gly Leu Pro Asn Thr Tyr Asn Thr Ile Ile Ser Arg
                 85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160
```

-continued

```
Glu Glu Tyr Ala Tyr Ile Lys Asn Asp Ile Gln Ile Ala Glu Ala
            165                 170                 175
Leu Leu Ile Gln Phe Lys Gln Gly Leu Asp Arg Met Thr Ala Gly Ser
        180                 185                 190
Asp Ser Leu Lys Gly Phe Lys Asp Ile Ile Thr Thr Lys Lys Phe Lys
            195                 200                 205
Lys Val Phe Pro Thr Leu Ser Leu Gly Leu Asp Lys Glu Val Arg Tyr
            210                 215                 220
Ala Tyr Arg Gly Gly Phe Thr Trp Leu Asn Asp Arg Phe Lys Glu Lys
225                 230                 235                 240
Glu Ile Gly Glu Gly Met Val Phe Asp Val Asn Ser Leu Tyr Pro Ala
            245                 250                 255
Gln Met Tyr Ser Arg Leu Leu Pro Tyr Gly Glu Pro Ile Val Phe Glu
            260                 265                 270
Gly Lys Tyr Val Trp Asp Glu Asp Tyr Pro Leu His Ile Gln His Ile
            275                 280                 285
Arg Cys Glu Phe Glu Leu Lys Glu Gly Tyr Ile Pro Thr Ile Gln Ile
            290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
            325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
            355                 360                 365
Tyr Ile Lys Thr Thr Ser Glu Gly Ala Ile Lys Gln Leu Ala Lys Leu
            370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
            405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
            435                 440                 445
Tyr Asp Arg Ile Ile Tyr Cys Asp Thr Asp Ser Ile His Leu Thr Gly
            450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
            485                 490                 495
Gln Lys Thr Tyr Ile Gln Asp Ile Tyr Met Lys Glu Val Asp Gly Lys
            500                 505                 510
Leu Val Glu Gly Ser Pro Asp Asp Tyr Thr Asp Ile Lys Phe Ser Val
            515                 520                 525
Lys Cys Ala Gly Met Thr Asp Lys Ile Lys Lys Glu Val Thr Phe Glu
            530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys Ser
            565                 570                 575
Gly Gly Ser Ala Trp Ser His Pro Gln Phe Glu Lys Gly Gly Gly Ser
```

```
                580             585             590
Gly Gly Gly Ser Gly Gly Ser Ala Trp Ser His Pro Gln Phe Glu Lys
            595                 600                 605

<210> SEQ ID NO 63
<211> LENGTH: 318
<212> TYPE: PRT
<213> ORGANISM: Herpes simplex virus 1

<400> SEQUENCE: 63

Thr Asp Ser Pro Gly Gly Val Ala Pro Ala Ser Pro Val Glu Asp Ala
1               5                   10                  15

Ser Asp Ala Ser Leu Gly Gln Pro Glu Glu Gly Ala Pro Cys Gln Val
            20                  25                  30

Val Leu Gln Gly Ala Glu Leu Asn Gly Ile Leu Gln Ala Phe Ala Pro
        35                  40                  45

Leu Arg Thr Ser Leu Leu Asp Ser Leu Leu Val Met Gly Asp Arg Gly
    50                  55                  60

Ile Leu Ile His Asn Thr Ile Phe Gly Glu Gln Val Phe Leu Pro Leu
65                  70                  75                  80

Glu His Ser Gln Phe Ser Arg Tyr Arg Trp Arg Gly Pro Thr Ala Ala
                85                  90                  95

Phe Leu Ser Leu Val Asp Gln Lys Arg Ser Leu Leu Ser Val Phe Arg
            100                 105                 110

Ala Asn Gln Tyr Pro Asp Leu Arg Arg Val Glu Leu Ala Ile Thr Gly
        115                 120                 125

Gln Ala Pro Phe Arg Thr Leu Val Gln Arg Ile Trp Thr Thr Thr Ser
    130                 135                 140

Asp Gly Glu Ala Val Glu Leu Ala Ser Glu Thr Leu Met Lys Arg Glu
145                 150                 155                 160

Leu Thr Ser Phe Val Val Leu Val Pro Gln Gly Thr Pro Asp Val Gln
                165                 170                 175

Leu Arg Leu Thr Arg Pro Gln Leu Thr Lys Val Leu Asn Ala Thr Gly
            180                 185                 190

Ala Asp Ser Ala Thr Pro Thr Thr Phe Glu Leu Gly Val Asn Gly Lys
        195                 200                 205

Phe Ser Val Phe Thr Thr Ser Thr Cys Val Thr Phe Ala Ala Arg Glu
    210                 215                 220

Glu Gly Val Ser Ser Thr Ser Thr Gln Val Gln Ile Leu Ser Asn
225                 230                 235                 240

Ala Leu Thr Lys Ala Gly Gln Ala Ala Asn Ala Lys Thr Val Tyr
                245                 250                 255

Gly Glu Asn Thr His Arg Thr Phe Ser Val Val Asp Asp Cys Ser
            260                 265                 270

Met Arg Ala Val Leu Arg Arg Leu Gln Val Gly Gly Thr Leu Lys
        275                 280                 285

Phe Phe Leu Thr Thr Pro Val Pro Ser Leu Cys Val Thr Ala Thr Gly
    290                 295                 300

Pro Asn Ala Val Ser Ala Val Phe Leu Leu Lys Pro Gln Lys
305                 310                 315

<210> SEQ ID NO 64
<211> LENGTH: 233
<212> TYPE: PRT
<213> ORGANISM: Bacteriophage RB69
```

-continued

```
<400> SEQUENCE: 64

Lys Gly Phe Ser Ser Glu Asp Lys Gly Glu Trp Lys Leu Lys Leu Asp
1               5                   10                  15

Ala Ser Gly Asn Gly Gln Ala Val Ile Arg Phe Leu Pro Ala Lys Thr
            20                  25                  30

Asp Asp Ala Leu Pro Phe Ala Ile Leu Val Asn His Gly Phe Lys Lys
        35                  40                  45

Asn Gly Lys Trp Tyr Ile Glu Thr Cys Ser Ser Thr His Gly Asp Tyr
    50                  55                  60

Asp Ser Cys Pro Val Cys Gln Tyr Ile Ser Lys Asn Asp Leu Tyr Asn
65                  70                  75                  80

Thr Asn Lys Thr Glu Tyr Ser Gln Leu Lys Arg Lys Thr Ser Tyr Trp
                85                  90                  95

Ala Asn Ile Leu Val Val Lys Asp Pro Gln Ala Pro Asn Glu Gly
            100                 105                 110

Lys Val Phe Lys Tyr Arg Phe Gly Lys Lys Ile Trp Asp Lys Ile Asn
        115                 120                 125

Ala Met Ile Ala Val Asp Thr Glu Met Gly Glu Thr Pro Val Asp Val
    130                 135                 140

Thr Cys Pro Trp Glu Gly Ala Asn Phe Val Leu Lys Val Lys Gln Val
145                 150                 155                 160

Ser Gly Phe Ser Asn Tyr Asp Glu Ser Lys Phe Leu Asn Gln Ser Ala
                165                 170                 175

Ile Pro Asn Ile Asp Asp Glu Ser Phe Gln Lys Glu Leu Phe Glu Gln
            180                 185                 190

Met Val Asp Leu Ser Glu Met Thr Ser Lys Asp Lys Phe Lys Ser Phe
        195                 200                 205

Glu Glu Leu Asn Thr Lys Phe Asn Gln Val Leu Gly Thr Ala Ala Leu
    210                 215                 220

Gly Gly Ala Ala Ala Ala Ala Ser
225                 230

<210> SEQ ID NO 65
<211> LENGTH: 210
<212> TYPE: PRT
<213> ORGANISM: Bacteriophage T7

<400> SEQUENCE: 65

Ala Lys Lys Ile Phe Thr Ser Ala Leu Gly Thr Ala Glu Pro Tyr Ala
1               5                   10                  15

Tyr Ile Ala Lys Pro Asp Tyr Gly Asn Glu Glu Arg Gly Phe Gly Asn
            20                  25                  30

Pro Arg Gly Val Tyr Lys Val Asp Leu Thr Ile Pro Asn Lys Asp Pro
        35                  40                  45

Arg Cys Gln Arg Met Val Asp Glu Ile Val Lys Cys His Glu Glu Ala
    50                  55                  60

Tyr Ala Ala Ala Val Glu Glu Tyr Glu Ala Asn Pro Pro Ala Val Ala
65                  70                  75                  80

Arg Gly Lys Lys Pro Leu Lys Pro Tyr Glu Gly Asp Met Pro Phe Phe
                85                  90                  95

Asp Asn Gly Asp Gly Thr Thr Thr Phe Lys Phe Lys Cys Tyr Ala Ser
            100                 105                 110

Phe Gln Asp Lys Lys Thr Lys Glu Thr Lys His Ile Asn Leu Val Val
        115                 120                 125
```

-continued

Val Asp Ser Lys Gly Lys Lys Met Glu Asp Val Pro Ile Ile Gly Gly
    130                 135                 140

Gly Ser Lys Leu Lys Val Lys Tyr Ser Leu Val Pro Tyr Lys Trp Asn
145                 150                 155                 160

Thr Ala Val Gly Ala Ser Val Lys Leu Gln Leu Glu Ser Val Met Leu
                165                 170                 175

Val Glu Leu Ala Thr Phe Gly Gly Glu Asp Trp Ala Asp Glu
            180                 185                 190

Val Glu Glu Asn Gly Tyr Val Ala Ser Gly Ser Ala Lys Ala Ser Lys
        195                 200                 205

Pro Arg
    210

<210> SEQ ID NO 66
<211> LENGTH: 99
<212> TYPE: PRT
<213> ORGANISM: Halorubrum lacusprofundi

<400> SEQUENCE: 66

Ser Gly Glu Glu Leu Leu Asp Leu Ala Gly Val Arg Asn Val Gly Arg
1               5                   10                  15

Lys Arg Ala Arg Arg Leu Phe Glu Ala Gly Ile Glu Thr Arg Ala Asp
            20                  25                  30

Leu Arg Glu Ala Asp Lys Ala Val Val Leu Gly Ala Leu Arg Gly Arg
        35                  40                  45

Glu Arg Thr Ala Glu Arg Ile Leu Glu His Ala Gly Arg Glu Asp Pro
    50                  55                  60

Ser Met Asp Asp Val Arg Pro Asp Lys Ser Ala Ser Ala Ala Ala Thr
65                  70                  75                  80

Ala Gly Ser Ala Ser Asp Glu Asp Gly Glu Gln Ala Ser Leu Gly
            85                  90                  95

Asp Phe Arg

<210> SEQ ID NO 67
<211> LENGTH: 102
<212> TYPE: PRT
<213> ORGANISM: Haloferax volcanii

<400> SEQUENCE: 67

Ser Gly Glu Glu Leu Leu Asp Leu Ala Gly Val Arg Gly Val Gly Arg
1               5                   10                  15

Lys Arg Ala Arg Arg Leu Phe Glu Ala Gly Val Glu Thr Arg Ala Asp
            20                  25                  30

Leu Arg Glu Ala Asp Lys Pro Arg Val Leu Ala Ala Leu Arg Gly Arg
        35                  40                  45

Arg Lys Thr Ala Glu Asn Ile Leu Glu Ala Ala Gly Arg Lys Asp Pro
    50                  55                  60

Ser Met Asp Ala Val Asp Glu Asp Ala Pro Asp Asp Ala Val Pro
65                  70                  75                  80

Asp Asp Ala Gly Phe Glu Thr Ala Lys Glu Arg Ala Asp Gln Gln Ala
            85                  90                  95

Ser Leu Gly Asp Phe Glu
        100

<210> SEQ ID NO 68
<211> LENGTH: 30
<212> TYPE: DNA

<210> SEQ ID NO 68
<211> LENGTH: 30 (implied)
<212> TYPE: DNA
<213> ORGANISM: Artificial sequence
<220> FEATURE:
<223> OTHER INFORMATION: Polynucleotide used in the Examples

<400> SEQUENCE: 68
ggtgaggagg atggtgctac ggagactagg                                    30

<210> SEQ ID NO 69
<211> LENGTH: 88
<212> TYPE: DNA
<213> ORGANISM: Artificial sequence
<220> FEATURE:
<223> OTHER INFORMATION: Polynucleotide used in the Examples

<400> SEQUENCE: 69
cgtggtcacg aggagctcgt cctcacctcg acgtctgcac gagcttttt tttttttttt    60 tttttttttt tttttttttt tttttttt                                      88

<210> SEQ ID NO 70
<211> LENGTH: 522
<212> TYPE: DNA
<213> ORGANISM: Artificial sequence
<220> FEATURE:
<223> OTHER INFORMATION: Polynucleotide used in the Examples

<400> SEQUENCE: 70
tttttttttt tttttttttt tttttttttt tttttttttt ttttgccat cagattgtgt    60 ttgttagtcg ctggttgttt ctgttggtgc tgatattgct tttgatgccg accctaaatt   120
ttttgcctgt ttggttcgct ttgagtcttc ttcggttccg actaccctcc cgactgccta   180
tgatgtttat cctttgaatg gtcgccatga tggtggttat tataccgtca aggactgtgt   240
gactattgac gtccttcccc gtacgccggg caataacgtt tatgttggtt tcatggtttg   300
gtctaacttt accgctacta aatgccgcgg attggtttcg ctgaatcagg ttattaaaga   360 gattattgt ctccagccac ttaagtgagg tgatttatgt ttggtgctat tgctggcggt    420
attgcttctg ctcttgctgg tggcgccatg tctaaattgt ttggaggcgg tcttttttccc   480 ccttttttccc ccttttttccc ccttttttccc ccttttttccc cc                  522

<210> SEQ ID NO 71
<211> LENGTH: 57
<212> TYPE: DNA
<213> ORGANISM: Artificial sequence
<220> FEATURE:
<223> OTHER INFORMATION: Polynucleotide used in the Examples

<400> SEQUENCE: 71
agcgactaac aaacacaatc tgatggcttt tttttttttt tttttttttt ttttttt      57

<210> SEQ ID NO 72
<211> LENGTH: 974
<212> TYPE: DNA
<213> ORGANISM: Artificial sequence
<220> FEATURE:
<223> OTHER INFORMATION: Polynucleotide used in the Examples

<400> SEQUENCE: 72
tttttttttt tttttttttt tttttttttt tttttttttt tttttttttt ggttgtttct    60
gttggtgctg atattgctgt gttctatgtc ttattctgtg tatgtatctt gtctgttagc   120
cccgattgtt accggataat tcgagctcgg tacccacccc ggttgataat cagaaaagcc   180
ccaaaaacag gaagattgta taagcaaata tttaaattgt aaacgttaat attttgttaa   240

```
aattcgcgtt aaattttttgt taaatcagct catttttttaa ccaataggcc gaaatcggca      300
aaatccctta taaatcaaaa gaatagaccg atataggggtt gagtgttgtt ccagtttgga      360
acaagagtcc agtattaaag aacgtggact ccaacgtcaa agggcgaaaa accgtctatc      420
agggcgatgg cccactacgt gaaccatcac cctaatcaag ttttttgggg tcgaggtgcc      480
gtaaagcact aaatcggaac cctaaaggga tgccccgatt tagagcttga cggggaaagc      540
cggcgaacgt ggcgagaaag gaagggaaga aagcgaaagg agcgggcgct agggcgctgg      600
caagtgtagc ggtcacgctg cgcgtaacca ccacacccgc cgcgcttaat gcgccgctac      660
agggcgcgtg gggatcctct agagtcgacc tgcaggcatg caagctatcc cgcaagaggc      720
ccggcagtac cggcataacc aagcctatgc ctacagcatc cagggtgacg gtgccgagga      780
tgacgatgag cgcattgtta gatttcatac acgtgcctg actgcgttag caatttaact      840
gtgataaact accgcattaa agctagctta tcgatgataa gctgtcaaac atgagaattc      900
ttgaagacga aagggcctcg tgatacgcct atttttatag gttaatgtca tgataataat      960
ggtttcttag acgt                                                         974

<210> SEQ ID NO 73
<211> LENGTH: 893
<212> TYPE: DNA
<213> ORGANISM: Artificial sequence
<220> FEATURE:
<223> OTHER INFORMATION: Polynucleotide used in the Examples

<400> SEQUENCE: 73
ctaagaaacc attattatca tgacattaac ctataaaaat aggcgtatca cgaggccctt       60
tcgtcttcaa gaattctcat gtttgacagc ttatcatcga taagctagct ttaatgcgt      120 agtttatcac agttaaattg ctaacgcagt caggcaccgt gtatgaaatc taacaatgcg     180
ctcatcgtca tcctcggcac cgtcaccctg gatgctgtag gcataggctt ggttatgccg     240
gtactgccgg gcctcttgcg ggatagcttg catgcctgca ggtcgactct agaggatccc     300
cacgcgccct gtagcggcgc attaagcgcg gcgggtgtgg tggttacgcg cagcgtgacc     360
gctacacttg ccagcgccct agcgcccgct cctttcgctt tcttcccttc ctttctcgcc     420
acgttcgccg gctttccccg tcaagctcta aatcggggca tccctttagg gttccgattt     480
agtgctttac ggcacctcga cccaaaaaaa cttgattagg gtgatggttc acgtagtggg     540
ccatcgccct gatagacggt ttttcgccct ttgacgttgg agtccacgtt ctttaatact     600
ggactcttgt tccaaactgg aacaacactc aaccctatct cggtctattc ttttgattta     660
taagggattt tgccgatttc ggcctattgg ttaaaaaatg agctgattta acaaaaattt     720
aacgcgaatt ttaacaaaat attaacgttt acaatttaaa tatttgctta tacaatcttc     780 ctgttttttgg ggcttttctg attatcaacc ggggtgggta ccgagctcga attatccggt     840
aacaatcggg gctaacagac aagatacata cacagaataa gacatagaac aca            893

<210> SEQ ID NO 74
<211> LENGTH: 28
<212> TYPE: DNA
<213> ORGANISM: Artificial sequence
<220> FEATURE:
<223> OTHER INFORMATION: Polynucleotide used in the Examples

<400> SEQUENCE: 74
gcaatatcag caccaacaga aacaacct                                          28
```

<210> SEQ ID NO 75
<211> LENGTH: 55
<212> TYPE: PRT
<213> ORGANISM: Artificial sequence
<220> FEATURE:
<223> OTHER INFORMATION: (HhH)2 domain

<400> SEQUENCE: 75

```
Trp Lys Glu Trp Leu Glu Arg Lys Val Gly Glu Gly Arg Ala Arg Arg
1               5                   10                  15

Leu Ile Glu Tyr Phe Gly Ser Ala Gly Glu Val Gly Lys Leu Val Glu
            20                  25                  30

Asn Ala Glu Val Ser Lys Leu Leu Glu Val Pro Gly Ile Gly Asp Glu
        35                  40                  45

Ala Val Ala Arg Leu Val Pro
    50                  55
```

<210> SEQ ID NO 76
<211> LENGTH: 107
<212> TYPE: PRT
<213> ORGANISM: Artificial sequence
<220> FEATURE:
<223> OTHER INFORMATION: (HhH)2-(HhH)2 domain

<400> SEQUENCE: 76

```
Trp Lys Glu Trp Leu Glu Arg Lys Val Gly Glu Gly Arg Ala Arg Arg
1               5                   10                  15

Leu Ile Glu Tyr Phe Gly Ser Ala Gly Glu Val Gly Lys Leu Val Glu
            20                  25                  30

Asn Ala Glu Val Ser Lys Leu Leu Glu Val Pro Gly Ile Gly Asp Glu
        35                  40                  45

Ala Val Ala Arg Leu Val Pro Gly Tyr Lys Thr Leu Arg Asp Ala Gly
    50                  55                  60

Leu Thr Pro Ala Glu Ala Glu Arg Val Leu Lys Arg Tyr Gly Ser Val
65                  70                  75                  80

Ser Lys Val Gln Glu Gly Ala Thr Pro Asp Glu Leu Arg Glu Leu Gly
                85                  90                  95

Leu Gly Asp Ala Lys Ile Ala Arg Ile Leu Gly
            100                 105
```

<210> SEQ ID NO 77
<211> LENGTH: 132
<212> TYPE: PRT
<213> ORGANISM: Homo sapiens

<400> SEQUENCE: 77

```
Glu Ser Glu Thr Thr Thr Ser Leu Val Leu Arg Ser Leu Asn Arg
1               5                   10                  15

Val His Leu Leu Gly Arg Val Gly Gln Asp Pro Val Leu Arg Gln Val
            20                  25                  30

Glu Gly Lys Asn Pro Val Thr Ile Phe Ser Leu Ala Thr Asn Glu Met
        35                  40                  45

Trp Arg Ser Gly Asp Ser Glu Val Tyr Gln Leu Gly Asp Val Ser Gln
    50                  55                  60

Lys Thr Thr Trp His Arg Ile Ser Val Phe Arg Pro Gly Leu Arg Asp
65                  70                  75                  80

Val Ala Tyr Gln Tyr Val Lys Lys Gly Ser Arg Ile Tyr Leu Glu Gly
                85                  90                  95
```

```
Lys Ile Asp Tyr Gly Glu Tyr Met Asp Lys Asn Asn Val Arg Arg Gln
            100                 105                 110

Ala Thr Thr Ile Ile Ala Asp Asn Ile Ile Phe Leu Ser Asp Gln Thr
            115                 120                 125

Lys Glu Lys Glu
        130

<210> SEQ ID NO 78
<211> LENGTH: 123
<212> TYPE: PRT
<213> ORGANISM: Bacteriophage phi-29

<400> SEQUENCE: 78

Glu Asn Thr Asn Ile Val Lys Ala Thr Phe Asp Thr Glu Thr Leu Glu
1               5                   10                  15

Gly Gln Ile Lys Ile Phe Asn Ala Gln Thr Gly Gly Gln Ser Phe
            20                  25                  30

Lys Asn Leu Pro Asp Gly Thr Ile Ile Glu Ala Asn Ala Ile Ala Gln
            35                  40                  45

Tyr Lys Gln Val Ser Asp Thr Tyr Gly Asp Ala Lys Glu Glu Thr Val
    50                  55                  60

Thr Thr Ile Phe Ala Ala Asp Gly Ser Leu Tyr Ser Ala Ile Ser Lys
65                  70                  75                  80

Thr Val Ala Glu Ala Ala Ser Asp Leu Ile Asp Leu Val Thr Arg His
                85                  90                  95

Lys Leu Glu Thr Phe Lys Val Lys Val Val Gln Gly Thr Ser Ser Lys
            100                 105                 110

Gly Asn Val Phe Phe Ser Leu Gln Leu Ser Leu
            115                 120

<210> SEQ ID NO 79
<211> LENGTH: 177
<212> TYPE: PRT
<213> ORGANISM: Escherichia coli

<400> SEQUENCE: 79

Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
            35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Gly Asn Ile Gly Gly
            115                 120                 125

Gly Gln Pro Gln Gly Gly Trp Gly Gln Pro Gln Pro Gln Gly Gly
            130                 135                 140

Asn Gln Phe Ser Gly Gly Ala Gln Ser Arg Pro Gln Gln Ser Ala Pro
145                 150                 155                 160
```

```
Ala Ala Pro Ser Asn Glu Pro Pro Met Asp Phe Asp Asp Ile Pro
            165                 170                 175

Phe

<210> SEQ ID NO 80
<211> LENGTH: 301
<212> TYPE: PRT
<213> ORGANISM: Bacteriophage T4

<400> SEQUENCE: 80

Met Phe Lys Arg Lys Ser Thr Ala Glu Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Asn Ala Gly Asn Gly Gln Ala Val Ile Arg Phe Leu
        35                  40                  45

Pro Ser Lys Asn Asp Glu Gln Ala Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asp Asn Lys Glu Tyr Ser Leu Val Lys Arg Lys
            100                 105                 110

Thr Ser Tyr Trp Ala Asn Ile Leu Val Val Lys Asp Pro Ala Ala Pro
        115                 120                 125

Glu Asn Glu Gly Lys Val Phe Lys Tyr Arg Phe Gly Lys Lys Ile Trp
    130                 135                 140

Asp Lys Ile Asn Ala Met Ile Ala Val Asp Val Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Gly Gln Val Met Gly
225                 230                 235                 240

Thr Ala Val Met Gly Gly Ala Ala Ala Thr Ala Ala Lys Lys Ala Asp
                245                 250                 255

Lys Val Ala Asp Asp Leu Asp Ala Phe Asn Val Asp Asp Phe Asn Thr
            260                 265                 270

Lys Thr Glu Asp Asp Phe Met Ser Ser Ser Ser Gly Ser Ser Ser Ser
        275                 280                 285

Ala Asp Asp Thr Asp Leu Asp Asp Leu Leu Asn Asp Leu
    290                 295                 300

<210> SEQ ID NO 81
<211> LENGTH: 177
<212> TYPE: PRT
<213> ORGANISM: Artificial sequence
<220> FEATURE:
<223> OTHER INFORMATION: EcoSSB-CterAla

<400> SEQUENCE: 81
```

```
Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Gly Asn Ile Gly Gly
                115                 120                 125

Gly Gln Pro Gln Gly Gly Trp Gly Gln Pro Gln Pro Gln Gly Gly
            130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Ala Phe Ala Ala Ala Ile Pro
                165                 170                 175

Phe
```

<210> SEQ ID NO 82
<211> LENGTH: 177
<212> TYPE: PRT
<213> ORGANISM: Artificial sequence
<220> FEATURE:
<223> OTHER INFORMATION: EcoSSB-CterNGGN

<400> SEQUENCE: 82

```
Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Gly Asn Ile Gly Gly
                115                 120                 125

Gly Gln Pro Gln Gly Gly Trp Gly Gln Pro Gln Pro Gln Gly Gly
            130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Asn Phe Gly Gly Asn Ile Pro
                165                 170                 175
```

Phe

<210> SEQ ID NO 83
<211> LENGTH: 152
<212> TYPE: PRT
<213> ORGANISM: Artificial sequence
<220> FEATURE:
<223> OTHER INFORMATION: EcoSSB-Q152del

<400> SEQUENCE: 83

```
Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Gly Asn Ile Gly Gly
        115                 120                 125

Gly Gln Pro Gln Gly Gly Trp Gly Gln Pro Gln Pro Gln Gln Gly Gly
    130                 135                 140

Asn Gln Phe Ser Gly Gly Ala Gln
145                 150
```

<210> SEQ ID NO 84
<211> LENGTH: 117
<212> TYPE: PRT
<213> ORGANISM: Artificial sequence
<220> FEATURE:
<223> OTHER INFORMATION: EcoSSB-G117del

<400> SEQUENCE: 84

```
Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly
        115
```

<210> SEQ ID NO 85
<211> LENGTH: 6

<212> TYPE: PRT
<213> ORGANISM: Artificial sequence
<220> FEATURE:
<223> OTHER INFORMATION: Linker

<400> SEQUENCE: 85

Gly Thr Gly Ser Gly Ala
1               5

<210> SEQ ID NO 86
<211> LENGTH: 6
<212> TYPE: PRT
<213> ORGANISM: Artificial sequence
<220> FEATURE:
<223> OTHER INFORMATION: Linker

<400> SEQUENCE: 86

Gly Thr Gly Ser Gly Thr
1               5

<210> SEQ ID NO 87
<211> LENGTH: 970
<212> TYPE: PRT
<213> ORGANISM: Citromicrobium bathyomarinum JL354

<400> SEQUENCE: 87

Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Ile Gly Asp Gly Ala Lys Arg Leu Gly Leu Glu Gly Lys Val
            35                  40                  45

Glu Ala Arg Ala Phe Asp Ala Leu Leu Arg Gly Glu Leu Pro Asp Gly
        50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
                100                 105                 110

His Trp Ala Glu Lys Asn Ala Ala Glu Thr Arg Val Val Glu Lys Gly
            115                 120                 125

Met Val Val Thr Gln Ala Thr Gly Asn Leu Ala Ile Gly Leu Phe Gln
130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
                180                 185                 190

Ala Arg Phe Arg Val Ala Val Glu Lys Leu Gly Tyr Glu Pro Gly Pro
            195                 200                 205

Val Leu Lys His Gly Asn Phe Glu Ala Arg Gly Ile Ser Arg Glu Gln
        210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

-continued

```
Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
        275                 280                 285

Ala Arg Thr Lys Ala Leu Gly Gln Gly Met Glu Ala Thr Arg Ile Gly
    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys
                325                 330                 335

Gln Asp Arg Gln Thr Ile Ala Ala Gln Ala Val Ala Ser Ala Val
            340                 345                 350

Arg His Leu Ser Gln Arg Glu Ala Ala Phe Glu Arg Thr Ala Leu Tyr
        355                 360                 365

Lys Ala Ala Leu Asp Phe Gly Leu Pro Thr Thr Ile Ala Asp Val Glu
    370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ser Val Gln Ala Ala Ala Leu
        435                 440                 445

Thr Gly Gln Gly Phe Arg Leu Asn Glu Gly Gln Leu Ala Ala Ala Arg
    450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
        515                 520                 525

Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
```

```
              675                 680                 685
Ala Val Asn Ala Ala Val Gln Gln Gly Leu Leu Ala Ser Arg Glu Ile
            690                 695                 700
Gly Pro Ala Lys Met Lys Leu Glu Val Leu Asp Arg Val Asn Thr Thr
705                 710                 715                 720
Arg Glu Glu Leu Arg His Leu Pro Ala Tyr Arg Ala Gly Arg Val Leu
                725                 730                 735
Glu Val Ser Arg Lys Gln Gln Ala Leu Gly Leu Phe Ile Gly Glu Tyr
            740                 745                 750
Arg Val Ile Gly Gln Asp Arg Lys Gly Lys Leu Val Glu Val Glu Asp
            755                 760                 765
Lys Arg Gly Lys Arg Phe Arg Phe Asp Pro Ala Arg Ile Arg Ala Gly
770                 775                 780
Lys Gly Asp Asp Asn Leu Thr Leu Leu Glu Pro Arg Lys Leu Glu Ile
785                 790                 795                 800
His Glu Gly Asp Arg Ile Arg Trp Thr Arg Asn Asp His Arg Arg Gly
                805                 810                 815
Leu Phe Asn Ala Asp Gln Ala Arg Val Val Glu Ile Ala Asn Gly Lys
            820                 825                 830
Val Thr Phe Glu Thr Ser Lys Gly Asp Leu Val Glu Leu Lys Lys Asp
            835                 840                 845
Asp Pro Met Leu Lys Arg Ile Asp Leu Ala Tyr Ala Leu Asn Val His
850                 855                 860
Met Ala Gln Gly Leu Thr Ser Asp Arg Gly Ile Ala Val Met Asp Ser
865                 870                 875                 880
Arg Glu Arg Asn Leu Ser Asn Gln Lys Thr Phe Leu Val Thr Val Thr
                885                 890                 895
Arg Leu Arg Asp His Leu Thr Leu Val Val Asp Ser Ala Asp Lys Leu
            900                 905                 910
Gly Ala Ala Val Ala Arg Asn Lys Gly Glu Lys Ala Ser Ala Ile Glu
            915                 920                 925
Val Thr Gly Ser Val Lys Pro Thr Ala Thr Lys Gly Ser Gly Val Asp
930                 935                 940
Gln Pro Lys Ser Val Glu Ala Asn Lys Ala Glu Lys Glu Leu Thr Arg
945                 950                 955                 960
Ser Lys Ser Lys Thr Leu Asp Phe Gly Ile
                965                 970

<210> SEQ ID NO 88
<211> LENGTH: 73
<212> TYPE: DNA
<213> ORGANISM: Artificial sequence
<220> FEATURE:
<223> OTHER INFORMATION: Polynucleotide used in the Examples

<400> SEQUENCE: 88
tttttttttt tttttttttt tttttttttt tttttttttt ttttttggtt gtttctgttg      60
gtgctgatat tgc                                                        73

<210> SEQ ID NO 89
<211> LENGTH: 984
<212> TYPE: PRT
<213> ORGANISM: Methanopyrus kandleri

<400> SEQUENCE: 89

Met Ala Leu Val Tyr Asp Ala Glu Phe Val Gly Ser Glu Arg Glu Phe
```

```
1               5                   10                  15
Glu Glu Glu Arg Glu Thr Phe Leu Lys Gly Val Lys Ala Tyr Asp Gly
                20                  25                  30

Val Leu Ala Thr Arg Tyr Leu Met Glu Arg Ser Ser Ala Lys Asn
                35                  40                  45

Asp Glu Glu Leu Leu Glu Leu His Gln Asn Phe Ile Leu Leu Thr Gly
50                  55                  60

Ser Tyr Ala Cys Ser Ile Asp Pro Thr Glu Asp Arg Tyr Gln Asn Val
65                  70                  75                  80

Ile Val Arg Gly Val Asn Phe Asp Glu Arg Val Gln Arg Leu Ser Thr
                85                  90                  95

Gly Gly Ser Pro Ala Arg Tyr Ala Ile Val Tyr Arg Arg Gly Trp Arg
                100                 105                 110

Ala Ile Ala Lys Ala Leu Asp Ile Asp Glu Glu Asp Val Pro Ala Ile
                115                 120                 125

Glu Val Arg Ala Val Lys Arg Asn Pro Leu Gln Pro Ala Leu Tyr Arg
                130                 135                 140

Ile Leu Val Arg Tyr Gly Arg Val Asp Leu Met Pro Val Thr Val Asp
145                 150                 155                 160

Glu Val Pro Pro Glu Met Ala Gly Glu Phe Glu Arg Leu Ile Glu Arg
                165                 170                 175

Tyr Asp Val Pro Ile Asp Glu Lys Glu Glu Arg Ile Leu Glu Ile Leu
                180                 185                 190

Arg Glu Asn Pro Trp Thr Pro His Asp Glu Ile Ala Arg Arg Leu Gly
                195                 200                 205

Leu Ser Val Ser Glu Val Glu Gly Glu Lys Asp Pro Glu Ser Ser Gly
210                 215                 220

Ile Tyr Ser Leu Trp Ser Arg Val Val Asn Ile Glu Tyr Asp Glu
225                 230                 235                 240

Arg Thr Ala Lys Arg His Val Lys Arg Arg Asp Arg Leu Leu Glu Glu
                245                 250                 255

Leu Tyr Glu His Leu Glu Glu Leu Ser Glu Arg Tyr Leu Arg His Pro
                260                 265                 270

Leu Thr Arg Arg Trp Ile Val Glu His Lys Arg Asp Ile Met Arg Arg
                275                 280                 285

Tyr Leu Glu Gln Arg Ile Val Glu Cys Ala Leu Lys Leu Gln Asp Arg
                290                 295                 300

Tyr Gly Ile Arg Glu Asp Val Ala Leu Cys Leu Ala Arg Ala Phe Asp
305                 310                 315                 320

Gly Ser Ile Ser Met Ile Ala Thr Thr Pro Tyr Arg Thr Leu Lys Asp
                325                 330                 335

Val Cys Pro Asp Leu Thr Leu Glu Glu Ala Lys Ser Val Asn Arg Thr
                340                 345                 350

Leu Ala Thr Leu Ile Asp Glu His Gly Leu Ser Pro Asp Ala Ala Asp
                355                 360                 365

Glu Leu Ile Glu His Phe Glu Ser Ile Ala Gly Ile Leu Ala Thr Asp
                370                 375                 380

Leu Glu Glu Ile Glu Arg Met Tyr Glu Glu Gly Arg Leu Ser Glu Glu
385                 390                 395                 400

Ala Tyr Arg Ala Ala Val Glu Ile Gln Leu Ala Glu Leu Thr Lys Lys
                405                 410                 415

Glu Gly Val Gly Arg Lys Thr Ala Glu Arg Leu Leu Arg Ala Phe Gly
                420                 425                 430
```

-continued

```
Asn Pro Glu Arg Val Lys Gln Leu Ala Arg Glu Phe Glu Ile Glu Lys
    435                 440                 445

Leu Ala Ser Val Glu Gly Val Gly Glu Arg Val Leu Arg Ser Leu Val
    450                 455                 460

Pro Gly Tyr Ala Ser Leu Ile Ser Ile Arg Gly Ile Asp Arg Glu Arg
465                 470                 475                 480

Ala Glu Arg Leu Leu Lys Lys Tyr Gly Tyr Ser Lys Val Arg Glu
                    485                 490                 495

Ala Gly Val Glu Glu Leu Arg Glu Asp Gly Leu Thr Asp Ala Gln Ile
                500                 505                 510

Arg Glu Leu Lys Gly Leu Lys Thr Leu Glu Ser Ile Val Gly Asp Leu
                515                 520                 525

Glu Lys Ala Asp Glu Leu Lys Arg Lys Tyr Gly Ser Ala Ser Ala Val
            530                 535                 540

Arg Arg Leu Pro Val Glu Glu Leu Arg Glu Leu Gly Phe Ser Asp Asp
545                 550                 555                 560

Glu Ile Ala Glu Ile Lys Gly Ile Pro Lys Lys Leu Arg Glu Ala Phe
                565                 570                 575

Asp Leu Glu Thr Ala Ala Glu Leu Tyr Glu Arg Tyr Gly Ser Leu Lys
                580                 585                 590

Glu Ile Gly Arg Arg Leu Ser Tyr Asp Asp Leu Leu Glu Leu Gly Ala
                595                 600                 605

Thr Pro Lys Ala Ala Ala Glu Ile Lys Gly Pro Glu Phe Lys Phe Leu
    610                 615                 620

Leu Asn Ile Glu Gly Val Gly Pro Lys Leu Ala Glu Arg Ile Leu Glu
625                 630                 635                 640

Ala Val Asp Tyr Asp Leu Glu Arg Leu Ala Ser Leu Asn Pro Glu Glu
                645                 650                 655

Leu Ala Glu Lys Val Glu Gly Leu Gly Glu Glu Leu Ala Glu Arg Val
                660                 665                 670

Val Tyr Ala Ala Arg Glu Arg Val Glu Ser Arg Arg Lys Ser Gly Arg
            675                 680                 685

Gln Glu Arg Ser Glu Glu Trp Lys Glu Trp Leu Glu Arg Lys Val
    690                 695                 700

Gly Glu Gly Arg Ala Arg Arg Leu Ile Glu Tyr Phe Gly Ser Ala Gly
705                 710                 715                 720

Glu Val Gly Lys Leu Val Glu Asn Ala Glu Val Ser Lys Leu Leu Glu
                725                 730                 735

Val Pro Gly Ile Gly Asp Glu Ala Ala Arg Leu Val Pro Gly Tyr
                740                 745                 750

Lys Thr Leu Arg Asp Ala Gly Leu Thr Pro Ala Glu Ala Glu Arg Val
            755                 760                 765

Leu Lys Arg Tyr Gly Ser Val Ser Lys Val Gln Glu Gly Ala Thr Pro
    770                 775                 780

Asp Glu Leu Arg Glu Leu Gly Leu Gly Asp Ala Lys Ile Ala Arg Ile
785                 790                 795                 800

Leu Gly Leu Arg Ser Leu Val Asn Lys Arg Leu Asp Val Asp Thr Ala
                805                 810                 815

Tyr Glu Leu Lys Arg Arg Tyr Gly Ser Val Ser Ala Val Arg Lys Ala
                820                 825                 830

Pro Val Lys Glu Leu Arg Glu Leu Gly Leu Ser Asp Arg Lys Ile Ala
            835                 840                 845
```

```
Arg Ile Lys Gly Ile Pro Glu Thr Met Leu Gln Val Arg Gly Met Ser
    850                 855                 860

Val Glu Lys Ala Glu Arg Leu Leu Glu Arg Phe Asp Thr Trp Thr Lys
865                 870                 875                 880

Val Lys Glu Ala Pro Val Ser Glu Leu Val Arg Val Pro Gly Val Gly
                885                 890                 895

Leu Ser Leu Val Lys Glu Ile Lys Ala Gln Val Asp Pro Ala Trp Lys
            900                 905                 910

Ala Leu Leu Asp Val Lys Gly Val Ser Pro Glu Leu Ala Asp Arg Leu
            915                 920                 925

Val Glu Glu Leu Gly Ser Pro Tyr Arg Val Leu Thr Ala Lys Lys Ser
    930                 935                 940

Asp Leu Met Arg Val Glu Arg Val Gly Pro Lys Leu Ala Glu Arg Ile
945                 950                 955                 960

Arg Ala Ala Gly Lys Arg Tyr Val Glu Glu Arg Ser Arg Glu
                965                 970                 975

Arg Ile Arg Arg Lys Leu Arg Gly
            980

<210> SEQ ID NO 90
<211> LENGTH: 1308
<212> TYPE: PRT
<213> ORGANISM: Artificial sequence
<220> FEATURE:
<223> OTHER INFORMATION: TrwC Cba-TopoV Mka

<400> SEQUENCE: 90

Met Leu Ser Val Ala Asn Val Arg Ser Pro Ser Ala Ala Ala Ser Tyr
1               5                   10                  15

Phe Ala Ser Asp Asn Tyr Tyr Ala Ser Asp Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
        115                 120                 125

Met Val Val Thr Gln Ala Thr Gly Asn Leu Ala Ile Gly Leu Phe Gln
    130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
    210                 215                 220
```

```
Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
            245                 250                 255

Ser Lys Glu Gly Ile Glu Asp Arg Ala Thr Leu Ser Lys Gln Trp Ser
        260                 265                 270

Glu Ala Ala Gln Ser Ile Gly Leu Asp Leu Lys Pro Leu Val Asp Arg
    275                 280                 285

Ala Arg Thr Lys Ala Leu Gly Gln Gly Met Glu Ala Thr Arg Ile Gly
290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Ser Val Leu Lys
            325                 330                 335

Gln Asp Arg Gln Thr Ile Ala Ala Ala Gln Ala Val Ala Ser Ala Val
            340                 345                 350

Arg His Leu Ser Gln Arg Glu Ala Ala Phe Glu Arg Thr Ala Leu Tyr
        355                 360                 365

Lys Ala Ala Leu Asp Phe Gly Leu Pro Thr Thr Ile Ala Asp Val Glu
370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
            405                 410                 415

Gln Arg Ile Leu Ser Glu Val Ala Ala Gly Lys Gly Asp Ser Ser Pro
        420                 425                 430

Ala Ile Thr Pro Gln Lys Ala Ala Ala Ser Val Gln Ala Ala Ala Leu
            435                 440                 445

Thr Gly Gln Gly Phe Arg Leu Asn Glu Gly Gln Leu Ala Ala Ala Arg
450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
            485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
        515                 520                 525

Phe Leu Gly Gly Trp Asn Lys Leu Leu Asp Asp Pro Gly Asn Val Ala
530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
            565                 570                 575

Leu Ala Asn Leu Ala Gly Val His Arg Leu Val Leu Ile Gly Asp Arg
        580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
            610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
```

```
            645                 650                 655
Asp Gly Ala Gln Val Ala Glu Thr Trp Leu Ala Leu Asp Lys Glu
        660                 665                 670

Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Ser Arg Glu Ile
        690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
            740                 745                 750

Arg Val Ile Gly Gln Asp Arg Lys Gly Lys Leu Val Glu Val Glu Asp
            755                 760                 765

Lys Arg Gly Lys Arg Phe Arg Phe Asp Pro Ala Arg Ile Arg Ala Gly
770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
                820                 825                 830

Val Thr Phe Glu Thr Ser Lys Gly Asp Leu Val Glu Leu Lys Lys Asp
                835                 840                 845

Asp Pro Met Leu Lys Arg Ile Asp Leu Ala Tyr Ala Leu Asn Val His
        850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
                900                 905                 910

Gly Ala Ala Val Ala Arg Asn Lys Gly Glu Lys Ala Ser Ala Ile Glu
            915                 920                 925

Val Thr Gly Ser Val Lys Pro Thr Ala Thr Lys Gly Ser Gly Val Asp
            930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile Ala Tyr Asp Val Gly Ala
                965                 970                 975

Ser Gly Arg Gln Glu Arg Ser Glu Glu Trp Lys Glu Trp Leu Glu
            980                 985                 990

Arg Lys Val Gly Glu Gly Arg Ala Arg Arg Leu Ile Glu Tyr Phe Gly
            995                 1000                1005

Ser Ala Gly Glu Val Gly Lys Leu Val Glu Asn Ala Glu Val Ser
        1010                1015                1020

Lys Leu Leu Glu Val Pro Gly Ile Gly Asp Glu Ala Val Ala Arg
        1025                1030                1035

Leu Val Pro Gly Tyr Lys Thr Leu Arg Asp Ala Gly Leu Thr Pro
        1040                1045                1050

Ala Glu Ala Glu Arg Val Leu Lys Arg Tyr Gly Ser Val Ser Lys
        1055                1060                1065
```

Val Gln Glu Gly Ala Thr Pro Asp Glu Leu Arg Glu Leu Gly Leu
    1070              1075              1080

Gly Asp Ala Lys Ile Ala Arg Ile Leu Gly Leu Arg Ser Leu Val
    1085              1090              1095

Asn Lys Arg Leu Asp Val Asp Thr Ala Tyr Glu Leu Lys Arg Arg
    1100              1105              1110

Tyr Gly Ser Val Ser Ala Val Arg Lys Ala Pro Val Lys Glu Leu
    1115              1120              1125

Arg Glu Leu Gly Leu Ser Asp Arg Lys Ile Ala Arg Ile Lys Gly
    1130              1135              1140

Ile Pro Glu Thr Met Leu Gln Val Arg Gly Met Ser Val Glu Lys
    1145              1150              1155

Ala Glu Arg Leu Leu Glu Arg Phe Asp Thr Trp Thr Lys Val Lys
    1160              1165              1170

Glu Ala Pro Val Ser Glu Leu Val Arg Val Pro Gly Val Gly Leu
    1175              1180              1185

Ser Leu Val Lys Glu Ile Lys Ala Gln Val Asp Pro Ala Trp Lys
    1190              1195              1200

Ala Leu Leu Asp Val Lys Gly Val Ser Pro Glu Leu Ala Asp Arg
    1205              1210              1215

Leu Val Glu Glu Leu Gly Ser Pro Tyr Arg Val Leu Thr Ala Lys
    1220              1225              1230

Lys Ser Asp Leu Met Arg Val Glu Arg Val Gly Pro Lys Leu Ala
    1235              1240              1245

Glu Arg Ile Arg Ala Ala Gly Lys Arg Tyr Val Glu Glu Arg Arg
    1250              1255              1260

Ser Arg Arg Glu Arg Ile Arg Arg Lys Leu Arg Gly Ser Gly Gly
    1265              1270              1275

Ser Ala Trp Ser His Pro Gln Phe Glu Lys Gly Gly Ser Gly
    1280              1285              1290

Gly Gly Ser Gly Gly Ser Ala Trp Ser His Pro Gln Phe Glu Lys
    1295              1300              1305

<210> SEQ ID NO 91
<211> LENGTH: 88
<212> TYPE: DNA
<213> ORGANISM: Artificial sequence
<220> FEATURE:
<223> OTHER INFORMATION: Polynucleotide used in the Examples

<400> SEQUENCE: 91
cgtggtcacg aggagctcgt cctcacctcg acgtctgcac gagcttttt tttttttttt    60 tttttttttt tttttttttt tttttttt                                      88

<210> SEQ ID NO 92
<211> LENGTH: 88
<212> TYPE: DNA
<213> ORGANISM: Artificial sequence
<220> FEATURE:
<223> OTHER INFORMATION: Polynucleotide used in the Examples

<400> SEQUENCE: 92
tttttttttt tttttttttt tttttttttt tttttttttt ttttgctcgt gcagacgtcg    60
aggtgaggac gagctcctcg tgaccacg                                       88

<210> SEQ ID NO 93

<211> LENGTH: 44
<212> TYPE: DNA
<213> ORGANISM: Artificial sequence
<220> FEATURE:
<223> OTHER INFORMATION: Polynucleotide used in the Examples

<400> SEQUENCE: 93
cgtggtcacg aggagctcgt cctcacctcg acgtctgcac gagc                              44

<210> SEQ ID NO 94
<211> LENGTH: 299
<212> TYPE: PRT
<213> ORGANISM: Methanopyrus kandleri

<400> SEQUENCE: 94

Ser Gly Arg Gln Glu Arg Ser Glu Glu Glu Trp Lys Glu Trp Leu Glu
1               5                   10                  15

Arg Lys Val Gly Glu Gly Arg Ala Arg Arg Leu Ile Glu Tyr Phe Gly
            20                  25                  30

Ser Ala Gly Glu Val Gly Lys Leu Val Glu Asn Ala Glu Val Ser Lys
        35                  40                  45

Leu Leu Glu Val Pro Gly Ile Gly Asp Glu Ala Val Ala Arg Leu Val
    50                  55                  60

Pro Gly Tyr Lys Thr Leu Arg Asp Ala Gly Leu Thr Pro Ala Glu Ala
65                  70                  75                  80

Glu Arg Val Leu Lys Arg Tyr Gly Ser Val Ser Lys Val Gln Glu Gly
                85                  90                  95

Ala Thr Pro Asp Glu Leu Arg Glu Leu Gly Leu Gly Asp Ala Lys Ile
            100                 105                 110

Ala Arg Ile Leu Gly Leu Arg Ser Leu Val Asn Lys Arg Leu Asp Val
        115                 120                 125

Asp Thr Ala Tyr Glu Leu Lys Arg Arg Tyr Gly Ser Val Ser Ala Val
    130                 135                 140

Arg Lys Ala Pro Val Lys Glu Leu Arg Glu Leu Gly Leu Ser Asp Arg
145                 150                 155                 160

Lys Ile Ala Arg Ile Lys Gly Ile Pro Glu Thr Met Leu Gln Val Arg
                165                 170                 175

Gly Met Ser Val Glu Lys Ala Glu Arg Leu Leu Glu Arg Phe Asp Thr
            180                 185                 190

Trp Thr Lys Val Lys Glu Ala Pro Val Ser Glu Leu Val Arg Val Pro
        195                 200                 205

Gly Val Gly Leu Ser Leu Val Lys Glu Ile Lys Ala Gln Val Asp Pro
    210                 215                 220

Ala Trp Lys Ala Leu Leu Asp Val Lys Gly Val Ser Pro Glu Leu Ala
225                 230                 235                 240

Asp Arg Leu Val Glu Glu Leu Gly Ser Pro Tyr Arg Val Leu Thr Ala
                245                 250                 255

Lys Lys Ser Asp Leu Met Arg Val Glu Arg Val Gly Pro Lys Leu Ala
            260                 265                 270

Glu Arg Ile Arg Ala Ala Gly Lys Arg Tyr Val Glu Glu Arg Arg Ser
        275                 280                 285

Arg Arg Glu Arg Ile Arg Arg Lys Leu Arg Gly
    290                 295

<210> SEQ ID NO 95
<211> LENGTH: 8
<212> TYPE: PRT

-continued

```
<213> ORGANISM: Artificial sequence
<220> FEATURE:
<223> OTHER INFORMATION: RecD-like motif I of TrwC Cba

<400> SEQUENCE: 95

Gly Ile Ala Gly Ala Gly Lys Ser
1               5

<210> SEQ ID NO 96
<211> LENGTH: 10
<212> TYPE: PRT
<213> ORGANISM: Artificial sequence
<220> FEATURE:
<223> OTHER INFORMATION: RecD-like motif V of TrwC Cba

<400> SEQUENCE: 96

Tyr Ala Leu Asn Val His Met Ala Gln Gly
1               5                   10

<210> SEQ ID NO 97
<211> LENGTH: 14
<212> TYPE: PRT
<213> ORGANISM: Artificial sequence
<220> FEATURE:
<223> OTHER INFORMATION: MobF motif III of TrwC Cba

<400> SEQUENCE: 97

His Asp Thr Asn Arg Asn Gln Glu Pro Asn Leu His Phe His
1               5                   10

<210> SEQ ID NO 98
<211> LENGTH: 943
<212> TYPE: PRT
<213> ORGANISM: Halothiobacillus neapolitanus c2

<400> SEQUENCE: 98

Met Leu Arg Ile Lys Asn Leu Lys Gly Asp Pro Ser Ala Ile Ile Asp
1               5                   10                  15

Tyr Ala Glu Asn Lys Lys Asn His Pro Asp Gln Lys Ser Gly Tyr Tyr
                20                  25                  30

Asp Ala Lys Gly Ala Pro Ser Ala Trp Gly Gly Ala Leu Ala Ala Asp
            35                  40                  45

Leu Gly Leu Ser Gly Ser Val Gln Ala Ala Asp Leu Lys Lys Leu Leu
        50                  55                  60

Ser Gly Glu Leu Ser Asp Gly Thr Arg Phe Ala Lys Glu Asp Pro Asp
65                  70                  75                  80

Arg Arg Leu Gly Ile Asp Met Ser Phe Ser Ala Pro Lys Ser Val Ser
                85                  90                  95

Leu Ala Ala Leu Val Gly Gly Asp Glu Arg Ile Ile Gln Ala His Asp
            100                 105                 110

Ala Ala Val Arg Thr Ala Met Ser Met Ile Glu Gln Glu Tyr Ala Thr
        115                 120                 125

Ala Arg Phe Gly His Ala Gly Arg Asn Val Val Cys Ser Gly Lys Leu
    130                 135                 140

Val Tyr Ala Ala Tyr Arg His Glu Asp Ala Arg Thr Val Asp Ile
145                 150                 155                 160

Ala Asp Pro Gln Leu His Thr His Cys Ile Val Ser Asn Ile Thr Ile
                165                 170                 175

Asp Pro Glu Thr Gly Lys Pro Arg Ser Ile Asp Phe Ala Trp Gly Gln
            180                 185                 190
```

-continued

```
Asp Gly Ile Lys Leu Ala Gly Ala Met Tyr Arg Ala Glu Leu Ala Arg
        195                 200                 205
Arg Leu Lys Glu Met Gly Tyr Glu Leu Arg Lys Ser Glu Glu Gly Phe
    210                 215                 220
Glu Leu Ala Gln Ile Ser Asp Glu Gln Val Glu Thr Phe Ser Arg Arg
225                 230                 235                 240
Arg Val Gln Val Asp Gln Ala Leu Glu Gln Gln Gly Thr Asp Arg Glu
                245                 250                 255
His Ala Ser Ser Glu Leu Lys Thr Ala Val Thr Leu Ala Thr Arg Gln
            260                 265                 270
Gly Lys Ala Gln Leu Ser Ala Glu Asp Gln Tyr Glu Glu Trp Gln Gln
        275                 280                 285
Arg Ala Ala Glu Ala Glu Leu Asp Leu Ser Gln Pro Val Gly Pro Arg
    290                 295                 300
Val Ser Val Thr Pro Pro Glu Ile Asp Leu Asp His Thr Phe Glu His
305                 310                 315                 320
Leu Ser Glu Arg Ala Ser Val Ile Asn Lys Asp Ala Val Arg Leu Asp
                325                 330                 335
Ala Leu Ile Asn His Met Ser Glu Gly Ala Thr Leu Ser Thr Val Asp
            340                 345                 350
Lys Ala Ile Gln Gly Ala Ala Val Thr Gly Asp Val Phe Glu Ile Glu
        355                 360                 365
Asp Gly Ile Lys Arg Lys Ile Ile Thr Arg Glu Thr Leu Lys Arg Glu
    370                 375                 380
Gln Gln Ile Leu Leu Ala Gln Gln Gly Arg Gly Val Asn Ser Val
385                 390                 395                 400
Leu Ile Gly Val Gly Asp Thr Lys His Leu Ile Glu Asp Ala Glu Gln
                405                 410                 415
Ala Gln Gly Phe Arg Phe Ser Glu Gly Gln Arg Ala Ile Asn Leu
            420                 425                 430
Thr Ala Thr Thr Thr Asp Gln Val Ser Gly Ile Val Gly Ala Ala Gly
        435                 440                 445
Ala Gly Lys Thr Thr Ala Met Lys Thr Val Ala Asp Leu Ala Lys Ser
    450                 455                 460
Gln Gly Leu Thr Val Val Gly Ile Ala Pro Ser Ser Ala Ala Ala Asp
465                 470                 475                 480
Glu Leu Lys Ser Ala Gly Ala Asp Asp Thr Met Thr Leu Ala Thr Phe
                485                 490                 495
Asn Leu Lys Gly Glu Ala Ala Gly Pro Arg Leu Leu Ile Leu Asp Glu
            500                 505                 510
Ala Gly Met Val Ser Ala Arg Asp Gly Glu Ala Leu Leu Lys Lys Leu
        515                 520                 525
Gly Lys Glu Asp Arg Leu Ile Phe Val Gly Asp Pro Lys Gln Leu Ala
    530                 535                 540
Ala Val Glu Ala Gly Ser Pro Phe Ala Gln Leu Met Arg Ser Gly Ala
545                 550                 555                 560
Ile Gln Tyr Ala Glu Ile Thr Glu Ile Asn Arg Gln Lys Asp Gln Lys
                565                 570                 575
Leu Leu Asp Ile Ala Gln His Phe Ala Lys Gly Lys Ala Glu Glu Ala
            580                 585                 590
Val Ala Leu Ala Thr Lys Tyr Val Thr Glu Val Pro Val Thr Leu Pro
        595                 600                 605
Asp Lys Pro Glu His Lys Ile Thr Arg Gln Ala Lys Thr Glu Ala Arg
```

```
                    610             615             620
Arg Leu Ala Ile Ala Ser Ala Thr Ala Lys Arg Tyr Leu Glu Leu Ser
625                 630             635                 640

Gln Glu Glu Arg Ala Thr Thr Leu Val Leu Ser Gly Thr Asn Ala Val
                645             650             655

Arg Lys Gln Val Asn Glu Gln Val Arg Lys Gly Leu Ile Asp Lys Gly
                660             665             670

Glu Ile Asn Gly Glu Ser Phe Thr Val Ser Thr Leu Asp Lys Ala Asp
                675             680             685

Met Thr Arg Ala Lys Met Arg Lys Ala Gly Asn Tyr Lys Pro Gly Gln
            690             695             700

Val Ile Lys Thr Ala Gly Lys Gln Ala Glu Gln Ser Glu Val Val Ala
705             710             715                 720

Val Asn Leu Asp Gln Asn Leu Ile Gln Val Lys Leu Ser Asp Gly Thr
                725             730             735

Leu Lys Ser Ile Asp Ala Ser Arg Phe Asp Val Lys Lys Thr Gln Val
                740             745             750

Phe Asn Pro Arg Gln Ile Asp Ile Ala Ala Gly Asp Lys Ile Ile Phe
                755             760             765

Thr Asn Asn Asp Gln Ala Thr Glu Thr Lys Asn Asn Gln Ile Gly Leu
            770             775             780

Ile Glu Glu Ile Lys Asp Gly Lys Ala Ile Ile Asn Ser Asn Gly Ala
785             790             795                 800

Lys Val Glu Ile Asp Ile Gln Arg Lys Leu His Ile Asp His Ala Tyr
                805             810             815

Cys Ile Thr Ile His Arg Ser Gln Gly Gln Thr Val Asp Ser Val Ile
                820             825             830

Val Ala Gly Glu Ala Ser Arg Thr Thr Ala Glu Ala Ala Tyr Val
                835             840             845

Ala Cys Thr Arg Glu Arg Tyr Lys Leu Glu Ile Thr Asp Asn Thr
850                 855             860

Glu Arg Leu Ser Lys Asn Trp Val Arg Tyr Ala Asp Arg Gln Thr Ala
865             870             875             880

Ala Glu Ala Leu Lys Ser Ser Glu Glu Lys Tyr Pro His Leu Asp Glu
                885             890             895

Ile Arg Glu Glu Leu Arg Arg Glu Leu Gln Gln Glu Leu Glu Arg Gln
                900             905             910

Glu Pro Thr Asn Ile Thr Pro Glu Leu Glu Ile Glu Met Glu Arg Ser
                915             920             925

Met Phe Asp Gln Tyr Thr Leu His Ser Arg Gln Pro Arg Ser Tyr
            930             935             940

<210> SEQ ID NO 99
<211> LENGTH: 8
<212> TYPE: PRT
<213> ORGANISM: Artificial sequence
<220> FEATURE:
<223> OTHER INFORMATION: RecD-like motif I of TrwC Hne

<400> SEQUENCE: 99

Gly Ala Ala Gly Ala Gly Lys Thr
1               5

<210> SEQ ID NO 100
<211> LENGTH: 10
<212> TYPE: PRT
```

```
<213> ORGANISM: Artificial sequence
<220> FEATURE:
<223> OTHER INFORMATION: RecD-like motif V of TrwC Hne

<400> SEQUENCE: 100

Tyr Cys Ile Thr Ile His Arg Ser Gln Gly
1               5                   10

<210> SEQ ID NO 101
<211> LENGTH: 18
<212> TYPE: PRT
<213> ORGANISM: Artificial sequence
<220> FEATURE:
<223> OTHER INFORMATION: MobF motif III of TrwC Hne

<400> SEQUENCE: 101

His Glu Asp Ala Arg Thr Val Asp Asp Ile Ala Asp Pro Gln Leu His
1               5                   10                  15

Thr His

<210> SEQ ID NO 102
<211> LENGTH: 960
<212> TYPE: PRT
<213> ORGANISM: Erythrobacter litoralis HTCC2594

<400> SEQUENCE: 102

Met Leu Ser Val Ala Asn Val Arg Ser Pro Thr Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Ile Gly Gly Gly Ala Lys Arg Leu Gly Leu Glu Gly Lys Val
            35                  40                  45

Glu Ala Lys Ala Phe Asp Ala Leu Leu Arg Gly Glu Leu Pro Asp Gly
        50                  55                  60

Ser Ser Val Gly Asn Pro Gly Gln Ala His Arg Pro Gly Thr Asp Leu
65                  70                  75                  80

Ser Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
                100                 105                 110

Gln Trp Ala Glu Lys Asn Ala Ala Glu Thr Arg Ile Val Glu Lys Gly
            115                 120                 125

Lys Met Val Thr Gln Ala Thr Gly Asn Leu Ala Val Gly Leu Phe Gln
130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
    210                 215                 220

Ile Met Ala Phe Ser Thr Arg Arg Lys Glu Val Leu Glu Ala Arg Arg
225                 230                 235                 240

Gly Pro Gly Leu Glu Ala Gly Arg Ile Ala Ala Leu Asp Thr Arg Ala
                245                 250                 255
```

```
Ser Lys Glu Glu Ile Glu Asp Arg Ala Thr Leu Gly Lys Gln Trp Ser
            260                 265                 270

Glu Thr Ala Gln Ser Ile Gly Leu Asp Leu Thr Pro Leu Val Asp Arg
            275                 280                 285

Ala Arg Thr Asn Ala Leu Gly Gln Ser Met Glu Ala Thr Arg Ile Gly
            290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys
                325                 330                 335

Gln Asp Arg Gln Thr Ile Ala Ala Gln Ala Val Ala Ser Ala Ile
            340                 345                 350

Arg His Leu Ser Gln Arg Glu Ala Ala Phe Glu Arg Thr Ala Leu Tyr
            355                 360                 365

Lys Ala Ala Leu Asp Phe Gly Leu Pro Ala Thr Ile Ala Asp Val Glu
    370                 375                 380

Lys Arg Thr Arg Ala Leu Val Arg Ser Gly Asp Leu Ile Ser Gly Lys
385                 390                 395                 400

Gly Glu His Lys Gly Trp Leu Ala Ser Arg Glu Ala Val Val Thr Glu
                405                 410                 415

Gln Arg Ile Leu Ser Glu Val Ala Ala Gly Lys Gly Asn Ser Ser Pro
            420                 425                 430

Ala Ile Glu Pro Gln Lys Ala Ala Ser Val Gln Ala Ala Ala Ala
            435                 440                 445

Thr Gly Gln Gly Phe Arg Leu Asn Glu Gly Gln Leu Ala Ala Ala Glu
    450                 455                 460

Leu Ile Leu Thr Ser Lys Asp Arg Thr Ile Ala Ile Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Glu Thr Gly Ile Gly Ser Gln Thr Leu Ala Arg
            515                 520                 525

Phe Leu Arg Gly Trp Thr Lys Leu Leu Gly Asp Pro Gly Asn Val Ala
    530                 535                 540

Leu Arg Thr Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
            595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ser Ala Gln Ala Gly Asp Val
625                 630                 635                 640

Arg Asn Ala Leu Arg His Leu Lys Ser His Thr Val Glu Ala Lys Gly
                645                 650                 655

Asp Gly Ala Gln Val Ala Ala Glu Thr Trp Leu Ala Leu Asp Lys Glu
            660                 665                 670
```

```
Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Asn Arg Glu Ile
    690                 695                 700

Gly Pro Gly Met Met Lys Leu Asp Val Leu Asp Arg Val Asn Ala Thr
705                 710                 715                 720

Arg Glu Glu Leu Arg His Leu Pro Ala Tyr Arg Ala Gly Gln Val Leu
                725                 730                 735

Glu Ile Ser Arg Lys Gln Ala Leu Gly Leu Ser Val Gly Glu Tyr
            740                 745                 750

Arg Val Leu Gly Gln Asp Arg Lys Gly Arg Leu Val Glu Val Glu Asp
        755                 760                 765

Lys Arg Gly Lys Arg Phe Arg Phe Asp Pro Ala Arg Ile Lys Ala Gly
    770                 775                 780

Lys Gly Asp Glu Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Ala Ile Ala Gly Gly Lys
            820                 825                 830

Ile Thr Phe Glu Thr Ser Gln Gly Asp Gln Val Glu Leu Lys Arg Asp
        835                 840                 845

Asp Pro Met Leu Lys Arg Ile Asp Leu Ala Tyr Ala Leu Asn Ala His
    850                 855                 860

Met Ala Gln Gly Leu Thr Ser Asp Arg Gly Ile Ala Val Met Thr Ser
865                 870                 875                 880

Ser Glu Arg Asn Leu Ser Asn Gln Lys Thr Phe Met Val Thr Val Thr
                885                 890                 895

Arg Leu Arg Asp His Leu Thr Leu Val Val Asp Asn Ala Glu Lys Leu
            900                 905                 910

Gly Ala Ala Val Ala Arg Asn Lys Gly Glu Lys Ala Ser Ala Leu Glu
        915                 920                 925

Val Thr Gly Ser Val Lys Ser Thr Ala Ala Lys Gly Ser Gly Val Asp
    930                 935                 940

Gln Leu Lys Pro Glu Glu Ala Asn Lys Ala Glu Lys Glu Leu Thr Arg
945                 950                 955                 960

<210> SEQ ID NO 103
<211> LENGTH: 10
<212> TYPE: PRT
<213> ORGANISM: Artificial sequence
<220> FEATURE:
<223> OTHER INFORMATION: RecD-like motif V of TrwC Eli

<400> SEQUENCE: 103

Tyr Ala Leu Asn Ala His Met Ala Gln Gly
1               5                   10

<210> SEQ ID NO 104
<211> LENGTH: 606
<212> TYPE: DNA
<213> ORGANISM: Artificial sequence
<220> FEATURE:
<223> OTHER INFORMATION: Polynucleotide used in the Examples

<400> SEQUENCE: 104
gccatcagat tgtgtttgtt agtcgctttt ttttttttgga attttttttt tggaattttt      60
```

```
ttttttgacgc tcagtaatgt gacgatagct gaaaactgta cgataaacgg tacgctgagg    120
gcggaaaaaa tcgtcgggga cattgtaaag gcggcgagcg cggcttttcc gcgccagcgt    180
gaaagcagtg tggactggcc gtcaggtacc cgtactgtca ccgtgaccga tgaccatcct    240
tttgatcgcc agatagtggt gcttccgctg acgtttcgcg gaagtaagcg tactgtcagc    300
ggcaggacaa cgtattcgat gtgttatctg aaagtactga tgaacggtgc ggtgatttat    360
gatggcgcgg cgaacgaggc ggtacaggtg ttctcccgta ttgttgacat gccagcgggt    420
cggggaaacg tgatcctgac gttcacgctt acgtccacac ggcattcggc agatattccg    480
ccgtatacgt ttgccagcga tgtgcaggtt atggtgatta agaaacaggc gctgggcatc    540
agcgtggtct gagtgtgaaa aaaaaggtac caaaaaaaac atcgtcgtga gtagtgaacc    600
gtaagc                                                               606
```

<210> SEQ ID NO 105
<211> LENGTH: 853
<212> TYPE: PRT
<213> ORGANISM: Escherichia coli

<400> SEQUENCE: 105

```
Met Ser Ala Ile Glu Asn Phe Asp Ala His Thr Pro Met Met Gln Gln
1               5                   10                  15

Tyr Leu Arg Leu Lys Ala Gln His Pro Glu Ile Leu Leu Phe Tyr Arg
            20                  25                  30

Met Gly Asp Phe Tyr Glu Leu Phe Tyr Asp Asp Ala Lys Arg Ala Ser
        35                  40                  45

Gln Leu Leu Asp Ile Ser Leu Thr Lys Arg Gly Ala Ser Ala Gly Glu
    50                  55                  60

Pro Ile Pro Met Ala Gly Ile Pro Tyr His Ala Val Glu Asn Tyr Leu
65                  70                  75                  80

Ala Lys Leu Val Asn Gln Gly Glu Ser Val Ala Ile Cys Glu Gln Ile
                85                  90                  95

Gly Asp Pro Ala Thr Ser Lys Gly Pro Val Glu Arg Lys Val Val Arg
            100                 105                 110

Ile Val Thr Pro Gly Thr Ile Ser Asp Glu Ala Leu Leu Gln Glu Arg
        115                 120                 125

Gln Asp Asn Leu Leu Ala Ala Ile Trp Gln Asp Ser Lys Gly Phe Gly
    130                 135                 140

Tyr Ala Thr Leu Asp Ile Ser Ser Gly Arg Phe Arg Leu Ser Glu Pro
145                 150                 155                 160

Ala Asp Arg Glu Thr Met Ala Ala Glu Leu Gln Arg Thr Asn Pro Ala
                165                 170                 175

Glu Leu Leu Tyr Ala Glu Asp Phe Ala Glu Met Ser Leu Ile Glu Gly
            180                 185                 190

Arg Arg Gly Leu Arg Arg Arg Pro Leu Trp Glu Phe Glu Ile Asp Thr
        195                 200                 205

Ala Arg Gln Gln Leu Asn Leu Gln Phe Gly Thr Arg Asp Leu Val Gly
    210                 215                 220

Phe Gly Val Glu Asn Ala Pro Arg Gly Leu Cys Ala Ala Gly Cys Leu
225                 230                 235                 240

Leu Gln Tyr Ala Lys Asp Thr Gln Arg Thr Thr Leu Pro His Ile Arg
                245                 250                 255

Ser Ile Thr Met Glu Arg Glu Gln Asp Ser Ile Ile Met Asp Ala Ala
            260                 265                 270
```

```
Thr Arg Arg Asn Leu Glu Ile Thr Gln Asn Leu Ala Gly Gly Ala Glu
            275                 280                 285

Asn Thr Leu Ala Ser Val Leu Asp Cys Thr Val Thr Pro Met Gly Ser
        290                 295                 300

Arg Met Leu Lys Arg Trp Leu His Met Pro Val Arg Asp Thr Arg Val
305                 310                 315                 320

Leu Leu Glu Arg Gln Gln Thr Ile Gly Ala Leu Gln Asp Phe Thr Ala
                325                 330                 335

Gly Leu Gln Pro Val Leu Arg Gln Val Gly Asp Leu Glu Arg Ile Leu
            340                 345                 350

Ala Arg Leu Ala Leu Arg Thr Ala Arg Pro Arg Asp Leu Ala Arg Met
        355                 360                 365

Arg His Ala Phe Gln Gln Leu Pro Glu Leu Arg Ala Gln Leu Glu Thr
    370                 375                 380

Val Asp Ser Ala Pro Val Gln Ala Leu Arg Glu Lys Met Gly Glu Phe
385                 390                 395                 400

Ala Glu Leu Arg Asp Leu Leu Glu Arg Ala Ile Ile Asp Thr Pro Pro
                405                 410                 415

Val Leu Val Arg Asp Gly Gly Val Ile Ala Ser Gly Tyr Asn Glu Glu
            420                 425                 430

Leu Asp Glu Trp Arg Ala Leu Ala Asp Gly Ala Thr Asp Tyr Leu Glu
        435                 440                 445

Arg Leu Glu Val Arg Glu Arg Glu Arg Thr Gly Leu Asp Thr Leu Lys
    450                 455                 460

Val Gly Phe Asn Ala Val His Gly Tyr Tyr Ile Gln Ile Ser Arg Gly
465                 470                 475                 480

Gln Ser His Leu Ala Pro Ile Asn Tyr Met Arg Arg Gln Thr Leu Lys
                485                 490                 495

Asn Ala Glu Arg Tyr Ile Ile Pro Glu Leu Lys Glu Tyr Glu Asp Lys
            500                 505                 510

Val Leu Thr Ser Lys Gly Lys Ala Leu Ala Leu Glu Lys Gln Leu Tyr
        515                 520                 525

Glu Glu Leu Phe Asp Leu Leu Leu Pro His Leu Glu Ala Leu Gln Gln
    530                 535                 540

Ser Ala Ser Ala Leu Ala Glu Leu Asp Val Leu Val Asn Leu Ala Glu
545                 550                 555                 560

Arg Ala Tyr Thr Leu Asn Tyr Thr Cys Pro Thr Phe Ile Asp Lys Pro
                565                 570                 575

Gly Ile Arg Ile Thr Glu Gly Arg His Pro Val Val Glu Gln Val Leu
            580                 585                 590

Asn Glu Pro Phe Ile Ala Asn Pro Leu Asn Leu Ser Pro Gln Arg Arg
        595                 600                 605

Met Leu Ile Ile Thr Gly Pro Asn Met Gly Gly Lys Ser Thr Tyr Met
    610                 615                 620

Arg Gln Thr Ala Leu Ile Ala Leu Met Ala Tyr Ile Gly Ser Tyr Val
625                 630                 635                 640

Pro Ala Gln Lys Val Glu Ile Gly Pro Ile Asp Arg Ile Phe Thr Arg
                645                 650                 655

Val Gly Ala Ala Asp Asp Leu Ala Ser Gly Arg Ser Thr Phe Met Val
            660                 665                 670

Glu Met Thr Glu Thr Ala Asn Ile Leu His Asn Ala Thr Glu Tyr Ser
        675                 680                 685

Leu Val Leu Met Asp Glu Ile Gly Arg Gly Thr Ser Thr Tyr Asp Gly
```

```
                    690                 695                 700
Leu Ser Leu Ala Trp Ala Cys Ala Glu Asn Leu Ala Asn Lys Ile Lys
705                 710                 715                 720

Ala Leu Thr Leu Phe Ala Thr His Tyr Phe Glu Leu Thr Gln Leu Pro
                    725                 730                 735

Glu Lys Met Glu Gly Val Ala Asn Val His Leu Asp Ala Leu Glu His
                740                 745                 750

Gly Asp Thr Ile Ala Phe Met His Ser Val Gln Asp Gly Ala Ala Ser
                755                 760                 765

Lys Ser Tyr Gly Leu Ala Val Ala Ala Leu Ala Gly Val Pro Lys Glu
                770                 775                 780

Val Ile Lys Arg Ala Arg Gln Lys Leu Arg Glu Leu Glu Ser Ile Ser
785                 790                 795                 800

Pro Asn Ala Ala Ala Thr Gln Val Asp Gly Thr Gln Met Ser Leu Leu
                    805                 810                 815

Ser Val Pro Glu Glu Thr Ser Pro Ala Val Glu Ala Leu Glu Asn Leu
                820                 825                 830

Asp Pro Asp Ser Leu Thr Pro Arg Gln Ala Leu Glu Trp Ile Tyr Arg
                835                 840                 845

Leu Lys Ser Leu Val
    850

<210> SEQ ID NO 106
<211> LENGTH: 64
<212> TYPE: PRT
<213> ORGANISM: Sulfolobus solfataricus

<400> SEQUENCE: 106

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
                20                  25                  30

Thr Tyr Asp Glu Gly Gly Gly Lys Thr Gly Arg Gly Ala Val Ser Glu
            35                  40                  45

Lys Asp Ala Pro Lys Glu Leu Leu Gln Met Leu Glu Lys Gln Lys Lys
        50                  55                  60

<210> SEQ ID NO 107
<211> LENGTH: 99
<212> TYPE: PRT
<213> ORGANISM: Sulfolobus solfataricus

<400> SEQUENCE: 107

Glu Lys Met Ser Ser Gly Thr Pro Thr Pro Ser Asn Val Val Leu Ile
1               5                   10                  15

Gly Lys Lys Pro Val Met Asn Tyr Val Leu Ala Ala Leu Thr Leu Leu
                20                  25                  30

Asn Gln Gly Val Ser Glu Ile Val Ile Lys Ala Arg Gly Arg Ala Ile
            35                  40                  45

Ser Lys Ala Val Asp Thr Val Glu Ile Val Arg Asn Arg Phe Leu Pro
        50                  55                  60

Asp Lys Ile Glu Ile Lys Ile Arg Val Gly Ser Gln Val Val Thr
65                  70                  75                  80

Ser Gln Asp Gly Arg Gln Ser Arg Val Ser Thr Ile Glu Ile Ala Ile
                85                  90                  95

Arg Lys Lys
```

<210> SEQ ID NO 108
<211> LENGTH: 88
<212> TYPE: PRT
<213> ORGANISM: Sulfolobus solfataricus

<400> SEQUENCE: 108

```
Thr Glu Lys Leu Asn Glu Ile Val Val Arg Lys Thr Lys Asn Val Glu
1               5                   10                  15

Asp His Val Leu Asp Val Ile Val Leu Phe Asn Gln Gly Ile Asp Glu
            20                  25                  30

Val Ile Leu Lys Gly Thr Gly Arg Glu Ile Ser Lys Ala Val Asp Val
        35                  40                  45

Tyr Asn Ser Leu Lys Asp Arg Leu Gly Asp Gly Val Gln Leu Val Asn
    50                  55                  60

Val Gln Thr Gly Ser Glu Val Arg Asp Arg Arg Ile Ser Tyr Ile
65                  70                  75                  80

Leu Leu Arg Leu Lys Arg Val Tyr
                85
```

<210> SEQ ID NO 109
<211> LENGTH: 107
<212> TYPE: PRT
<213> ORGANISM: Escherichia coli

<400> SEQUENCE: 109

```
Ala Gln Gln Ser Pro Tyr Ser Ala Ala Met Ala Glu Gln Arg His Gln
1               5                   10                  15

Glu Trp Leu Arg Phe Val Asp Leu Leu Lys Asn Ala Tyr Gln Asn Asp
            20                  25                  30

Leu His Leu Pro Leu Leu Asn Leu Met Leu Thr Pro Asp Glu Arg Glu
            35                  40                  45

Ala Leu Gly Thr Arg Val Arg Ile Val Glu Glu Leu Leu Arg Gly Glu
        50                  55                  60

Met Ser Gln Arg Glu Leu Lys Asn Glu Leu Gly Ala Gly Ile Ala Thr
65                  70                  75                  80

Ile Thr Arg Gly Ser Asn Ser Leu Lys Ala Ala Pro Val Glu Leu Arg
                85                  90                  95

Gln Trp Leu Glu Glu Val Leu Leu Lys Ser Asp
            100                 105
```

<210> SEQ ID NO 110
<211> LENGTH: 237
<212> TYPE: PRT
<213> ORGANISM: Bacteriophage lambda

<400> SEQUENCE: 110

```
Met Ser Thr Lys Lys Lys Pro Leu Thr Gln Glu Gln Leu Glu Asp Ala
1               5                   10                  15

Arg Arg Leu Lys Ala Ile Tyr Glu Lys Lys Lys Asn Glu Leu Gly Leu
            20                  25                  30

Ser Gln Glu Ser Val Ala Asp Lys Met Gly Met Gly Gln Ser Gly Val
            35                  40                  45

Gly Ala Leu Phe Asn Gly Ile Asn Ala Leu Asn Ala Tyr Asn Ala Ala
        50                  55                  60

Leu Leu Ala Lys Ile Leu Lys Val Ser Val Glu Glu Phe Ser Pro Ser
65                  70                  75                  80
```

```
Ile Ala Arg Glu Ile Tyr Glu Met Tyr Glu Ala Val Ser Met Gln Pro
            85                  90                  95

Ser Leu Arg Ser Glu Tyr Glu Tyr Pro Val Phe Ser His Val Gln Ala
            100                 105                 110

Gly Met Phe Ser Pro Glu Leu Arg Thr Phe Thr Lys Gly Asp Ala Glu
            115                 120                 125

Arg Trp Val Ser Thr Thr Lys Lys Ala Ser Asp Ser Ala Phe Trp Leu
            130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Asp Glu Phe Thr Phe
                180                 185                 190

Lys Lys Leu Ile Arg Asp Ser Gly Gln Val Phe Leu Gln Pro Leu Asn
                195                 200                 205

Pro Gln Tyr Pro Met Ile Pro Cys Asn Glu Ser Cys Ser Val Val Gly
            210                 215                 220

Lys Val Ile Ala Ser Gln Trp Pro Glu Glu Thr Phe Gly
225                 230                 235
```

<210> SEQ ID NO 111
<211> LENGTH: 60
<212> TYPE: PRT
<213> ORGANISM: Crenarchaea

<400> SEQUENCE: 111

```
Met Ser Ser Gly Lys Lys Pro Val Lys Val Lys Thr Pro Ala Gly Lys
1               5                   10                  15

Glu Ala Glu Leu Val Pro Glu Lys Val Trp Ala Leu Ala Pro Lys Gly
            20                  25                  30

Arg Lys Gly Val Lys Ile Gly Leu Phe Lys Asp Pro Glu Thr Gly Lys
            35                  40                  45

Tyr Phe Arg His Lys Leu Pro Asp Asp Tyr Pro Ile
            50                  55                  60
```

<210> SEQ ID NO 112
<211> LENGTH: 136
<212> TYPE: PRT
<213> ORGANISM: Homo sapiens

<400> SEQUENCE: 112

```
Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
            35                  40                  45

Leu Arg Glu Ile Arg Arg Tyr Gln Lys Ser Thr Glu Leu Leu Ile Arg
            50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
            100                 105                 110
```

```
Ile His Ala Lys Arg Val Thr Ile Met Pro Lys Asp Ile Gln Leu Ala
            115                 120                 125

Arg Arg Ile Arg Gly Glu Arg Ala
    130                 135

<210> SEQ ID NO 113
<211> LENGTH: 89
<212> TYPE: PRT
<213> ORGANISM: Bacteriophage T4

<400> SEQUENCE: 113

Met Ala Lys Lys Glu Met Val Glu Phe Asp Glu Ala Ile His Gly Glu
1               5                   10                  15

Asp Leu Ala Lys Phe Ile Lys Glu Ala Ser Asp His Lys Leu Lys Ile
            20                  25                  30

Ser Gly Tyr Asn Glu Leu Ile Lys Asp Ile Arg Ile Arg Ala Lys Asp
        35                  40                  45

Glu Leu Gly Val Asp Gly Lys Met Phe Asn Arg Leu Leu Ala Leu Tyr
    50                  55                  60

His Lys Asp Asn Arg Asp Val Phe Glu Ala Glu Thr Glu Glu Val Val
65                  70                  75                  80

Glu Leu Tyr Asp Thr Val Phe Ser Lys
                85

<210> SEQ ID NO 114
<211> LENGTH: 339
<212> TYPE: PRT
<213> ORGANISM: Homo sapiens

<400> SEQUENCE: 114

Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Ala Glu Ala Ala Lys
65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
            100                 105                 110

Leu Gln Gly Gly Ile Glu Thr Gly Ser Ile Thr Glu Met Phe Gly Glu
        115                 120                 125

Phe Arg Thr Gly Lys Thr Gln Ile Cys His Thr Leu Ala Val Thr Cys
    130                 135                 140

Gln Leu Pro Ile Asp Arg Gly Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
            180                 185                 190

Arg Ala Phe Asn Thr Asp His Gln Thr Gln Leu Leu Tyr Gln Ala Ser
        195                 200                 205
```

```
Ala Met Met Val Glu Ser Arg Tyr Ala Leu Leu Ile Val Asp Ser Ala
    210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Leu Arg Leu Ala
                245                 250                 255

Asp Glu Phe Gly Val Ala Val Val Ile Thr Asn Gln Val Val Ala Gln
            260                 265                 270

Val Asp Gly Ala Ala Met Phe Ala Asp Pro Lys Lys Pro Ile Gly
        275                 280                 285

Gly Asn Ile Ile Ala His Ala Ser Thr Thr Arg Leu Tyr Leu Arg Lys
    290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                325                 330                 335

Ala Lys Asp

<210> SEQ ID NO 115
<211> LENGTH: 375
<212> TYPE: PRT
<213> ORGANISM: Citromicrobium bathyomarinum JL354

<400> SEQUENCE: 115

Met Lys Ala Thr Ile Glu Arg Ala Thr Leu Leu Arg Cys Leu Ser His
1               5                   10                  15

Val Gln Ser Val Val Glu Arg Arg Asn Thr Ile Pro Ile Leu Ser Asn
                20                  25                  30

Val Leu Ile Asp Ala Asp Ala Gly Gly Gly Val Lys Val Met Ala Thr
            35                  40                  45

Asp Leu Asp Leu Gln Val Val Glu Thr Met Thr Ala Ala Ser Val Glu
        50                  55                  60

Ser Gly Ala Ile Thr Val Ser Ala His Leu Leu Phe Asp Ile Ala
65                  70                  75                  80

Arg Lys Leu Pro Asp Gly Ser Gln Val Ser Leu Glu Thr Ala Asp Asn
                85                  90                  95

Arg Met Val Val Lys Ala Gly Arg Ser Arg Phe Gln Leu Pro Thr Leu
            100                 105                 110

Pro Arg Asp Asp Phe Pro Val Ile Val Glu Gly Glu Leu Pro Thr Ser
        115                 120                 125

Phe Glu Leu Pro Ala Arg Glu Leu Ala Glu Met Ile Asp Arg Thr Arg
    130                 135                 140

Phe Ala Ile Ser Thr Glu Glu Thr Arg Tyr Tyr Leu Asn Gly Ile Phe
145                 150                 155                 160

Leu His Val Ser Asp Glu Ala Arg Pro Val Leu Lys Ala Ala Thr
                165                 170                 175

Asp Gly His Arg Leu Ala Arg Tyr Thr Leu Asp Arg Pro Glu Gly Ala
            180                 185                 190

Glu Gly Met Pro Asp Val Ile Val Pro Arg Lys Ala Val Gly Glu Leu
        195                 200                 205

Arg Lys Leu Leu Glu Glu Ala Leu Asp Ser Asn Val Gln Ile Asp Leu
    210                 215                 220

Ser Ala Ser Lys Ile Arg Phe Ala Leu Gly Gly Glu Gly Gly Val Val
225                 230                 235                 240
```

-continued

```
Leu Thr Ser Lys Leu Ile Asp Gly Thr Phe Pro Asp Tyr Ser Arg Val
            245             250             255

Ile Pro Thr Gly Asn Asp Lys Leu Leu Arg Leu Asp Pro Lys Ala Phe
            260             265             270

Phe Gln Gly Val Asp Arg Val Ala Thr Ile Ala Thr Glu Lys Thr Arg
        275             280             285

Ala Val Lys Met Gly Leu Asp Glu Asp Lys Val Thr Leu Ser Val Thr
    290             295             300

Ser Pro Asp Asn Gly Thr Ala Ala Glu Glu Ile Ala Ala Glu Tyr Lys
305             310             315             320

Ala Glu Gly Phe Glu Ile Gly Phe Asn Ala Asn Tyr Leu Lys Asp Ile
            325             330             335

Leu Gly Gln Ile Asp Ser Asp Thr Val Glu Leu His Leu Ala Asp Ala
            340             345             350

Gly Ala Pro Thr Leu Ile Arg Arg Asp Glu Asn Ser Pro Ala Leu Tyr
        355             360             365

Val Leu Met Pro Met Arg Val
370             375
```

ENZYME CONSTRUCT

RELATED APPLICATIONS

This application is a 35 U.S.C. 371 national stage filing of International Application PCT/GB2013/051928, filed Jul. 18, 2013, which claims priority to United States Patent Application Nos. 61/774,694 and 61/673,446, filed on Mar. 8, 2013 and Jul. 19, 2012, respectively. The contents of the aforementioned applications are hereby incorporated by reference.

FIELD OF THE INVENTION

The invention relates to methods using constructs comprising a helicase and an additional polynucleotide binding moiety. The helicase is attached to the polynucleotide binding moiety and the construct has the ability to control the movement of a polynucleotide. The constructs can be used to control the movement of polynucleotides and are particularly useful for sequencing polynucleotides.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identity of the nucleotides are derived. Strand sequencing can involve the use of a nucleotide handling protein to control the movement of the polynucleotide through the pore.

SUMMARY OF THE INVENTION

The inventors have surprisingly demonstrated that attaching an additional polynucleotide binding moiety to a helicase, such as attaching two or more helicases together, results in a construct that has an improved ability to control the movement of a polynucleotide. In particular, the inventors have surprisingly demonstrated that such constructs will strongly bind to a long polynucleotide, such as a polynucleotide comprising 400 nucleotides or more, and will control the movement of most of, if not all of, the polynucleotide without disengaging. This allows the effective control of the movement of the polynucleotide, especially during Strand Sequencing.

Accordingly, the invention provides a method of characterising a target polynucleotide, comprising:

(a) contacting the target polynucleotide with a transmembrane pore and a construct comprising a helicase and an additional polynucleotide binding moiety, wherein the helicase is attached to the polynucleotide binding moiety and the construct has the ability to control the movement of a polynucleotide, such that the construct controls the movement of the target polynucleotide through the pore; and (b) taking one or more measurements as the polynucleotide moves with respect to the pore wherein the measurements are indicative of one or more characteristics of the target polynucleotide and thereby characterising the target polynucleotide.

The invention also provides:

a construct comprising two or more helicases, wherein the helicases are attached together and the construct has the ability to control the movement of a polynucleotide;

a polynucleotide sequence which encodes a construct of the invention, wherein the two or more helicases are genetically fused;

a method of controlling the movement of a polynucleotide, comprising contacting the polynucleotide with a construct of the invention and thereby controlling the movement of the polynucleotide;

a method of forming a sensor for characterising a target polynucleotide, comprising forming a complex between a pore and a construct as defined above and thereby forming a sensor for characterising the target polynucleotide;

a sensor for characterising a target polynucleotide, comprising a complex between a pore and a construct as defined above;

use of a construct as defined above to control the movement of a target polynucleotide through a pore;

a kit for characterising a target polynucleotide comprising (a) a pore and (b) a construct as defined above;

an apparatus for characterising target polynucleotides in a sample, comprising a plurality of pores and a plurality of constructs as defined above; and a method of producing a construct of the invention, comprising attaching two or more helicases together and thereby producing the construct.

DESCRIPTION OF THE SEQUENCE LISTING

Figure 1:
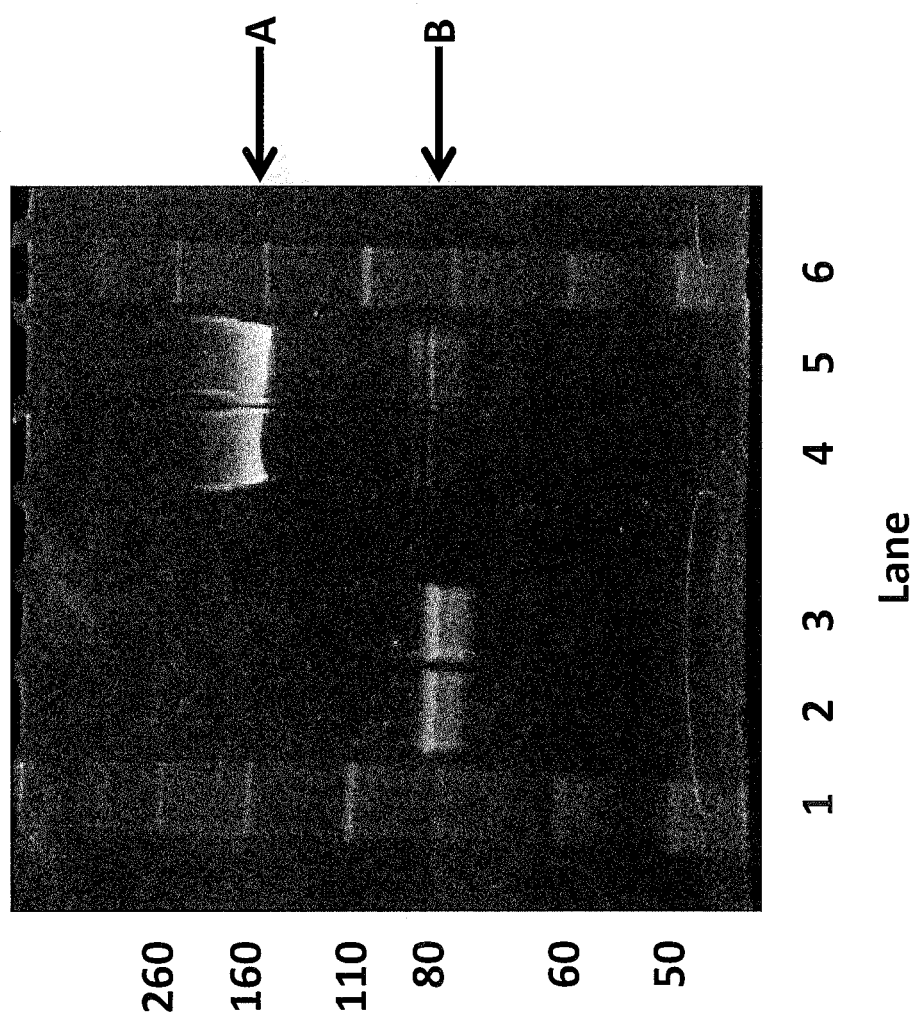
FIG. 1 shows a gel of the monomer and dimers of a number of Hel308 Mbu helicase constructs. Lanes 1 and 6 show an appropriate protein ladder. Lane 2 corresponds to the Hel308 Mbu (R687A/A700C) monomer (SEQ ID NO: 10 with the mutations R687A/A700C), Lane 3 corresponds to Hel308 Mbu(R681A/R687A/A700C) monomer (SEQ ID NO: 10 with the mutations R681A/R687A/A700C), Lane 4 corresponds to Hel308 Mbu(R687A/A700C)-2 kDa dimer (where each monomer unit comprises SEQ ID NO: 10 with the mutations R687A/A700C, with one monomer unit being linked to the other via position 700 of each monomer unit using a 2 kDa PEG linker) and Lane 5 corresponds to Hel308 Mbu(R681A/R687A/A700C)-2 kDa dimer (where each monomer unit comprises SEQ ID NO: 10 with the mutations R681A/R687A/A700C, with one monomer unit being linked to the other via position 700 of each monomer unit using a 2 kDa PEG linker). The band labelled A corresponds to the monomer and the band labelled B corresponds to the dimer.

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the amino acid sequence of the Hel308 motif.

SEQ ID NO: 9 shows the amino acid sequence of the extended Hel308 motif.

SEQ ID NO: 10 shows the amino acid sequence of Hel308 Mbu.

SEQ ID NO: 11 shows the Hel308 motif of Hel308 Mbu and Hel308 Mhu.

SEQ ID NO: 12 shows the extended Hel308 motif of Hel308 Mbu and Hel308 Mhu.

SEQ ID NO: 13 shows the amino acid sequence of Hel308 Csy.

SEQ ID NO: 14 shows the Hel308 motif of Hel308 Csy.

SEQ ID NO: 15 shows the extended Hel308 motif of Hel308 Csy.

SEQ ID NO: 16 shows the amino acid sequence of Hel308 Tga.

SEQ ID NO: 17 shows the Hel308 motif of Hel308 Tga.

SEQ ID NO: 18 shows the extended Hel308 motif of Hel308 Tga.

SEQ ID NO: 19 shows the amino acid sequence of Hel308 Mhu.

SEQ ID NO: 20 shows the RecD-like motif I.

SEQ ID NOs: 21, 22 and 23 show the extended RecD-like motif I.

SEQ ID NO: 24 shows the RecD motif I.

SEQ ID NO: 25 shows a preferred RecD motif I, namely G-G-P-G-T-G-K-T.

SEQ ID NOs: 26, 27 and 28 show the extended RecD motif I.

SEQ ID NO: 29 shows the RecD-like motif V.

SEQ ID NO: 30 shows the RecD motif V.

SEQ ID NOs: 31-38 show the MobF motif III.

SEQ ID NOs: 39-45 shows the MobQ motif III.

SEQ ID NO: 46 shows the amino acid sequence of TraI Eco.

SEQ ID NO: 47 shows the RecD-like motif I of TraI Eco.

SEQ ID NO: 48 shows the RecD-like motif V of TraI Eco.

SEQ ID NO: 49 shows the MobF motif III of TraI Eco.

SEQ ID NO: 50 shows the XPD motif V.

SEQ ID NO: 51 shows XPD motif VI.

SEQ ID NO: 52 shows the amino acid sequence of XPD Mbu.

SEQ ID NO: 53 shows the XPD motif V of XPD Mbu.

SEQ ID NO: 54 shows XPD motif VI of XPD Mbu.

SEQ ID NO: 55 shows the amino acid sequence of a preferred HhH domain.

SEQ ID NO: 56 shows the amino acid sequence of the SSB from the bacteriophage RB69, which is encoded by the gp32 gene.

SEQ ID NO: 57 shows the amino acid sequence of the SSB from the bacteriophage T7, which is encoded by the gp2.5 gene.

SEQ ID NO: 58 shows the amino acid sequence of the UL42 processivity factor from Herpes virus 1.

SEQ ID NO: 59 shows the amino acid sequence of subunit 1 of PCNA.

SEQ ID NO: 60 shows the amino acid sequence of subunit 2 of PCNA.

SEQ ID NO: 61 shows the amino acid sequence of subunit 3 of PCNA.

SEQ ID NO: 62 shows the amino acid sequence of Phi29 DNA polymerase.

SEQ ID NO: 63 shows the amino acid sequence (from 1 to 319) of the UL42 processivity factor from the Herpes virus 1.

SEQ ID NO: 64 shows the amino acid sequence of the SSB from the bacteriophage RB69, i.e. SEQ ID NO: 56, with its C terminus deleted (gp32RB69CD).

SEQ ID NO: 65 shows the amino acid sequence (from 1 to 210) of the SSB from the bacteriophage T7 (gp2.5T7-R211Del). The full length protein is shown in SEQ ID NO: 57.

SEQ ID NO: 66 shows the amino acid sequence of the $5^{th}$ domain of Hel308 Hla.

SEQ ID NO: 67 shows the amino acid sequence of the $5^{th}$ domain of Hel308 Hvo.

SEQ ID NO: 68 shows the polynucleotide sequence of a DNA strand used in helicase dimer production.

SEQ ID NO: 69 shows the polynucleotide sequence of a DNA strand used in a helicase fluorescent assay.

SEQ ID NO: 70 shows the polynucleotide sequence of a ssDNA strand used in Examples 5, 6 and 7. At the 5' end of SEQ ID NO: 70 there are four 2'-O-methyl uracil bases attached to a 50T leader sequence to aid capture by the nanopore.

SEQ ID NO: 71 shows the polynucleotide sequence of a ssDNA strand used in Examples 5, 6 and 7.

SEQ ID NOs: 72 and 73 show polynucleotide sequences of ssDNA strands used in Example 8.

SEQ ID NO: 74 shows the polynucleotide sequence of a ssDNA strand used in Example 8.

SEQ ID NO: 75 shows the amino acid sequence of the (HhH)2 domain.

SEQ ID NO: 76 shows the amino acid sequence of the (HhH)2-(HhH)2 domain.

SEQ ID NO: 77 shows the amino acid sequence of the human mitochondrial SSB (HsmtSSB).

SEQ ID NO: 78 shows the amino acid sequence of the p5 protein from Phi29 DNA polymerase.

SEQ ID NO: 79 shows the amino acid sequence of the wild-type SSB from *E. coli*.

SEQ ID NO: 80 shows the amino acid sequence of the ssb from the bacteriophage T4, which is encoded by the gp32 gene.

SEQ ID NO: 81 shows the amino acid sequence of EcoSSB-CterAla.

SEQ ID NO: 82 shows the amino acid sequence of EcoSSB-CterNGGN.

SEQ ID NO: 83 shows the amino acid sequence of EcoSSB-Q152del.

SEQ ID NO: 84 shows the amino acid sequence of EcoSSB-G117del.

SEQ ID NO: 85 shows the GTGSGA linker.

SEQ ID NO: 86 shows the GTGSGT linker.

SEQ ID NO: 87 shows the amino acid sequence TrwC Cba.

SEQ ID NO: 88 shows part of the polynucleotide sequence used in Example 9. Attached to the 5' end of this sequence is 28 iSpC3 spacers units the last of which has an additional two T's attached to the 5' end of the spacer group. Attached to the 3' end of this sequence is four iSpC3 spacer units which are attached to the 5' end of SEQ ID NO: 104.

SEQ ID NO: 89 shows the amino acid sequence of Topoisomerase V Mka (*Methanopyrus Kandleri*).

SEQ ID NO: 90 shows the amino acid sequence of TrwC Cba-TopoV Mka, where TrwC Cba is attached by the linker AYDVGA to domains H-L of Topoisomerase V Mka.

SEQ ID NOs: 91-93 show the polynucleotide sequences used in Example 10.

SEQ ID NO: 94 shows the amino acid sequence of domains H-L of Topoisomerase V Mka (*Methanopyrus Kandleri*).

SEQ ID NOs: 95 to 103 show some of the TraI sequences shown in Table 2.

SEQ ID NO: 104 shows part of the polynucleotide sequence used in Example 9. Attached to the 5' end of this sequence is four iSpC3 spacer units, the last of which is attached to SEQ ID NO: 88. Attached to the 5' end of SEQ ID NO: 88 is 28 iSpC3 spacer units the last of which has an additional two T's attached to the 5' end of the spacer group.

SEQ ID NO: 105 shows the amino acid sequence of Mutant S (*Escherichia coli*).

SEQ ID NO: 106 shows the amino acid sequence of Sso7d (*Sufolobus solfataricus*).

SEQ ID NO: 107 shows the amino acid sequence of Sso10b1 (*Sulfolobus solfataricus* P2).

SEQ ID NO: 108 shows the amino acid sequence of Sso10b2 (*Sulfolobus solfataricus* P2).

SEQ ID NO: 109 shows the amino acid sequence of Tryptophan repressor (*Escherichia coli*).

SEQ ID NO: 110 shows the amino acid sequence of Lambda repressor (*Enterobacteria phage lambda*).

SEQ ID NO: 111 shows the amino acid sequence of Cren7 (*Histone crenarchaea* Cren7 Sso).

SEQ ID NO: 112 shows the amino acid sequence of human histone (*Homo sapiens*).

SEQ ID NO: 113 shows the amino acid sequence of dsbA (*Enterobacteria phage* T4).

SEQ ID NO: 114 shows the amino acid sequence of Rad51 (*Homo sapiens*).

SEQ ID NO: 115 shows the amino acid sequence of PCNA sliding clamp (*Citromicrobium bathyomarinum* JL354).

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a construct" includes "constructs", reference to "a helicase" includes two or more such helicases, reference to "a transmembrane protein pore" includes two or more such pores, and the like.

All publications, patents and patent applications cited herein, whether supra or infra, are hereby incorporated by reference in their entirety.

Constructs for Use in the Invention

The present invention provides methods using a construct that is helpful for controlling the movement of a polynucleotide. The construct comprises a helicase and an additional polynucleotide binding moiety. The helicase is attached to the polynucleotide binding moiety. The construct has the ability to control the movement of a polynucleotide. The construct is artificial or non-natural.

As discussed in more detail below, the construct may comprise two or more helicases (i.e. the additional polynucleotide binding moiety is one or more additional helicases). In such embodiments, each helicase in the construct is capable of functioning on its own as a helicase. The construct itself is not a multimeric or oligomeric helicase, such as dimeric helicase. In other words, the construct itself is not a helicase that naturally exists as a multimer or an oligomer, such as a dimer. The construct may comprise a multimeric, such as dimeric, helicase, but it must be attached to an additional polynucleotide binding moiety, such as another helicase. The helicase is preferably monomeric. The helicase is preferably not a helicase domain from a helicase enzyme. This is discussed in more detail below.

The constructs described herein are useful tools for controlling the movement of a polynucleotide during Strand Sequencing. A problem which occurs in sequencing polynucleotides, particularly those of 500 nucleotides or more, is that the molecular motor which is controlling translocation of the polynucleotide may disengage from the polynucleotide. This allows the polynucleotide to be pulled through the pore rapidly and in an uncontrolled manner in the direction of the applied field. The constructs described herein are less likely to disengage from the polynucleotide being sequenced. The construct can provide increased read lengths of the polynucleotide as it controls the translocation of the polynucleotide through a nanopore. The ability to translocate an entire polynucleotide through a nanopore under the control of a construct described herein allows characteristics of the polynucleotide, such as its sequence, to be estimated with improved accuracy and speed over known methods. This becomes more important as strand lengths increase and molecular motors are required with improved processivity. The constructs described herein are particularly effective in controlling the translocation of target polynucleotides of 500 nucleotides or more, for example 1000 nucleotides, 5000, 10000, 20000, 50000, 100000 or more.

A targeted construct that binds to a specific polynucleotide sequence can also be designed. As discussed in more detail below, the polynucleotide binding moiety may bind to a specific polynucleotide sequence and thereby target the helicase portion of the construct to the specific sequence.

The constructs described herein are also useful tools for isothermal polymerase chain reaction (PCR). In such methods, the strands of double stranded DNA are typically first separated by a construct described herein and coated by single stranded DNA (ssDNA)-binding proteins. In the second step, two sequence specific primers typically hybridise to each border of the DNA template. DNA polymerases may then be used to extend the primers annealed to the templates to produce a double stranded DNA and the two newly synthesized DNA products may then be used as substrates by the constructs described herein entering the next round of the reaction. Thus, a simultaneous chain reaction develops, resulting in exponential amplification of the selected target sequence.

The construct has the ability to control the movement of a polynucleotide. The ability of a construct to control the movement of a polynucleotide can be assayed using any method known in the art. For instance, the construct may be contacted with a polynucleotide and the position of the polynucleotide may be determined using standard methods. The ability of a construct to control the movement of a polynucleotide is typically assayed as described in the Examples.

The construct may be isolated, substantially isolated, purified or substantially purified. A construct is isolated or purified if it is completely free of any other components, such as lipids, polynucleotides or pore monomers. A construct is substantially isolated if it is mixed with carriers or diluents which will not interfere with its intended use. For instance, a construct is substantially isolated or substantially purified if it is present in a form that comprises less than 10%, less than 5%, less than 2% or less than 1% of other components, such as lipids, polynucleotides or pore monomers.

Attachment

The helicase is attached to the additional polynucleotide binding moiety. The helicase is preferably covalently attached to the additional polynucleotide binding moiety. The helicase may be attached to the moiety at more than one, such as two or three, points.

The helicase can be covalently attached to the moiety using any method known in the art. The helicase and moiety may be produced separately and then attached together. The two components may be attached in any configuration. For instance, they may be attached via their terminal (i.e. amino or carboxy terminal) amino acids. Suitable configurations include, but are not limited to, the amino terminus of the moiety being attached to the carboxy terminus of the helicase and vice versa. Alternatively, the two components may be attached via amino acids within their sequences. For instance, the moiety may be attached to one or more amino acids in a loop region of the helicase. In a preferred embodiment, terminal amino acids of the moiety are attached to one or more amino acids in the loop region of a helicase. Terminal amino acids and loop regions can be identified using methods known in the art (Edman P., Acta Chemica Scandinavia, (1950), 283-293). For instance, loop regions can be identified using protein modeling. This exploits the fact that protein structures are more conserved than protein sequences amongst homologues. Hence, producing atomic resolution models of proteins is dependent upon the identification of one or more protein structures that are likely to resemble the structure of the query sequence. In order to assess whether a suitable protein structure exists to use as a "template" to build a protein model, a search is performed on the protein data bank (PDB) database. A protein structure is considered a suitable template if it shares a reasonable level of sequence identity with the query sequence. If such a template exists, then the template sequence is "aligned" with the query sequence, i.e. residues in the query sequence are mapped onto the template residues. The sequence alignment and template structure are then used to produce a structural model of the query sequence. Hence, the quality of a protein model is dependent upon the quality of the sequence alignment and the template structure.

The two components may be attached via their naturally occurring amino acids, such as cysteines, threonines, serines, aspartates, asparagines, glutamates and glutamines. Naturally occurring amino acids may be modified to facilitate attachment. For instance, the naturally occurring amino acids may be modified by acylation, phosphorylation, glycosylation or farnesylation. Other suitable modifications are known in the art. Modifications to naturally occurring amino acids may be post-translation modifications. The two components may be attached via amino acids that have been introduced into their sequences. Such amino acids are preferably introduced by substitution. The introduced amino acid may be cysteine or a non-natural amino acid that facilitates attachment. Suitable non-natural amino acids include, but are not limited to, 4-azido-L-phenylalanine (Faz), and any one of the amino acids numbered 1-71 included in FIG. 1 of Liu C. C. and Schultz P. G., Annu. Rev. Biochem., 2010, 79, 413-444. The introduced amino acids may be modified as discussed above.

In a preferred embodiment, the helicase is chemically attached to the moiety, for instance via a linker molecule. Linker molecules are discussed in more detail below. One suitable method of chemical attachment is cysteine linkage. This is discussed in more detail below.

The helicase may be transiently attached to the moiety by a hexa-his tag or Ni-NTA. The helicase and moiety may also be modified such that they transiently attach to each other.

In another preferred embodiment, the helicase is genetically fused to the moiety. A helicase is genetically fused to a moiety if the whole construct is expressed from a single polynucleotide sequence. The coding sequences of the helicase and moiety may be combined in any way to form a single polynucleotide sequence encoding the construct. Genetic fusion of a pore to a nucleic acid binding protein is discussed in International Application No. PCT/GB09/001679 (published as WO 2010/004265).

The helicase and moiety may be genetically fused in any configuration. The helicase and moiety may be fused via their terminal amino acids. For instance, the amino terminus of the moiety may be fused to the carboxy terminus of the helicase and vice versa. The amino acid sequence of the moiety is preferably added in frame into the amino acid sequence of the helicase. In other words, the moiety is preferably inserted within the sequence of the helicase. In such embodiments, the helicase and moiety are typically attached at two points, i.e. via the amino and carboxy terminal amino acids of the moiety. If the moiety is inserted within the sequence of the helicase, it is preferred that the amino and carboxy terminal amino acids of the moiety are in close proximity and are each attached to adjacent amino acids in the sequence of the helicase or variant thereof. In a preferred embodiment, the moiety is inserted into a loop region of the helicase.

The construct retains the ability of the helicase to control the movement of a polynucleotide. This ability of the helicase is typically provided by its three dimensional structure that is typically provided by its β-strands and α-helices. The α-helices and β-strands are typically connected by loop regions. In order to avoid affecting the ability of the helicase to control the movement of a polynucleotide, the moiety is preferably genetically fused to either end of the helicase or inserted into a surface-exposed loop region of the helicase. The loop regions of specific helicases can be identified using methods known in the art. For instance, the loop regions can be identified using protein modelling, x-ray diffraction measurement of the protein in a crystalline state (Rupp B (2009). Biomolecular Crystallography: Principles, Practice and Application to Structural Biology. New York: Garland Science), nuclear magnetic resonance (NMR) spectroscopy of the protein in solution (Mark Rance; Cavanagh, John; Wayne J. Fairbrother; Arthur W. Hunt III; Skelton, Nicholas J. (2007). Protein NMR spectroscopy: principles and practice (2nd ed.). Boston: Academic Press) or cryo-electron microscopy of the protein in a frozen-hydrated state (van Heel M, Gowen B, Matadeen R, Orlova E V, Finn R, Pape T, Cohen D, Stark H, Schmidt R, Schatz M, Patwardhan A (2000). "Single-particle electron cryo-microscopy: towards atomic resolution.". Q Rev Biophys. 33: 307-69. Structural information of proteins determined by above mentioned methods are publicly available from the protein bank (PDB) database.

For Hel308 helicases (SEQ ID NOs: 10, 13, 16 and 19), β-strands can only be found in the two RecA-like engine domains (domains 1 and 2). These domains are responsible for coupling the hydrolysis of the fuel nucleotide (normally ATP) with movement. The important domains for ratcheting along a polynucleotide are domains 3 and 4, but above all domain 4. Interestingly, both of domains 3 and 4 comprise only α-helices. There is an important α-helix in domain 4 called the ratchet helix. As a result, in the Hel308 embodiments of the invention, the moiety is preferably not genetically fused to any of the α-helixes.

In another embodiment, the helicase is attached to the moiety using intein-Tag sequences. Two proteins can be joined by genetically encoding compatible split intein-Tag sequences at the end of each protein. The inteins do not require catalysts or enzymes but self release while joining the two proteins. The join is traceless, leaving a single peptide chain. This method is generally for joining termini of proteins.

The helicase may be attached directly to the moiety. The helicase is preferably attached to the moiety using one or more, such as two or three, linkers. The one or more linkers may be designed to constrain the mobility of the moiety. The linkers may be attached to one or more reactive cysteine residues, reactive lysine residues or non-natural amino acids in the helicase and/or moiety. The non-natural amino acid may be any of those discussed above. The non-natural amino acid is preferably 4-azido-L-phenylalanine (Faz). Suitable linkers are well-known in the art.

The helicase is preferably attached to the moiety using one or more chemical crosslinkers or one or more peptide linkers. Suitable chemical crosslinkers are well-known in the art. Suitable chemical crosslinkers include, but are not limited to, those including the following functional groups: maleimide, active esters, succinimide, azide, alkyne (such as dibenzocyclooctynol (DIBO or DBCO), difluoro cycloalkynes and linear alkynes), phosphine (such as those used in traceless and non-traceless Staudinger ligations), haloacetyl (such as iodoacetamide), phosgene type reagents, sulphonyl chloride reagents, isothiocyanates, acyl halides, hydrazines, disulphides, vinyl sulfones, aziridines and photoreactive reagents (such as aryl azides, diaziridines). The crosslinker is preferably not bis(sulfosuccinimidyl) suberate (BS$^3$). The helicase and the moiety are preferably not crosslinked using formaldehyde.

Reactions between amino acids and functional groups may be spontaneous, such as cysteine/maleimide, or may require external reagents, such as Cu(I) for linking azide and linear alkynes.

Linkers can comprise any molecule that stretches across the distance required. Linkers can vary in length from one carbon (phosgene-type linkers) to many Angstroms. Examples of linear molecules, include but are not limited to, are polyethyleneglycols (PEGs), polypeptides, polysaccharides, deoxyribonucleic acid (DNA), peptide nucleic acid (PNA), threose nucleic acid (TNA), glycerol nucleic acid (GNA), saturated and unsaturated hydrocarbons, polyamides. These linkers may be inert or reactive, in particular they may be chemically cleavable at a defined position, or may be themselves modified with a fluorophore or ligand. The linker is preferably resistant to dithiothreitol (DTT).

Cleavable linkers can be used as an aid to separation of constructs from non-attached components and can be used to further control the synthesis reaction. For example, a heterobifunctional linker may react with the helicase, but not the moiety. If the free end of the linker can be used to bind the helicase protein to a surface, the unreacted helicases from the first reaction can be removed from the mixture. Subsequently, the linker can be cleaved to expose a group that reacts with the moiety. In addition, by following this sequence of linkage reactions, conditions may be optimised first for the reaction to the helicase, then for the reaction to the moiety after cleavage of the linker. The second reaction would also be much more directed towards the correct site of reaction with the moiety because the linker would be confined to the region to which it is already attached.

Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate, 2,5-dioxopyrrolidin-1-yl 8-(pyridin-2-yldisulfanyl)octananoate, di-maleimide PEG 1k, di-maleimide PEG 3.4k, di-maleimide PEG 5k, di-maleimide PEG 10k, bis(maleimido)ethane (BMOE), bis-maleimidohexane (BMH), 1,4-bis-maleimidobutane (BMB), 1,4 bis-maleimidyl-2,3-dihydroxybutane (BMDB), BM[PEO]2 (1,8-bis-maleimidodiethyleneglycol), BM[PEO]3 (1,11-bis-maleimidotriethylene glycol), tris[2-maleimidoethyl]amine (TMEA), DTME dithiobismaleimidoethane, bis-maleimide PEG3, bis-maleimide PEG11, DBCO-maleimide, DBCO-PEG4-maleimide, DBCO-PEG4-NH2, DBCO-PEG4-NHS, DBCO-NHS, DBCO-PEG-DBCO 2.8 kDa, DBCO-PEG-DBCO 4.0 kDa, DBCO-15 atoms-DBCO, DBCO-26 atoms-DBCO, DBCO-35 atoms-DBCO, DBCO-PEG4-S-S-PEG3-biotin, DBCO-S-S-PEG3-biotin and DBCO-S-S-PEG11-biotin. The most preferred crosslinkers are succinimidyl 3-(2-pyridyldithio)propionate (SPDP) and maleimide-PEG(2 kDa)-maleimide (alpha, omega-bis-maleimido poly(ethylene glycol)).

The helicase may be covalently attached to the bifunctional crosslinker before the helicase/crosslinker complex is covalently attached to the moiety. Alternatively, the moiety may be covalently attached to the bifunctional crosslinker before the bifunctional crosslinker/moiety complex is attached to the helicase. The helicase and moiety may be covalently attached to the chemical crosslinker at the same time.

The helicase may be attached to the moiety using two different linkers that are specific for each other. One of the linkers is attached to the helicase and the other is attached to the moiety. Once mixed together, the linkers should react to form a construct described herein. The helicase may be attached to the moiety using the hybridization linkers described in International Application No. PCT/GB10/000132 (published as WO 2010/086602). In particular, the helicase may be attached to the moiety using two or more linkers each comprising a hybridizable region and a group capable of forming a covalent bond. The hybridizable regions in the linkers hybridize and link the moieties. The linked moieties are then coupled via the formation of covalent bonds between the groups. Any of the specific linkers disclosed in International Application No. PCT/GB10/000132 (published as WO 2010/086602) may be used in accordance with the invention.

The helicase and the moiety may be modified and then attached using a chemical crosslinker that is specific for the two modifications. Any of the crosslinkers discussed above may be used.

Alternatively, the linkers preferably comprise amino acid sequences. Such linkers are peptide linkers. The length, flexibility and hydrophilicity of the peptide linker are typically designed such that it does not to disturb the functions of the helicase and moiety. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$, $(SG)_8$, $(SG)_{10}$, $(SG)_{15}$ or $(SG)_{20}$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

The linkers may be labeled. Suitable labels include, but are not limited to, fluorescent molecules (such as Cy3 or AlexaFluor®555), radioisotopes, e.g. $^{125}I$, $^{35}S$, enzymes, antibodies, antigens, polynucleotides and ligands such as biotin. Such labels allow the amount of linker to be quantified. The label could also be a cleavable purification tag, such as biotin, or a specific sequence to show up in an identification method, such as a peptide that is not present in the protein itself, but that is released by trypsin digestion.

A preferred method of attaching the helicase to the moiety is via cysteine linkage. This can be mediated by a bi-functional chemical linker or by a polypeptide linker with a terminal presented cysteine residue. Linkage can occur via natural cysteines in the helicase and/or moiety. Alternatively, cysteines can be introduced into the helicase and/or moiety. If the helicase is attached to the moiety via cysteine linkage, the one or more cysteines have preferably been introduced to the helicase and/or moiety by substitution.

The length, reactivity, specificity, rigidity and solubility of any bi-functional linker may be designed to ensure that the moiety is positioned correctly in relation to the helicase and the function of both the helicase and moiety is retained. Suitable linkers include bismaleimide crosslinkers, such as 1,4-bis(maleimido)butane (BMB) or bis(maleimido)hexane. One drawback of bi-functional linkers is the requirement of the helicase and moiety to contain no further surface accessible cysteine residues if attachment at specific sites is preferred, as binding of the bi-functional linker to surface accessible cysteine residues may be difficult to control and may affect substrate binding or activity. If the helicase and/or moiety does contain several accessible cysteine residues, modification of the helicase and/or moiety may be required to remove them while ensuring the modifications do not affect the folding or activity of the helicase and moiety. This is discussed in International Application No. PCT/GB10/000133 (published as WO 2010/086603). In a preferred embodiment, a reactive cysteine is presented on a peptide linker that is genetically attached to the moiety. This means that additional modifications will not necessarily be needed to remove other accessible cysteine residues from the moiety. The reactivity of cysteine residues may be enhanced by modification of the adjacent residues, for example on a peptide linker. For instance, the basic groups of flanking arginine, histidine or lysine residues will change the pKa of the cysteines thiol group to that of the more reactive $S^-$ group. The reactivity of cysteine residues may be protected by thiol protective groups such as 5,5'-dithiobis-(2-nitrobenzoic acid) (dTNB). These may be reacted with one or more cysteine residues of the moiety or helicase, either as a monomer or part of an oligomer, before a linker is attached. Selective deprotection of surface accessible cysteines may be possible using reducing reagents immobilized on beads (for example immobilized tris(2-carboxyethyl)phosphine, TCEP). Cysteine linkage of two or more helicases is discussed in more detail below.

Another preferred method of attaching the helicase to the moiety is via 4-azido-L-phenylalanine (Faz) linkage. This can be mediated by a bi-functional chemical linker or by a polypeptide linker with a terminal presented Faz residue. The one or more Faz residues have preferably been introduced to the helicase and/or moiety by substitution. Faz linkage of two or more helicases is discussed in more detail below.

Cross-linkage of helicases or moieties to themselves may be prevented by keeping the concentration of linker in a vast excess of the helicase and/or moiety. Alternatively, a "lock and key" arrangement may be used in which two linkers are used. Only one end of each linker may react together to form a longer linker and the other ends of the linker each react with a different part of the construct (i.e. helicase or moiety). This is discussed in more detail below.

The site of attachment is selected such that, when the construct is contacted with a polynucleotide, both the helicase and the moiety can bind to the polynucleotide and control its movement.

Attachment can be facilitated using the polynucleotide binding activities of the helicase and the moiety. For instance, complementary polynucleotides can be used to bring the helicase and moiety together as they hybridize. The helicase can be bound to one polynucleotide and the moiety can be bound to the complementary polynucleotide. The two polynucleotides can then be allowed to hybridise to each other. This will bring the helicase into close contact with the moiety, making the linking reaction more efficient. This is especially helpful for attaching two or more helicases in the correct orientation for controlling movement of a target polynucleotide. An example of complementary polynucleotides that may be used are shown below.

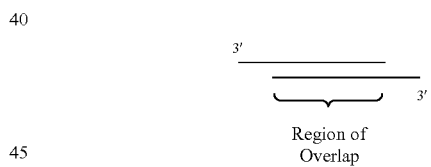

Region of Overlap

For helicase-Phi29 constructs the DNA below could be used.

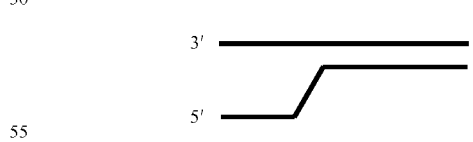

Tags can be added to the construct to make purification of the construct easier. These tags can then be chemically or enzymatically cleaved off, if their removal is necessary. Fluorophores or chromophores can also be included, and these could also be cleavable.

A simple way to purify the construct is to include a different purification tag on each protein (i.e. the helicase and the moiety), such as a hexa-His-tag and a Strep-tag®. If the two proteins are different from one another, this method is particularly useful. The use of two tags enables only the species with both tags to be purified easily.

If the two proteins do not have two different tags, other methods may be used. For instance, proteins with free surface cysteines or proteins with linkers attached that have not reacted to form a construct could be removed, for instance using an iodoacetamide resin for maleimide linkers.

Constructs can also be purified from unreacted proteins on the basis of a different DNA processivity property. In particular, a construct can be purified from unreacted proteins on the basis of an increased affinity for a polynucleotide, a reduced likelihood of disengaging from a polynucleotide once bound and/or an increased read length of a polynucleotide as it controls the translocation of the polynucleotide through a nanopore Helicase Any helicase may be used in the constructs described herein. Helicases are often known as translocases and the two terms may be used interchangeably. Suitable helicases are well-known in the art (M. E. Fairman-Williams et al., Curr. Opin. Struct Biol., 2010, 20 (3), 313-324, T. M. Lohman et al., Nature Reviews Molecular Cell Biology, 2008, 9, 391-401). The helicase is typically a member of one of superfamilies 1 to 6. The helicase is preferably a member of any of the Moiety Classification (EC) groups 3.6.1.- and 2.7.7.-. The helicase is preferably an ATP-dependent DNA helicase (EC group 3.6.4.12), an ATP-dependent RNA helicase (EC group 3.6.4.13) or an ATP-independent RNA helicase.

The helicase may be a multimeric or oligomeric helicase. In other words, the helicase may need to form a multimer or an oligomer, such as a dimer, to function. However, as discussed above, the construct itself cannot be a multimeric or oligomeric helicase. The multimeric or oligomeric helicase must be attached to an additional polynucleotide binding moiety. The helicase is preferably monomeric. In other words, the helicase preferably does not need to form a multimer or an oligomer, such as a dimer, to function. Hel308, RecD, TraI and XPD helicases are all monomeric helicases. These are discussed in more detail below. The helicase is preferably not the hepatitis C virus NS3 helicase (also known as NS3h). NS3 helicase acts as an oligomer and so is not monomeric.

Monomeric helicases may comprise several domains attached together. For instance, TraI helicases and TraI subgroup helicases may contain two RecD helicase domains, a relaxase domain and a C-terminal domain. The domains typically form a monomeric helicase that is capable of functioning without forming oligomers.

The helicase is typically an entire helicase, such as an entire Hel308, RecD, TraI or XPD helicase. The helicase is preferably not a helicase domain from a helicase enzyme. For instance, the helicase is preferably not a RecD domain or the helicase domain from the Brome mosaic virus (BMV) viral replication protein 1a. The construct cannot itself be a helicase comprising two or more helicase domains attached together, such as a TraI helicase comprising two RecD domains attached together. The construct may comprise a helicase comprising two or more helicase domains, such as TraI helicase, but it must be attached to an additional polynucleotide binding moiety. The helicase is preferably capable of binding to the target polynucleotide at an internal nucleotide. An internal nucleotide is a nucleotide which is not a terminal nucleotide in the target polynucleotide. For example, it is not a 3' terminal nucleotide or a 5' terminal nucleotide. All nucleotides in a circular polynucleotide are internal nucleotides.

Generally, a helicase which is capable of binding at an internal nucleotide is also capable of binding at a terminal nucleotide, but the tendency for some helicases to bind at an internal nucleotide will be greater than others. For a helicase suitable for use in the invention, typically at least 10% of its binding to a polynucleotide will be at an internal nucleotide. Typically, at least 20%, at least 30%, at least 40% or at least 50% of its binding will be at an internal nucleotide. Binding at a terminal nucleotide may involve binding to both a terminal nucleotide and adjacent internal nucleotides at the same time. For the purposes of the invention, this is not binding to the target polynucleotide at an internal nucleotide. In other words, the helicase used in the invention is not only capable of binding to a terminal nucleotide in combination with one or more adjacent internal nucleotides. The helicase must be capable of binding to an internal nucleotide without concurrent binding to a terminal nucleotide.

A helicase which is capable of binding at an internal nucleotide may bind to more than one internal nucleotide. Typically, the helicase binds to at least 2 internal nucleotides, for example at least 3, at least 4, at least 5, at least 10 or at least 15 internal nucleotides. Typically the helicase binds to at least 2 adjacent internal nucleotides, for example at least 3, at least 4, at least 5, at least 10 or at least 15 adjacent internal nucleotides. The at least 2 internal nucleotides may be adjacent or non-adjacent.

The ability of a helicase to bind to a polynucleotide at an internal nucleotide may be determined by carrying out a comparative assay. The ability of a motor to bind to a control polynucleotide A is compared to the ability to bind to the same polynucleotide but with a blocking group attached at the terminal nucleotide (polynucleotide B). The blocking group prevents any binding at the terminal nucleotide of strand B, and thus allows only internal binding of a helicase.

Examples of helicases which are capable of binding at an internal nucleotide include, but are not limited to, Hel308 Tga, Hel308 Mhu and Hel308 Csy. Hence, the molecular motor preferably comprises (a) the sequence of Hel308 Tga (i.e. SEQ ID NO: 16) or a variant thereof or (b) the sequence of Hel308 Csy (i.e. SEQ ID NO: 13) or a variant thereof or (c) the sequence of Hel308 Mhu (i.e. SEQ ID NO: 19) or a variant thereof. Variants of these sequences are discussed in more detail below. Variants preferably comprise one or more substituted cysteine residues and/or one or more substituted Faz residues to facilitate attachment as discussed above.

The helicase is preferably a Hel308 helicase. Hel308 helicases are monomeric because they function without forming oligomers. Any Hel308 helicase may be used in accordance with the invention. Hel308 helicases are also known as ski2-like helicases and the two terms can be used interchangeably. Suitable Hel308 helicases are disclosed in Table 4 of U.S. Patent Application Nos. 61/549,998 and 61/599,244 and International Application No. PCT/GB2012/052579 (published as WO 2013/057495).

The Hel308 helicase typically comprises the amino acid motif Q-X1-X2-G-R-A-G-R (hereinafter called the Hel308 motif; SEQ ID NO: 8). The Hel308 motif is typically part of the helicase motif VI (Tuteja and Tuteja, Eur. J. Biochem. 271, 1849-1863 (2004)). X1 may be C, M or L. X1 is preferably C. X2 may be any amino acid residue. X2 is typically a hydrophobic or neutral residue. X2 may be A, F, M, C, V, L, I, S, T, P or R. X2 is preferably A, F, M, C, V, L, I, S, T or P. X2 is more preferably A, M or L. X2 is most preferably A or M.

The Hel308 helicase preferably comprises the motif Q-X1-X2-G-R-A-G-R-P (hereinafter called the extended Hel308 motif; SEQ ID NO: 9) wherein X1 and X2 are as described above.

The most preferred Hel308 motifs and extended Hel308 motifs are shown in the Table 1 below.

TABLE 1

Preferred Hel308 helicases and their motifs

| SEQ ID NO: | Helicase | Names | % Identity to Hel308 Mbu | Hel308 motif | Extended Hel308 motif |
|---|---|---|---|---|---|
| 10 | Hel308 Mbu | Methanococcoides burtonii | — | QMAGRAGR (SEQ ID NO: 11) | QMAGRAGRP (SEQ ID NO: 12) |
| 13 | Hel308 Csy | Cenarchaeum symbiosum | 34% | QLCGRAGR (SEQ ID NO: 14) | QLCGRAGRP (SEQ ID NO: 15) |
| 16 | Hel308 Tga | Thermococcus gammatolerans EJ3 | 38% | QMMGRAGR (SEQ ID NO: 17) | QMMGRAGRP (SEQ ID NO: 18) |
| 19 | Hel308 Mhu | Methanospirillum hungatei JF-1 | 40% | QMAGRAGR (SEQ ID NO: 11) | QMAGRAGRP (SEQ ID NO: 12) |

The most preferred Hel308 motif is shown in SEQ ID NO: 17. The most preferred extended Hel308 motif is shown in SEQ ID NO: 18. Other preferred Hel308 motifs and extended Hel308 motifs are found in Table 5 of U.S. Patent Application Nos. 61/549,998 and 61/599,244 and International Application No. PCT/GB2012/052579 (published as WO 2013/057495).

The Hel308 helicase preferably comprises the sequence of Hel308 Mbu (i.e. SEQ ID NO: 10) or a variant thereof. The Hel308 helicase more preferably comprises (a) the sequence of Hel308 Tga (i.e. SEQ ID NO: 16) or a variant thereof, (b) the sequence of Hel308 Csy (i.e. SEQ ID NO: 13) or a variant thereof or (c) the sequence of Hel308 Mhu (i.e. SEQ ID NO: 19) or a variant thereof. The Hel308 helicase most preferably comprises the sequence shown in SEQ ID NO: 16 or a variant thereof.

A variant of a Hel308 helicase is an enzyme that has an amino acid sequence which varies from that of the wild-type helicase and which retains polynucleotide binding activity. In particular, a variant of SEQ ID NO: 10, 13, 16 or 19 is an enzyme that has an amino acid sequence which varies from that of SEQ ID NO: 10, 13, 16 or 19 and which retains polynucleotide binding activity. Polynucleotide binding activity can be determined using methods known in the art. Suitable methods include, but are not limited to, fluorescence anisotropy, tryptophan fluorescence and electrophoretic mobility shift assay (EMSA). For instance, the ability of a variant to bind a single stranded polynucleotide can be determined as described in the Examples.

The variant retains helicase activity. This can be measured in various ways. For instance, the ability of the variant to translocate along a polynucleotide can be measured using electrophysiology, a fluorescence assay or ATP hydrolysis.

The variant may include modifications that facilitate handling of the polynucleotide encoding the helicase and/or facilitate its activity at high salt concentrations and/or room temperature. Variants typically differ from the wild-type helicase in regions outside of the Hel308 motif or extended Hel308 motif discussed above. However, variants may include modifications within these motif(s).

Over the entire length of the amino acid sequence of SEQ ID NO: 10, 13, 16 or 19, a variant will preferably be at least 30% homologous to that sequence based on amino acid identity. More preferably, the variant polypeptide may be at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 10, 13, 16 or 19 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed below with reference to SEQ ID NOs: 2 and 4.

A variant of SEQ ID NO: 10, 13, 16 or 19 preferably comprises the Hel308 motif or extended Hel308 motif of the wild-type sequence as shown in Table 1 above. However, a variant may comprise the Hel308 motif or extended Hel308 motif from a different wild-type sequence. For instance, a variant of SEQ ID NO: 12 may comprise the Hel308 motif or extended Hel308 motif from SEQ ID NO: 13 (i.e. SEQ ID NO: 14 or 15). Variants of SEQ ID NO: 10, 13, 16 or 19 may also include modifications within the Hel308 motif or extended Hel308 motif of the relevant wild-type sequence. Suitable modifications at X1 and X2 are discussed above when defining the two motifs. A variant of SEQ ID NO: 10, 13, 16 or 19 preferably comprises one or more substituted cysteine residues and/or one or more substituted Faz residues to facilitate attachment as discussed above.

A variant of SEQ ID NO: 10 may lack the first 19 amino acids of SEQ ID NO: 10 and/or lack the last 33 amino acids of SEQ ID NO: 10. A variant of SEQ ID NO: 10 preferably comprises a sequence which is at least 70%, at least 75%, at least 80%, at least 85%, at least 90% or more preferably at least 95%, at least 97% or at least 99% homologous based on amino acid identity with amino acids 20 to 211 or 20 to 727 of SEQ ID NO: 10.

SEQ ID NO: 10 (Hel308 Mbu) contains five natural cysteine residues. However, all of these residues are located within or around the DNA binding grove of the enzyme. Once a DNA strand is bound within the enzyme, these natural cysteine residues become less accessible for external modifications. This allows specific cysteine mutants of SEQ ID NO: 10 to be designed and attached to the moiety using cysteine linkage as discussed above. Preferred variants of SEQ ID NO: 10 have one or more of the following substitutions: A29C, Q221C, Q442C, T569C, A577C, A700C and S708C. The introduction of a cysteine residue at one or more of these positions facilitates cysteine linkage as discussed above. Other preferred variants of SEQ ID NO: 10 have one or more of the following substitutions: M2Faz, R10Faz, F15Faz, A29Faz, R185Faz, A268Faz, E284Faz, Y387Faz, F400Faz, Y455Faz, E464Faz, E573Faz, A577Faz, E649Faz, A700Faz, Y720Faz, Q442Faz and S708Faz. The introduction of a Faz residue at one or more of these positions facilitates Faz linkage as discussed above.

The helicase is preferably a RecD helicase. RecD helicases are monomeric because they function without forming oligomers. Any RecD helicase may be used in accordance with the invention. The structures of RecD helicases are known in the art (FEBS J. 2008 April; 275(8):1835-51. Epub 2008 Mar. 9. ATPase activity of RecD is essential for growth of the Antarctic *Pseudomonas syringae* Lz4W at low temperature. Satapathy A K, Pavankumar T L, Bhattacharjya S, Sankaranarayanan R, Ray M K; EMS Microbiol Rev. 2009 May; 33(3):657-87. The diversity of conjugative relaxases and its application in plasmid classification. Garcillán-Barcia M P, Francia M V, de la Cruz F; J Biol Chem. 2011 Apr. 8;286(14):12670-82. Epub 2011 Feb. 2. Functional characterization of the multidomain F plasmid TraI relaxase-helicase. Cheng Y, McNamara D E, Miley M J, Nash R P, Redinbo M R).

The RecD helicase typically comprises the amino acid motif X1-X2-X3-G-X4-X5-X6-X7 (hereinafter called the RecD-like motif I; SEQ ID NO: 20), wherein X1 is G, S or A, X2 is any amino acid, X3 is P, A, S or G, X4 is T, A, V, S or C, X5 is G or A, X6 is K or R and X7 is T or S. X1 is preferably G. X2 is preferably G, I, Y or A. X2 is more preferably G. X3 is preferably P or A. X4 is preferably T, A, V or C. X4 is preferably T, V or C. X5 is preferably G. X6 is preferably K. X7 is preferably T or S. The RecD helicase preferably comprises Q-(X8)$_{16-18}$-X1-X2-X3-G-X4-X5-X6-X7 (hereinafter called the extended RecD-like motif I; SEQ ID NOs: 21, 22 and 23), wherein X1 to X7 are as defined above and X8 is any amino acid. There are preferably 16 X8 residues (i.e. (X8)$_{16}$) in the extended RecD-like motif I. Suitable sequences for (X8)$_{16}$ can be identified in SEQ ID NOs: 14, 17, 20, 23, 26, 29, 32, 35, 38, 41, 44, 47 and 50 of U.S. Patent Application No. 61/581,332 and SEQ ID NOs: 18, 21, 24, 25, 28, 30, 32, 35, 37, 39, 41, 42 and 44 of International Application No. PCT/GB2012/053274 (published as WO 2012/098562).

The RecD helicase preferably comprises the amino acid motif G-G-P-G-Xa-G-K-Xb (hereinafter called the RecD motif I; SEQ ID NO: 24) wherein Xa is T, V or C and Xb is T or S. Xa is preferably T. Xb is preferably T. The Rec-D helicase preferably comprises the sequence G-G-P-G-T-G-K-T (SEQ ID NO: 25). The RecD helicase more preferably comprises the amino acid motif Q-(X8)$_{16-18}$-G-G-P-G-Xa-G-K-Xb (hereinafter called the extended RecD motif I; SEQ ID NOs: 26, 27 and 28), wherein Xa and Xb are as defined above and X8 is any amino acid. There are preferably 16 X8 residues (i.e. (X8)$_{16}$) in the extended RecD motif I. Suitable sequences for (X8)$_{16}$ can be identified in SEQ ID NOs: 14, 17, 20, 23, 26, 29, 32, 35, 38, 41, 44, 47 and 50 of U.S. Patent Application No. 61/581,332 and SEQ ID NOs: 18, 21, 24, 25, 28, 30, 32, 35, 37, 39, 41, 42 and 44 of International Application No. PCT/GB2012/053274 (published as WO 2012/098562).

The RecD helicase typically comprises the amino acid motif X1-X2-X3-X4-X5-(X6)$_3$-Q-X7 (hereinafter called the RecD-like motif V; SEQ ID NO: 29), wherein X1 is Y, W or F, X2 is A, T, S, M, C or V, X3 is any amino acid, X4 is T, N or S, X5 is A, T, G, S, V or I, X6 is any amino acid and X7 is G or S. X1 is preferably Y. X2 is preferably A, M, C or V. X2 is more preferably A. X3 is preferably I, M or L. X3 is more preferably I or L. X4 is preferably T or S. X4 is more preferably T. X5 is preferably A, V or I. X5 is more preferably V or I. X5 is most preferably V. (X6)$_3$ is preferably H-K-S, H-M-A, H-G-A or H-R-S. (X6)$_3$ is more preferably H-K-S. X7 is preferably G. The RecD helicase preferably comprises the amino acid motif Xa-Xb-Xc-Xd-Xe-H-K-S-Q-G (hereinafter called the RecD motif V; SEQ ID NO: 30), wherein Xa is Y, W or F, Xb is A, M, C or V, Xc is I, M or L, Xd is T or S and Xe is V or I. Xa is preferably Y. Xb is preferably A. Xd is preferably T. Xd is preferably V. Preferred RecD motifs I are shown in Table 5 of U.S. Patent Application No. 61/581,332 and International Application No. PCT/GB2012/053274 (published as WO 2012/098562). Preferred RecD-like motifs I are shown in Table 7 of U.S. Patent Application No. 61/581,332 and International Application No. PCT/GB2012/053274 (published as WO 2012/098562). Preferred RecD-like motifs V are shown in Tables 5 and 7 of U.S. Patent Application No. 61/581,332 and International Application No. PCT/GB2012/053274 (published as WO 2012/098562).

The RecD helicase is preferably one of the helicases shown in Table 4 or 5 of U.S. Patent Application No. 61/581,332 and International Application No. PCT/GB2012/053274 (published as WO 2012/098562) or a variant thereof. Variants are described in U.S. Patent Application No. 61/581,332 and International Application No. PCT/GB2012/053274 (published as WO 2012/098562).

The RecD helicase is preferably a TraI helicase or a TraI subgroup helicase. TraI helicases and TraI subgroup helicases are monomeric because they function without forming oligomers. TraI helicases and TraI subgroup helicases may contain two RecD helicase domains, a relaxase domain and a C-terminal domain. The TraI subgroup helicase is preferably a TrwC helicase. The TraI helicase or TraI subgroup helicase is preferably one of the helicases shown in Table 6 of U.S. Patent Application No. 61/581,332 and International Application No. PCT/GB2012/053274 (published as WO 2012/098562) or a variant thereof. Variants are described in U.S. Patent Application No. 61/581,332 and International Application No. PCT/GB2012/053274 (published as WO 2012/098562).

The TraI helicase or a TraI subgroup helicase typically comprises a RecD-like motif I as defined above (SEQ ID NO: 20) and/or a RecD-like motif V as defined above (SEQ ID NO: 29). The TraI helicase or a TraI subgroup helicase preferably comprises both a RecD-like motif I (SEQ ID NO: 20) and a RecD-like motif V (SEQ ID NO: 29). The TraI helicase or a TraI subgroup helicase typically further comprises one of the following two motifs:

The amino acid motif H-(X1)$_2$-X2-R-(X3)$_{5-12}$-H-X4-H (hereinafter called the MobF motif III; SEQ ID NOs: 31-38), wherein X1 and X2 are any amino acid and X2 and X4 are independently selected from any amino acid except D, E, K and R. (X1)$_2$ is of course X1a-X1b. X1a and X1b can be the same of different amino acid. X1a is preferably D or E. X1b is preferably T or D. (X1)$_2$ is preferably DT or ED. (X1)$_2$ is most preferably DT. The 5 to 12 amino acids in (X3)$_{5-12}$ can be the same or different. X2 and X4 are independently selected from G, P, A, V, L, I, M, C, F, Y, W, H, Q, N, S and T. X2 and X4 are preferably not charged. X2 and X4 are preferably not H. X2 is more preferably N, S or A. X2 is most preferably N. X4 is most preferably F or T. (X3)$_{5-12}$ is preferably 6 or 10 residues in length. Suitable embodiments of (X3)$_{5-12}$ can be derived from SEQ ID NOs: 58, 62, 66 and 70 shown in Table 7 of U.S. Patent Application No. 61/581,332 and SEQ ID NOs:

61, 65, 69, 73, 74, 82, 86, 90, 94, 98, 102, 110, 112, 113, 114, 117, 121, 124, 125, 129, 133, 136, 140, 144, 147, 151, 152, 156, 160, 164 and 168 of International Application No. PCT/GB2012/053274 (published as WO 2012/098562).

The amino acid motif G-X1-X2-X3-X4-X5-X6-X7-H-(X8)$_{6-12}$-H-X9 (hereinafter called the MobQ motif III; SEQ ID NOs: 39-45), wherein X1, X2, X3, X5, X6, X7 and X9 are independently selected from any amino acid except D, E, K and R, X4 is D or E and X8 is any amino acid. X1, X2, X3, X5, X6, X7 and X9 are independently selected from G, P, A, V, L, I, M, C, F, Y, W, H, Q, N, S and T. X1, X2, X3, X5, X6, X7 and X9 are preferably not charged. X1, X2, X3, X5, X6, X7 and X9 are preferably not H. The 6 to 12 amino acids in (X8)$_{6-12}$ can be the same or different. Preferred MobF motifs III are shown in Table 7 of U.S. Patent Application No. 61/581,332 and International Application No. PCT/GB2012/053274 (published as WO 2012/098562).

The TraI helicase or TraI subgroup helicase is more preferably one of the helicases shown in Table 6 or 7 of U.S. Patent Application No. 61/581,332 and International Application No. PCT/GB2012/053274 (published as WO 2012/098562) or a variant thereof. The TraI helicase most preferably comprises the sequence shown in SEQ ID NO: 46 or a variant thereof. SEQ ID NO: 46 is TraI Eco (NCBI Reference Sequence: NP_061483.1; Genbank AAQ98619.1; SEQ ID NO: 46). TraI Eco comprises the following motifs: RecD-like motif I (GYAGVGKT; SEQ ID NO: 47), RecD-like motif V (YAITAHGAQG; SEQ ID NO: 48) and Mob F motif III (HDTSRDQEPQLHTH; SEQ ID NO: 49).

The TraI helicase or TraI subgroup helicase more preferably comprises the sequence of one of the helicases shown in Table 2 below, i.e. one of SEQ ID NOs: 46, 87, 98 and 102, or a variant thereof.

A variant of a RecD helicase, TraI helicase or TraI subgroup helicase is an enzyme that has an amino acid sequence which varies from that of the wild-type helicase and which retains polynucleotide binding activity. This can be measured as described above. In particular, a variant of SEQ ID NO: 46, 87, 98 or 102 is an enzyme that has an amino acid sequence which varies from that of SEQ ID NO: 46, 87, 98 or 102 and which retains polynucleotide binding activity. The variant retains helicase activity. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of the motifs discussed above. However, variants may include modifications within these motif(s).

Over the entire length of the amino acid sequence of any one of SEQ ID NOs: 46, 87, 98 and 102, a variant will preferably be at least 10% homologous to that sequence based on amino acid identity. More preferably, the variant polypeptide may be at least 20%, at least 25%, at least 30%, at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 46, 87, 98 or 102 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed above with reference to SEQ ID NOs: 2 and 4.

A variant of any one of SEQ ID NOs: 46, 87, 98 and 102 preferably comprises the RecD-like motif I and/or RecD-like motif V of the wild-type sequence. However, a variant of SEQ ID NO: 46, 87, 98 or 102 may comprise the RecD-like motif I and/or extended RecD-like motif V from a different wild-type sequence. For instance, a variant may comprise any one of the preferred motifs shown in Tables 5 and 7 of U.S. Patent Application No. 61/581,332 and International Application No. PCT/GB2012/053274 (published as WO 2012/098562). Variants of SEQ ID NO: 46, 87, 98 or 102 may also include modifications within the RecD-like motifs I and V of the wild-type sequence. A variant of SEQ ID NO: 46, 87, 98 or 102 preferably comprises one or more

TABLE 2

More preferred TraI helicase and TraI subgroup helicases

| SEQ ID NO | Name | Strain | NCBI ref | % Identity to TraI Eco | RecD-like motif I (SEQ ID NO:) | RecD-like motif V (SEQ ID NO:) | Mob F motif III (SEQ ID NO:) |
|---|---|---|---|---|---|---|---|
| 46 | TraI Eco | *Escherichia coli* | NCBI Reference Sequence: NP_061483.1 Genbank AAQ98619.1 | — | GYAGVGKT (47) | YAITAHGAQG (48) | HDTSRDQEPQLHTH 49) |
| 87 | TrwC Cba | *Citromicrobium bathyomarinum* JL354 | NCBI Reference Sequence: ZP_06861556.1 | 15% | GIAGAGKS (95) | YALNVHMAQG (96) | HDTNRNQEPNLHFH (97) |
| 98 | TrwC Hne | *Halothiobacillus neapolitanus* c2 | NCBI Reference Sequence: YP_003262832.1 | 11.5% | GAAGAGKT (99) | YCITIHRSQG (100) | HEDARTVDDIADPQLHTH (101) |
| 102 | TrwC Eli | *Erythrobacter litoralis* HTCC2594 | NCBI Reference Sequence: YP_457045.1 | 16% | GIAGAGKS (95) | YALNAHMAQG (103) | HDTNRNQEPNLHFH (97) | substituted cysteine residues and/or one or more substituted Faz residues to facilitate attachment as discussed above.

The helicase is preferably an XPD helicase. XPD helicases are monomeric because they function without forming oligomers. Any XPD helicase may be used in accordance with the invention. XPD helicases are also known as Rad3 helicases and the two terms can be used interchangeably.

The structures of XPD helicases are known in the art (Cell. 2008 May 30; 133(5):801-12. Structure of the DNA repair helicase XPD. Liu H, Rudolf J, Johnson K A, McMahon S A, Oke M, Carter L, McRobbie A M, Brown S E, Naismith J H, White M F). The XPD helicase typically comprises the amino acid motif X1-X2-X3-G-X4-X5-X6-E-G (hereinafter called XPD motif V; SEQ ID NO: 50). X1, X2, X5 and X6 are independently selected from any amino acid except D, E, K and R. X1, X2, X5 and X6 are independently selected from G, P, A, V, L, I, M, C, F, Y, W, H, Q, N, S and T. X1, X2, X5 and X6 are preferably not charged. X1, X2, X5 and X6 are preferably not H. X1 is more preferably V, L, I, S or Y. X5 is more preferably V, L, I, N or F. X6 is more preferably S or A. X3 and X4 may be any amino acid residue. X4 is preferably K, R or T.

The XPD helicase typically comprises the amino acid motif Q-Xa-Xb-G-R-Xc-Xd-R-$(Xe)_3$-Xf-$(Xg)_7$-D-Xh-R (hereinafter called XPD motif VI; SEQ ID NO: 51). Xa, Xe and Xg may be any amino acid residue. Xb, Xc and Xd are independently selected from any amino acid except D, E, K and R. Xb, Xc and Xd are typically independently selected from G, P, A, V, L, I, M, C, F, Y, W, H, Q, N, S and T. Xb, Xc and Xd are preferably not charged. Xb, Xc and Xd are preferably not H. Xb is more preferably V, A, L, I or M. Xc is more preferably V, A, L, I, M or C. Xd is more preferably I, H, L, F, M or V. Xf may be D or E. $(Xg)_7$ is $X_{g1}$, $X_{g2}$, $X_{g3}$, $X_{g4}$, $X_{g5}$, $X_{g6}$ and $X_{g7}$. $X_{g2}$ is preferably G, A, S or C. $X_{g5}$ is preferably F, V, L, I, M, A, W or Y. $X_{g6}$ is preferably L, F, Y, M, I or V. $X_{g7}$ is preferably A, C, V, L, I, M or S.

The XPD helicase preferably comprises XPD motifs V and VI. The most preferred XPD motifs V and VI are shown in Table 5 of U.S. Patent Application No. 61/581,340 and International Application No. PCT/GB2012/053273 (published as WO 2012/098561).

The XPD helicase preferably further comprises an iron sulphide (FeS) core between two Walker A and B motifs (motifs I and II). An FeS core typically comprises an iron atom coordinated between the sulphide groups of cysteine residues. The FeS core is typically tetrahedral.

The XPD helicase is preferably one of the helicases shown in Table 4 or 5 of U.S. Patent Application No. 61/581,340 and International Application No. PCT/GB2012/053273 (published as WO 2012/098561) or a variant thereof. The XPD helicase most preferably comprises the sequence shown in SEQ ID NO: 52 or a variant thereof. SEQ ID NO: 52 is XPD Mbu (*Methanococcoides burtonii*; YP_566221.1; GI:91773529). XPD Mbu comprises YLWGTLSEG (Motif V; SEQ ID NO: 53) and QAMGRV-VRSPTDYGARILLDGR (Motif VI; SEQ ID NO: 54).

A variant of a XPD helicase is an enzyme that has an amino acid sequence which varies from that of the wild-type helicase and which retains polynucleotide binding activity. This can be measured as described above. In particular, a variant of SEQ ID NO: 52 is an enzyme that has an amino acid sequence which varies from that of SEQ ID NO: 52 and which retains polynucleotide binding activity. The variant retains helicase activity. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of XPD motifs V and VI discussed above. However, variants may include modifications within one or both of these motifs.

Over the entire length of the amino acid sequence of SEQ ID NO: 52, such as SEQ ID NO: 10, a variant will preferably be at least 10%, preferably 30% homologous to that sequence based on amino acid identity. More preferably, the variant polypeptide may be at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 52 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed above with reference to SEQ ID NOs: 2 and 4.

A variant of SEQ ID NO: 52 preferably comprises the XPD motif V and/or the XPD motif VI of the wild-type sequence. A variant of SEQ ID NO: 52 more preferably comprises both XPD motifs V and VI of SEQ ID NO: 52. However, a variant of SEQ ID NO: 52 may comprise XPD motifs V and/or VI from a different wild-type sequence. For instance, a variant of SEQ ID NO: 52 may comprise any one of the preferred motifs shown in Table 5 of U.S. Patent Application No. 61/581,340 and International Application No. PCT/GB2012/053273 (published as WO 2012/098561). Variants of SEQ ID NO: 52 may also include modifications within XPD motif V and/or XPD motif VI of the wild-type sequence. Suitable modifications to these motifs are discussed above when defining the two motifs. A variant of SEQ ID NO: 52 preferably comprises one or more substituted cysteine residues and/or one or more substituted Faz residues to facilitate attachment as discussed above.

The helicase may be any of the modified helicases described and claimed in U.S. Provisional Application No. 61/673,452 (filed 19 Jul. 2012), U.S. Provisional Application No. 61/774,862 (filed 8 Mar. 2013) and the International Application being filed concurrently with this application (Oxford Nanopore Ref: ONT IP 033).

The helicase is more preferably a Hel308 helicase in which one or more cysteine residues and/or one or more non-natural amino acids have been introduced at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10), wherein the helicase retains its ability to control the movement of a polynucleotide.

The Hel308 helicase preferably comprises a variant of one of SEQ ID NOs: 10, 13, 16 or 19 which comprises one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10).

The Hel308 helicase preferably comprises a variant of one of SEQ ID NOs: 10, 13, 16 or 19 which comprises one or more cysteine residues and/or one or more non-natural amino acids at one or more of the positions which correspond to D274, E284, E285, S288, S615, K717, Y720, E287, T289, G290, E291, N316 and K319 in Hel308 Mbu (SEQ ID NO: 10).

Tables 3a and 3b below show the positions in other Hel308 helicases which correspond to D274, E284, E285, S288, S615, K717, Y720, E287, T289, G290, E291, N316 and K319 in Hel308 Mbu (SEQ ID NO: 10). The lack of a corresponding position in another Hel308 helicase is marked as a "-".

TABLE 3a

Positions which correspond to D274, E284, E285, S288, S615, K717 and Y720 in Hel308 Mbu (SEQ ID NO: 10).

| SEQ ID NO: | Hel308 homologue | A | B | C | D | E | F | G |
|---|---|---|---|---|---|---|---|---|
| 10 | Mbu | D274 | E284 | E285 | S288 | S615 | K717 | Y720 |
| 13 | Csy | D280 | K290 | I291 | S294 | P589 | T694 | N697 |
| 16 | Tga | L266 | S276 | L277 | Q280 | P583 | K689 | D692 |
| 19 | Mhu | S269 | Q277 | E278 | R281 | S583 | G685 | R688 |

TABLE 3b

Positions which correspond to E287, T289, G290, E291, N316 and K319 in Hel308 Mbu (SEQ ID NO: 10).

| SEQ ID NO: | Hel308 homologue | H | I | J | K | L | M |
|---|---|---|---|---|---|---|---|
| 10 | Mbu | E287 | T289 | G290 | E291 | N316 | K319 |
| 13 | Csy | S293 | G295 | G296 | E297 | D322 | S325 |
| 16 | Tga | S279 | L281 | E282 | D283 | V308 | T311 |
| 19 | Mhu | R280 | L282 | R283 | D284 | Q309 | T312 |

The Hel308 helicase preferably comprises a variant of one of SEQ ID NOs: 10, 13, 16 or 19 which comprises one or more cysteine residues and/or one or more non-natural amino acids at one or more of the positions which correspond to D274, E284, E285, S288, S615, K717 and Y720 in Hel308 Mbu (SEQ ID NO: 10). The helicase may comprise one or more cysteine residues and/or one or more non-natural amino acids at any of the following combinations of the positions labelled A to G in each row of Table 3a: {A}, {B}, {C}, {D}, {G}, {E}, {F}, {A and B}, {A and C}, {A and D}, {A and G}, {A and E}, {A and F}, {B and C}, {B and D}, {B and G}, {B and E}, {B and F}, {C and D}, {C and G}, {C and E}, {C and F}, {D and G}, {D and E}, {D and F}, {G and E}, {G and F}, {E and F}, {A, B and C}, {A, B and D}, {A, B and G}, {A, B and E}, {A, B and F}, {A, C and D}, {A, C and G}, {A, C and E}, {A, C and F}, {A, D and G}, {A, D and E}, {A, D and F}, {A, G and E}, {A, G and F}, {A, E and F}, {B, C and D}, {B, C and G}, {B, C and E}, {B, C and F}, {B, D and G}, {B, D and E}, {B, D and F}, {B, G and E}, {B, G and F}, {B, E and F}, {C, D and G}, {C, D and E}, {C, D and F}, {C, G and E}, {C, G and F}, {C, E and F}, {D, G and E}, {D, G and F}, {D, E and F}, {G, E and F}, {A, B, C and D}, {A, B, C and G}, {A, B, C and E}, {A, B, C and F}, {A, B, D and G}, {A, B, D and E}, {A, B, D and F}, {A, B, G and E}, {A, B, G and F}, {A, B, E and F}, {A, C, D and G}, {A, C, D and E}, {A, C, D and F}, {A, C, G and E}, {A, C, G and F}, {A, C, E and F}, {A, D, G and E}, {A, D, G and F}, {A, D, E and F}, {A, G, E and F}, {B, C, D and G}, {B, C, D and E}, {B, C, D and F}, {B, C, G and E}, {B, C, G and F}, {B, C, E and F}, {B, D, G and E}, {B, D, G and F}, {B, D, E and F}, {B, G, E and F}, {C, D, G and E}, {C, D, G and F}, {C, D, E and F}, {C, G, E and F}, {D, G, E and F}, {A, B, C, D and G}, {A, B, C, D and E}, {A, B, C, D and F}, {A, B, C, D, E and F}, {A, B, C, G and E}, {A, B, C, G and F}, {A, B, C, E and F}, {A, B, D, G and E}, {A, B, D, G and F}, {A, B, D, E and F}, {A, C, D, G and E}, {A, C, D, G and F}, {B, C, D, G and E}, {B, C, D, G and F}, or {A, B, C, D, G, E and F}.

The Hel308 helicase more preferably comprises a variant of one of SEQ ID NOs: 10, 13, 16 or 19 which comprises one or more cysteine residues and/or one or more non-natural amino acids at one or more of the positions which correspond to D274, E284, E285, S288 and S615 in Hel308 Mbu (SEQ ID NO: 10).

Polynucleotide Binding Moiety

The constructs described herein comprise an additional polynucleotide binding moiety. A polynucleotide binding moiety is a polypeptide that is capable of binding to a polynucleotide. The moiety is preferably capable of specific binding to defined polynucleotide sequence. In other words, the moiety preferably binds to a specific polynucleotide sequence, but displays at least 10 fold less binding to different sequences or more preferably at least 100 fold less binding to different sequences or most preferably at least 1000 fold less binding to different sequences. The different sequence may be a random sequence. In some embodiments, the moiety binds to a specific polynucleotide sequence, but binding to different sequences cannot be measured. Moieties that bind to specific sequences can be used to design constructs that are targeted to such sequences.

The moiety typically interacts with and modifies at least one property of a polynucleotide. The moiety may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag. Suitable labels are described above. The target polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

It is preferred that the tertiary structure of the moiety is known. Knowledge of the three dimensional structure of the moiety allows modifications to be made to the moiety to facilitate its function in the construct.

The moiety may be any size and have any structure. For instance, the moiety may be an oligomer, such as a dimer or trimer. The moiety is preferably a small, globular polypeptide formed from one monomer. Such moieties are easy to handle and are less likely to interfere with the ability of the helicase to control the movement of the polynucleotide, particularly if fused to or inserted into the sequence of the helicase.

The amino and carboxy terminii of the moiety are preferably in close proximity. The amino and carboxy terminii of the moiety are more preferably presented on same face of the moiety. Such embodiments facilitate insertion of the moiety into the sequence of the helicase. For instance, if the amino and carboxy terminii of the moiety are in close proximity, each can be attached by genetic fusion to adjacent amino acids in the sequence of the helicase.

It is also preferred that the location and function of the active site of the moiety is known. This prevents modifications being made to the active site that abolish the activity of the moiety. It also allows the moiety to be attached to the helicase so that the moiety binds to the polynucleotide and controls its movement. Knowledge of the way in which a moiety may bind to and orient polynucleotides also allows an effective construct to be designed.

The constructs described herein are useful in Strand Sequencing. The moiety preferably binds the polynucleotide in a buffer background which is compatible with Strand Sequencing and the discrimination of the nucleotides. The moiety preferably has at least residual activity in a salt concentration well above the normal physiological level, such as from 100 mM to 2M. The moiety is more preferably modified to increase its activity at high salt concentrations. The moiety may also be modified to improve its processivity, stability and shelf life.

Suitable modifications can be determined from the characterisation of polynucleotide binding moieties from extremphiles such as halophilic, moderately halophilic bacteria, thermophilic and moderately thermophilic organisms, as well as directed evolution approaches to altering the salt tolerance, stability and temperature dependence of mesophilic or thermophilic exonucleases.

The polynucleotide binding moiety preferably comprises one or more domains independently selected from helix-hairpin-helix (HhH) domains, eukaryotic single-stranded binding proteins (SSBs), bacterial SSBs, archaeal SSBs, viral SSBs, double-stranded binding proteins, sliding clamps, processivity factors, DNA binding loops, replication initiation proteins, telomere binding proteins, repressors, zinc fingers and proliferating cell nuclear antigens (PCNAs).

The helix-hairpin-helix (HhH) domains are polypeptide motifs that bind DNA in a sequence non-specific manner. They have been shown to confer salt stability and processivity when fused to polymerases, as well as increasing their thermal stability. Suitable domains include domain H (residues 696-751) and domain HI (residues 696-802) from Topoisomerase V from *Methanopyrus kandleri* (SEQ ID NO: 89). As discussed below, the polynucleotide binding moiety may be domains H-L of SEQ ID NO: 89 as shown in SEQ ID NO: 94. Topoisomerase V from *Methanopyrus kandleri* is an example of a double-stranded binding protein as discussed below.

The HhH domain preferably comprises the sequence shown in SEQ ID NO: 55 or 75 or 76 or a variant thereof. This domain increases the processivity and the salt tolerance of a helicase when used in a construct described herein. A variant of SEQ ID NO: 55 or 75 or 76 is a protein that has an amino acid sequence which varies from that of SEQ ID NO: 55 or 75 or 76 and which retains polynucleotide binding activity. This can be measured as described above. A variant typically has at least 50% homology to SEQ ID NO: 55 or 75 or 76 based on amino acid identity over its entire sequence (or any of the % homologies discussed above in relation to helicases) and retains polynucleotide binding activity. A variant may differ from SEQ ID NO: 55 or 75 or 76 in any of the ways discussed above in relation to helicases or below in relation to pores. A variant preferably comprises one or more substituted cysteine residues and/or one or more substituted Faz residues to facilitate attachment to the helicase as discussed above.

SSBs bind single stranded DNA with high affinity in a sequence non-specific manner. They exist in all domains of life in a variety of forms and bind DNA either as monomers or multimers. Using amino acid sequence alignment and logorithms (such as Hidden Markov models) SSBs can be classified according to their sequence homology. The Pfam family, PF00436, includes proteins that all show sequence similarity to known SSBs. This group of SSBs can then be further classified according to the Structural Classification of Proteins (SCOP). SSBs fall into the following lineage: Class; All beta proteins, Fold; OB-fold, Superfamily: Nucleic acid-binding proteins, Family; Single strand DNA-binding domain, SSB. Within this family SSBs can be classified according to subfamilies, with several type species often characterised within each subfamily.

The SSB may be from a eukaryote, such as from humans, mice, rats, fungi, protozoa or plants, from a prokaryote, such as bacteria and archaea, or from a virus.

Eukaryotic SSBs are known as replication protein A (RPAs). In most cases, they are hetero-trimers formed of different size units. Some of the larger units (e.g. RPA70 of *Saccharomyces cerevisiae*) are stable and bind ssDNA in monomeric form.

Bacterial SSBs bind DNA as stable homo-tetramers (e.g. *E. coli, Mycobacterium smegmatis* and *Helicobacter pylori*) or homo-dimers (e.g. *Deinococcus radiodurans* and *Thermotoga maritima*). The SSBs from archaeal genomes are considered to be related with eukaryotic RPAs. Few of them, such as the SSB encoded by the crenarchaeote *Sulfolobus solfataricus*, are homo-tetramers. The SSBs from most other species are closer related to the replication proteins from eukaryotes and are referred to as RPAs. In some of these species they have been shown to be monomeric (*Methanococcus jannaschii* and *Methanothermobacter thermoautotrophicum*). Still, other species of Archaea, including *Archaeoglobus fulgidus* and *Methanococcoides burtonii*, appear to each contain two open reading frames with sequence similarity to RPAs. There is no evidence at protein level and no published data regarding their DNA binding capabilities or oligomeric state. However, the presence of two oligonucleotide/oligosaccharide (OB) folds in each of these genes (three OB folds in the case of one of the *M. burtonii* ORFs) suggests that they also bind single stranded DNA.

Viral SSBs bind DNA as monomers. This, as well as their relatively small size renders them amenable to genetic fusion to other proteins, for instance via a flexible peptide linker. Alternatively, the SSBs can be expressed separately and attached to other proteins by chemical methods (e.g. cysteines, unnatural amino-acids). This is discussed in more detail below.

The SSB is preferably either (i) an SSB comprising a carboxy-terminal (C-terminal) region which does not have a net negative charge or (ii) a modified SSB comprising one or more modifications in its C-terminal region which decreases the net negative charge of the C-terminal region. Such SSBs do not block the transmembrane pore and therefore allow characterization of the target polynucleotide.

Examples of SSBs comprising a C-terminal region which does not have a net negative charge include, but are not limited to, the human mitochondrial SSB (HsmtSSB; SEQ ID NO: 77), the human replication protein A 70 kDa subunit, the human replication protein A 14 kDa subunit, the telomere end binding protein alpha subunit from *Oxytricha nova*, the core domain of telomere end binding protein beta subunit from *Oxytricha nova*, the protection of telomeres protein 1 (Pot1) from *Schizosaccharomyces pombe*, the human Pot1, the OB-fold domains of BRCA2 from mouse or rat, the p5 protein from phi29 (SEQ ID NO: 78) or a variant of any of those proteins. A variant is a protein that has an amino acid sequence which varies from that of the wild-type protein and which retains single stranded polynucleotide binding activity. Polynucleotide binding activity can be determined using methods known in the art (and as described above). For instance, the ability of a variant to bind a single stranded polynucleotide can be determined as described in the Examples.

A variant of SEQ ID NO 77 or 78 typically has at least 50% homology to SEQ ID NO: 77 or 78 based on amino acid identity over its entire sequence (or any of the % homologies discussed above in relation to helicases) and retains single stranded polynucleotide binding activity. A variant may differ from SEQ ID NO: 77 or 78 in any of the ways discussed above in relation to helicases. In particular, a variant may have one or more conservative substitutions as shown in Tables 8 and 9.

Examples of SSBs which require one or more modifications in their C-terminal region to decrease the net negative charge include, but are not limited to, the SSB of *E. coli* (EcoSSB; SEQ ID NO: 79), the SSB of *Mycobacterium tuberculosis*, the SSB of *Deinococcus radiodurans*, the SSB of *Thermus thermophiles*, the SSB from *Sulfolobus solfataricus*, the human replication protein A 32 kDa subunit (RPA32) fragment, the CDC13 SSB from *Saccharomyces cerevisiae*, the Primosomal replication protein N (PriB) from *E. coli*, the PriB from *Arabidopsis thaliana*, the hypothetical protein At4g28440, the SSB from T4 (gp32; SEQ ID NO: 80), the SSB from RB69 (gp32; SEQ ID NO: 56), the SSB from T7 (gp2.5; SEQ ID NO: 57) or a variant of any of these proteins. Hence, the SSB used in the method of the invention may be derived from any of these proteins.

In addition to the one or more modifications in the C-terminal region, the SSB used in the method may include additional modifications which are outside the C-terminal region or do not decrease the net negative charge of the C-terminal region. In other words, the SSB used in the method of the invention is derived from a variant of a wild-type protein. A variant is a protein that has an amino acid sequence which varies from that of the wild-type protein and which retains single stranded polynucleotide binding activity. Polynucleotide binding activity can be determined as discussed above.

The SSB used in the invention may be derived from a variant of SEQ ID NO: 56, 57, 79 or 80. In other words, a variant of SEQ ID NO: 56, 57, 79 or 80 may be used as the starting point for the SSB used in the invention, but the SSB actually used further includes one or more modifications in its C-terminal region which decreases the net negative charge of the C-terminal region. A variant of SEQ ID NO: 56, 57, 79 or 80 typically has at least 50% homology to SEQ ID NO: 56, 57, 79 or 80 based on amino acid identity over its entire sequence (or any of the % homologies discussed above in relation to helicases) and retains single stranded polynucleotide binding activity. A variant may differ from SEQ ID NO: 56, 57, 79 or 80 in any of the ways discussed above in relation to helicases. In particular, a variant may have one or more conservative substitutions as shown in Tables 8 and 9.

It is straightforward to identify the C-terminal region of the SSB in accordance with normal protein N to C nomenclature. The C-terminal region of the SSB is preferably about the last third of the SSB at the C-terminal end, such as the last third of the SSB at the C-terminal end. The C-terminal region of the SSB is more preferably about the last quarter, fifth or eighth of the SSB at the C-terminal end, such as the last quarter, fifth or eighth of the SSB at the C-terminal end. The last third, quarter, fifth or eighth of the SSB may be measured in terms of numbers of amino acids or in terms of actual length of the primary structure of the SSB protein. The length of the various amino acids in the N to C direction are known in the art.

The C-terminal region is preferably from about the last 10 to about the last 60 amino acids of the C-terminal end of the SSB. The C-terminal region is more preferably about the last 15, about the last 20, about the last 25, about the last 30, about the last 35, about the last 40, about the last 45, about the last 50 or about the last 55 amino acids of the C-terminal end of the SSB.

The C-terminal region typically comprises a glycine and/or proline rich region. This proline/glycine rich region gives the C-terminal region flexibility and can be used to identify the C-terminal region.

Suitable modifications for decreasing the net negative charge are disclosed in U.S. Provisional Application No. 61/673,457 (filed 19 Jul. 2012), U.S. Provisional Application No. 61/774,688 (filed 8 Mar. 2013) and the International application being filed concurrently with this application (Oxford Nanopore Ref: ONT IP 035). The SSB may be any of the SSBs disclosed in the US Provisional Applications and the International application.

The modified SSB most preferably comprises a sequence selected from those shown in SEQ ID NOs: 64, 65 and 81 to 84.

Double-stranded binding proteins bind double stranded DNA with high affinity. Suitable double-stranded binding proteins include, but are not limited to Mutator S (MutS; NCBI Reference Sequence: NP_417213.1; SEQ ID NO: 105), Sso7d (*Sufolobus solfataricus* P2; NCBI Reference Sequence: NP_343889.1; SEQ ID NO: 106; Nucleic Acids Research, 2004, Vol 32, No. 3, 1197-1207), Sso10b1 (NCBI Reference Sequence: NP_342446.1; SEQ ID NO: 107), Sso10b2 (NCBI Reference Sequence: NP_342448.1; SEQ ID NO: 108), Tryptophan repressor (Trp repressor; NCBI Reference Sequence: NP_291006.1; SEQ ID NO: 109), Lambda repressor (NCBI Reference Sequence: NP_040628.1; SEQ ID NO: 110), Cren7 (NCBI Reference Sequence: NP_342459.1; SEQ ID NO: 111), major histone classes H1/H5, H2A, H2B, H3 and H4 (NCBI Reference Sequence: NP_066403.2, SEQ ID NO: 112), dsbA (NCBI Reference Sequence: NP_049858.1; SEQ ID NO: 113), Rad51 (NCBI Reference Sequence: NP_002866.2; SEQ ID NO: 114), sliding clamps and Topoisomerase V Mka (SEQ ID NO: 89) or a variant of any of these proteins. A variant of SEQ ID NO: 89, 105, 106, 107, 108, 109, 110, 111, 112, 113 or 114 typically has at least 50% homology to SEQ ID NO: 89, 105, 106, 107, 108, 109, 110, 111, 112, 113 or 114 based on amino acid identity over its entire sequence (or any of the % homologies discussed above in relation to helicases) and retains single stranded polynucleotide binding activity. A variant may differ from SEQ ID NO: 89, 105, 106, 107, 108, 109, 110, 111, 112, 113 or 114 in any of the ways discussed above in relation to helicases. In particular, a variant may have one or more conservative substitutions as shown in Tables 8 and 9. Most polymerases achieve processivity by interacting with sliding clamps. In general, these are multimeric proteins (homo-dimers or homo-trimers) that encircle dsDNA. These sliding clamps require accessory proteins (clamp loaders) to assemble them around the DNA helix in an ATP-dependent process. They also do not contact DNA directly, acting as a topological tether. As sliding clamps interact with their cognate polymerases in a specific manner via a polymerase domain, this fragment could be fused to the helicase in order to incite recruitment of helicases onto the sliding clamp. This interaction could be further stabilized by the generation of a covalent bond (introduction of cysteines or unnatural amino-acids).

Related to DNA sliding clamps, processivity factors are viral proteins that anchor their cognate polymerases to DNA, leading to a dramatic increase the length of the fragments generated. They can be monomeric (as is the case for UL42 from Herpes simplex virus 1) or multimeric (UL44 from Cytomegalovirus is a dimer), they do not form closed rings around the DNA strand and they contact DNA directly. UL42 has been shown to increase processivity without reducing the rate of its corresponding polymerase, suggesting that it interacts with DNA in a different mode to SSBs. The UL42 preferably comprises the sequence shown in SEQ ID NO: 58 or SEQ ID NO: 63 or a variant thereof. A variant of SEQ ID NO: 58 or 63 is a protein that has an amino acid sequence which varies from that of SEQ ID NO: 58 or 63 and which retains polynucleotide binding activity. This can be measured as described above. A variant typically has at least 50% homology to SEQ ID NO: 58 or 63 based on amino acid identity over its entire sequence (or any of the % homologies discussed above in relation to helicases) and retains polynucleotide binding activity. A variant may differ from SEQ ID NO: 58 or SEQ ID NO: 63 in any of the ways discussed above in relation to helicases or below in relation to pores. A variant preferably comprises one or more substituted cysteine residues and/or one or more substituted Faz residues to facilitate attachment to the helicase as discussed above.

Attaching UL42 to a helicase could be done via genetic fusion or chemical attachment (cysteines, unnatural amino-acids). As the polymerase polypeptide that binds UL42 is visible in the crystal structure, these 35 amino acids (residues 1200-1235) could be fused onto the C-terminus of the helicase and the natural affinity between this polypeptide and the processivity factor used to form a complex. The interaction could be stabilized by introducing a covalent interaction (cysteines or unnatural amino-acids). One option is to utilize a natural UL42 cysteine (C300) that is located close to the polypeptide interaction site and introduce a point mutation into the polymerase polypeptide (e.g. L1234C).

A reported method of increasing polymerase processivity is by exploiting the interaction between *E. coli* thioredoxin (Trx) and the thioredoxin binding domain (TBD) of bacteriophage T7 DNA polymerase (residues 258-333). The binding of Trx to TBD causes the polypeptide to change conformation to one that binds DNA. TBD is believed to clamp down onto a DNA strand and limit the polymerase off-rate, thus increasing processivity. Chimeric polymerases have been made by transferring TBD onto a non-processive polymerase, resulting in 1000 fold increase in polymerised fragment length. There were no attempts to attach TBD to any other class of proteins, but a covalent link between TBD and Trx was engineered and can be used to stabilise the interaction.

Some helicases use accessory proteins in-vivo to achieve processivity (e.g. cisA from phage Φx174 and geneII protein from phage M13 for *E. coli* Rep helicase). Some of these proteins have been shown to interact with more than one helicase (e.g. MutL acts on both UvrD and Rep, though not to the same extent). These proteins have intrinsic DNA binding capabilities, some of them recognizing a specific DNA sequence. The ability of some of these accessory proteins to covalently attach themselves to a specific DNA sequence could also be used to create a set starting point for the helicase activity.

The proteins that protect the ends of chromosomes bind to telomeric ssDNA sequences in a highly specific manner. This ability could either be exploited as is or by using point mutations to abolish the sequence specificity.

Small DNA binding motifs (such as helix-turn-helix) recognize specific DNA sequences. In the case of the bacteriophage 434 repressor, a 62 residue fragment was engineered and shown to retain DNA binding abilities and specificity.

An abundant motif in eukaryotic proteins, zinc fingers consist of around 30 amino-acids that bind DNA in a specific manner. Typically each zinc finger recognizes only three DNA bases, but multiple fingers can be linked to obtain recognition of a longer sequence.

Proliferating cell nuclear antigens (PCNAs) form a very tight clamp (doughnut) which slides up and down the dsDNA or ssDNA. The PCNA from crenarchaeota is unique in being a hetero-trimer so it is possible to functionalise one subunit and retain activity. Its subunits are shown in SEQ ID NOs: 59, 60 and 61. The PCNA is preferably a trimer comprising the sequences shown in SEQ ID NOs: 59, 60 and 61 or a variant thereof. PCNA sliding clamp (NCBI Reference Sequence: ZP_06863050.1; SEQ ID NO: 115) forms a dimer. The pCNA is preferably a dimer comprising SEQ ID NO: 115 or a variant thereof. A variant is a protein that has an amino acid sequence which varies from that of SEQ ID NO: 59, 60, 61 and 115 and which retains polynucleotide binding activity. This can be measured as described above. A variant is typically a trimer comprising sequences that have at least 50% homology to SEQ ID NOs: 59, 60, 61 and 115 respectively based on amino acid identity over their entire sequences (or any of the % homologies discussed above in relation to helicases) and which retains polynucleotide binding activity. A variant may comprise sequences which differ from SEQ ID NO: 59, 60, 61 or 115 in any of the ways discussed above in relation to helicases or below in relation to pores. A variant preferably comprises one or more substituted cysteine residues and/or one or more substituted Faz residues to facilitate attachment to the helicase as discussed above. In a preferred embodiment, subunits 1 and 2 (i.e. SEQ ID NOs: 59 and 60 or variants thereof) are attached, such as genetically fused, and the resulting protein is attached to a helicase to form a construct. During use of the construct, subunit 3 (i.e. SEQ ID NO: 61 or a variant thereof) may be added to complete the PCNA clamp (or doughnut) once the construct has bound the polynucleotide. In a preferred embodiment, one monomer (i.e. SEQ ID NO: 111 or variants thereof) is attached, such as genetically fused, and the resulting protein is attached to a helicase to form a construct of the invention. During use of the construct, the second monomer (i.e. SEQ ID NO: 111 or a variant thereof) may be added to complete the the PCNA clamp (or doughnut) once the construct has bound the polynucleotide.

The polynucleotide binding motif may be selected from any of those shown in Table 4 below.

TABLE 4

Suitable polynucleotide binding motifs

| No. | Name | Class | Organism | Structure | Sequence | Functional form | MW (Da) | Notes |
|---|---|---|---|---|---|---|---|---|
| 1 | SSBEco | ssb | *Escherichia coli* | 1QVC, 1EYG | P0AGE0 | homo-tetramer | 18975 | |
| 2 | SSBBhe | ssb | *Bartonella henselae* | 3LGJ, 3PGZ | Q6G302 | homo-tetramer | 16737 | structure only |
| 3 | SSBCbu | ssb | *Coxiella burnetii* | 3TQY | Q83EP4 | homo-tetramer | 17437 | structure only |
| 4 | SSBTma | ssb | *Thermathoga maritima* | 1Z9F | Q9WZ73 | homo-dimer | 16298 | small, thermostable, salt independent DNA binding |
| 5 | SSBHpy | ssb | *Helicobacter pylori* | 2VW9 | O25841 | homo-tetramer | 20143 | |
| 6 | SSBDra | ssb | *Deinococcus radiodurans* | 1SE8 | Q9RY51 | homo-dimer | 32722 | |
| 7 | SSBTaq | ssb | *Thermus aquaticus* | 2FXQ | Q9KH06 | homo-dimer | 30026 | |
| 8 | SSBMsm | ssb | *Mycobacterium smegmatis* | 3A5U, 1X3E | Q9AFI5 | homo-tetramer | 17401 | tetramer more stable than *E. coli*, binding less salt dependent |
| 9 | SSBSso | ssb/RPA | *Sulfolobus solfataricus* | 1O7I | Q97W73 | homo-tetramer | 16138 | similarities with RPA |
| 10 | SSBMHsmt | ssb | *Homo sapiens* | 3ULL | Q04837 | homo-tetramer | 17260 | |
| 11 | SSBMle | ssb | *Mycobacterium leprae* | 3AFP | P46390 | homo-tetramer | 17701 | |
| 12 | gp32T4 | ssb | Bacteriohage T4 | 1GPC | P03695 | monomer | 33506 | Homo-dimer in the absence of DNA, monomer when binding DNA. |
| 13 | gp32RB69 | ssb | Bacteriophage RB69 | 2A1K | Q7Y265 | monomer | 33118 | |
| 14 | gp2.5T7 | ssb | Bacteriophage T7 | 1JE5 | P03696 | monomer | 25694 | |
| 15 | UL42 | processivity factor | Herpes virus 1 | 1DML | P10226 | monomer | 51159 | binds ssDNA dsDNA, structure shows link with polymerase |
| 16 | UL44 | processivity factor | Herpes virus 5 (cytomegalovirus) | 1YYP | P16790 | homo-dimer | 46233 | forms C shaped clamp on DNA |
| 17 | pf8 | processivity factor | KSHV | 3I2M | Q77ZG5 | homo-dimer | 42378 | |
| 18 | RPAMja | RPA | *Methanococcus jannaschii* | 3DM3 | Q58559 | monomer | 73842 | contains 4 OB folds. Structure of fragment |
| 19 | RPAMma | RPA | *Methanococcus maripaludis* | 3E0E, 2K5V | Q6LYF9 | monomer | 71388 | Core domain structure |
| 20 | RPAMth | RPA | *Methanothermobacter thermoautotrophicus* | | | monomer | 120000 | Shown to interact directly with Hel308. Sequence from paper. |
| 21 | RPA70Sce | RPA | *Saccharomyces cerevisiae* | 1YNX | P22336 | hetero-trimer | 70348 | unit has two OB folds and binds DNA |
| 22 | RPAMbu1 | RPA | *Methanococcoides burtonii* | | Q12V72 | ? | 41227 | three OB folds identified |

TABLE 4-continued

Suitable polynucleotide binding motifs

| No. | Name | Class | Organism | Structure | Sequence | Functional form | MW (Da) | Notes |
|---|---|---|---|---|---|---|---|---|
| 23 | RPAMbu2 | RPA | *Methanococcoides burtonii* | | Q12W96 | ? | 47082 | two OB folds identified |
| 24 | RPA70Hsa | RPA | *Homo sapiens* | 1JMC | P27694 | hetero-trimer | 68138 | |
| 25 | RPA14Hsa | RPA | *Homo sapiens* | 3KDF | P35244 | hetero-trimer | 13569 | in complex with RPA32 |
| 26 | gp45T4 | sliding clamp | Bacteriophage T4 | 1CZD | P04525 | homo-trimer | 24858 | ring shape threads DNA |
| 27 | BetaEco | sliding clamp | *E. coli* | 3BEP | P0A988 | homo-dimer | 40587 | ring shape threads DNA, may bind ssDNA in poket |
| 28 | PCNASce | sliding clamp | *Saccharomyces cerevisiae* | 1PLQ, 3K4X | P15873 | homo-dimer | 28916 | ring shape threads DNA |
| 29 | PCNATko | sliding clamp | *Thermococcus kodakaraensis* | 3LX1 | Q5JF32 | homo-dimer | 28239 | |
| 30 | PCNAHvo | sliding clamp | *Haloferax volcanii* | 3IFV | D0VWY8 | homo-dimer | 26672 | |
| 31 | PCNAPfu | sliding clamp | *Pyrococcus furiosus* | 1GE8 | O73947 | homo-dimer | 28005 | |
| 32 | PCNAMbu | sliding clamp | *Methanococcoides burtonii* | | Q12U18 | homo-dimer | 27121 | Inferred from homology |
| 33 | BetaMtu | sliding clamp | *Mycobacterium tuberculosis* | 3P16 | Q50790 | homo-dimer | 42113 | |
| 34 | BetaTma | sliding clamp | *Thermotoga maritima* | 1VPK | Q9WYA0 | homo-dimer | 40948 | |
| 35 | BetaSpy | sliding clamp | *Streptococcus pyrogenes* | 2AVT | Q9EVR1 | homo-dimer | 41867 | |
| 36 | gp45RB69 | sliding clamp | Bacteriophage RB69 | 1B77 | O80164 | homo-trimer | 25111 | Structure shows interaction with polypeptide fom polymerase |
| 37 | p55Hsa | DNA binding protein | *Homo sapiens* (mitochondrial) | 2G4C, 3IKL, 3IKM | Q9UHN | monomer | 54911 | interacts with specific polymerase domain |
| 38 | p55Dme | DNA binding protein | *Drosophylla melanogaster* | | Q9VJV8 | monomer | 41027 | associates with polymerase Gamma conferring salt tolerance, processivity and increased activity |
| 39 | p55Xla | DNA binding protein | *Xenopus laevis* | | Q9W6G7 | monomer | 52283 | |
| 40 | RepDSau | replication initiation protein | *Staphylococcus aureus* | | P08115 | homo-dimer | 37874 | increases processivity of PcrA, covalently and specifically links DNA |
| 41 | G2P | replication initiation protein | Enterobacteria phage 1 | | P69546 | monomer | 46168 | increases processivity of Rep, covalently and specifically links DNA |
| 42 | MutLEco | mismatch repair protein | *Escherichia coli* | 1BKN, 1B62, 1B63 | P23367 | homo-dimer | 67924 | increases processivity of UvrD (and Rep) |
| 43 | KuMtu | DNA repair protein | *Mycobacterium tuberculosis* | | O05866 | homo-dimer | 30904 | increases processivity of UvrD1. Structure available for human Ku |
| 44 | OnTEBP | telomere binding protein | *Oxytricha nova*-Alpha | 1OTC | P29549 | hetero-dimer | 56082 | Specific biding to 3' end T4G4T4G4. Alpha subunit may be enough |
| | | | *Oxytricha nova*-Beta | | P16458 | | 41446 | |
| 45 | EcrTEBP | telomere binding protein | *Euplotes crassus* | | Q06183 | monomer | 53360 | Homolog to OnTEBP with no Beta subunit in genome |
| 46 | TteTEBP | telomere binding protein | *Tetrachymena termophila* Alpha | | Q23FB9 | hetero-dimer | 53073 | Homolog to OnTEBP-Alpha |
| | | | *Tetrachymena termophila* Beta | | Q23FH0 | | 54757 | May be homolog to OnTEBP Beta |
| 47 | pot1Spo | telomere binding proteins | *Schizosaccharomyces pombe* | | O13988 | monomer | 64111 | related to TEBP |

TABLE 4-continued

Suitable polynucleotide binding motifs

| No. | Name | Class | Organism | Structure | Sequence | Functional form | MW (Da) | Notes |
|---|---|---|---|---|---|---|---|---|
| 48 | Cdc13pSce | telomere binding proteins | *Saccharomyces cerevisiae* | | C7GSV7 | monomer | 104936 | specific binding to telomeric DNA |
| 49 | C1 | repressor | Bacteriophage 434 | | P16117 | homo-dimer | 10426 | binds DNA specifically as homo-dimer |
| 50 | LexA | repressor | *Escherichia coli* | 1LEB | P0A7C2 | homo-dimer | 22358 | binds DNA specifically as homo-dimer |

The polynucleotide binding moiety is preferably derived from a polynucleotide binding enzyme. A polynucleotide binding enzyme is a polypeptide that is capable of binding to a polynucleotide and interacting with and modifying at least one property of the polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide binding moiety does not need to display enzymatic activity as long as it is capable of binding the polynucleotide and controlling its movement. For instance, the moiety may be derived from an enzyme that has been modified to remove its enzymatic activity or may be used under conditions which prevent it from acting as an enzyme.

The polynucleotide binding moiety is preferably derived from a nucleolytic enzyme. The enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are exonucleases, polymerases, helicases and topoisomerases, such as gyrases. Suitable exonucleases include, but are not limited to, exonuclease I from *E. coli*, exonuclease III enzyme from *E. coli*, RecJ from *T. thermophilus* and bacteriophage lambda exonuclease and variants thereof.

The polymerase is preferably a member of any of the Moiety Classification (EC) groups 2.7.7.6, 2.7.7.7, 2.7.7.19, 2.7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The polynucleotide binding moiety is preferably derived from Phi29 DNA polymerase (SEQ ID NO: 62). The moiety may comprise the sequence shown in SEQ ID NO: 62 or a variant thereof. A variant of SEQ ID NO: 62 is an enzyme that has an amino acid sequence which varies from that of SEQ ID NO: 62 and which retains polynucleotide binding activity. The variant may include modifications that facilitate binding of the polynucleotide and/or facilitate its activity at high salt concentrations and/or room temperature.

Over the entire length of the amino acid sequence of SEQ ID NO: 62, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 62 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described below. The variant may differ from the wild-type sequence in any of the ways discussed below with reference to SEQ ID NOs: 2 and 4.

The helicase may be any of those discussed above. Helicase dimers and multimers are discussed in detail below. The polynucleotide binding moiety may be a polynucleotide binding domain derived from a helicase. For instance, the polynucleotide binding moiety preferably comprises the sequence shown in SEQ ID NO: 66 or 67 or a variant thereof. A variant of SEQ ID NO: 66 or 67 is a protein that has an amino acid sequence which varies from that of SEQ ID NO: 66 or 67 and which retains polynucleotide binding activity. This can be measured as described above. The variant may include modifications that facilitate binding of the polynucleotide and/or facilitate its activity at high salt concentrations and/or room temperature.

Over the entire length of the amino acid sequence of SEQ ID NO: 66 or 67, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 66 or 67 over the entire sequence. There may be at least 80%, for example at least 85%, 90% or 95%, amino acid identity over a stretch of 40 or more, for example 50, 60, 70 or 80 or more, contiguous amino acids ("hard homology"). Homology is determined as described above. The variant may differ from the wild-type sequence in any of the ways discussed below with reference to SEQ ID NOs: 2 and 4.

The topoisomerase is preferably a member of any of the Moiety Classification (EC) groups 5.99.1.2 and 5.99.1.3.

The polynucleotide binding moiety may be any of the enzymes discussed above. The construct preferably does not comprise a helicase attached to a polymerase, a topoisomerase or a primase. The construct preferably does not comprise two or more NS3 helicases attached together. The construct more preferably does not comprise two or more NS3 helicases attached together using bis(sulfosuccinimidyl) suberate (BS³).

The moiety may be labelled with a revealing label. The label may be any of those described above.

The moiety may be isolated from any moiety-producing organism, such as *E. coli, T. thermophilus* or bacteriophage, or made synthetically or by recombinant means. For example, the moiety may be synthesized by in vitro translation and transcription as described below. The moiety may be produced in large scale following purification as described below.

Preferred Constructs

As will be clear from the discussion above, the polynucleotide binding moiety is preferably derived from a helicase. For instance, it may be a polynucleotide domain from a helicase. The moiety more preferably comprises one or more helicases. The helicases may be any of those discussed above. In such embodiments, the constructs of course comprise two or more helicases attached together. The invention provides a construct comprising two or more helicases attached together. As discussed above, each helicase must be capable of functioning as a helicase on its own. Any of the embodiments discussed above with reference to the constructs that may be used in the method of the invention, and in particular the types of helicases that may be used and the methods of attachment, are equally applicable to the constructs of the invention. The two or more helicases are preferably monomeric helicases. The two or more helicases are preferably not two or more helicase domains from helicase enzymes.

The construct of the invention preferably does not comprise two or more NS3 helicases attached together. The construct of the invention more preferably does not comprise two or more NS3 helicases attached together using bis(sulfosuccinimidyl) suberate (BS³).

The construct may comprise two, three, four, five or more helicases. In other words, the constructs of the invention may comprise a helicase dimer, a helicase trimer, a helicase tetramer, a helicase pentamer and the like.

The two or more helicases can be attached together in any orientation. Identical or similar helicases may be attached via the same amino acid residue (i.e. same position) or spatially proximate amino acid residues (i.e. spatially proximate positions) in each helicase. This is termed the "head-to-head" formation. Alternatively, identical or similar helicases may be attached via amino acid residues (or positions) on opposite or different sides of each helicase. This is termed the "head-to-tail" formation. Helicase trimers comprising three identical or similar helicases may comprise both the head-to-head and head-to-tail formations.

The two or more helicases may be different from one another (i.e. the construct is a hetero-dimer, -trimer, -tetramer or -pentamer etc.). For instance, the constructs of the invention may comprise: (a) one or more Hel308 helicases and one or more XPD helicases; (b) one or more Hel308 helicases and one or more RecD helicases; (c) one or more Hel308 helicases and one or more TraI helicases; (d) one or more XPD helicases and one or more RecD helicases; (e) one or more XPD helicases and one or more TraI helicases; or (f) one or more RecD helicases and one or more TraI helicases. The construct may comprise two different variants of the same helicase. For instance, the construct may comprise two variants of one of the helicases discussed above with one or more cysteine residues or Faz residues introduced at different positions in each variant. In this instance, the helicases can be in a head-to-tail formation. In a preferred embodiment, a variant of SEQ ID NO: 10 comprising Q442C may be attached via cysteine linkage to a variant of SEQ ID NO: 10 comprising Q557C. Cys mutants of Hel308Mbu can also be made into hetero-dimers if necessary. In this approach, two different Cys mutant pairs such as Hel308Mbu-Q442C and Hel308Mbu-Q577C can be linked in head-to-tail fashion. Hetero-dimers can be formed in two possible ways. The first involves the use of a homo-bifunctional linker as discussed above. One of the helicase variants can be modified with a large excess of linker in such a way that one linker is attached to one molecule of the protein. This linker modified variant can then be purified away from unmodified proteins, possible homo-dimers and unreacted linkers to react with the other helicase variant. The resulting dimer can then be purified away from other species.

The second involves the use of hetero-bifunctional linkers. For example, one of the helicase variants can be modified with a first PEG linker containing maleimide or iodoacetamide functional group at one end and a cyclooctyne functional group (DIBO) at the other end. An example of this is shown below:

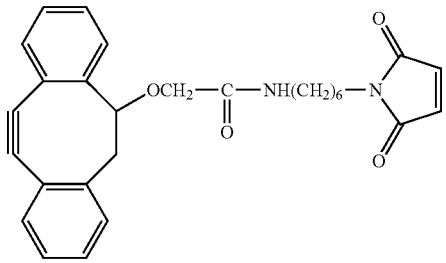

The second helicase variant can be modified with a second PEG linker containing maleimide or iodoacetamide functional group at one end and an azide functional group at the other end. An example is show below:

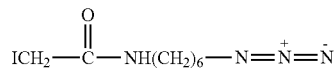

The two helicase variants with two different linkers can then be purified and clicked together (using Cu²⁺ free click chemistry) to make a dimer. Copper free click chemistry has been used in these applications because of its desirable properties. For example, it is fast, clean and not poisonous towards proteins. However, other suitable bio-orthogonal chemistries include, but are not limited to, Staudinger chemistry, hydrazine or hydrazide/aldehyde or ketone reagents (HyNic+4FB chemistry, including all Solulink™ reagents), Diels-Alder reagent pairs and boronic acid/salicyhydroxamate reagents.

These two ways of linking two different variants of the same helicase are also valid for any of the constructs discussed above in which the helicase and the moiety are different from one another, such as dimers of two different helicases and a helicase-polymerase dimer.

Similar methodology may also be used for linking different Faz variants. One Faz variant (such as SEQ ID NO: 10 comprising Q442C) can be modified with a large excess of linker in such a way that one linker is attached to one molecule of the protein. This linker modified Faz variant can then be purified away from unmodified proteins, possible homo-dimers and unreacted linkers to react with the second Faz variant (such as SEQ ID NO: 10 comprising Q577Faz). The resulting dimer can then be purified away from other species.

Hetero-dimers can also be made by linking cysteine variants and Faz variants of the same helicase or different helicases. For example, any of the above cysteine variants (such as SEQ ID NO: 10 comprising Q442C) can be used to make dimers with any of the above Faz variants (such SEQ ID NO: 10 comprising Q577Faz). Hetero-bifunctional PEG linkers with maleimide or iodoacetamide functionalities at one end and DBCO functionality at the other end can be used in this combination of mutants. An example of such a linker is shown below (DBCO-PEG4-maleimide):

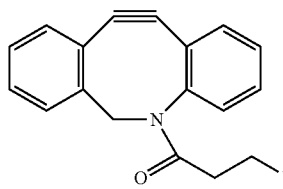

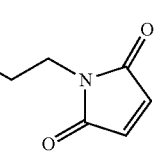

The length of the linker can be varied by changing the number of PEG units between the two functional groups.

Helicase hetero-trimers can comprise three different types of helicases selected from Hel308 helicases, XPD helicases, RecD helicases, TraI helicases and variants thereof. The same is true for oligomers comprising more than three helicases. The two or more helicases within a construct may be different variants of the same helicase, such as different more. PEG linkers are suitable because they have favourable properties such as water solubility. Other non PEG linkers can also be used in cysteine linkage.

By using similar approaches, identical Faz variants can also be made into homo-dimers. Homo-bifunctional linkers with DIBO functional groups can be used to link two molecules of the same Faz variant to make homo-dimers using $Cu^{2+}$ free click chemistry. An example of a linker is given below:

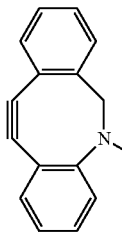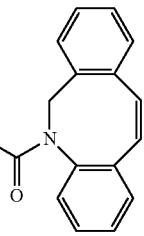

variants of SEQ ID NO: 10, 13, 16 or 19. The different variants may be modified at different positions to facilitate attachment via the different positions. The hetero-trimers may therefore be in a head-to-tail and head-to-head formation.

The two or more helicases in the constructs of the invention may be the same as one another (i.e. the construct is a homo-dimer, -trimer, -tetramer or -pentamer etc.) Homo-oligomers can comprise two or more Hel308 helicases, two or more XPD helicases, two or more RecD helicases, two or more TraI helicases or two or more of any of the variants discussed above. In such embodiments, the helicases are preferably attached using the same amino acid residue (i.e. same position) in each helicase. The helicases are therefore attached head-to-head. The helicases may be linked using a cysteine residue or a Faz residue that has been substituted into the helicases at the same position. Cysteine residues in identical helicase variants can be linked using a homo-bifunctional linker containing thiol reactive groups such as maleimide or iodoacetamide. These functional groups can be at the end of a polyethyleneglycol (PEG) chain as in the following example:

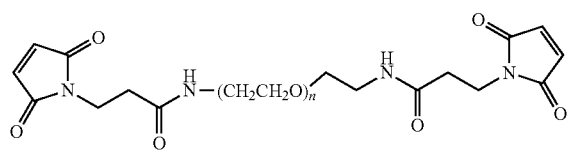

The length of the linker can be varied to suit the required applications. For example, n can be 2, 3, 4, 8, 11, 12, 16 or The length of the PEG linker can vary to include 2, 4, 8, 12, 16 or more PEG units. Such linkers can also be made to incorporate a florescent tag to ease quantifications. Such fluorescence tags can also be incorporated into Maleimide linkers.

Preferred constructs of the invention are shown in the Table 5 below.

| Preferred constructs of the invention |
|---|
| Hel308Mbu-A700C dimer 2 kDa |
| Hel308Mbu-A700C dimer 3.4 kDa |
| Hel308Mbu-Q442C 2 kDa linker homodimer |
| Hel308Mbu-Q442C 3.4 kDa linker homodimer |
| Hel308Mbu-A700C 2 kDa linker homodimer |
| Hel308Mbu-A700C-strepII. 2 kDa PEG homodimer |
| Hel308Mhu-WT 2 kDa Dimer |
| Helicase 2 k dimer (Hel308Mbu R681A, R687A, A700C - STrEP ) |
| Helicase 2 k dimer (Hel308Mbu R687A, A700C - STrEP) |
| Hel308Mhu-WT 2 kDa Dimer |
| Hel308Tga N674C Dimer 2 kDa |
| Hel308Tga N674C Dimer 2 kDa tests for assay |
| Hel308 Tga-R657A-N674C-STrEP Dimer 2 kDa |

Preferred constructs of the invention are shown in the Table 6 below. Each row shows a preferred construct in which the helicase in the left-hand column is attached to additional polynucleotide binding moiety in the right-hand column in accordance with the invention.

| Helicase | Additional polynucleotide binding moiety |
|---|---|
| Hel308 helicase as defined above (preferably SEQ ID NO: 10, 13, 16 or 19 or a variant thereof as defined above) | Polymerase preferably SEQ ID NO: 62 or a variant thereof as defined above) |
| TraI helicase as defined above (preferably SEQ ID NO: 46, 87, 98 and 102 or a variant thereof as defined above) | Polymerase preferably SEQ ID NO: 62 or a variant thereof as defined above) |
| Hel308 helicase as defined above (preferably SEQ ID NO: 10, 13, 16 or 19 or a variant thereof as defined above) | Hel308 helicase as defined above preferably SEQ NO: 10, 13, 16 or 19 or a variant thereof as defined above) |
| TraI helicase as defined above (preferably SEQ ID NO: 46, 87, 98 and 102 or a variant thereof as defined above) | TraI helicase as defined above preferably SEQ ID NO: 46, 87, 98 and 102 or a variant thereof as defined above) |
| Hel308 helicase as defined above (preferably SEQ ID NO: 10, 13, 16 or 19 or a variant thereof as defined above) | TraI helicase as defined above (preferably SEQ ID NO: 46, 87, 98 and 102 or a variant thereof as defined above) |
| TraI helicase as defined above (preferably SEQ ID NO: 46, 87, 98 and 102 or a variant thereof as defined above) | Hel308 helicase as defined above preferably SEQ ID NO: 10, 13, 16 or 19 or a variant thereof as defined above) |

The invention also provides a construct comprising a helicase and an amino acid sequence comprising SEQ ID NO: 94 (H-L domains from Topoisomerase V from *Methanopyrus kandleri*; SEQ ID NO: 89) or a variant thereof having at least 80% homology to SEQ ID NO: 94 based on amino acid identity over the entire sequence of SEQ ID NO: 94, wherein the helicase is attached to the amino acid sequence and the construct has the ability to control the movement of a polynucleotide. The helicase may be attached to the amino acid sequence in any of the ways discussed above.

The construct preferably comprises SEQ ID NO: 90 or a variant thereof having at least 80% homology to SEQ ID NO: 90 based on amino acid identity over the entire sequence of SEQ ID NO: 90.

Over the entire length of the amino acid sequence of SEQ ID NO: 94 or 90, a variant will preferably be at least 80% homologous to that sequence based on amino acid identity. More preferably, the variant polypeptide may be at least 85%, at least 90% and more preferably at least 95%, 97% or 99% homologous based on amino acid identity to the amino acid sequence of SEQ ID NO: 94 or 90 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described below. The variant may differ from the wild-type sequence in any of the ways discussed below with reference to SEQ ID NOs: 2 and 4.

Polynucleotide Sequences

The present invention also provides polynucleotide sequences which encode a construct in which the two or more helicases are genetically fused. It is straightforward to generate such polynucleotide sequences using standard techniques. A polynucleotide sequence encoding a helicase may be either fused to or inserted into a polynucleotide sequence encoding another helicase. The fusion or insertion is typically in frame. If a polynucleotide sequence encoding a helicase is inserted into a polynucleotide sequence encoding another helicase, the sequence encoding the moiety is typically flanked at both ends by restriction endonuclease sites, such as those recognized by BspE1. It may also be flanked at both ends by polynucleotide sequences encoding linkers, such as 5 to 10 codons each encoding serine or glycine.

Polynucleotide sequences may be isolated and replicated using standard methods in the art. Chromosomal DNA may be extracted from a helicase producing organism, such as *Methanococcoides burtonii*, and/or a moiety producing organism, such as *E. coli, T. thermophilus* or bacteriophage. The gene encoding the helicase and moiety may be amplified using PCR involving specific primers. The amplified sequences may then be incorporated into a recombinant replicable vector such as a cloning vector. The vector may be used to replicate the polynucleotide in a compatible host cell. Thus polynucleotide sequences encoding a helicase and/or moiety may be made by introducing a polynucleotide encoding a helicase and/or moiety into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into a suitable expression vector. In an expression vector, the polynucleotide sequence encoding a construct is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, trc, lac, ara or $\lambda_L$ promoter is typically used.

The host cell typically expresses the construct at a high level. Host cells transformed with a polynucleotide sequence encoding a construct will be chosen to be compatible with the expression vector used to transform the cell. The host cell is typically bacterial and preferably *E. coli*. Any cell with a λ DE3 lysogen, for example C41 (DE3), BL21 (DE3), JM109 (DE3), B834 (DE3), TUNER, Origami and Origami B, can express a vector comprising the T7 promoter.

Methods of the Invention

The invention provides a method of controlling the movement of a target polynucleotide using a construct of the invention, i.e. a construct comprising two or more helicases attached together. The method comprises contacting the target polynucleotide with a construct of the invention and thereby controlling the movement of the polynucleotide. The method is preferably carried out with a potential applied across the pore. As discussed in more detail below, the applied potential typically results in the formation of a complex between the pore and the construct. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The invention also provides a method of characterising a target polynucleotide. The method comprises (a) contacting the target polynucleotide with a transmembrane pore and a construct described herein such that the construct controls the movement of the target polynucleotide through the pore. The method also comprises (b) taking one or more measurements as the polynucleotide moves with respect to the pore wherein the measurements are indicative of one or more characteristics of the target polynucleotide and thereby characterising the target polynucleotide.

Steps (a) and (b) are preferably carried out with a potential applied across the pore as discussed above. In some instances, the current passing through the pore as the polynucleotide moves with respect to the pore is used to determine the sequence of the target polynucleotide. This is Strand Sequencing.

The method of the invention is for characterising a target polynucleotide. A polynucleotide is defined above.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic layer may be a monolayer or a bilayer. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/

004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro. The polynucleotide may be coupled to the membrane. This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The polynucleotide may be coupled directly to the membrane. The polynucleotide is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the helicase. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the helicase's active site. If the coupling is transient, then when the coupled end randomly becomes free of the bilayer, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the polynucleotide is coupled to an amphiphilic layer. Coupling of polynucleotides to synthetic lipid bilayers has been carried out previously with various different tethering strategies. These are summarised in Table 7 below.

TABLE 7

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies. " *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer with a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the amplified target DNA will contain a reactive group for coupling.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA MspB, MspC or MspD, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et at (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et at (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 8 below. Where amino acids have similar polarity, this can also be determined by reference to the hydropathy scale for amino acid side chains in Table 9.

TABLE 8

Chemical properties of amino acids

| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gty | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic neutral |

TABLE 9

Hydropathy scale

| Side Chain | Hydropathy |
| --- | --- |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described above.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the construct. The variant preferably comprises one or more reactive cysteine residues that facilitate attachment to the construct. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

The construct may be covalently attached to the pore. The construct is preferably not covalently attached to the pore. The application of a voltage to the pore and construct typically results in the formation of a sensor that is capable of sequencing target polynucleotides. This is discussed in more detail below.

Any of the proteins described herein, i.e. the transmembrane protein pores or constructs, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin hetero-oligomers (Chem Biol. 1997 July; 4(7): 497-505).

The pore and/or construct may be labelled with a revealing label. The revealing label may be any suitable label which allows the pore to be detected. Suitable labels include, but are not limited to, fluorescent molecules, radioisotopes, e.g. $^{125}I$, $^{35}S$, enzymes, antibodies, antigens, polynucleotides and ligands such as biotin.

Proteins may be made synthetically or by recombinant means. For example, the pore and/or construct may be synthesized by in vitro translation and transcription (IVTT). The amino acid sequence of the pore and/or construct may be modified to include non-naturally occurring amino acids or to increase the stability of the protein. When a protein is produced by synthetic means, such amino acids may be introduced during production. The pore and/or construct may also be altered following either synthetic or recombinant production.

The pore and/or construct may also be produced using D-amino acids. For instance, the pore or construct may comprise a mixture of L-amino acids and D-amino acids. This is conventional in the art for producing such proteins or peptides.

The pore and/or construct may also contain other non-specific modifications as long as they do not interfere with pore formation or construct function. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

The pore and construct can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore and/or construct may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore and/or construct may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured for example by determining the number of interactions between the target polynucleotide and the pore or the duration of interaction between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:

(a) contacting the target polynucleotide with a transmembrane pore and a construct described herein such that the target polynucleotide moves through the pore and the construct controls the movement of the target polynucleotide through the pore; and (b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. Hel308, XPD, RecD and TraI helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method may be carried out in the presence of free nucleotides or free nucleotide analogues and/or an enzyme cofactor that facilitates the action of the construct. The method may also be carried out in the absence of free nucleotides or free nucleotide analogues and in the absence of an enzyme cofactor. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The target polynucleotide may be contacted with the construct and the pore in any order. In is preferred that, when the target polynucleotide is contacted with the construct and the pore, the target polynucleotide firstly forms a complex with the construct. When the voltage is applied across the pore, the target polynucleotide/construct complex then forms a complex with the pore and controls the movement of the polynucleotide through the pore.

As discussed above, helicases may work in two modes with respect to the pore. The constructs described herein comprising such helicases can also work in two modes. First, the method is preferably carried out using the construct such that it moves the target sequence through the pore with the field resulting from the applied voltage. In this mode the 5' end of the DNA is first captured in the pore, and the construct moves the DNA into the pore such that the target sequence is passed through the pore with the field until it finally translocates through to the trans side of the bilayer. Alternatively, the method is preferably carried out such that the construct moves the target sequence through the pore against the field resulting from the applied voltage. In this mode the 3' end of the DNA is first captured in the pore, and the construct moves the DNA through the pore such that the target sequence is pulled out of the pore against the applied field until finally ejected back to the cis side of the bilayer.

Other Methods

The invention also provides a method of forming a sensor for characterising a target polynucleotide. The method comprises forming a complex between a pore and a construct described herein. The complex may be formed by contacting the pore and the construct in the presence of the target polynucleotide and then applying a potential across the pore. The applied potential may be a chemical potential or a voltage potential as described above. Alternatively, the complex may be formed by covalently attaching the pore to the construct. Methods for covalent attachment are known in the art and disclosed, for example, in International Application Nos. PCT/GB09/001679 (published as WO 2010/004265) and PCT/GB10/000133 (published as WO 2010/086603). The complex is a sensor for characterising the target polynucleotide. The method preferably comprises forming a complex between a pore derived from Msp and a construct described herein. Any of the embodiments discussed above with reference to the methods of the invention equally apply to this method. The invention also provides a sensor produced using the method of the invention.

Kits

The present invention also provides a kit for characterising a target polynucleotide. The kit comprises (a) a pore and (b) a construct described herein. Any of the embodiments discussed above with reference to the method of the invention equally apply to the kits.

The kit may further comprise the components of a membrane, such as the phospholipids needed to form an amphiphilic layer, such as a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising a target polynucleotide. The apparatus comprises a plurality of pores and a plurality of constructs described herein. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention.

The apparatus is preferably set up to carry out the method of the invention.

The apparatus preferably comprises:

a sensor device that is capable of supporting the plurality of pores and being operable to perform polynucleotide characterisation using the pores and constructs; and at least one reservoir for holding material for performing the characterisation.

The apparatus preferably comprises:

a sensor device that is capable of supporting the membrane and plurality of pores and being operable to perform polynucleotide characterising using the pores and constructs;

at least one reservoir for holding material for performing the characterising;

a fluidics system configured to controllably supply material from the at least one reservoir to the sensor device; and one or more containers for receiving respective samples, the fluidics system being configured to supply the samples selectively from the one or more containers to the sensor device. The apparatus may be any of those described in International Application No. PCT/GB08/004127 (published as WO 2009/077734), PCT/GB10/000789 (published as WO 2010/122293), International Application No. PCT/GB10/002206 (not yet published) or International Application No. PCT/US99/25679 (published as WO 00/28312).

Methods of Producing Constructs of the Invention

The invention also provides a method of producing a construct of the invention. In one embodiment, the method comprises attaching, preferably covalently attaching, two or more helicases. In another embodiment, the method comprises attaching, preferably covalently attaching, a helicase to an amino acid sequence comprising SEQ ID NO: 94 or a variant thereof having at least 80% homology to SEQ ID NO: 94 based on amino acid identity over the entire sequence of SEQ ID NO: 94 and thereby producing the construct. Any of the helicases discussed above can be used in the methods. The site of and method of attachment are selected as discussed above.

The method may further comprise determining whether or not the construct is capable of controlling the movement of a polynucleotide. Assays for doing this are described above. If the movement of a polynucleotide can be controlled, the helicases have been attached correctly and a construct of the invention has been produced. If the movement of a polynucleotide cannot be controlled, a construct of the invention has not been produced.

The following Example illustrates the invention.

EXAMPLE 1

In this Example and all of the following Examples, bismaleimide-functionalized PEG linkers are identified with reference to their molecular weight. For instance, "2 kDa", "2 kDA linker" or "2 kDA PEG linker" refers to a bismaleimide-functionalized PEG linker having a molecular weight of 2 kDa.

This Example describes the method of synthesising the Hel308 Mbu(R687A/A700C)-2 kDa dimer (where each monomer unit comprises SEQ ID NO: 10 with the mutations R687A/A700C, with one monomer unit being linked to the other via position 700 of each monomer unit using a 2 kDa PEG linker) and the Hel308 Mbu(R681A/R687A/A700C)-2 kDa dimer (where each monomer unit comprises SEQ ID NO: 10 with the mutations R681A/R687A/A700C, with one monomer unit being linked to the other via position 700 of each monomer unit using a 2 kDa PEG linker). In the case of these dimers the A700C is the added mutation that serves as the connection for the linker in the dimer proteins (Mbu/R687A A700C-2 kDa PEG linker-A700C Mbu/R687A and Mbu/R681A/R687A A700C-2 kDa PEG linker-A700C Mbu/R681A/R687A). 5 cysteines are naturally present in Hel308Mbu (SEQ ID NO: 10) but these are not very reactive and, therefore, the reaction is almost completely centered on A700C.

DTT was added to Hel308Mbu R687A/A700C (2 mg/mL) (SEQ ID NO: 10 with the mutations R687A/A700C) to 5 mM and placed on a rotator for 30 min. The reduced protein was buffer exchanged into 100 mM potassium phosphate, 500 mM NaCl, 5 mM EDTA, 0.1% tween20, pH7.2. 30 mer ssDNA (SEQ ID NO: 68) was added to the helicase (10 fold excess) to protect the internal cysteines and increase the likelihood of the protein remaining stable. The protein/DNA solution was diluted to 1.5 mg/mL with buffer, placed under an atmosphere of nitrogen and incubated at room temperature for 30 min. 0.016 mM bismaleimide-PEG (2 kDa) was added and the reaction allowed to proceed at room temperature under an atmosphere of nitrogen for 2 h. 10 mM DTT was added to quench the reaction and break up any disulfide bridged species. The Hel308 Mbu(R687A/A700C)-2 kDa mutant dimer was purified immediately using an initial Strep-tactin step to remove DNA and reagents, followed by an anion-exchange chromatography step to separate the dimer from all other species present in solution.

An AKTA purifier machine was used for the purifications. Strep purification was performed on a 1 mL StrepTactin Sepharose High Performance column. The protein solution was buffer exchanged into binding buffer (50 mM Tris, 500 mM NaCl, 2 mM EDTA, 2 mM DTT, 0.05% tween20, pH 8.0) before being loaded onto the column. After an initial wash step to remove all unbound material, the protein was washed with the same buffer containing 2 M salt to dissociate the DNA from the protein before eluting it with 10 mM desthiobiotin in buffer. The eluted protein was buffer exchanged into LOW buffer (50 mM Tris, 80 mM NaCl, 2 mM DTT, 0.05% tween20, pH 8.0) to prepare it for the separation between the dimer and all other species present in solution. The ion exchange step was performed on a GE Mini Q PC 3.2/3 column with a flow rate of 0.4 mL/min, on a gradient between LOW and HIGH buffer (50 mM Tris, 2 M NaCl, 2 mM DTT, 0.05% tween20, pH 8.0). The start, middle and end of the eluted dimer peak were pooled separately and given separate ID numbers. All three were activity assayed before the middle peak was used for tests in electrophysiology. FIG. 1 shows a gel of the Hel308 Mbu (R687A/A700C) monomer (SEQ ID NO: 10 with the mutations R687A/A700C, lane 2) and the Hel308 Mbu(R687A/A700C)-2 kDa dimer (lane 4). The above procedure can be used in order to form the Hel308 Mbu(R681A/R687A/A700C)-2 kDa dimer (FIG. 1, Lane 5) from the Hel308 Mbu(R681A/R687A/A700C) monomer (SEQ ID NO: 10 with the mutations R681A/R687A/A700C, FIG. 1, Lane 3).

EXAMPLE 2

This Example describes the method of synthesising the Hel308 Mhu multimer (multiple units of SEQ ID NO: 19). There are no added mutations on Hel308Mhu (SEQ ID NO: 19), so the cysteines contained in the WT are used as the sites for linkage.

DTT was added to Hel308 Mhu (1.83 mg/mL) (SEQ ID NO: 19) to 10 mM and placed on a rotator for 30 min. The reduced protein was buffer exchanged into 100 mM potassium phosphate, 500 mM NaCl, 5 mM EDTA, 0.1% tween20, pH7.2. 30mer ssDNA (SEQ ID NO: 68) was added to the helicase (6 fold excess) to protect the internal cysteines and increase the likelihood of the protein remaining stable. The protein/DNA solution was diluted to 1.6 mg/mL with buffer, placed under an atmosphere of nitrogen and incubated at room temperature for 30 min. 0.0095 mM bismaleimide-PEG (2 kDa) was added and the reaction allowed to proceed at room temperature under an atmosphere of nitrogen for 2 h. 10 mM DTT was added to quench the reaction and break up any disulfide bridged species. The Hel308 Mhu multimer was purified immediately using an initial Strep-tactin step to remove DNA and reagents, followed by anion-exchange and gel filtration chromatography steps to remove the monomer from all other species present in solution.

Figure 2:
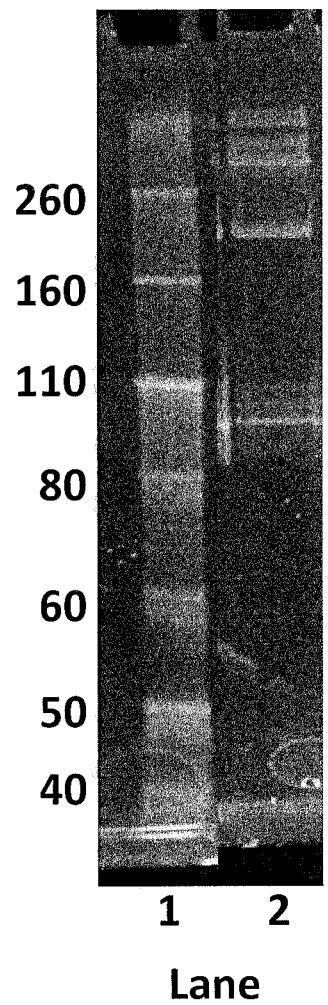
FIG. 2 shows a gel of the Hel308 Mhu multimer. Lane 1 shows an appropriate protein ladder and Lane 2 corresponds to the Hel308 Mhu multimer (multiple units of SEQ ID NO: 19).

An AKTA purifier machine was used for the purifications. Strep purification was performed on a 5 mL StrepTactin Sepharose High Performance column. The protein solution was buffer exchanged into binding buffer (50 mM Tris, 500 mM NaCl, 0.1% tween20, pH 8.0) before being loaded onto the column. After an initial wash step, to remove all unbound material, the protein was washed with the same buffer containing 2 M NaCl to dissociate the DNA from the protein, before eluting it with 10 mM desthiobiotin in buffer. The eluted protein was buffer exchanged into LOW buffer (50 mM Tris, 80 mM NaCl, 2 mM DTT, 0.05% tween20, pH 8.0) to prepare it for the separation between the dimer and all other species present in solution. The ion exchange step was performed on a GE Mono Q 5/50 GL column with a flow rate of 1 mL/min, on a gradient between LOW and HIGH buffer (50 mM Tris, 2 M NaCl, 2 mM DTT, 0.05% tween20, pH 8.0). The elution peak was further purified by anion exchange on the same column 3 times. The collected elution peak from the last purification step was collected, concentrated to 0.25 mL, buffer, exchanged into 50 mM Tris, 500 mM NaCl, 2 mM DTT, pH 8.0 and purified by gel filtration on a Superdex™ 10/300 GL column. The final protein had an approximate 1:1:1:1 ratio of monomer:dimer:trimer:multimers (ONT Ref—ONLP4454). FIG. 2 shows a gel of the Hel308 Mhu multimer sample (lane 2).

EXAMPLE 3

This Example describes the method of synthesising the Hel308 Tga(R657A/N674C)-2 kDa dimer (where each monomer unit comprises SEQ ID NO: 16 with the mutations R657A/N674C, with one monomer unit being linked to the other via position 674 of each monomer unit using a 2 kDa PEG linker). In the case of this dimer the N674C is the added mutation that serves as the connection for the linker in the dimer protein (Tga N674C-2 kDa PEG linker-N674C Tga).

DTT was added Hel308 Tga(R657A/N674C) (2 mg/mL) (where each monomer unit comprises SEQ ID NO: 16 with the mutations R657A/N674C, with one monomer unit being linked to the other via position 674 of each monomer unit using a 2 kDa PEG linker) to 10 mM and placed on a rotator for 30 min. The reduced protein was buffer exchanged into 100 mM potassium phosphate, 500 mM NaCl, 5 mM EDTA, 0.1% tween20, pH7.2. 30mer ssDNA (SEQ ID NO: 68) was added to the helicase to increase the likelihood of the protein remaining stable. The protein/DNA solution was diluted to 1.6 mg/mL with buffer, placed under an atmosphere of nitrogen and incubated at room temperature for 30 min. 0.038 mM bismaleimide-PEG (2 kDa) was added and the reaction allowed to proceed at 23° C. under an atmosphere of nitrogen for 2.5 h. 10 mM DTT was added to quench the reaction and break up any disulfide bridged species. The Hel308 Tga(R657A/N674C) mutant dimer was purified immediately using an initial Strep-tactin step to remove DNA and reagents, followed by an anion-exchange chromatography step to separate dimer from all other species present in solution.

Figure 3:
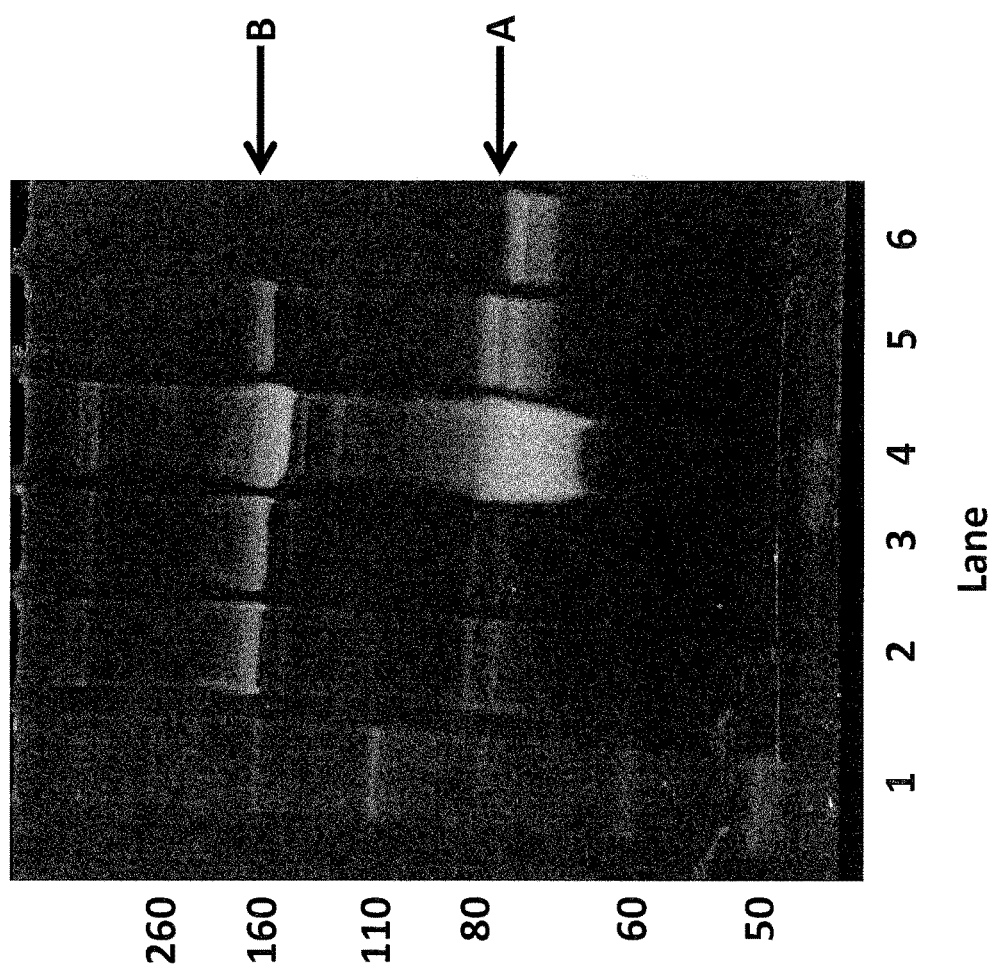
FIG. 3 shows a gel of the Hel308 Tga(R657A/N674C)-2 kDa dimer and monomer at various stages during formation and purification (Lane 1=protein ladder, Lane 2=Hel308 Tga(R657A/N674C)-2 kDa dimer after heating at 90° C. for 10 min, Lane 3=Hel308 Tga(R657A/N674C)-2 kDa dimer (where each monomer unit comprises SEQ ID NO: 16 with the mutations R657A/N674C, with one monomer unit being linked to the other via position 674 of each monomer unit using a 2 kDa PEG linker), Lane 4=elution peak from a Strep-Tactin Sepharose purification, Lane 5=initial reaction mixture and Lane 6=Hel308 Tga(R657A/N674C) monomer (SEQ ID NO: 16 with the mutations R657A/N674C)). The band labelled A corresponds to the monomer and the band labelled B corresponds to the dimer.

An AKTA purifier machine was used for the purifications. Strep purification was performed on a 5 mL StrepTactin Sepharose High Performance column. The protein solution was buffer exchanged into binding buffer (50 mM Tris, 200 mM NaCl, 1 mM MgCl2, 2 mM DTT, 0.05% tween20, pH 8.0) before being loaded onto the column. After an initial wash step, to remove all unbound material, the protein was washed with the same buffer containing 4 mM ATP, to remove DNA from the protein, before eluting it with 10 mM desthiobiotin in buffer. The eluted protein was concentrated to 0.25 mL, buffer exchanged into 50 mM Tris, 250 mM NaCl, 2 mM DTT, 1 mM MgCl2, 0.05% tween20, pH 8.0 and purified by gel filtration on a Superdex™ 10/300 GL column. FIG. 3 shows a gel of the Hel308 Tga(R657A/N674C)-2 kDa dimer and monomer at various stages during formation and purification (Lane 1=protein ladder, Lane 2=Hel308 Tga(R657A/N674C)-2 kDa dimer after heat treatment, Lane 3=Hel308 Tga(R657A/N674C)-2 kDa dimer (where each monomer unit comprises SEQ ID NO: 16 with the mutations R657A/N674C, with one monomer unit being linked to the other via position 674 of each monomer unit using a 2 kDa PEG linker), Lane 4=strep elution, Lane 5=initial reaction mixture and Lane 6=Hel308 Tga(R657A/N674C) monomer (SEQ ID NO: 16 with the mutations R657A/N674C)).

EXAMPLE 4

This Example compares the DNA binding ability of various Hel308 Mbu helicase constructs with that of the Hel308 Mbu monomer (SEQ ID NO: 10) using a fluorescence based assay.

Figure 4:
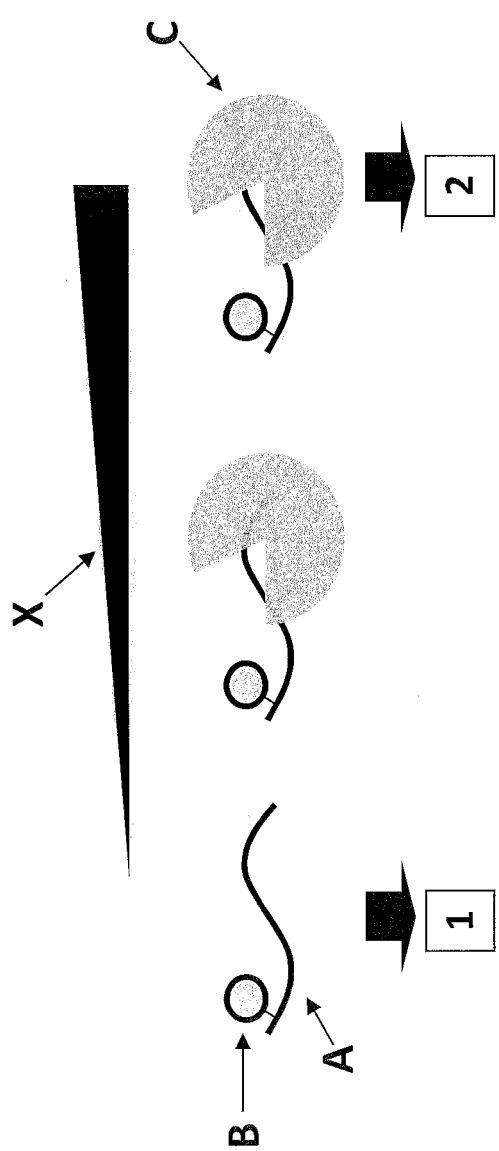
FIG. 4 shows a fluorescence assay for testing helicase/DNA binding. A custom fluorescent substrate was used to assay the ability of various helicases to bind to single-stranded DNA. The 88 nt single-stranded DNA substrate (1 nM final, SEQ ID NO: 69, labelled A) has a carboxyfluorescein (FAM) base at its 5' end (circle labelled B). As the helicase (labelled C) binds to the oligonucleotide in buffered solution (400 mM NaCl, 10 mM Hepes, pH8.0, 1 mM $MgCl_2$), the fluorescence anisotropy (a property relating to the rate of free rotation of the oligonucleotide in solution) increases. The lower the amount of helicase needed to effect an increase in anisotropy, the tighter the binding affinity between the DNA and helicase. Situation 1 with no enzyme bound has a faster rotation and low anisotropy, whereas, situation 2 with enzyme bound has slower rotation and high anisotropy. The black bar labelled X corresponds to increasing helicase concentration (the thicker the bar the higher the helicase concentration).
Figure 5:
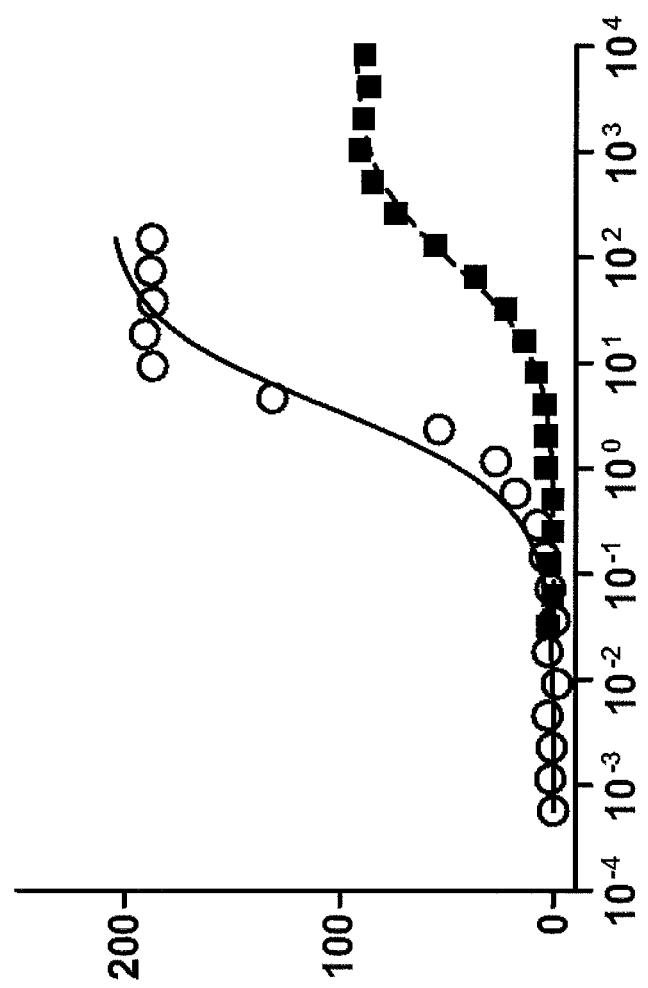
FIG. 5 shows the change in anisotropy of the DNA oligonucleotide (SEQ ID NO: 69, which has a carboxyfluorescein base at its 5' end) with increasing amounts of various Hel308 Mbu constructs (y-axis label=Anisotropy (blank subtracted), x-axis label=Protein Concentration (nM)). The data with black square points correspond to the Hel308 Mbu monomer (SEQ ID NO: 10). The data with the empty circles correspond to the Hel308 Mbu A700C 2 kDa dimer (where each monomer unit comprises SEQ ID NO: 10 with the mutation A700C, with one monomer unit being linked to the other via position 700 of each monomer unit using a 2 kDa PEG linker). A lower concentration of the Hel308 Mbu A700C 2 kDa dimer is required to effect an increase in anisotropy, therefore, the dimer has a higher binding affinity for the DNA than the monomer.
Figure 6:
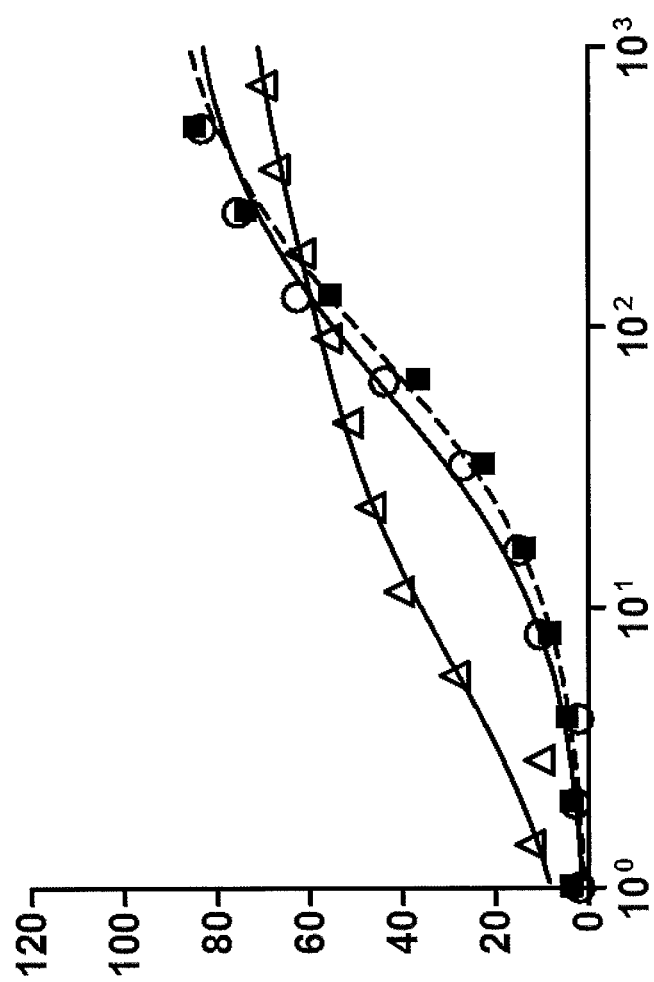
FIG. 6 shows the change in anisotropy of the DNA oligonucleotide (SEQ ID NO: 69, which has a carboxyfluorescein base at its 5' end) with increasing amounts of various Hel308 (Mbu) constructs (y-axis label=Anisotropy (blank subtracted), x-axis label=Protein Concentration (nM)). The data with black square points correspond to the Hel308 Mbu monomer (SEQ ID NO: 10). The data with the empty circles correspond to Hel308 Mbu-GTGSGA-(HhH)2 (where a helicase monomer unit (SEQ ID NO: 10) is attached by the linker sequence GTGSGA to a HhH2 domain (SEQ ID NO: 75)) and the data with the empty triangles correspond to Hel308 Mbu-GTGSGA-(HhH)2-(HhH)2 (where a helicase monomer unit (SEQ ID NO: 10) is attached by the linker sequence GTGSGA to a (HhH)2-(HhH)2 domain (SEQ ID NO: 76)). The Hel308 Mbu helicases with additional helix-hairpin-helix binding domains attached show an increase in anisotropy at a lower concentration than the monomer. This indicates that the Hel308 Mbu constructs with additional binding domains have a stronger binding affinity for DNA than the monomer. The Hel308 Mbu-GTGSGA-(HhH)2-(HhH)2, which has four HhH domains, was observed to bind DNA more tightly than Hel308 Mbu-GTGSGA-(HhH)2 which only has two HhH domains.
Figure 7:
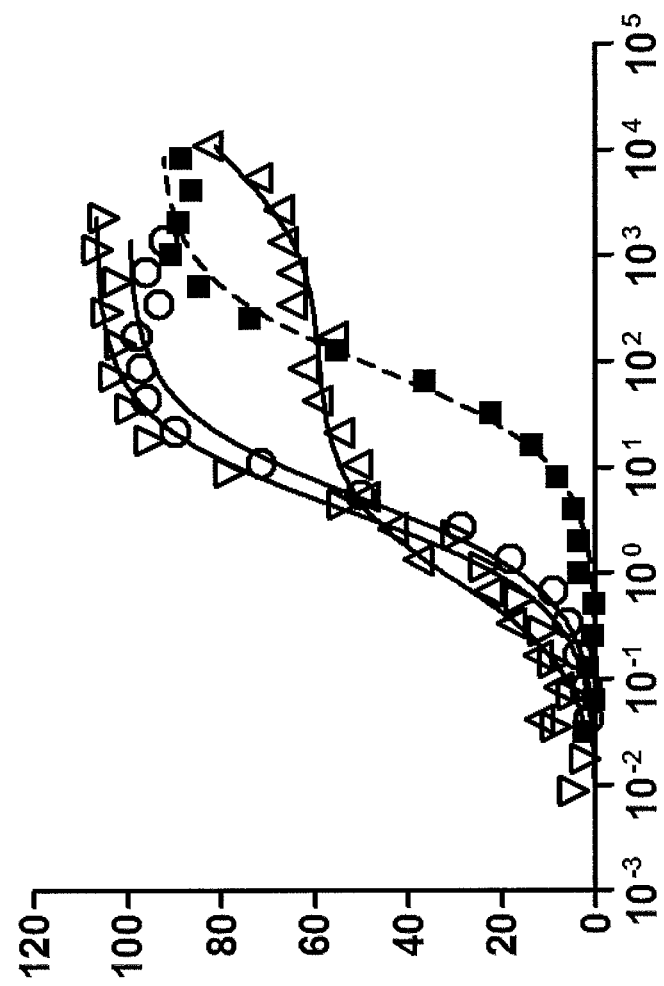
FIG. 7 shows the change in anisotropy of the DNA oligonucleotide (SEQ ID NO: 69, which has a carboxyfluorescein base at its 5' end) with increasing amounts of various Hel308 (Mbu) constructs (y-axis label=Anisotropy (blank subtracted), x-axis label=Protein Concentration (nM)). The data with black square points correspond to the Hel308 Mbu monomer (SEQ ID NO: 10). The data with the empty circles correspond to Hel308 Mbu-GTGSGA-UL42HV1-I320Del (where a helicase monomer unit (SEQ ID NO: 10) is attached by the linker sequence GTGSGA to UL42HV1-I320Del (SEQ ID NO: 63)), the data with the empty triangles pointing up correspond to Hel308 Mbu-GTGSGA-gp32RB69CD (where a helicase monomer unit (SEQ ID NO: 10) is attached by the linker sequence GTGSGA to gp32RB69CD (SEQ ID NO: 64)) and the data with empty triangles pointing down correspond to Hel308 Mbu-GTGSGA-gp2.5T7-R211Del (where a helicase monomer unit (SEQ ID NO: 10) is attached by the linker sequence GTGSGA to gp2.5T7-R211Del (SEQ ID NO: 65)). All of the Hel308 Mbu helicases which have additional binding domains attached (Hel308 Mbu-GTGSGA-UL42HV1-I320Del, Hel308 Mbu-GTGSGA-gp32RB69CD and Hel308 Mbu-GTGSGA-gp2.5T7-R211Del) show an increase in anisotropy at a lower concentration than the monomer. This indicates that the Hel308 Mbu constructs with additional binding domains have a stronger binding affinity for DNA than the monomer.

A custom fluorescent substrate was used to assay the ability of various helicases to bind to single-stranded DNA. The 88 nt single-stranded DNA substrate (1 nM final, SEQ ID NO: 69) has a carboxyfluorescein (FAM) base at its 5' end. As helicase binds to the oligonucleotide in a buffered solution (400 mM NaCl, 10 mM Hepes, pH8.0, 1 mM MgCl$_2$), the fluorescence anisotropy (a property relating to the rate of free rotation of the oligonucleotide in solution) increases. The lower the amount of helicase needed to affect an increase in anisotropy, the tighter the binding affinity between the DNA and helicase (FIG. 4). FIGS. 5-8 show the change in anisotropy of the DNA oligonucleotide (SEQ ID NO: 69, which has a carboxyfluorescein base at its 5' end) with increasing amounts of various Hel308 (Mbu) constructs. All of the constructs tested show an increase in anisotropy at a lower concentration than the monomer. The constructs tested were:

1. Hel308 Mbu A700C 2 kDa dimer (helicase dimer where each monomer unit comprises SEQ ID NO: 10 with the mutation A700C, with one monomer unit being linked to the other via position 700 of each monomer unit using a 2 kDa PEG linker),
2. Hel308 Mbu-GTGSGA-(HhH)2 (where a helicase monomer unit (SEQ ID NO: 10) is attached by the linker sequence GTGSGA to a helix-hairpin-helix (HhH2) domain (SEQ ID NO: 75)),
3. Hel308 Mbu-GTGSGA-(HhH)2-(HhH)2 (where a helicase monomer unit (SEQ ID NO: 10) is attached by the linker sequence GTGSGA to a (HhH)2-(HhH)2 domain (SEQ ID NO: 76) where HhH is a helix-hairpin-helix domain),
4. Hel308 Mbu-GTGSGA-UL42HV1-I320Del (where a helicase monomer unit (SEQ ID NO: 10) is attached by the linker sequence GTGSGA to processivity factor UL42HV1-I320Del (SEQ ID NO: 63)),
5. Hel308 Mbu-GTGSGA-gp32RB69CD (where a helicase monomer unit (SEQ ID NO: 10) is attached by the linker sequence GTGSGA to SSB gp32RB69CD (SEQ ID NO: 64)),
6. Hel308 Mbu-GTGSGA-gp2.5T7-R211Del (where a helicase monomer unit (SEQ ID NO: 10) is attached by the linker sequence GTGSGA to SSB gp2.5T7-R211Del (SEQ ID NO: 65)) and
7. (gp32RB69CD)-Hel308 Mbu) (where the SSB gp32RB69CD (SEQ ID NO: 64) is attached by the linker sequence GTGSGT to the helicase monomer unit (SEQ ID NO: 10)).

Figure 8:
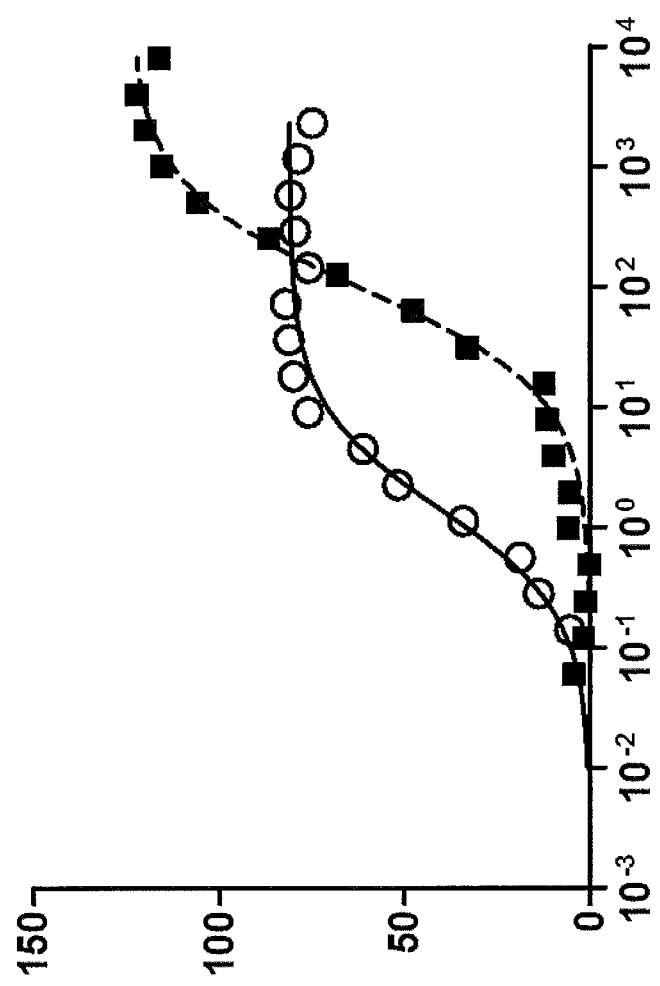
FIG. 8 shows the change in anisotropy of the DNA oligonucleotide (SEQ ID NO: 69, which has a carboxyfluorescein base at its 5' end) with increasing amounts of various Hel308 (Mbu) constructs (y-axis label=Anisotropy (blank subtracted), x-axis label=Protein Concentration (nM)). The data with black square points correspond to the Hel308 Mbu monomer. The data with the empty circles correspond to (gp32RB69CD)-Hel308 Mbu (where the gp32RB69CD (SEQ ID NO: 64) is attached by the linker sequence GTGSGT to the helicase monomer unit (SEQ ID NO: 10)). The (gp32RB69CD)-Hel308 Mbu helicase construct shows an increase in anisotropy at a lower concentration than the monomer, indicating tighter binding to the DNA was observed in comparison to the monomer.
Figure 9:
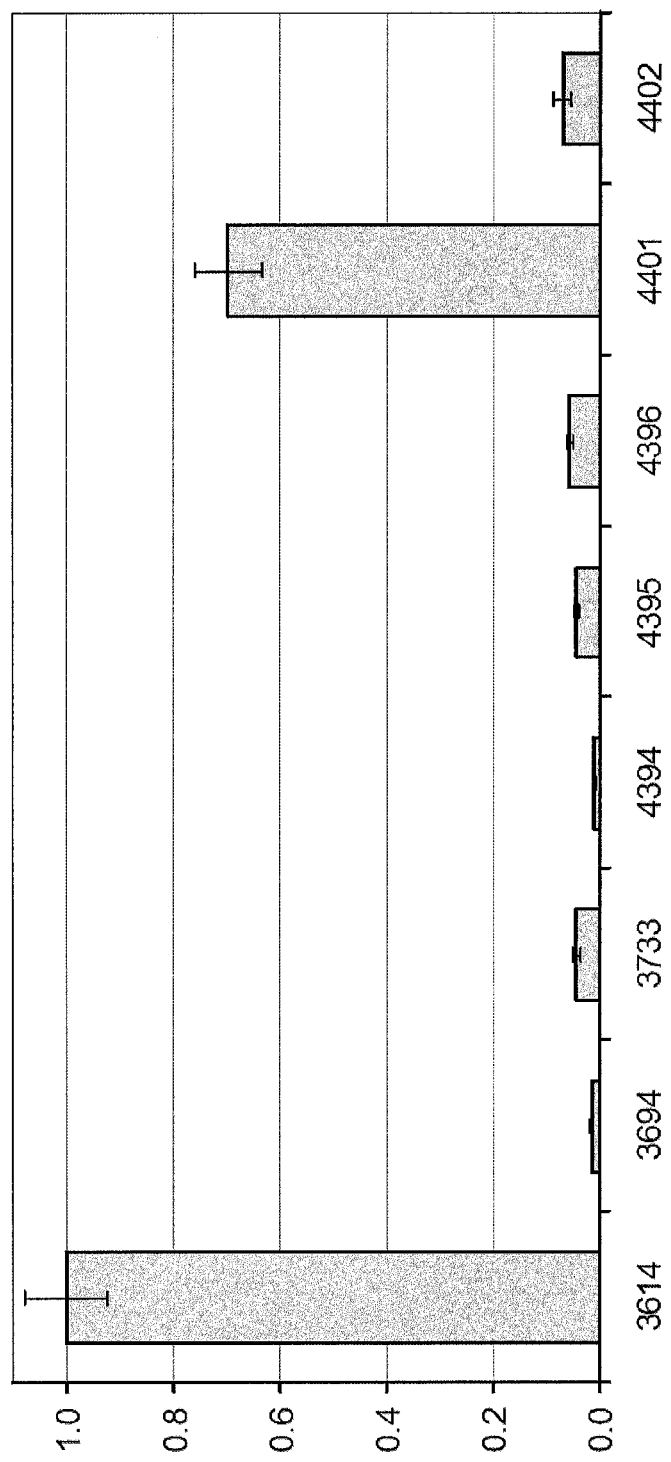
FIG. 9 shows relative equilibrium dissociation constants ($K_d$) (with respect to the Hel308 Mbu monomer) for various Hel308 (Mbu) constructs, obtained through fitting two phase dissociation binding curves through the data shown in FIGS. 5-8 using Graphpad Prism software (y-axis label=Relative $K_d$, x-axis label=Ref. Number). The reference numbers correspond to the following Hel308 (Mbu) constructs— 3614=Hel308 (Mbu), 3694=(gp32-RB69CD)-Hel308 Mbu, 3733=Hel308 (Mbu)-A700C 2 kDa PEG dimer, 4401=Hel308 (Mbu)-GTGSGA-(HhH)2, 4402=Hel308 (Mbu)-GTGSGA-(HhH)2-(HhH)2, 4394=Hel308 (Mbu)-GTGSGA-gp32RB69CD, 4395=Hel308 (Mbu)-GTGSGA-gp2.5T7-R112Del and 4396=Hel308 (Mbu)-GTGSGA-UL42HV1-I320Del. All of the helicase constructs with additional binding domains attached show a lower equilibrium dissociation constant than the Hel308 Mbu monomer alone.

FIG. 9 shows the relative equilibrium dissociation constants ($K_d$) (with respect to Hel308 Mbu monomer (SEQ ID NO: 10)) for various Hel308 (Mbu) constructs obtained through fitting two phase dissociation binding curves through the data shown in FIGS. 5-8 using Graphpad Prism software. All of the helicase constructs with additional binding domains attached show a lower equilibrium dissociation constant than the Hel308 Mbu monomer (SEQ ID NO: 10) alone. Therefore, the Hel308 Mbu helicase with additional binding constructs all show stronger binding to DNA than the Hel308 Mbu monomer.

EXAMPLE 5

Figure 10:
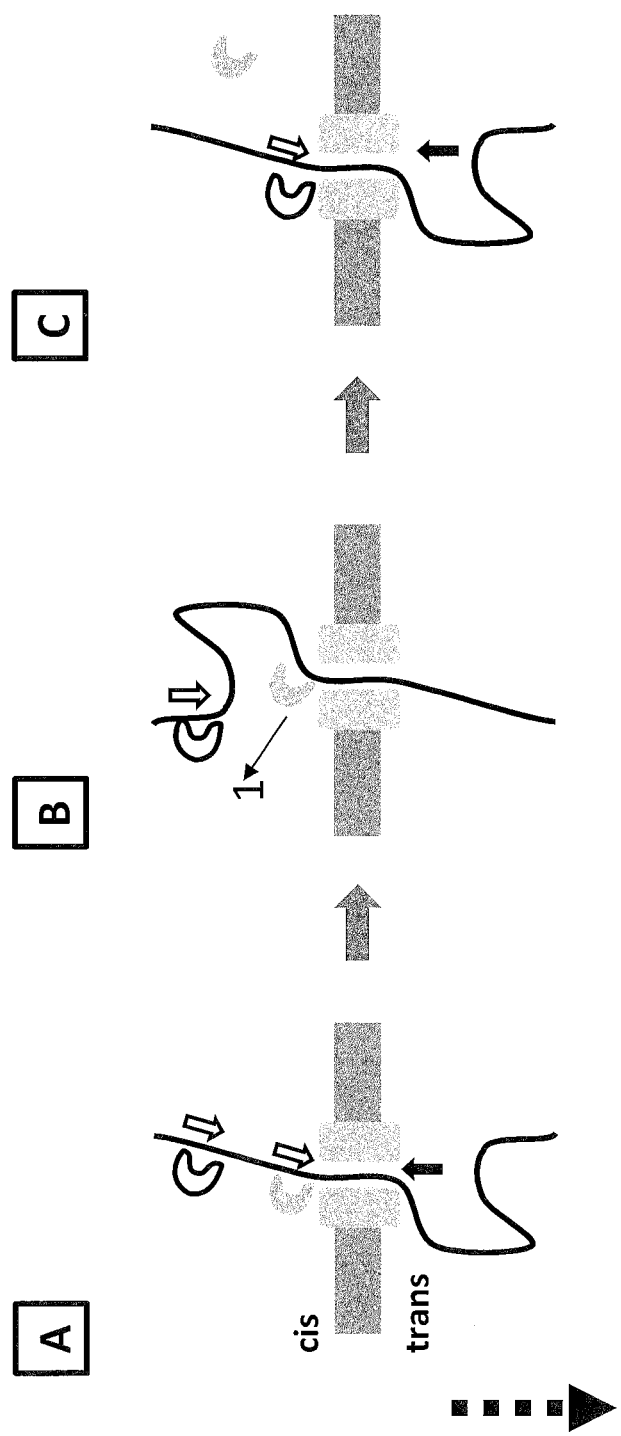
FIG. 10 shows a schematic of helicase monomers controlling the movement of a polynucleotide through a nanopore in a membrane. A) Under an applied field (the direction of the applied field is indicated by the dashed black arrow), DNA in the cis compartment is captured by the nanopore, and translocates through the nanopore until the first helicase (grey semi-circle) contacts the top of the nanopore. After this point, the helicase will move along the DNA (in the presence of dNTP and suitable metal ion) controlling the movement of the DNA through the nanopore (the direction of the enzyme movement is indicated by the non-filled arrow). In the implementation shown, the DNA strand is captured by the 5' end by the pore, and the enzymes move 3' to 5' pulling the DNA against the field. As long as the enzyme does not dissociate, the strands will all end in the same way at the 5' end and will finally be ejected back to the cis side. Alternatively, strands captured by the 3' end by the nanopore will be fed into the pore by the enzyme moving 3' to 5' along the DNA, and will ultimately be ejected into the trans side. With enzymes that show 5' to 3' polarity, these modes are reversed. B) With enzyme monomers, if one of the enzymes dissociates (indicated by arrow 1) the DNA will start to translocate through the pore in the opposite direction due to the applied field pulling the DNA into the cis compartment. C) The DNA will continue to move with the applied field until a second helicase (black outlined semi-circle) contacts the top of the nanopore.

This Example compares the ability of a Hel308 Mbu monomer (SEQ ID NO: 10), to control the movement of intact DNA strands (400 mer) through a nanopore, to that of the Hel308 Mbu A700C 2 kDa dimer (where each monomer unit comprises SEQ ID NO: 10 with the mutation A700C, with one monomer unit being linked to the other via position 700 of each monomer unit using a 2 kDa PEG linker). The general method for controlled DNA translocation by the monomer is shown in FIG. 10 and by the dimer in FIG. 11.
Materials and Methods
400 mer DNA Sequences:

Primers were designed to amplify a ~400 bp fragment of PhiX174. Each of the 5'-ends of these primers included a 50 nucleotide non-complimentary region, either a homopolymeric stretch or repeating units of 10 nucleotide homopolymeric sections. These serve as identifiers for controlled translocation of the strand through a nanopore, as well as determining the directionality of translocation. In addition, the 5'-end of the forward primer was "capped" to include four 2'-O-methyl-uracil (mU) nucleotides and the 5'-end of the reverse primer was chemically phosphorylated. These primer modifications then allow for the controlled digestion of predominantly only the antisense strand, using lambda exonuclease. The mU capping protects the sense strand from nuclease digestion whilst the PO4 at the 5' of the antisense strand promotes it. Therefore after incubation with lambda exonuclease only the sense strand of the duplex remains intact, now as single stranded DNA (ssDNA). The generated ssDNA was then PAGE purified as previously described.

Figure 12:
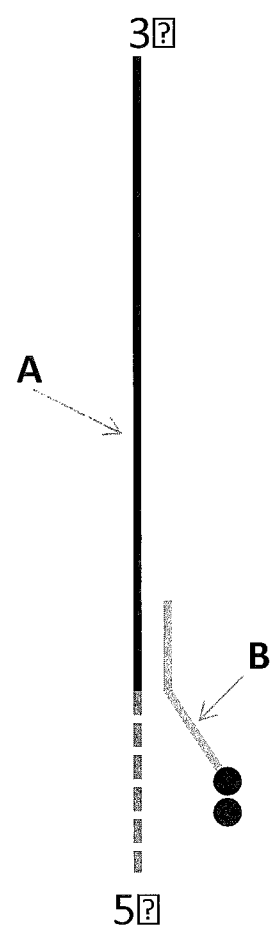
FIG. 12 shows the DNA substrate design used in Examples 5, 6 and 7. Strand A corresponds to SEQ ID NO: 70 (a 400mer) and Strand B corresponds to SEQ ID NO: 71 (primer which has a cholesterol tag at the 3' end (indicated by the two black circles)).

The DNA substrate design used in all the experiments described here is shown in FIG. 12. The DNA substrate consists of a 400base section of ssDNA from PhiX, with, at the 5' end of the sequence, four 2'-O-methyl uracil bases attached to a 50T 5'-leader to aid capture by the nanopore (SEQ ID NO: 70, at the 5' end of SEQ ID NO: 70 there are four 2'-O-methyl uracil bases attached to a 50T leader sequence to aid capture by the nanopore). Annealed to this strand just after the 50T leader is a primer containing a 3' cholesterol TEG (SEQ ID NO: 71) to enrich the DNA on the surface of the bilayer, and thus improve capture efficiency.
Buffered solution: 1 M KCl, 10 mM Hepes pH8.0, 1 mM ATP, 10 mM MgCl$_2$, 1 mM DTT
Nanopore: E. coli MS(B1-L88N)8 MspA (SEQ ID NO: 2, with the mutation L88N)
Monomer Enzyme: Hel308 Mbu (SEQ ID NO: 10) added at 100 nM final.
Dimer Enzyme: Hel308 Mbu A700C 2 kDa homodimer (where each monomer unit comprises SEQ ID NO: 10 with the mutation A700C, with one monomer unit being linked to the other via position 700 of each monomer unit using a 2 kDa PEG linker) added at 10 nM final.

Electrical measurements were acquired from single MspA nanopores inserted in 1,2-diphytanoyl-glycero-3-phosphocholine lipid (Avanti Polar Lipids) bilayers. Bilayers were formed across ~100 um diameter apertures in 20 um thick PTFE films (in custom Delrin chambers) via the Montal-Mueller technique, separating two 1 mL buffered solutions. All experiments were carried out in the stated buffered solution. Single-channel currents were measured on Axopatch 200B amplifiers (Molecular Devices) equipped with 1440A digitizers. Ag/AgCl electrodes were connected to the buffered solutions so that the cis compartment (to which both nanopore and enzyme/DNA are added) is connected to the ground of the Axopatch headstage, and the trans compartment is connected to the active electrode of the headstage.

Figure 13:
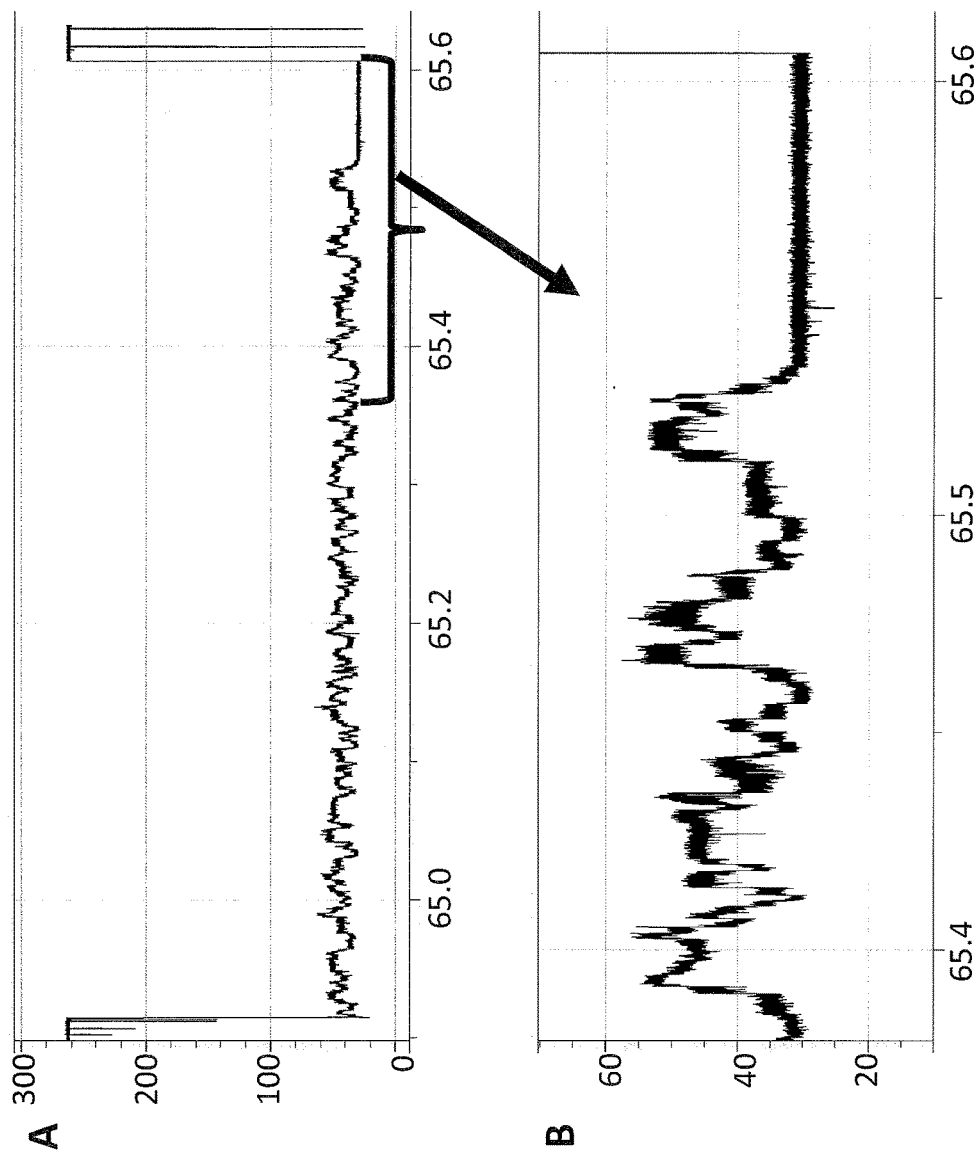
FIG. 13 shows that helicase monomers are able to move DNA through a nanopore in a controlled fashion, producing stepwise changes in current as the DNA moves through the nanopore. Example of current traces (y-axis label=Current (pA), x-axis label=Time (min) for traces A and B) observed when a monomer helicase controls the translocation of DNA (120 mV, 1 M KCl, 10 mM Hepes pH 8.0, 0.15 nM 400 mer DNA, 100 nM Hel308 Mbu monomer (SEQ ID NO: 10), 1 mM DTT, 1 mM ATP, 10 mM $MgCl_2$) through an MS(B1-L88N)8 MspA nanopore (8 monomer units as shown in SEQ ID NO: 2, with the mutation L88N). A) Section of current vs. time acquisition of a Hel308 Mbu monomer controlled 400 mer DNA movement. Under an applied potential DNA with helicase bound is captured by the nanopore. This produces blocks in current from the open-pore level (~260 pA) to a DNA level (~20-60 pA). The DNA level then shows stepwise changes in current as the enzyme moves the DNA through the pore. The example helicase-controlled DNA movement shown ends in a characteristic long polyT level before exiting the nanopore. B) Expanded view of the helicase-controlled DNA movements ending in the characteristic polyT level.

After achieving a single pore in the bilayer DTT (1 mM) and MgCl2 were added to the cis chamber and mixed well. DNA construct and helicase were then added to 100 uL of buffer and pre-incubated for 5 mins (DNA=1.5 nM (SEQ ID NO's: 70 and 71 (which has a 3' cholesterol TEG)), monomer enzyme=1 uM or dimer enzyme=0.1 uM). This pre-incubation mix was added to 900 uL of buffer in the cis compartment of the electrophysiology chamber to initiate capture of the helicase-DNA complexes in the MspA nanopore (to give final concentrations of DNA=0.15 nM, monomer enzyme=0.1 uM or dimer enzyme=0.01 uM). Helicase ATPase activity was initiated as required by the addition of dNTP (1 mM final ATP) to the cis compartment. Experiments were carried out at a constant potential of +120 mV.
Results and Discussion The addition of helicase monomer-DNA substrate to MspA nanopores (as shown in FIG. 10) produces characteristic current blocks as shown in FIG. 13. For a given substrate, we observe a characteristic pattern of current transitions for each helicase controlled DNA movement that reflects the DNA sequence. DNA without a helicase bound to it interacts transiently with the nanopore producing short-lived blocks in current (<<1 seconds). DNA with Hel308 Mbu monomer (SEQ ID NO: 10) bound and active (i.e. moving along the DNA strand under ATPase action) produces long characteristic blocks levels with stepwise changes in current as shown in FIG. 13. Different DNA motifs in the nanopore give rise to unique current block levels.

Figure 11:
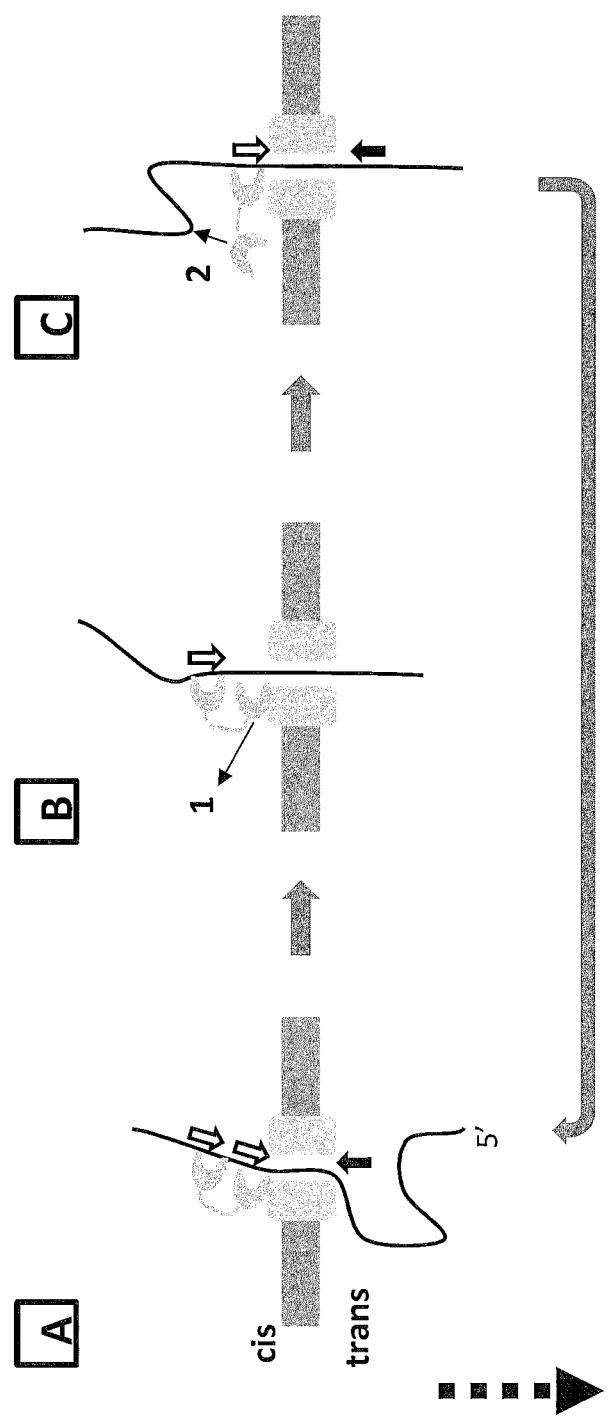
FIG. 11 shows a schematic of a helicase-helicase dimer controlling the movement of a polynucleotide through a nanopore in a membrane. A) Under an applied field (the direction of the applied field is indicated by the dashed black arrow), DNA in the cis compartment is captured by the nanopore, and translocates through the nanopore until the helicase contacts the top of the nanopore. After this point, the helicase will move along the DNA (in the presence of dNTP and suitable metal ion) controlling the movement of the DNA through the nanopore. In the implementation shown, the DNA strand is captured at the 5' end by the pore, and the enzymes move 3' to 5' pulling the DNA against the field. As long as the enzyme does not dissociate, the strands will all end in the same way at the 5' end and will finally be ejected back to the cis side. Alternatively, strands captured at the 3' end by the nanopore will be fed into the pore by the enzyme moving 3' to 5' along the DNA, and will ultimately be ejected into the trans side. With 5' to 3' enzymes these modes are reversed. B) With enzyme dimers, if one of the enzymes dissociates (indicated by arrow 1) it will remain attached to the other enzyme and thus remain local to the DNA. C) This enhances rebinding of the dissociated enzyme to the DNA, where it can continue to move along the DNA. This enhanced rebinding improves the chances that the dimer construct will remain on the DNA and eventually move to the end of the DNA, thus improving overall processivity. The enzyme re-binding is indicated by arrow 2. It is possible to observe transitions from C) back to A) if the enzyme on top of the pore dissociates from the DNA. The DNA will be pulled back through the pore by the applied field until it reaches the attached trailing enzyme. The dissociated enzyme can then re-attach itself. This process is highlighted by the pale grey arrow going from C) back to A).
Figure 14:
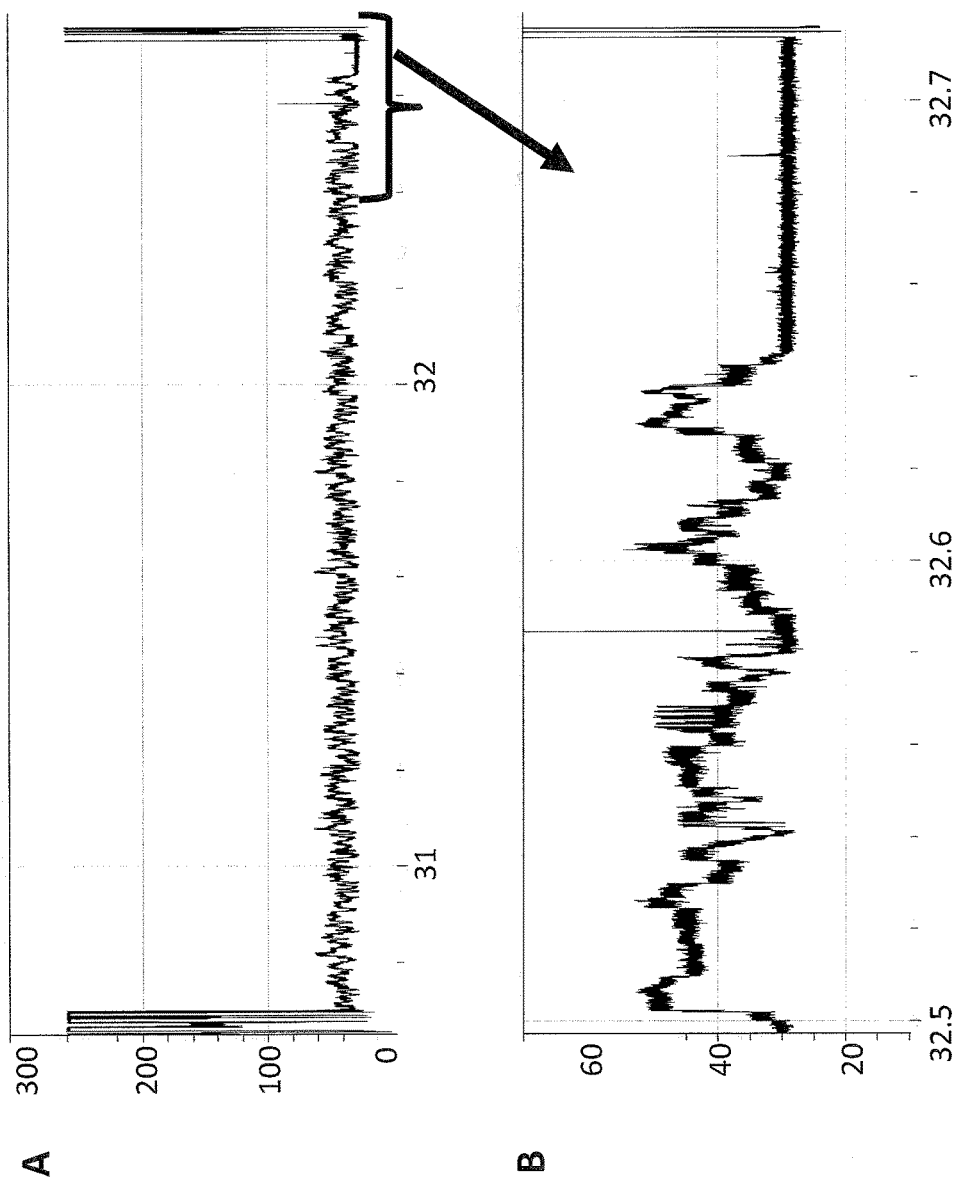
FIG. 14 shows that helicase-helicase dimers are able to move DNA through a nanopore in a controlled fashion, producing stepwise changes in current as the DNA moves through the nanopore. Example of current traces (y-axis label=Current (pA), x-axis label=Time (min) for traces A and B) observed when a dimer helicase controls the translocation of DNA (120 mV, 1 M KCl, 10 mM Hepes pH 8.0, 0.15 nM 400 mer DNA, 10 nM Hel308 Mbu A700C 2 kDa dimer (where each monomer unit comprises SEQ ID NO: 10 with the mutation A700C, with one monomer unit being linked to the other via position 700 of each monomer unit using a 2 kDa PEG linker), 1 mM DTT, 1 mM ATP, 10 mM $MgCl_2$) through an MS(B1-L88N)8 MspA nanopore (SEQ ID NO: 2, with the mutation L88N). A) Section of current vs. time acquisition of a Hel308 Mbu A700C 2 kDa dimer controlled 400 mer DNA movement. Under an applied potential DNA with helicase bound is captured by the nanopore. This produces blocks in current from the open-pore level (~260 pA) to a DNA level (~20-60 pA). The DNA level then shows stepwise changes in current as the enzyme moves the DNA through the pore. The example helicase-controlled DNA movement shown ends in a characteristic long polyT level before exiting the nanopore. B) Expanded view of the helicase-controlled DNA movements ending in the characteristic polyT level.

The addition of helicase dimer-DNA substrate to MspA nanopores (as shown in FIG. 11) produces characteristic current blocks as shown in FIG. 14. DNA with Hel308 Mbu A700C 2 kDa dimer (where each monomer unit comprises SEQ ID NO: 10 with the mutation A700C, with one monomer unit being linked to the other via position 700 of each monomer unit using a 2 kDa PEG linker) bound and active (i.e. moving along the DNA strand under ATPase action) produces long characteristic blocks levels with stepwise changes in current as shown in FIG. 14. It is also possible to employ a ten-times lower concentration of dimer and still observe these characteristic current blocks.

Figure 15:
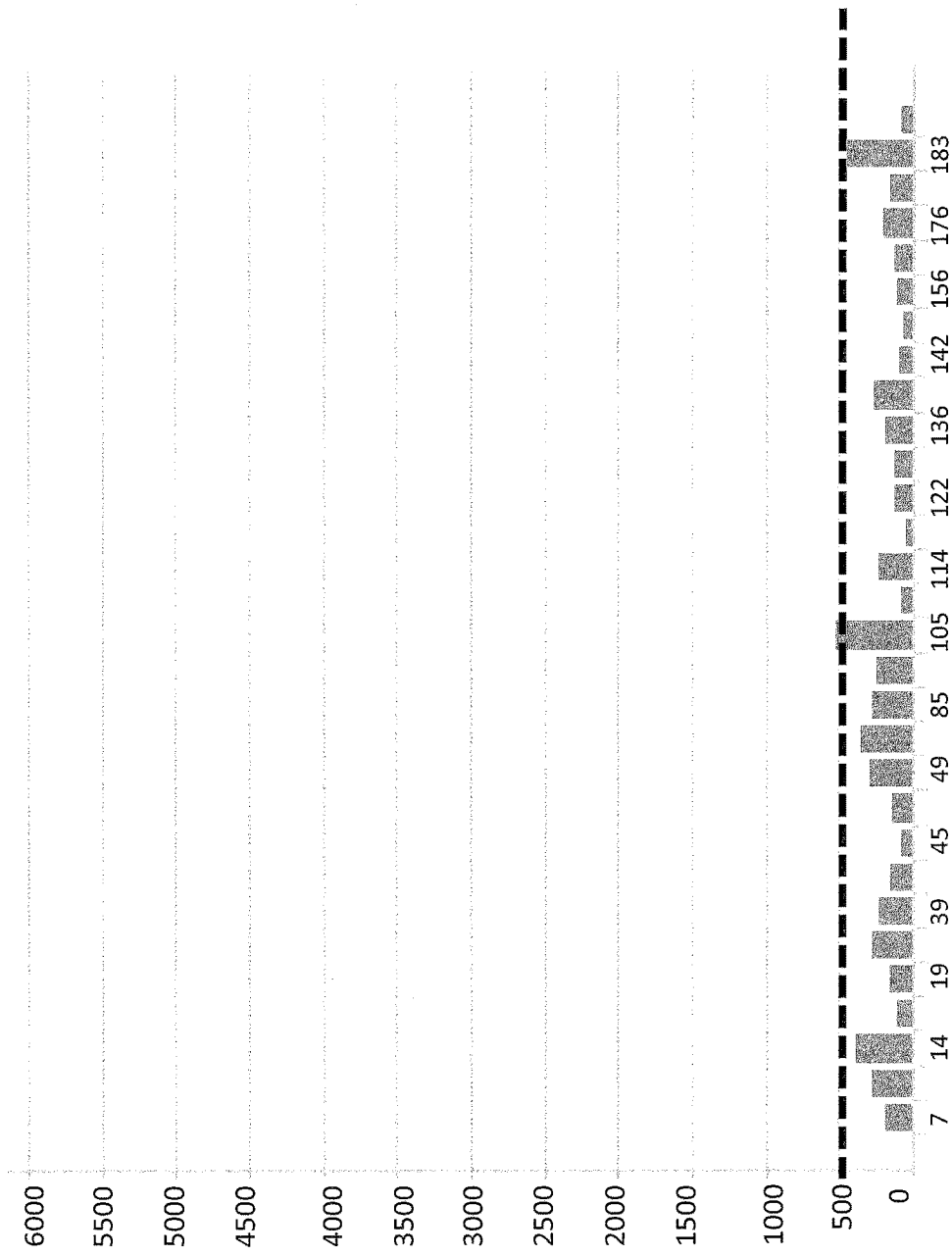
FIG. 15 shows the overall length of the strand movements (number of states, which corresponds to the number of bases moved) for an experiment using monomer Hel308 Mbu (SEQ ID NO: 10) to control DNA movement through a nanopore (+120 mV, 1 M KCl, 10 mM Hepes pH 8.0, 0.15 nM 400 mer DNA, 100 nM Hel308 Mbu monomer, 1 mM DTT, 1 mM ATP, 10 mM $MgCl_2$, MS(B1-L88N)8 MspA, y-axis label=Number of States, x-axis label=Strand). A dotted line highlights the number of states corresponding to 500. For the monomer run 37% of the helicase-controlled DNA movements measured reached the polyT at the end of the DNA strand.
Figure 16:
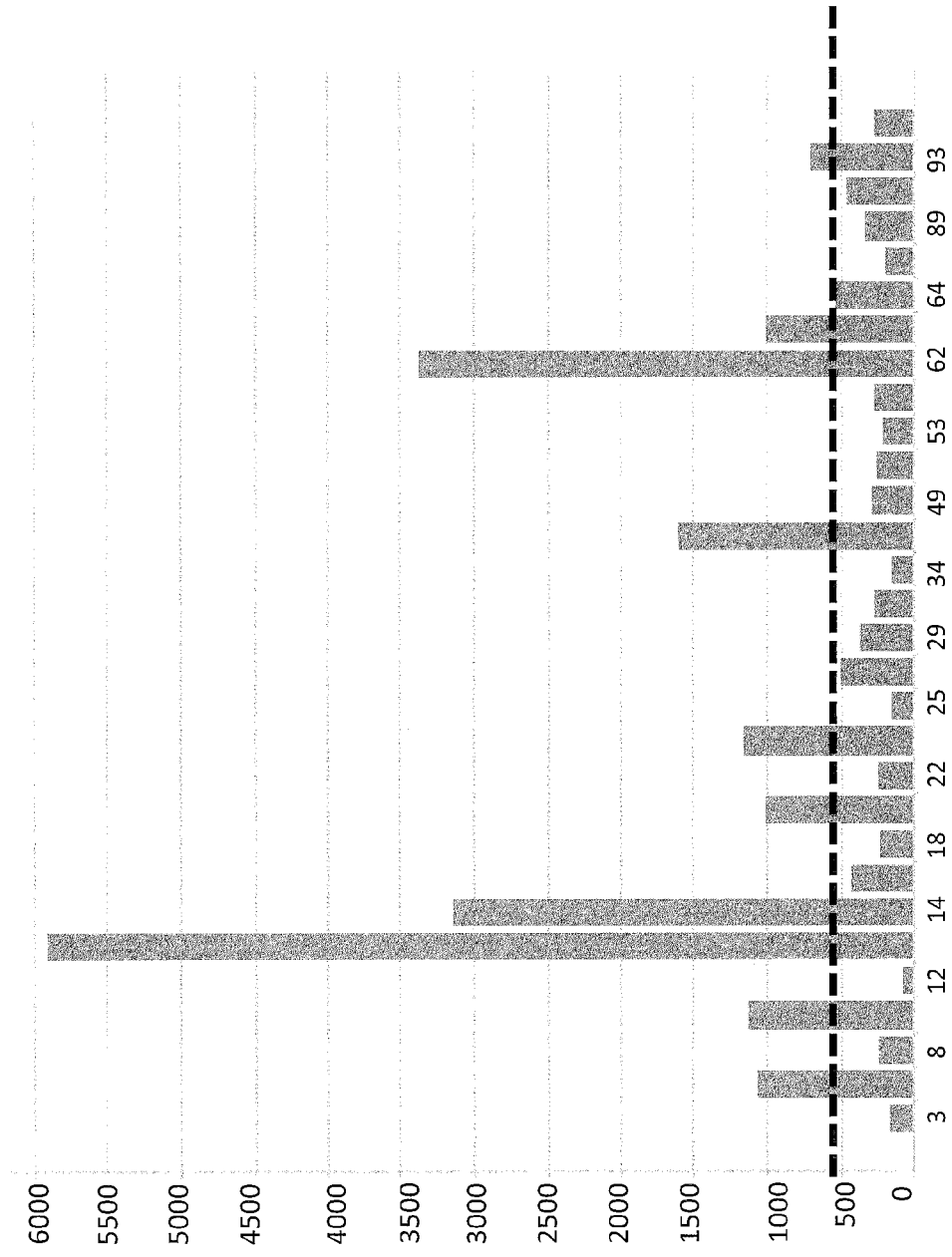
FIG. 16 shows the overall length of the strand movements (number of states, which corresponds to the number of bases moved) for an experiment using Hel308 Mbu A700C 2 kDa dimer (where each monomer unit comprises SEQ ID NO: 10 with the mutation A700C, with one monomer unit being linked to the other via position 700 of each monomer unit via a 2 kDa PEG linker) to control DNA movement through a nanopore (+120 mV, 1 M KCl, 10 mM Hepes pH 8.0, 0.15 nM 400 mer DNA, 10 nM Hel308 Mbu A700C 2 kDa dimer, 1 mM DTT, 1 mM ATP, 10 mM $MgCl_2$, MS(B1-L88N)8 MspA, y-axis label=Number of States, x-axis label=Strand). DNA movements controlled by a dimer are typically much longer than those controlled by a monomer helicase (a dotted line highlights the number of states corresponding to 500). This indicates enzyme rebinding and therefore reduced enzyme dissociation. For the dimer run 47% of the helicase-controlled DNA movements measured reached the polyT, showing the reduced dissociation and improved processivity of the dimer.
Figure 17:
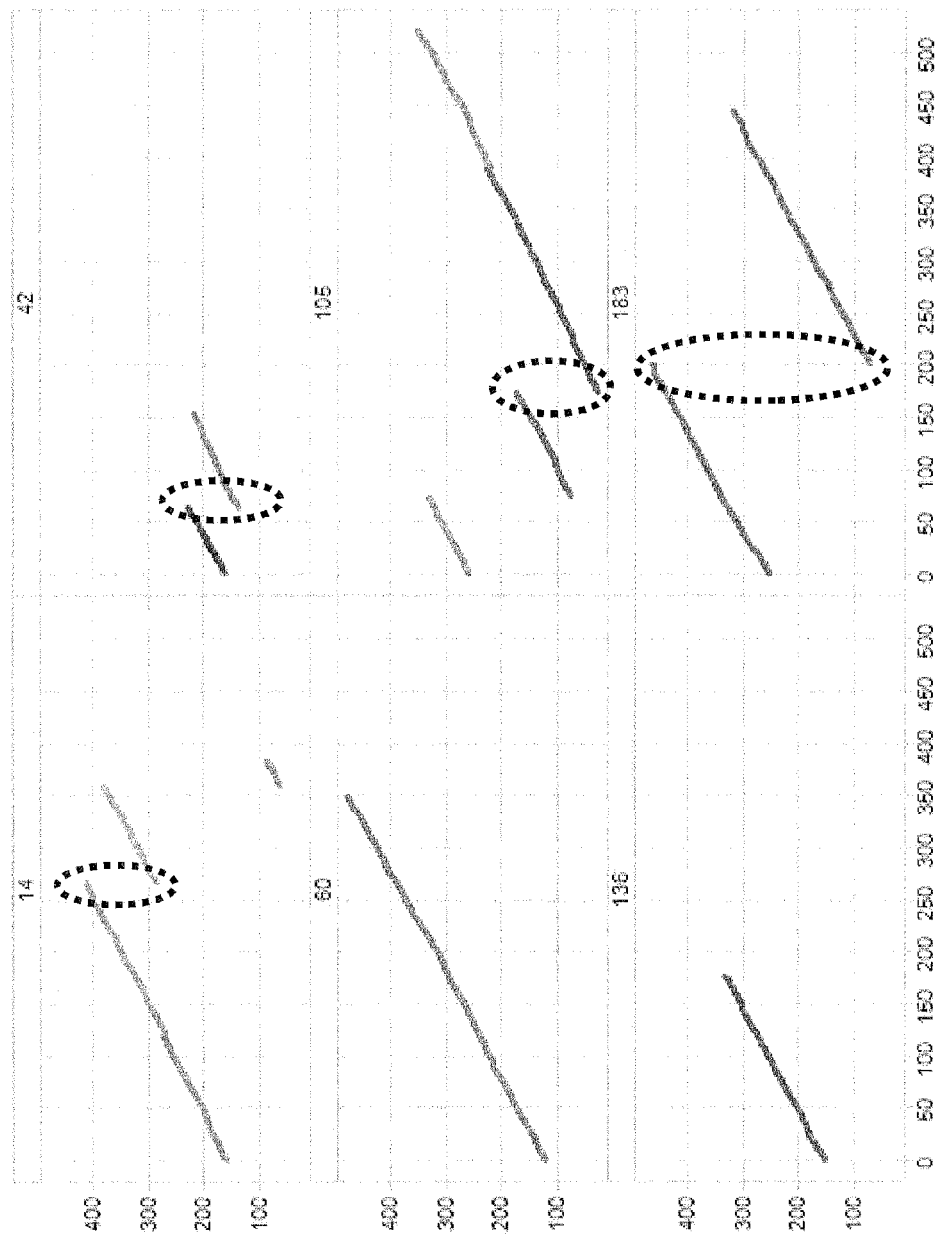
FIG. 17 shows six examples of the position in the known DNA sequence (y-axis label=Position in Sequence) of the state-fitted data for the Hel308 Mbu monomer controlled strand movements as a function of the state index x-axis label=State Index). The Hel308 Mbu monomer (SEQ ID NO: 10) data show processive linear movement through the sequence, with periodic dislocations back to previous parts of the sequence, which are the result of enzyme dissociation and the DNA slipping back under the applied field until encountering a trailing enzyme. Many of the helicase-controlled DNA movements do not make it to the end of the sequence due to enzyme dissociation.
Figure 18:
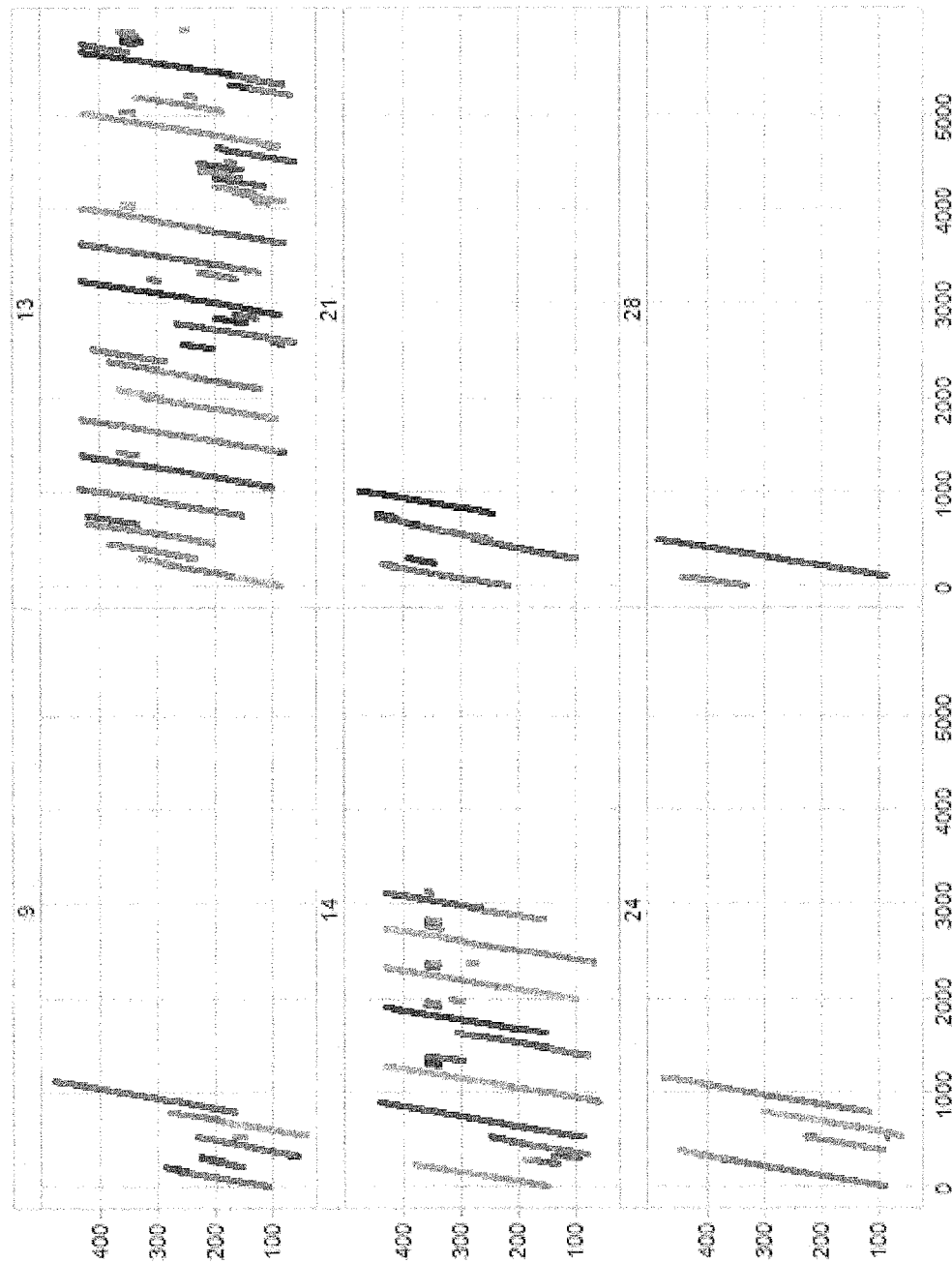
FIG. 18 shows six examples of the position in the known DNA sequence (y-axis label=Position in Sequence) of the state-fitted data for the Hel308 Mbu A700C 2 kDa homodimer (where each monomer unit comprises SEQ ID NO: 10 with the mutation A700C, with one monomer unit being linked to the other via position 700 of each monomer unit using a 2 kDa PEG linker) controlled strand movements as a function of the state index x-axis label=State Index). The dimer data show processive linear movement through the sequence, with periodic dislocations back to previous parts of the sequence, which are the result of enzyme dissociation. However, unlike the monomer data the enzymes proceed to control the movement of the DNA for much longer, and after dissociation the enzyme re-binds to the DNA.

The current blocks produced when the Hel308 Mbu monomer (SEQ ID NO: 10) controls translocation of the 400 mer DNA strand through the pore are similar to those produced by the Hel308 Mbu A700C 2 kDa dimer (where each monomer unit comprises SEQ ID NO: 10 with the mutation A700C, with one monomer unit being linked to the other via position 700 of each monomer unit using a 2 kDa PEG linker). However, when you compare the overall length of the helicase controlled strand movements for two experiments (run under identical conditions with either monomer Hel308 Mbu or Hel308 Mbu A700C 2 kDa dimer) then the helicase controlled DNA movements with the dimer are typically much longer (FIG. 16) than those observed by the monomer (FIG. 15). This indicates enzyme rebinding and therefore reduced enzyme dissociation. In addition, for the monomer run 37% of the helicase controlled DNA movements measured reached the polyT at the end of the DNA strand, whereas, for the dimer run 47% of the helicase controlled DNA movements measured reached the polyT, showing the reduced dissociation and improved processivity of the dimer. FIGS. 8 and 9 each show six examples of the position in the known DNA sequence (vertical axis) of the state-fitted data for the strand movements as a function of the state index (horizontal axis), when DNA motion is controlled by either the Hel308 Mbu monomer (FIG. 17) or the Hel308 Mbu A700C 2 kDa dimer (FIG. 18). The monomer data shows processive linear movement through the sequence, with periodic dislocations back to previous parts of the sequence (highlighted with a dashed circle), which are the result of enzyme dissociation and the DNA slipping back under the applied field until it encounters a trailing enzyme. Many of the helicase controlled DNA movements do not make it to the end of the sequence due to enzyme dissociation. Whereas for the dimer data the enzymes proceed to control the movement of the DNA for much longer, and after dissociation the enzyme re-binds to the DNA.

EXAMPLE 6

This Example shows that two different Hel308 Mbu homodimers, that are connected via different amino-acid positions and with different length linkers (2 kb and 3.4 kb linkers) in comparison to the Hel308 Mbu A700C 2 kDa homodimer discussed in Example 5, were also capable of controlling the movement of intact DNA strands (400 mer) through a nanopore. The general method for controlled DNA translocation by the dimer is shown in FIG. 11.

Buffered solution: 400 mM KCl, 10 mM Hepes pH8.0, 1 mM ATP, 1 mM $MgCl_2$, 1 mM DTT Nanopore: *E. coli* MS(B1-L88N)8 MspA (SEQ ID NO: 2 with the mutation L88N)

Dimer Enzymes: Hel308 Mbu Q442C 2 kDa linker homodimer (where each monomer unit comprises SEQ ID NO: 10 with the mutation Q442C, with one monomer unit being linked to the other via position 442 of each monomer unit using a 2 kDa PEG linker) added at approximately 1 nM final and Hel308 Mbu Q442C 3.4 kDa linker homodimer (where each monomer unit comprises SEQ ID NO: 10 with the mutation Q442C, with one monomer unit being linked to the other via position 442 of each monomer unit using a 3.4 kDa PEG linker) added at approximately 1 nM final.

Electrical experiments were set up as described in Example 5 in order to achieve a single pore inserted into a lipid bilayer. After achieving a single pore in the bilayer, DTT (1 mM) and $MgCl_2$ (1 mM) were added to the cis chamber and mixed well. DNA polynucleotide SEQ ID NO's: 70 and 71 (which has a 3' cholesterol TEG) (DNA=0.15 nM), ATP (1 mM) and either Hel308 Mbu Q442C 2 kDa linker homodimer or Hel308 Mbu Q442C 3.4 kDa linker homodimer were then added to the cis compartment of the electrophysiology chamber to initiate capture of the helicase-DNA complexes in the MspA nanopore. Experiments were carried out at a constant potential of +180 mV.

Results and Discussion

Figure 19:
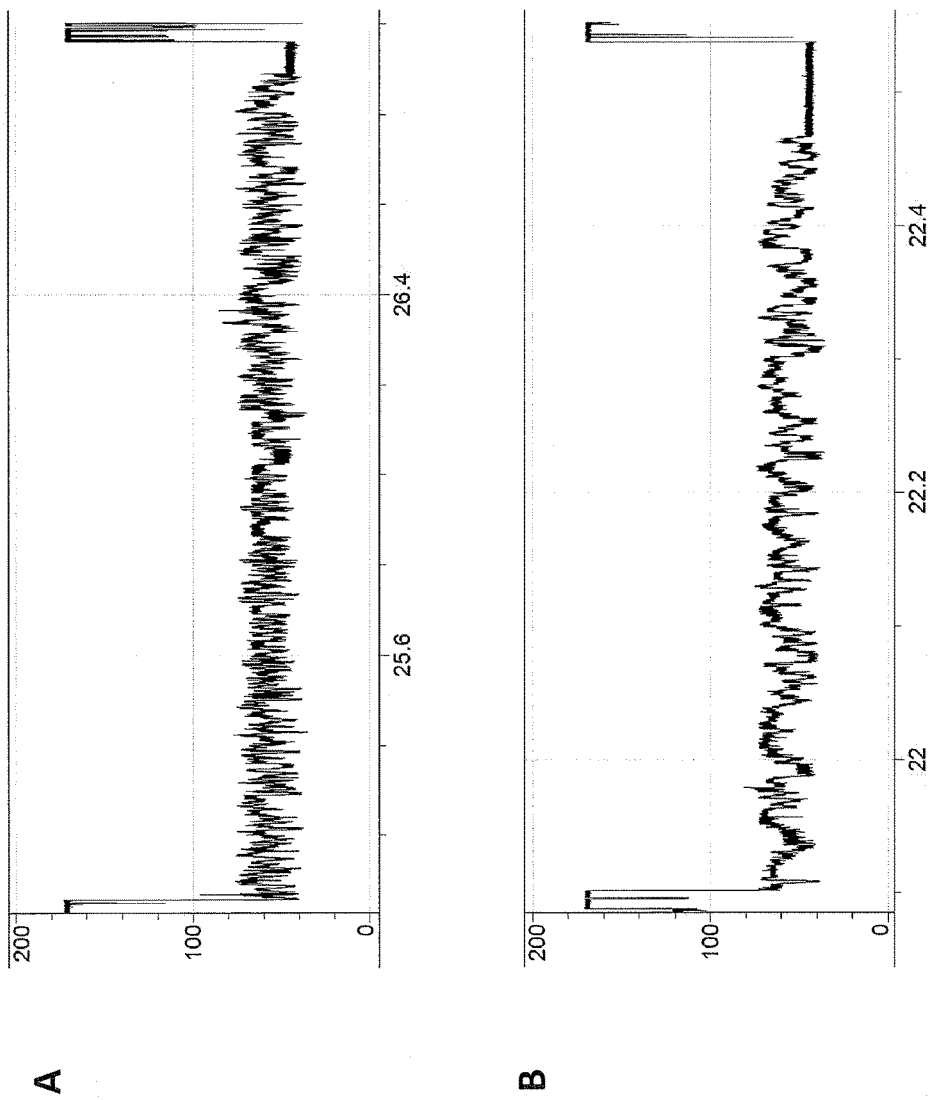
FIG. 19 shows helicase-helicase dimers are able to move DNA through a nanopore in a controlled fashion, producing stepwise changes in current as the DNA moves through the nanopore. Example current traces (y-axis label=Current (pA), x-axis label=Time (min) for traces A and B) observed when a dimer helicase controls the translocation of DNA (180 mV, 400 mM KCl, 10 mM Hepes pH 8.0, 0.15 nM 400 mer DNA, approximately 1 nM Hel308 Mbu Q442C 2 kDa linker homodimer (where each monomer unit comprises SEQ ID NO: 10 with the mutation Q442C, with one monomer unit being linked to the other via position 442 of each monomer unit using a 2 kDa PEG linker) or 1 nM Hel308 Mbu Q442C 3.4 kDa linker homodimer (where each monomer unit comprises SEQ ID NO: 10 with the mutation Q442C, with one monomer unit being linked to the other via position 442 of each monomer unit using a 3.4 kDa PEG linker), 1 mM DTT, 1 mM ATP, 1 mM $MgCl_2$) through an MS(B1-L88N)8 MspA nanopore. A) Section of current vs. time acquisition of a Hel308 Mbu Q442C 2 kDa linker homodimer controlled 400mer DNA movement. Under an applied potential DNA with helicase bound is captured by the nanopore. This produces blocks in current from the open-pore level (~170 pA) to a DNA level (~40-80 pA). The DNA level then shows stepwise changes in current as the enzyme moves the DNA through the pore. The example helicase-controlled DNA movement shown ends in a characteristic long polyT level before exiting the nanopore. B) Section of current vs. time acquisition of a Hel308 Mbu Q442C 3.4 kDa linker homodimer controlled 400mer DNA movement. Under an applied potential DNA with helicase bound is captured by the nanopore. This produces blocks in current from the open-pore level (~170 pA) to a DNA level (~40-80 pA). The DNA level then shows stepwise changes in current as the enzyme moves the DNA through the pore. The example helicase-controlled DNA movement shown ends in a characteristic long polyT level before exiting the nanopore.

The use of the Hel308 Mbu Q442C 2 kDa linker homodimer (where each monomer unit comprises SEQ ID NO: 10 with the mutation Q442C, with one monomer unit being linked to the other via position 442 of each monomer unit using a 2 kDa PEG linker) helicase, to control DNA substrate translocation through MspA nanopores, produces characteristic current blocks as shown in FIG. 19A. For a given substrate, we observe a characteristic pattern of current transitions for each helicase controlled DNA movement that reflects the DNA sequence. DNA without a helicase bound to it interacts transiently with the nanopore producing short-lived blocks in current (<<1 seconds). DNA with helicase dimer bound and active (i.e. moving along the DNA strand under ATPase action) produces long characteristic blocks levels with stepwise changes in current as shown in FIG. 19A. Different DNA motifs in the nanopore give rise to unique current block levels. The use of the Hel308 Mbu Q442C 3.4 kDa linker homodimer helicase (where each monomer unit comprises SEQ ID NO: 10 with the mutation Q442C, with one monomer unit being linked to the other via position 442 of each monomer unit using a 3.4 kDa PEG linker), to control DNA movement through MspA nanopores, also produces characteristic current blocks as shown in FIG. 19B. This illustrates that it is possible to attach two helicases together at different positions using two different linker lengths and still retain enzyme activity.

EXAMPLE 7

This Example shows helicase-controlled DNA movement through nanopores using helicases with an additional binding domain fused to the C-terminus. The two Examples shown are Hel308 Mbu with an additional $5^{th}$ domain from Hel308 Hla (where a helicase monomer unit (SEQ ID NO: 10) is attached to the $5^{th}$ domain of Hel308 Hla (SEQ ID NO: 66)) or Hel308 Hvo (where a helicase monomer unit (SEQ ID NO: 10) is attached to the $5^{th}$ domain of Hel308 Hvo (SEQ ID NO: 67)) genetically fused to the C-terminus.

Buffered solution: 400 mM NaCl, 10 mM Hepes pH8.0, 1 mM ATP, 1 mM $MgCl_2$, 1 mM DTT Nanopore: *E. coli* MS(B1-L88N)8 MspA (SEQ ID NO: 2 with the mutation L88N)

Dimer Enzymes: Hel308 Mbu+$5^{th}$ domain Hel308 Hla (where a helicase monomer unit (SEQ ID NO: 10) is attached to the $5^{th}$ domain of Hel308 Hla (SEQ ID NO: 66)) added at 100 nM final and Hel308 Mbu+$5^{th}$ domain Hel308 Hvo (where a helicase monomer unit (SEQ ID NO: 10) is attached to the $5^{th}$ domain of Hel308 Hvo (SEQ ID NO: 67)) added at 100 nM final.

Electrical experiments were set up as described in Example 5 in order to achieve a single pore inserted into a lipid bilayer. After achieving a single pore in the bilayer DTT (1 mM) and MgCl$_2$ (1 mM) were added to the cis chamber and mixed well. A control recording at +140 mV was run for 5 minutes. DNA polynucleotide SEQ ID NO's: 70 and 71 (which has a 3' cholesterol TEG) (DNA=0.6 nM) and either Hel308 Mbu+5$^{th}$ domain Hel308 Hla (100 nM, where a helicase monomer unit (SEQ ID NO: 10) is attached to the 5$^{th}$ domain of Hel308 Hla (SEQ ID NO: 66)) or Hel308 Mbu+5$^{th}$ domain Hel308 Hvo (100 nM, where a helicase monomer unit (SEQ ID NO: 10) is attached to the 5$^{th}$ domain of Hel308 Hvo (SEQ ID NO: 67)) were then added to the cis compartment of the electrophysiology chamber to initiate capture of the helicase-DNA complexes in the MspA nanopore. A second control recording at +140 mV was run for 10 minutes. Finally helicase ATPase activity was initiated as required by the addition of ATP (1 mM) to the cis compartment. Experiments were carried out at a constant potential of +140 mV.

Results and Discussion

Figure 20:
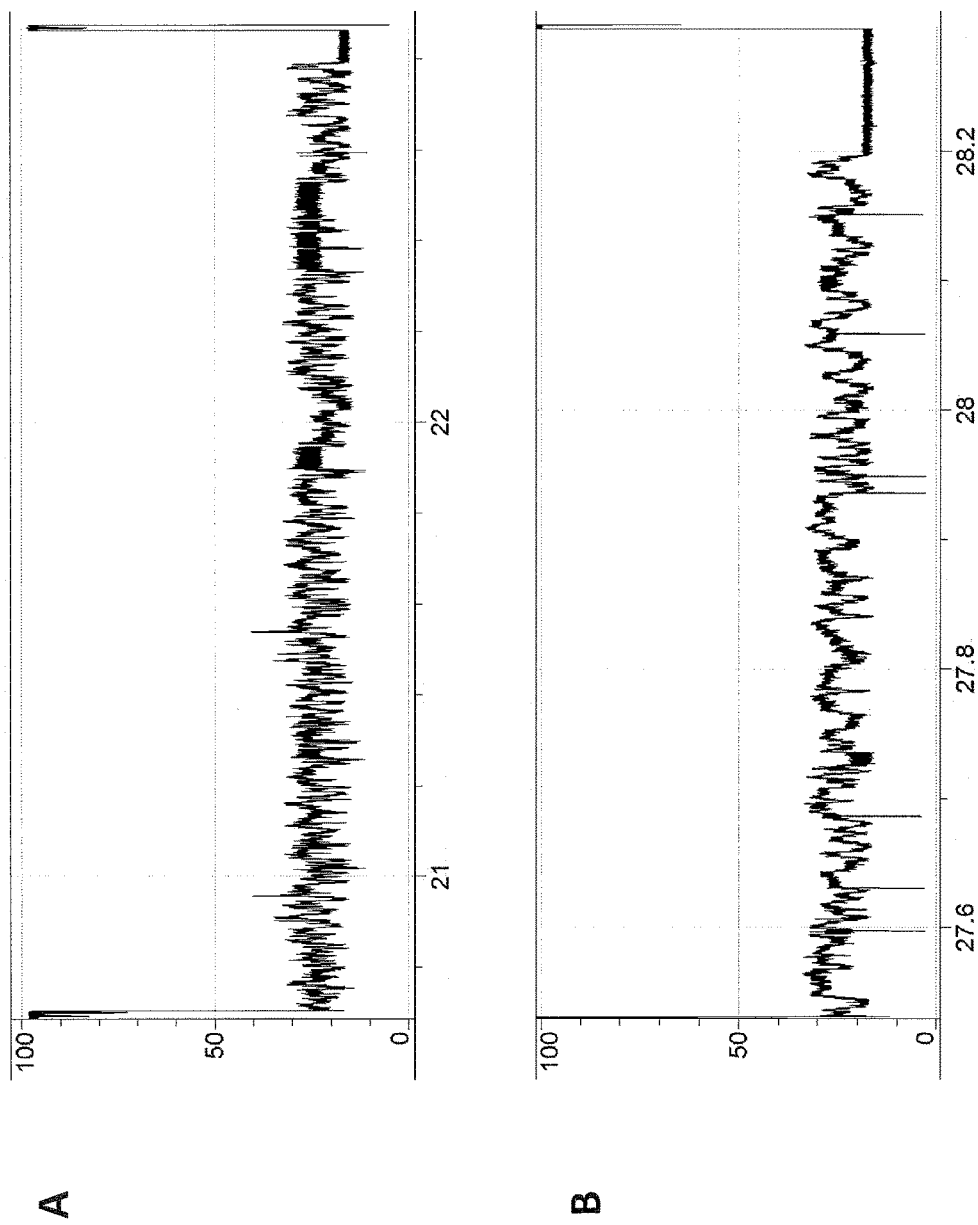
FIG. 20 shows helicases attached to an additional binding domain are able to move DNA through a nanopore in a controlled fashion, producing stepwise changes in current as the DNA moves through the nanopore. Example current traces (y-axis label=Current (pA), x-axis label=Time (min) for traces A and B) observed when a helicase-controls the translocation of DNA (140 mV, 400 mM NaCl, 10 mM Hepes pH 8.0, 0.6 nM 400 mer DNA, 100 nM Hel308 Mbu+$5^{th}$ domain Hel308 Hla (where a helicase monomer unit (SEQ ID NO: 10) is attached to the $5^{th}$ domain of Hel308 Hla (SEQ ID NO: 66)) or 100 nM Hel308 Mbu+$5^{th}$ domain Hel308 Hvo (where a helicase monomer unit (SEQ ID NO: 10) is attached to the $5^{th}$ domain of Hel308 Hvo (SEQ ID NO: 67)), 1 mM DTT, 1 mM ATP, 1 mM $MgCl_2$) through an MS(B1-L88N)8 MspA nanopore. A) Section of current vs. time acquisition of a Hel308 Mbu+$5^{th}$ domain Hel308 Hla controlled 400 mer DNA movement. Under an applied potential DNA with helicase bound is captured by the nanopore. This produces blocks in current from the open-pore level (~100 pA) to a DNA level (~10-40 pA). The DNA level then shows stepwise changes in current as the enzyme moves the DNA through the pore. The example helicase-controlled DNA movement shown ends in a characteristic long polyT level before exiting the nanopore. B) Section of current vs. time acquisition of a Hel308 Mbu+$5^{th}$ domain Hel308 Hvo controlled 400 mer DNA movement. Under an applied potential DNA with helicase bound is captured by the nanopore. This produces blocks in current from the open-pore level (~100 pA) to a DNA level (~10-40 pA). The DNA level then shows stepwise changes in current as the enzyme moves the DNA through the pore. The example helicase-controlled DNA movement shown ends in a characteristic long polyT level before exiting the nanopore.

The use of the Hel308 Mbu+5$^{th}$ domain Hel308 Hla helicase (where a helicase monomer unit (SEQ ID NO: 10) is attached to the 5$^{th}$ domain of Hel308 Hla (SEQ ID NO: 66)), to control DNA substrate translocation through MspA nanopores, produces characteristic current blocks as shown in FIG. 20A. For a given substrate, we observe a characteristic pattern of current transitions for each helicase controlled DNA movement that reflects the DNA sequence. DNA without a helicase bound to it interacts transiently with the nanopore producing short-lived blocks in current (<<1 seconds). DNA with Hel308 Mbu+5$^{th}$ domain Hel308 Hla helicase bound and active (i.e. moving along the DNA strand under ATPase action) produces long characteristic blocks levels with stepwise changes in current as shown in FIG. 20A. Different DNA motifs in the nanopore give rise to unique current block levels. The use of the Hel308 Mbu+5$^{th}$ domain Hel308 Hvo helicase (where a helicase monomer unit (SEQ ID NO: 10) is attached to the 5$^{th}$ domain of Hel308 Hvo (SEQ ID NO: 67)), to control DNA movement through MspA nanopores, also produces characteristic current blocks as shown in FIG. 20B. This illustrates that it is possible to attach an additional binding domain of a helicase to another helicase and still retain enzyme activity.

EXAMPLE 8

This Example shows helicase-controlled DNA movement through nanopores using helicases with additional Helix-hairpin-Helix (HhH) domains attached. The two examples shown are Hel308 Mbu with either two or four helix-hairpin-helix domains attached at the C-terminus.

Materials and Methods

Figure 21:
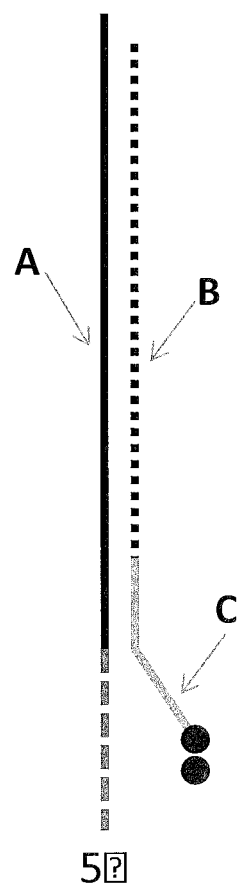
FIG. 21 shows the DNA substrate design used in Example 8. Strand A corresponds to SEQ ID NO: 72 (a 900mer) and Strand B corresponds to SEQ ID NO: 73 (anti-sense sequence minus a 4 base-pair leader). Strand C corresponds to SEQ ID NO: 74 (primer which has a cholesterol tag at the 3' end (indicated by the two black circles)).

The DNA was formed by ligating a 50-polyT 5' leader to a ~900base fragment of PhiX dsDNA. The leader also contains a complementary section to which SEQ ID NO: 74 (which at the 3' end of the sequence has six iSp18 spacers attached to two thymine residues and a 3' cholesterol TEG) was hybridized to allow the DNA to be tethered to the bilayer. Finally the 3' end of the PhiX dsDNA was digested with AatII digestion enzyme to yield a 4nt 3'-overhang of ACGT (see FIG. 21 for diagram of the DNA substrate design).

Buffered solution: 400 mM NaCl, 100 mM Hepes pH8.0, 10 mM potassium ferrocyanide, 10 mM potassium ferricyanide, 1 mM ATP, 1 mM MgCl$_2$, Nanopore: E. coli MS(B1-G75S-G77S-L88N-Q126R)8 MspA (SEQ ID NO:2 with the mutations G75S/G77S/L88N/Q126R)

Dimer Enzymes: Hel308 Mbu-GTGSGA-(HhH)2 (where a helicase monomer unit (SEQ ID NO: 10) is attached by the linker sequence GTGSGA to a HhH2 domain (SEQ ID NO: 75)) added at 100 nM final and Hel308 Mbu-GTGSGA-(HhH)2-(HhH)2 (where a helicase monomer unit (SEQ ID NO: 10) is attached by the linker sequence GTGSGA to a (HhH)2-(HhH)2 domain (SEQ ID NO:76)) added at 100 nM final.

Electrical experiments were set up as described in Example 5 in order to achieve a single pore inserted into a lipid bilayer, however, platinum electrodes were employed instead of Ag/AgCl electrodes. After achieving a single pore in the bilayer, MgCl$_2$ (1 mM) and ATP (1 mM) were added to the chamber. A control recording at +140 mV was run for 5 minutes. DNA polynucleotide SEQ ID NO's 72, 73 and 74 (which at the 3' end of the sequence has six iSp18 spacers attached to two thymine residues and a 3' cholesterol TEG) (DNA=0.1 nM) were added to the cis compartment of the electrophysiology chamber and DNA translocation events were observed. Finally, either Hel308 Mbu-GTGSGA-(HhH)2 (100 nM, where a helicase monomer unit (SEQ ID NO: 10) is attached by the linker sequence GTGSGA to a HhH2 domain (SEQ ID NO: 75)) or Hel308 Mbu-GTGSGA-(HhH)2-(HhH)2 (100 nM, where a helicase monomer unit (SEQ ID NO: 10) is attached by the linker sequence GTGSGA to a (HhH)2-(HhH)2 domain (SEQ ID NO: 76)) was then added to the cis compartment of the electrophysiology chamber to initiate capture of the helicase-DNA complexes in the MspA nanopore. Experiments were carried out at a constant potential of +140 mV.

Results and Discussion

Figure 22:
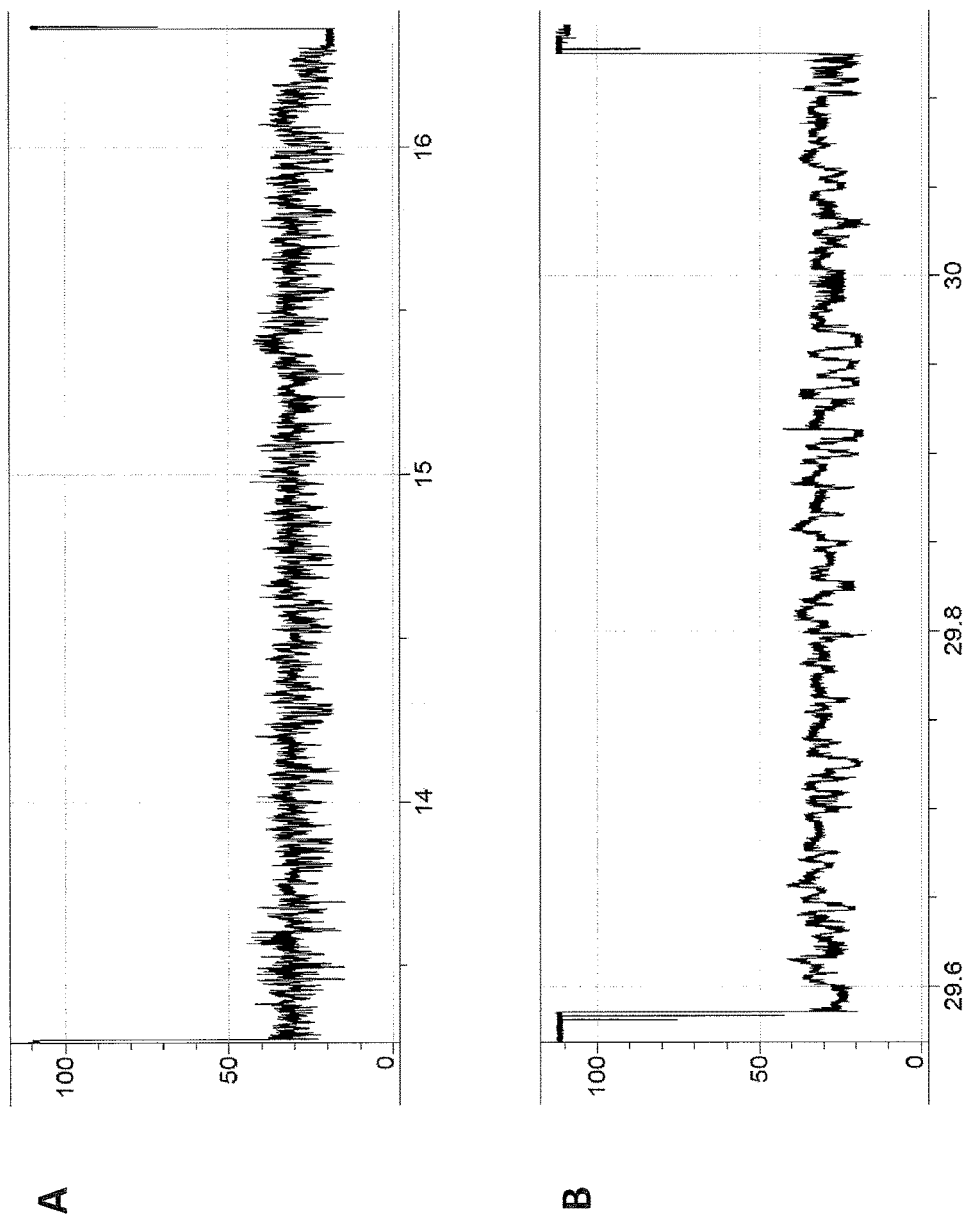
FIG. 22 shows helicases attached to additional helix-harpin-helix binding domains are able to move DNA through a nanopore in a controlled fashion, producing stepwise changes in current as the DNA moves through the nanopore. Example current traces (y-axis label=Current (pA), x-axis label=Time (min) for traces A and B) observed when a helicase controls the translocation of DNA (140 mV, 400 mM NaCl, 100 mM Hepes pH 8.0, 0.1 nM 900 mer DNA, 100 nM Hel308 Mbu-GTGSGA-(HhH)2 (where a helicase monomer unit (SEQ ID NO: 10) is attached by the linker sequence GTGSGA to a HhH2 domain (SEQ ID NO: 75)) or 100 nM Hel308 Mbu-GTGSGA-(HhH)2-(HhH)2 (where a helicase monomer unit (SEQ ID NO: 10) is attached by the linker sequence GTGSGA to a (HhH)2-(HhH)2 domain (SEQ ID NO: 76)), 10 mM potassium ferrocyanide, 10 mM potassium ferricyanide, 1 mM ATP, 1 mM $MgCl_2$) through an MS(B1-G75S-G77S-L88N-Q126R)8 MspA nanopore (8 monomer units as shown in SEQ ID NO: 2 with the mutations G75S/G77S/L88N/Q126R)). A) Section of current vs. time acquisition of a Hel308 Mbu-GTGSGA-(HhH)2 controlled 900 mer DNA movement. Under an applied potential DNA with helicase bound is captured by the nanopore. This produces blocks in the current from the open-pore level (~110 pA) to a DNA level (~10-40 pA). The DNA level then shows stepwise changes in current as the enzyme moves the DNA through the pore. The example helicase-controlled DNA movement shown ends in a characteristic long polyT level before exiting the nanopore. B) Section of current vs. time acquisition of a Hel308 Mbu-GTGSGA-(HhH)2-(HhH)2 controlled 900 mer DNA movement. Under an applied potential DNA with helicase bound is captured by the nanopore. This produces blocks in current from the open-pore level (~110 pA) to a DNA level (~10-40 pA). The DNA level then shows stepwise changes in current as the enzyme moves the DNA through the pore. The example helicase-controlled DNA movement shown ends in a characteristic long polyT level before exiting the nanopore.

The use of Hel308 Mbu-GTGSGA-(HhH)2 (where a helicase monomer unit (SEQ ID NO: 10) is attached by the linker sequence GTGSGA to a HhH2 domain (SEQ ID NO: 75)), to control DNA substrate translocation through MspA nanopores, produces characteristic current blocks as shown in FIG. 22A. For a given substrate, we observe a characteristic pattern of current transitions for each helicase controlled DNA movement that reflects the DNA sequence. DNA without helicase bound interacts transiently with the nanopore producing short-lived blocks in current (<<1 seconds). DNA with Hel308 Mbu-GTGSGA-(HhH)2 bound and active (i.e. moving along the DNA strand under ATPase action) produces long characteristic blocks levels with stepwise changes in current as shown in FIG. 22A. Different DNA motifs in the nanopore give rise to unique current block levels. The use of the Hel308 Mbu-GTGSGA-(HhH)2-(HhH)2 (where a helicase monomer unit (SEQ ID NO: 10) is attached by the linker sequence GTGSGA to a (HhH)2-(HhH)2 domain (SEQ ID NO: 76)), to control DNA movement through MspA nanopores, also produces characteristic current blocks as shown in FIG. 22B. This illustrates that it is possible to attach additional helix-hairpin-helix domains to a helicase and still retain enzyme activity.

EXAMPLE 9

This Example compares the ability of a TrwC Cba monomer (SEQ ID NO: 87), to control the movement of intact DNA strands (attached to the 5' end of SEQ ID NO: 88 is 28 iSpC3 spacers units the last of which has an additional two T's attached to the 5' end of the spacer group, attached to the 3' end of SEQ ID NO: 88 is a further four iSpC3 spacers which are attached to the 5' end of SEQ ID NO: 104) through a nanopore, to that of the TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker). The dimer results in a greater percentage of long dwell helicase-controlled DNA movement (a long dwell movement is a helicase-controlled DNA movement which is more than three standard deviations away from the mean of the major population of helicase-controlled DNA movements) than the monomer.

Materials and Methods

Prior to setting up the experiment, the DNA (1 nM, attached to the 5' end of SEQ ID NO: 88 is 28 iSpC3 spacers units the last of which has an additional two T's attached to the 5' end of the spacer group, attached to the 3' end of SEQ ID NO: 88 is a further four iSpC3 spacers which are attached to the 5' end of SEQ ID NO: 104) and the enzyme (either a TrwC Cba monomer (1 nM, SEQ ID NO: 87) or TrwC Cba Q276C-3.4 kDa dimer (0.3 nM, where each monomer unit comprises SEQ ID NO: 87 with the mutation Q276C, with one monomer unit being linked to the other via position 276 of each monomer unit using a 3.4 kDa PEG linker)) were pre-incubated together for >16 hours.

Electrical measurements were acquired from single MspA nanopores MS(G75S/G77S/L88N/D90N/D91N/D93N/D118R/Q126R/D134R/E139K)8 MspA (SEQ ID NO: 2 with the mutations G75 S/G77S/L88N/D90N/D91N/D93N/D118R/Q126R/D134R/E139K) inserted in block copolymer in buffer (625 mM KCl, 100 mM Hepes, 75 mM Potassium Ferrocyanide (II), 25 mM Potassium ferricyanide (III), pH 8). $MgCl_2$ (10 mM) and dTTP (5 mM) were mixed together with buffer (625 mM KCl, 100 mM Hepes, 75 mM Potassium Ferrocyanide (II), 25 mM Potassium ferricyanide (III), pH 8) and then added to the DNA (attached to the 5' end of SEQ ID NO: 88 is 28 iSpC3 spacers units the last of which has an additional two T's attached to the 5' end of the spacer group, attached to the 3' end of SEQ ID NO: 88 is a further four iSpC3 spacers which are attached to the 5' end of SEQ ID NO: 104), enzyme pre-mix (either a TrwC Cba monomer (1 nM, SEQ ID NO: 87) or TrwC Cba Q276C-3.4 kDa dimer (1 nM, where each monomer unit comprises SEQ ID NO: 87 with the mutation Q276C, with one monomer unit being linked to the other via position 276 of each monomer unit using a 3.4 kDa PEG linker)). After achieving a single pore in the bilayer, the pre-mix was added to the single nanopore experimental system. Experiments were carried out at a constant potential of +120 mV and helicase-controlled DNA movement was monitored.

Results and Discussion

Helicase controlled DNA movement was observed for the helicase TrwC Cba monomer (SEQ ID NO: 87) and TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker). Of the helicase-controlled DNA movements observed there is a major population which accounts for around 95% of movements detected, however, there is a small percentage of movements which are significantly longer in dwell time (more than three standard deviations away from the mean of the major population of helicase-controlled DNA movements). These longer movements allow improved data analysis. When the TrwC Cba Q276C-3.4 kDa dimer (1 nM, where each monomer unit comprises SEQ ID NO: 87 with the mutation Q276C, with one monomer unit being linked to the other via position 276 of each monomer unit using a 3.4 kDa PEG linker) was used to control DNA movement then a much higher percentage (20% for the TrwC Cba Q276C-3.4 kDa dimer in comparison to and 5% for the TrwC Cba monomer) of these longer dwell time movements (more than three standard deviations away from the mean of the major population of helicase-controlled DNA movements) was observed. The use of the dimer helicase provides an advantage over the monomer as it allows improved data analysis in the nanopore sequencing system.

EXAMPLE 10

This Example illustrates the salt tolerance of a TrwC Cba-TopoV Mka (where TrwC Cba is attached by the linker AYDVGA to domains H-L of Topoisomerase V Mka full sequence shown in SEQ ID NO: 90) using a fluorescence assay for testing enzyme activity.

Materials and Methods

Figure 23:
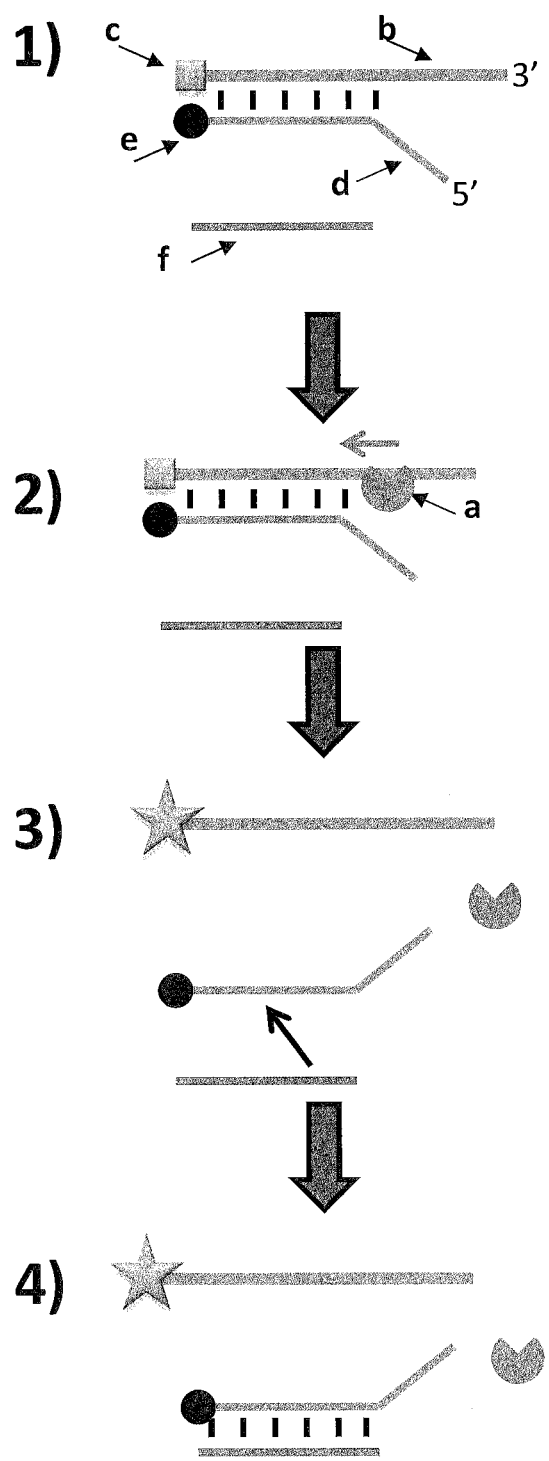
FIG. 23 Fluorescence assay for testing enzyme activity. A custom fluorescent substrate was used to assay the ability of the helicase/helicase dimer (a) to displace hybridised dsDNA. 1) The fluorescent substrate strand (50 nM final, SEQ ID NO: 91 and 92) has both a 3' and 5' ssDNA overhang, and a 44 base section of hybridised dsDNA. The upper strand (b) has a carboxyfluorescein base (c) at the 5' end (labeled 5 in SEQ ID NO: 91), and the hybridised complement (d) has a black-hole quencher (BHQ-1) base (e) at the 3' end (labeled 6 in SEQ ID NO: 92). When hybridised, the fluorescence from the fluorescein is quenched by the local BHQ-1, and the substrate is essentially non-fluorescent. 1 µM of a capture strand (f, SEQ ID NO: 93) that is part-complementary to the lower strand of the fluorescent substrate is included in the assay. 2) In the presence of ATP (1 mM) and MgCl$_2$ (1 mM), helicase (100 nM) added to the substrate binds to the 3' tail of the fluorescent substrate, moves along the upper strand, and displaces the complementary strand (d) as shown. 3) Once the complementary strand with BHQ-1 is fully displaced the fluorescein on the major strand fluoresces. 4) Displaced lower strand (d) preferentially anneals to an excess of capture strand (f) to prevent re-annealing of initial substrate and loss of fluorescence.

A custom fluorescent substrate was used to assay the ability of the TrwC Cba-Topo V Mka (where TrwC Cba is attached by the linker AYDVGA to domains H-L of Topoisomerase V Mka full sequence shown in SEQ ID NO: 90) to displace hybridised dsDNA. As shown in 1) of FIG. 23, the fluorescent substrate strand (50 nM final) has both a 3' and 5' ssDNA overhang, and a 44 base section of hybridised dsDNA. The upper strand, containing the 3' ssDNA overhang, has a carboxyfluorescein base (labelled 5 in SEQ ID NO: 91) at the 5' end, and the hybrised complement has a black-hole quencher (BHQ-1) base (labelled 6 in SEQ ID NO: 92) at the 3' end. When hybridised the fluorescence from the fluorescein is quenched by the local BHQ-1, and the substrate is essentially non-fluorescent. 1 µM of a capture strand (SEQ ID NO: 93) that is part-complementary to the lower strand of the fluorescent substrate is included in the assay. As shown in 2), in the presence of ATP (1 mM) and $MgCl_2$ (1 mM), helicase (100 nM) added to the substrate binds to the 3' tail of the fluorescent substrate, moves along the upper strand, and displaces the complementary strand. As shown in 3), once the complementary strand with BHQ-1 is fully displaced the fluorescein on the major strand fluoresces. As shown in 4), the displaced strand preferentially anneals to an excess of capture strand to prevent re-annealing of initial substrate and loss of fluorescence.

Results and Discussion

Figure 24:
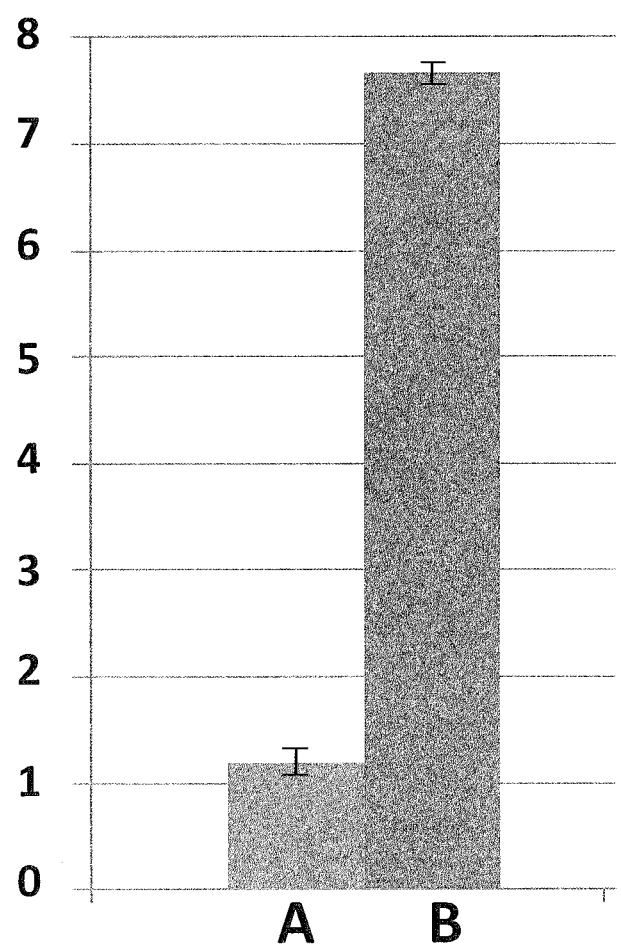
FIG. 24 Graph (y-axis=1000×dsDNA turnover (molecules/min/enz), x-axis=enzyme) of the initial rate of activity in buffer solutions (10 mM Hepes pH 8.0, 1 mM ATP, 1 mM MgCl$_2$, 50 nM fluorescent substrate DNA (SEQ ID NOs: 91 and 92), 1 µM capture DNA (SEQ ID NO: 93)) for the TrwC Cba monomer (labeled A, SEQ ID NO: 87) and the TrwC Cba-TopoV Mka (labeled B, where TrwC Cba is attached by the linker AYDVGA to domains H-L of Topoisomerase V Mka full sequence shown in SEQ ID NO: 90) at 400 mM of NaCl.

The graph in FIG. 24 shows the initial rate of activity in buffer solution (10 mM Hepes pH 8.0, 1 mM ATP, 1 mM $MgCl_2$, 50 nM fluorescent substrate DNA (SEQ ID NOs: 91 and 92), 1 µM capture DNA (SEQ ID NO: 93)) for the TrwC Cba monomer (labeled A in FIG. 24; SEQ ID NO: 87) and the TrwC Cba-Topo V Mka (labeled B in FIG. 24; where TrwC Cba is attached by the linker AYDVGA to domains H-L of Topoisomerase V Mka full sequence shown in SEQ ID NO: 90) at 400 mM of NaCl. At the salt concentration investigated the TrwC Cba-Topo V Mka (where TrwC Cba is attached by the linker AYDVGA to domains H-L of Topoisomerase V Mka full sequence shown in SEQ ID NO: 90) exhibited a higher rate of dsDNA turnover than the TrwC Cba monomer (SEQ ID NO: 87) (see FIG. 24).

EXAMPLE 11

This Example describes the method of synthesising the TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker).

Materials and Methods

DTT was added TrwC Cba Q276C monomer (2 mg/mL, where each monomer unit comprises SEQ ID NO: 87 with the mutation Q276C) to 10 mM and placed on a rotator for 30 min. The reduced protein was buffer exchanged into 100 mM potassium phosphate, 500 mM NaCl, 5 mM EDTA, 0.1% tween20, pH7.2. TrwC Cba Q276C monomer (2 mg/mL) (where each monomer unit comprises SEQ ID NO: 87 with the mutation Q276C) at 2 mg/ml was added to bismaleimide-PEG (3.4 kDa; 0.038 mM) was added and the reaction allowed to proceed at 23° C. under an atmosphere of nitrogen for 2.5 h. DTT (10 mM) was added to quench the reaction and break up any disulfide bridged species. The TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker) was purified immediately using an initial Strep-tactin step to remove reagents, followed by GF-chromatography step to separate dimer from all other species present in solution.

Figure 25:
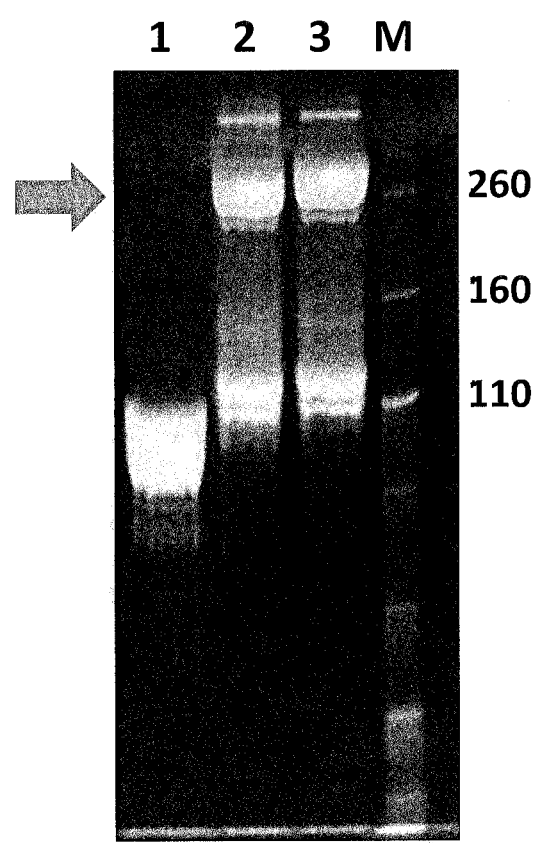
FIG. 25 shows a gel of the TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker) and TrwC Cba Q276C monomer (where each monomer unit comprises SEQ ID NO: 87 with the mutation Q276C) at various stages during formation and purification. Lane M=protein ladder, Lane 1=E3-Q276C monomer starting material, Lanes 2 and 3=reaction mix. The band which corresponds to TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker) is indicated by a grey arrow.
Figure 26:
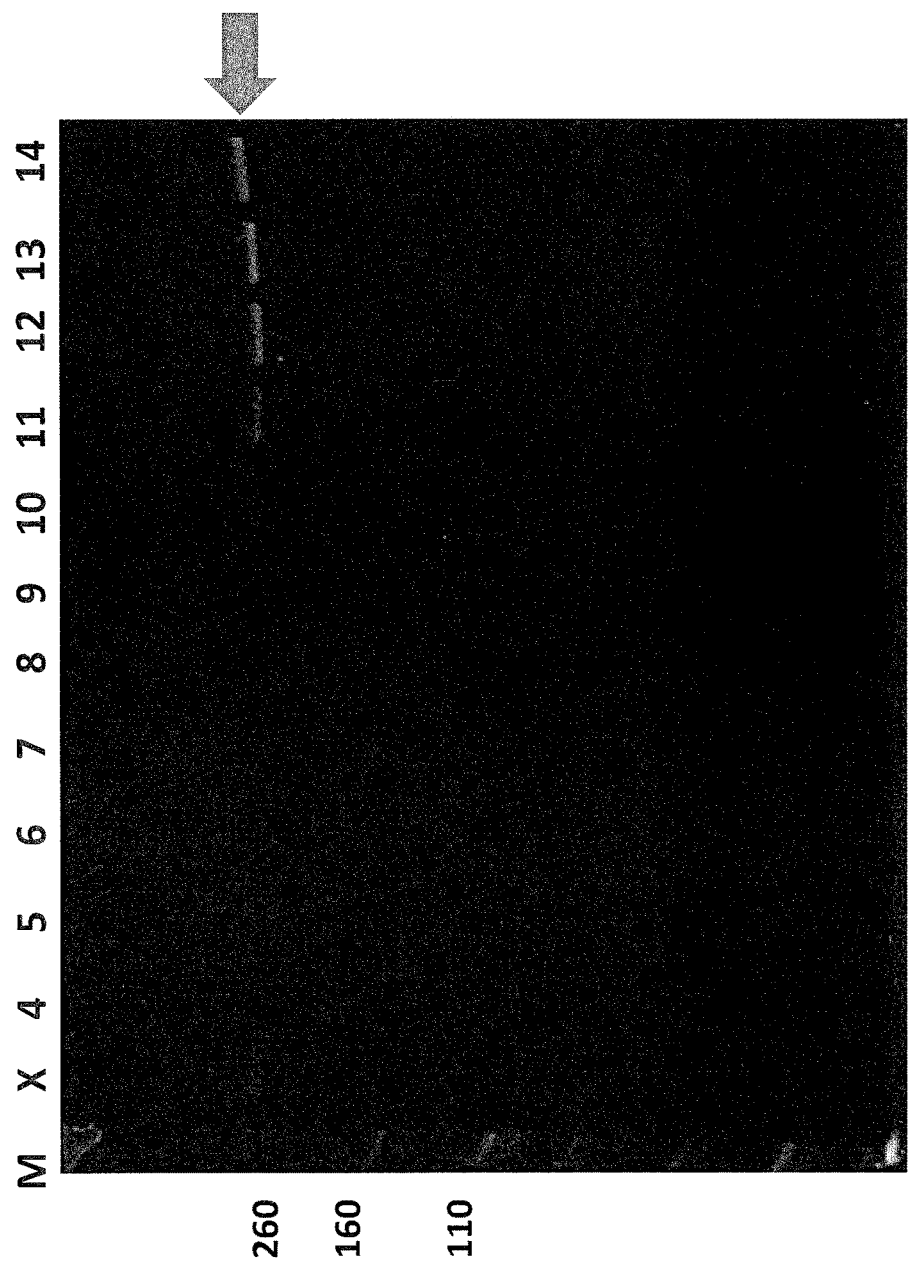
FIG. 26 shows a gel of the TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker) and TrwC Cba Q276C monomer (where each monomer unit comprises SEQ ID NO: 87 with the mutation Q276C) at various stages during formation and purification. Lane M=protein ladder, Lane X=reference lane for TrwC Cba Q276C-3.4 kDa dimer, lanes 4-14 contain purified fractions from the elution of TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker)). The band which corresponds to TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker) is indicated by a grey arrow.

An AKTA purifier machine was used for the purifications. Strep purification was performed on a 5 mL StrepTactin Sepharose High Performance column. The protein solution was buffer exchanged into binding buffer (50 mM Tris, 200 mM NaCl, 1 mM MgCl2, 2 mM DTT, 0.05% tween20, pH 8.0) before being loaded onto the column. After an initial wash step to remove all unbound material it was eluted with 10 mM desthiobiotin in buffer. The eluted protein was concentrated to 0.25 mL, buffer exchanged into 50 mM Tris, 250 mM NaCl, 2 mM DTT, 1 mM MgCl2, 0.05% tween20, pH 8.0 and purified by gel filtration on a Superdex™ 10/300 GL column. FIGS. 25 and 26 show gels of the TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker) and TrwC Cba Q276C monomer (where each monomer unit comprises SEQ ID NO: 87 with the mutation Q276C) at various stages during formation and purification (FIG. 25—Lane M=protein ladder, Lane 1=E3-Q276C monomer starting material, Lane 2=reaction mix, Lane 3=reaction mix. FIG. 26—Lane M=protein ladder, Lane X=reference lane for TrwC Cba Q276C-3.4 kDa dimer, lanes 4-14 contain purified fractions from the elution of TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker)). The band which corresponds to TrwC Cba Q276C-3.4 kDa dimer (where each monomer unit comprises SEQ ID NO: 87 with the mutation Q276C, with one monomer unit being linked to the other via position 276 of each monomer unit using a 3.4 kDa PEG linker) is indicated by a grey arrow in both FIGS. 25 and 26.

Using an analogous procedure to that described in this example, it was possible to make the following TrwC Cba Q276C-1 kDa dimer (where each monomer unit comprises SEQ ID NO: 87 with the mutation Q276C, with one monomer unit being linked to the other via position 276 of each monomer unit using a 1 kDa PEG linker).

EXAMPLE 12

Figure 27:
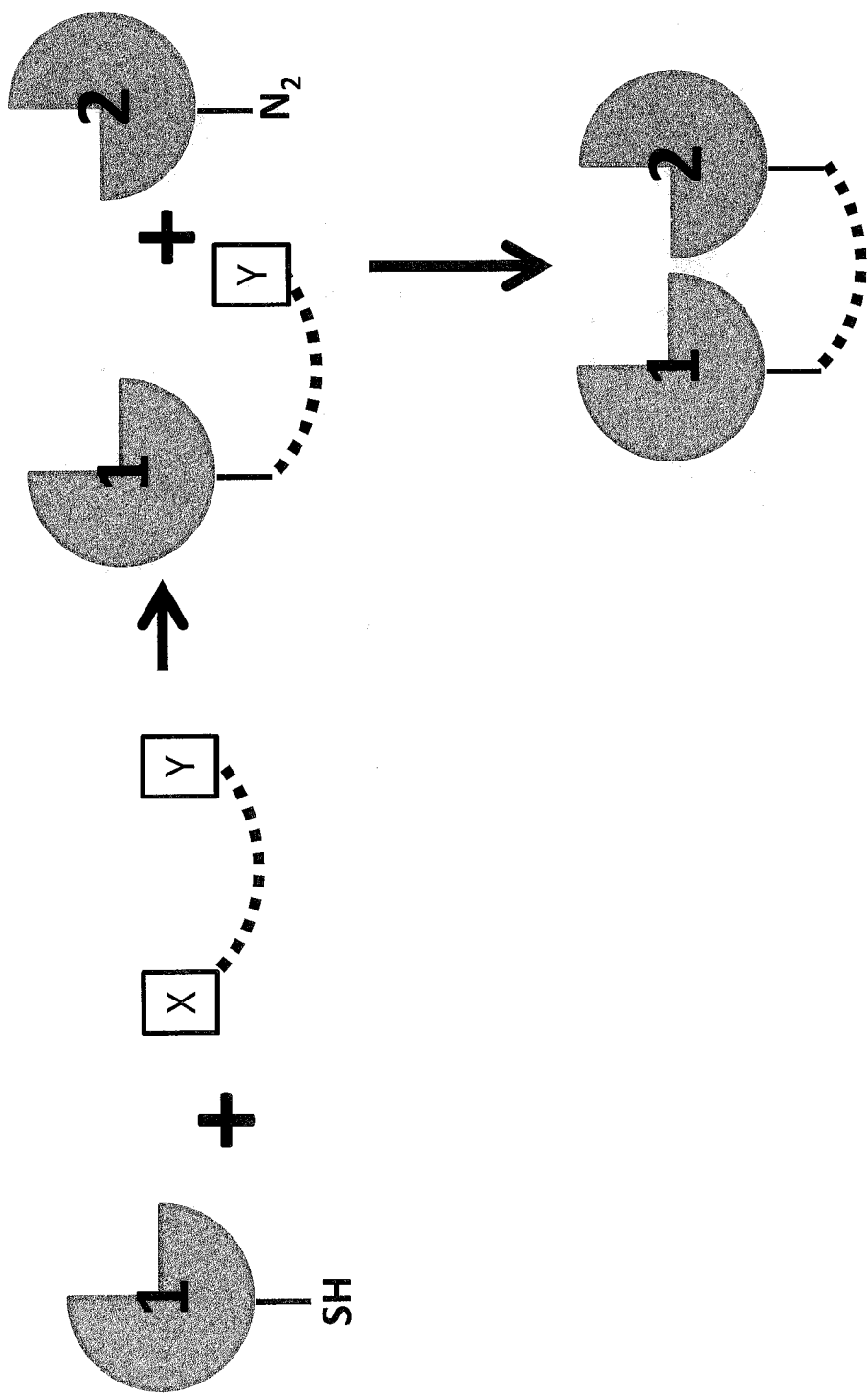
FIG. 27 shows a cartoon representation of the chemical reaction steps which are necessary to form the Hel308Mbu-A577Faz-PEG4 linker-TrwC Cba Q276C dimer (where the Hel308Mbu monomer unit (labeled 2) comprises SEQ ID NO: 10 with the amino acid at position 577 mutated to a 4-azido-L-phenylalanine (Faz), which is attached by PEG4 linker (black dotted line) to TrwC Cba monomer unit (labeled 1) SEQ ID NO: 87 with the mutation Q276C, where the linker is attached to each monomer at position 577 on Hel 308 Mbu monomer and position 276 on TrwC Cba). Step one reacts the cysteine at position 276 on the surface of TrwC Cba with the maleimide functional group (labelled X) at one end of the PEG4 linker. Step two reacts the 4-azido-L-phenylalanine (Faz) amino acid at position 577 on the surface of Hel308Mbu with the DBCO functional group (labelled Y) at the other end of the PEG4 linker using click chemistry.

This Example describes the method of synthesising the Hel308Mbu-A577Faz-PEG4 linker-TrwC Cba Q276C dimer (where the Hel308Mbu monomer unit comprises SEQ ID NO: 10 with the amino acid at position 577 mutated to a 4-azido-L-phenylalanine (Faz), which is attached by PEG4 linker to TrwC Cba monomer unit SEQ ID NO: 87 with the mutation Q276C, where the linker is attached to each monomer at position 577 on Hel 308 Mbu monomer and position 276 on TrwC Cba). A cartoon representation of the method to attach the two monomer units is shown in FIG. 27.

Materials and Methods

Figure 28:
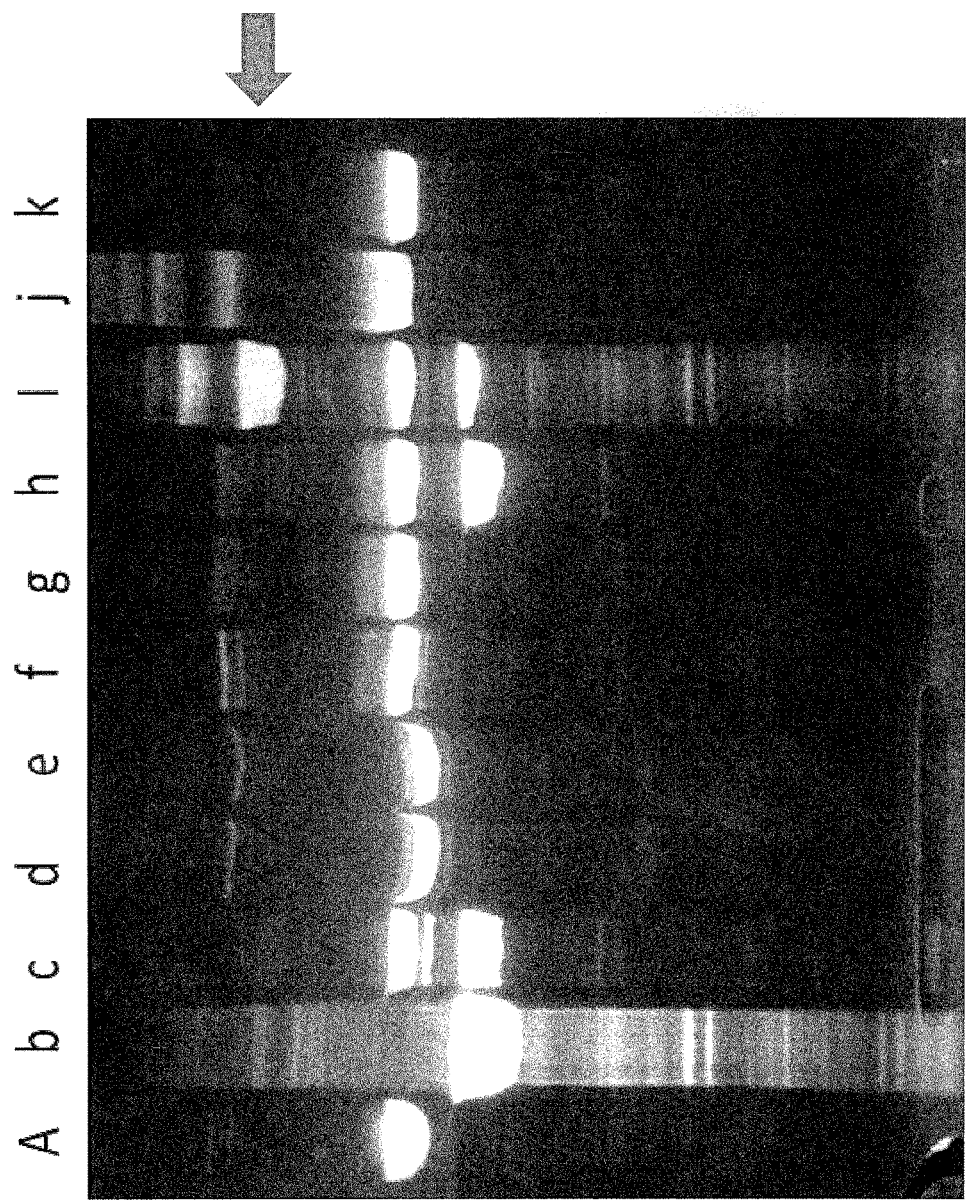
FIG. 28 shows a 4-12% gel of samples from Example 12. The sample in each lane is as follows—lane a) TrwC Cba-Q276C monomer (SEQ ID NO: 87 with the mutation Q276C), lane b) Hel308 Mbu-A577Faz (where each monomer unit comprises SEQ ID NO: 10 with the mutation A577Faz), lane c) TrwC Cba-Q276C monomer (SEQ ID NO: 87 with the mutation Q276C)+Hel308 Mbu-A577Faz (where each monomer unit comprises SEQ ID NO: 10 with the mutation A577Faz), lane d) TrwC Cba-Q276C monomer (SEQ ID NO: 87 with the mutation Q276C)+5 kDa PEG, lane e) TrwC Cba-Q276C monomer (SEQ ID NO: 87 with the mutation Q276C)+5 kDa PEG with an azide attached, lane f) TrwC Cba-Q276C monomer (SEQ ID NO: 87 with the mutation Q276C)+Azide Alexa Fluor® 555 (Life Technologies, used to check for non-specific interactions between the fluorophore and TrwC Cba-Q276C monomer), lane g) TrwC Cba-Q276C monomer (SEQ ID NO: 87 with the mutation Q276C)+Mal-PEG4-DBCO, lane h) TrwC Cba-Q276C-PEG4-DBCO (SEQ ID NO: 87 with the mutation Q276C which is attached to the PEG4-DBCO linker)+Hel308 Mbu (SEQ ID NO: 10), lane i) Hel308Mbu-A577Faz-PEG4 linker-TrwC Cba Q276C dimer (where the Hel308Mbu monomer unit comprises SEQ ID NO: 10 with the amino acid at position 577 mutated to a 4-azido-L-phenylalanine (Faz), which is attached by PEG4 linker to TrwC Cba monomer unit SEQ ID NO: 87 with the mutation Q276C, where the linker is attached to each monomer at position 577 on Hel 308 Mbu monomer and position 276 on TrwC Cba) plus unreacted TrwC Cba-Q276C monomer (SEQ ID NO: 87 with the mutation Q276C)+Mal-PEG4-DBCO+Hel308 Mbu-A577Faz monomer (where each monomer unit comprises SEQ ID NO: 10 with the mutation A577Faz), lane j) TrwC Cba-Q276C monomer (SEQ ID NO: 87 with the mutation Q276C)+Mal-PEG4-DBCO+5 kDa PEG with an azide attached, lane k) TrwC Cba-Q276C monomer (SEQ ID NO: 87 with the mutation Q276C)+Mal-PEG4-DBCO+Azide Alexa Fluor® 555 (Life Technologies, used to check for non-specific interactions between the fluorophore and TrwC Cba-Q276C monomer). The band corresponding to the desired dimer product (Hel308Mbu-A577Faz-PEG4 linker-TrwC Cba Q276C dimer (where the Hel308Mbu monomer unit comprises SEQ ID NO: 10 with the amino acid at position 577 mutated to a 4-azido-L-phenylalanine (Faz), which is attached by PEG4 linker to TrwC Cba monomer unit SEQ ID NO: 87 with the mutation Q276C, where the linker is attached to each monomer at position 577 on Hel 308 Mbu monomer and position 276 on TrwC Cba)) is indicated by a grey arrow.

DTT (10 mM) was added to TrwC Cba Q276C monomer (0.9 mg/mL, 1 mL, where each monomer unit comprises SEQ ID NO: 87 with the mutation Q276C) and the sample left at room temperature for 1 hour. Buffer exchange of the TrwC Cba Q276C monomer (0.9 mg/mL, where each monomer unit comprises SEQ ID NO: 87 with the mutation Q276C) sample was performed twice using 40K Zeba columns in 100 mM Tris 400 mM NaCl pH 7.5. Mal-PEG4-DBCO (500 µM) was added to the buffer exchanged TrwC Cba Q276C monomer (0.9 mg/mL, where each monomer unit comprises SEQ ID NO: 87 with the mutation Q276C) and the sample left at room temperature for 3 hours. The TrwC Cba Q276C monomer (0.9 mg/mL, where each monomer unit comprises SEQ ID NO: 87 with the mutation Q276C) Mal-PEG4-DBCO was then buffer exchanged twice, into 100 mM Tris 400 mM NaCl pH 7.5, using 40K Zeba columns. Hel308 Mbu-A577Faz (1.1 mg/mL, 1 mL, where each monomer unit comprises SEQ ID NO: 10 with the mutation A577Faz) was buffer exchanged into 100 mM Tris 400 mM NaCl pH 7.5 using a 40K Zeba column. The two buffer exchanged proteins were mixed together and left at room temperature for 3 hours. Finally, the following samples were then run on a 4-12% gel (shown in FIG. 28) lane a) TrwC Cba-Q276C monomer (SEQ ID NO: 87 with the mutation Q276C), lane b) Hel308 Mbu-A577Faz (where each monomer unit comprises SEQ ID NO: 10 with the mutation A577Faz), lane c) TrwC Cba-Q276C monomer (SEQ ID NO: 87 with the mutation Q276C)+Hel308 Mbu-A577Faz (where each monomer unit comprises SEQ ID NO: 10 with the mutation A577Faz), lane d) TrwC Cba-Q276C monomer (SEQ ID NO: 87 with the mutation Q276C)+5 kDa PEG, lane e) TrwC Cba-Q276C monomer (SEQ ID NO: 87 with the mutation Q276C)+5 kDa PEG with an azide attached, lane f) TrwC Cba-Q276C monomer (SEQ ID NO: 87 with the mutation Q276C)+Azide Alexa Fluor® 555 (Life Technologies, used to check for non-specific interactions between the fluorophore and TrwC Cba-Q276C monomer), lane g) TrwC Cba-Q276C monomer (SEQ ID NO: 87 with the mutation Q276C)+Mal-PEG4-DBCO, lane h) TrwC Cba-Q276C-PEG4-DBCO (SEQ ID NO: 87 with the mutation Q276C which is attached to the PEG4-DBCO linker)+Hel308 Mbu (SEQ ID NO: 10), lane i) Hel308Mbu-A577Faz-PEG4 linker-TrwC Cba Q276C dimer (where the Hel308Mbu monomer unit comprises SEQ ID NO: 10 with the amino acid at position 577 mutated to a 4-azido-L-phenylalanine (Faz), which is attached by PEG4 linker to TrwC Cba monomer unit SEQ ID NO: 87 with the mutation Q276C, where the linker is attached to each monomer at position 577 on Hel 308 Mbu monomer and position 276 on TrwC Cba) plus unreacted TrwC Cba-Q276C monomer (SEQ ID NO: 87 with the mutation Q276C)+Mal-PEG4-DBCO+Hel308 Mbu-A577Faz monomer (where each monomer unit comprises SEQ ID NO: 10 with the mutation A577Faz), lane j) TrwC Cba-Q276C monomer (SEQ ID NO: 87 with the mutation Q276C)+Mal-PEG4-DBCO+5 kDa PEG with an azide attached, lane k) TrwC Cba-Q276C monomer (SEQ ID NO: 87 with the mutation Q276C)+Mal-PEG4-DBCO+Azide Alexa Fluor® 555 (Life Technologies, used to check for non-specific interactions between the fluorophore and TrwC Cba-Q276C monomer).

The invention claimed is:

1. A method of characterizing a target polynucleotide, comprising:
   (a) contacting the target polynucleotide with a transmembrane pore and a construct comprising a helicase and an additional polynucleotide binding moiety, wherein the helicase is attached to the additional polynucleotide binding moiety and the construct has the ability to control the movement of a polynucleotide, such that the construct controls the movement of the target polynucleotide through the pore; and
   (b) taking one or more measurements as the polynucleotide moves with respect to the pore wherein the measurements are indicative of one or more characteristics of the target polynucleotide and thereby characterizing the target polynucleotide,
   wherein the helicase and the additional polynucleotide binding moiety are covalently attached, are chemically attached or are genetically fused, and
   wherein the additional polynucleotide binding moiety (a) comprises one or more helicases, (b) comprises one or more domains independently selected from helix-hairpin-helix (HhH) domains, eukaryotic single-stranded binding proteins (SSBs), bacterial SSBs, archaeal SSBs, viral SSBs, double-stranded binding proteins, sliding clamps, processivity factors, DNA binding loops, replication initiation proteins, telomere binding proteins, repressors, zinc fingers, and proliferating cell nuclear antigens (PCNAs), or (c) is derived from an exonuclease, polymerase, or topoisomerase.

2. The method according to claim 1, wherein the helicase and the additional polynucleotide binding moiety are attached by one or more linkers or are attached by one or more linkers which are amino acid sequences.

3. The method according to claim 1, wherein the additional polynucleotide binding moiety comprises one or more helicases.

4. The method according to claim 3, wherein the helicase is of the same type as the one or more helicases of the additional polynucleotide binding moiety.

5. The method according to claim 3, wherein the helicase is different from the one or more helicases of the additional polynucleotide binding moiety.

6. The method according to claim 3, wherein the helicases are attached to one another using the same amino acid residue in each helicase.

7. The method according to claim 1, wherein the additional polynucleotide binding moiety (b) comprises one or more domains independently selected from helix-hairpin-helix (HhH) domains, eukaryotic single-stranded binding proteins (SSBs), bacterial SSBs, archaeal SSBs, viral SSBs, double-stranded binding proteins, sliding clamps, processivity factors, DNA binding loops, replication initiation proteins, telomere binding proteins, repressors, zinc fingers, and proliferating cell nuclear antigens (PCNAs) or (c) is derived from an exonuclease, polymerase, or topoisomerase.

8. The method according to claim 1, wherein the additional polynucleotide binding moiety is selected from those shown in Table 4 and variants thereof or the polymerase is Phi29 polymerase (SEQ ID NO: 62) or a variant thereof.

9. The method according to claim 3, wherein the helicases are independently selected from superfamilies 1 to 6.

10. The method according to claim 3, wherein the helicases are independently monomeric.

11. The method according to claim 3, wherein the helicases are independently selected from Hel308 helicases, RecD helicases, TraI helicases, TraI subgroup helicases, XPD helicases, and variants thereof.

12. The method according to claim 9, wherein:
   (a) the Hel308 helicase comprises the amino acid motif Q-X1-X2-G-R-A-G-R (SEQ ID NO: 8), wherein X1 is C, M or L and X2 is any amino acid residue;
   (b) wherein the RecD helicase comprises:
      (i) the amino acid motif X1-X2-X3-G-X4-X5-X6-X7 (SEQ ID NO: 20), wherein X1 is G, S or A, X2 is any amino acid, X3 is P, A, S or G, X4 is T, A, V, S or C, X5 is G or A, X6 is K or R and X7 is T or S; and/or
      (ii) the amino acid motif X1-X2-X3-X4-X5-(X6)$_3$-Q-X7 (SEQ ID NO: 29), wherein X1 is Y, W or F, X2 is A, T, S, M, C or V, X$_3$ is any amino acid, X4 is T, N, or S, X5 is A, T, G, S, V or I, X6 is any amino acid and X7 is G or S;

(c) the TraI helicase or TraI subgroup helicase comprises:
(i) the amino acid motif H-(X1)$_2$-X2-R-(X3)$_{5-12}$-H-X4-H (SEQ ID NOs: 31-38), wherein X1 and X3 are any amino acid and X2 and X4 are independently selected from any amino acid except D, E, K and R; or
(ii) the amino acid motif G-X1-X2-X3-X4-X5-X6-X7-H-(X8)$_{6-12}$-H-X9 (SEQ ID NOs: 39-45), wherein X1, X2, X3, X5, X6, X7 and X9 are independently selected from any amino acid except D, E, K and R, X4 is D or E and X8 is any amino acid; or
(d) the XPD helicase comprises:
(i) the amino acid motif X1-X2-X3-G-X4-X5-X6-E-G (SEQ ID NO: 50), wherein X1, X2, X5 and X6 are independently selected from any amino acid except D, E, K and R and wherein X3 and X4 is any amino acid residue; and/or
(ii) the amino acid motif Q-Xa-Xb-G-R-Xc-Xd-R-(Xe)3-Xf-(Xg)7-D-N-R (SEQ ID NO: 51), wherein Xa, Xe and Xg is any amino acid residue and wherein Xb, Xc and Xd are independently selected from any amino acid except D, E, K and R, and wherein Xf is D or E.

13. The method according to claim 12, wherein (a) X2 in Hel308 helicase is A, F, M, C, V, L, I, S, T or P; (b) the Hel308 helicase is one of the helicases shown in Table 1 or a variant thereof having helicase activity; (c) the Hel308 helicase comprises (i) the sequence shown in SEQ ID NOs: 10, 13, 16, or 19 or (ii) a variant thereof having at least 80% sequence identity to SEQ ID NOs: 10, 13, 16, or 19 over the entire sequence and retaining helicase activity; (d) the TraI helicase comprises (i) the sequence shown in SEQ ID NO: 46, 87, 98, or 102 or (ii) a variant thereof having at least 80% sequence identity to SEQ ID NO: 46, 87, 98, or 102 over the entire sequence and retaining helicase activity; (e) X1, X2, X5 and X6 and/or Xb, Xc and Xd in the XPD helicase are independently selected from G, P, A, V, L, I, M, C, F, Y, W, H, Q, N, S and T; or (f) the XPD helicase comprises (i) the sequence shown in SEQ ID NO: 52 or (ii) a variant thereof having at least 80% sequence identity to SEQ ID NO: 52 over the entire sequence and retaining helicase activity.

14. The method according to claim 3, wherein at least one of the helicases is modified to facilitate the attachment by the introduction of one or more non-native cysteine residues and/or one or more 4-azido-L-phenylalanine (Faz) residues.

15. The method according to claim 1, wherein the one or more characteristics are selected from (i) the length of the target polynucleotide, (ii) the identity of the target polynucleotide, (iii) the sequence of the target polynucleotide, (iv) the secondary structure of the target polynucleotide, (v) whether or not the target polynucleotide is modified and (vi) whether or not the target polynucleotide is modified by methylation, by oxidation, by damage, with one or more proteins or with one or more labels, tags or spacers.

16. The method according to claim 1, wherein the one or more characteristics of the target polynucleotide are measured by an electrical measurement, an optical measurement, a current measurement, an impedance measurement, a tunneling measurement and/or a field effect transistor (FET) measurement.

17. The method according to claim 1, wherein the method comprises measuring the current passing through the pore as the polynucleotide moves with respect to the pore wherein the current is indicative of one or more characteristics of the target polynucleotide and thereby characterizing the target polynucleotide.

18. The method according to claim 1, wherein the method further comprises the step of applying a voltage across the pore to form a complex between the pore and the construct.

19. The method according to claim 1, wherein at least a portion of the polynucleotide is double stranded.

20. The method according to claim 1, wherein the pore is a transmembrane protein pore, a solid state pore or is derived from a hemolysin, leukocidin, *Mycobacterium smegmatis* porin A (MspA), MspB, MspC, MspD, outer membrane porin F (OmpF), outer membrane porin G (OmpG), outer membrane phospholipase A, *Neisseria* autotransporter lipoprotein (NalP) and WZA.

\* \* \* \* \*

UNITED STATES PATENT AND TRADEMARK OFFICE
CERTIFICATE OF CORRECTION

| | | |
|---|---|---|
| PATENT NO. | : 9,797,009 B2 | |
| APPLICATION NO. | : 14/415533 | |
| DATED | : October 24, 2017 | |
| INVENTOR(S) | : Andrew Heron et al. | |

It is certified that error appears in the above-identified patent and that said Letters Patent is hereby corrected as shown below:

In the Claims

Claim 11, at Column 226, Line number 52, should read:
--RecD helicases, TraI helicases, TraI subgroup helicases,--

Claim 12, at Column 227, Line number 1, should read:
--(c) the TraI helicase or TraI subgroup helicase comprises:--

Claim 12, at Column 227, Line numbers 17-18, should read:
--(ii) the amino acid motif Q-Xa-Xb-G-R-Xc-Xd-R-(Xe)$_3$-Xf-(Xg)$_7$-D-N-R (SEQ ID NO: 51), wherein Xa, Xe--

Claim 13, at Column 227, Line number 29, should read:
--entire sequence and retaining helicase activity; (d) the TraI--

Signed and Sealed this
Thirteenth Day of February, 2018

Andrei Iancu
*Director of the United States Patent and Trademark Office*